US011541027B2

(12) United States Patent
Bacha et al.

(10) Patent No.: US 11,541,027 B2
(45) Date of Patent: Jan. 3, 2023

(54) USE OF DIANHYDROGALACTITOL AND ANALOGS OR DERIVATIVES THEREOF IN COMBINATION WITH PLATINUM-CONTAINING ANTINEOPLASTIC AGENTS TO TREAT NON-SMALL-CELL CARCINOMA OF THE LUNG AND BRAIN METASTASES

(71) Applicant: DelMar Pharmaceuticals, Inc., Vancouver (CA)

(72) Inventors: Jeffrey A. Bacha, Vancouver (CA); Dennis M. Brown, Menlo Park, CA (US); Anne Steinø, Vancouver (CA)

(73) Assignee: DEL MAR PHARMACEUTICALS (BC) LTD., Vancouver (CA)

( * ) Notice: Subject to any disclaimer, the term of this patent is extended or adjusted under 35 U.S.C. 154(b) by 0 days.

(21) Appl. No.: 14/710,240

(22) Filed: May 12, 2015

(65) Prior Publication Data
US 2016/0008316 A1 Jan. 14, 2016
US 2019/0269646 A9 Sep. 5, 2019

Related U.S. Application Data

(63) Continuation-in-part of application No. PCT/US2015/024462, filed on Apr. 6, 2015.

(60) Provisional application No. 62/062,246, filed on Oct. 10, 2014, provisional application No. 61/975,587, filed on Apr. 4, 2014.

(51) Int. Cl.
| *A61K 31/336* | (2006.01) |
| *A61K 33/243* | (2019.01) |
| *A61K 9/00* | (2006.01) |
| *A61K 9/51* | (2006.01) |
| *A61K 9/08* | (2006.01) |
| *A61K 9/16* | (2006.01) |
| *A61K 9/127* | (2006.01) |
| *A61K 9/48* | (2006.01) |
| *A61K 9/20* | (2006.01) |
| *A61K 9/06* | (2006.01) |
| *A61K 9/10* | (2006.01) |
| *A61K 9/02* | (2006.01) |
| *A61K 31/04* | (2006.01) |
| *A61K 9/19* | (2006.01) |
| *A61K 9/70* | (2006.01) |
| *A61K 45/06* | (2006.01) |
| *C12Q 1/6886* | (2018.01) |

(52) U.S. Cl.
CPC .............. *A61K 31/336* (2013.01); *A61K 9/00* (2013.01); *A61K 9/0014* (2013.01); *A61K 9/0019* (2013.01); *A61K 9/0056* (2013.01); *A61K 9/0095* (2013.01); *A61K 9/02* (2013.01); *A61K 9/06* (2013.01); *A61K 9/08* (2013.01); *A61K 9/10* (2013.01); *A61K 9/127* (2013.01); *A61K 9/1605* (2013.01); *A61K 9/19* (2013.01); *A61K 9/2004* (2013.01); *A61K 9/4808* (2013.01); *A61K 9/5107* (2013.01); *A61K 9/7023* (2013.01); *A61K 31/04* (2013.01); *A61K 33/243* (2019.01); *A61K 45/06* (2013.01); *C12Q 1/6886* (2013.01); *C12Q 2600/156* (2013.01); *C12Q 2600/158* (2013.01)

(58) Field of Classification Search
CPC ..... A61K 31/336; A61K 33/24; A61K 33/243
See application file for complete search history.

(56) References Cited

U.S. PATENT DOCUMENTS

| 4,801,575 A | 1/1989 | Pardridge |
| 4,853,221 A | 8/1989 | Elslager et al. |
| 5,035,878 A | 7/1991 | Borch et al. |
| 5,294,430 A | 3/1994 | Borch et al. |
| 5,597,798 A | 1/1997 | Howell et al. |
| 5,756,512 A | 5/1998 | Johnson |
| 5,795,871 A | 8/1998 | Narita et al. |
| 6,232,307 B1 | 5/2001 | Miller et al. |
| 6,287,792 B1 | 9/2001 | Pardridge et al. |
| 6,335,156 B1 | 1/2002 | Hermeking et al. |
| 6,372,250 B1 | 4/2002 | Pardridge |

(Continued)

FOREIGN PATENT DOCUMENTS

| CN | 101869558 A | 10/2010 |
| JP | 2015-504048 A | 2/2015 |

(Continued)

OTHER PUBLICATIONS

Eagan et al., A role of cis-dichlorodiamineplatinum(II) in squamous cell lung cancer, 1980, Cancer Treatment Reports, vol. 64, No. 1, pp. 87-91, Abstract Only Provided.*
Stewart et al., Tumor and host factors that may limit efficacy of chemotherapy in non-small cell and small cell lung cancer, 2010, Critical Reviews in Oncology/Hematology, vol. 75, pp. 173-234.*
Weill et al. Adenoviral-mediated p53 Gene Transfer to Non-small cell lung cancer through endobronchial injection, 2000, Chest, vol. 118, pp. 966-970.*

(Continued)

*Primary Examiner* — James D. Anderson
(74) *Attorney, Agent, or Firm* — Christensen O'Connor Johnson Kindness PLLC

(57) ABSTRACT

The use of dianhydrogalactitol provides a novel therapeutic modality for the treatment of non-small-cell lung carcinoma (NSCLC) and ovarian cancer, as well as other types of malignancy, including brain metastases of NSCLC. Dianhydrogalactitol acts as an alkylating agent on DNA that creates $N^7$ methylation. Dianhydrogalactitol is effective in suppressing the growth of cancer stem cells and is active against tumors that are refractory to temozolomide, cisplatin, and tyrosine kinase inhibitors; the drug acts independently of the MGMT repair mechanism. Dianhydrogalactitol can be used together with other anti-neoplastic agents and can possess additive or super-additive effects.

33 Claims, 20 Drawing Sheets

(56) References Cited

U.S. PATENT DOCUMENTS

| | | |
|---|---|---|
| 6,443,898 B1 | 9/2002 | Unger et al. |
| 6,573,292 B1 | 6/2003 | Nardella |
| 6,740,523 B2 | 5/2004 | Hermeking et al. |
| 6,921,772 B2 | 7/2005 | Nardella |
| 7,074,575 B2 | 7/2006 | Chandrasekher et al. |
| 7,101,576 B2 | 9/2006 | Hovey et al. |
| 7,314,886 B2 | 1/2008 | Chao et al. |
| 7,323,164 B2 | 1/2008 | Chandrasekher et al. |
| 7,388,079 B2 | 6/2008 | Pardridge et al. |
| 7,446,122 B2 | 11/2008 | Chao et al. |
| 7,507,536 B2 | 3/2009 | Van Criekinge et al. |
| 7,507,800 B2 | 3/2009 | van Ommen et al. |
| 7,619,005 B2 | 11/2009 | Epstein et al. |
| 7,655,414 B2 | 2/2010 | Brennscheidt et al. |
| 7,728,042 B2 | 6/2010 | Eros et al. |
| 7,825,129 B2 | 11/2010 | Pellicciari et al. |
| 7,879,896 B2 | 2/2011 | Allegretti et al. |
| 7,910,314 B2 | 3/2011 | Frackelton, Jr. et al. |
| 7,928,105 B2 | 4/2011 | Gangloff et al. |
| 7,956,064 B2 | 6/2011 | Chua et al. |
| 7,968,514 B2 | 6/2011 | Coelingh Bennink et al. |
| 7,994,184 B2 | 8/2011 | Rabizadeh et al. |
| 8,008,491 B2 | 8/2011 | Jiang et al. |
| 8,030,060 B2 | 10/2011 | Guo |
| 8,058,275 B2 | 11/2011 | Xu et al. |
| 8,088,760 B2 | 1/2012 | Chu et al. |
| 8,119,654 B2 | 2/2012 | Jagtap et al. |
| 8,124,095 B2 | 2/2012 | Pardridge et al. |
| 8,133,692 B2 | 3/2012 | Jove et al. |
| 8,183,250 B2 | 5/2012 | Penning et al. |
| 8,188,103 B2 | 5/2012 | Van Der Aa et al. |
| 8,211,643 B2 | 7/2012 | Tsao et al. |
| 8,217,070 B2 | 7/2012 | Zhu et al. |
| 8,236,802 B2 | 8/2012 | Xu et al. |
| 8,247,416 B2 | 8/2012 | Menear et al. |
| 8,268,827 B2 | 9/2012 | Branca et al. |
| 8,268,889 B2 | 9/2012 | Kloog et al. |
| 8,277,807 B2 | 10/2012 | Gallagher et al. |
| 8,299,088 B2 | 10/2012 | Matteucci et al. |
| 8,299,256 B2 | 10/2012 | Vialard et al. |
| 8,309,573 B2 | 11/2012 | Fujio et al. |
| 8,323,906 B2 | 12/2012 | Veiby et al. |
| 8,324,282 B2 | 12/2012 | Gerson et al. |
| 8,338,477 B2 | 12/2012 | Duncan et al. |
| 8,362,072 B2 | 1/2013 | Jensen et al. |
| 8,377,888 B2 | 2/2013 | Costa et al. |
| 8,404,829 B2 | 3/2013 | Gray et al. |
| 8,465,929 B2 | 6/2013 | Fung et al. |
| 8,476,026 B2 | 7/2013 | Alex et al. |
| 8,476,420 B2 | 7/2013 | Showe et al. |
| 8,529,900 B2 | 9/2013 | Alifano et al. |
| 8,541,433 B2 | 9/2013 | Clozel et al. |
| 8,575,191 B2 | 11/2013 | Chen et al. |
| 8,623,592 B2 | 1/2014 | Schoeberl et al. |
| 8,642,347 B2 | 2/2014 | Ye et al. |
| 8,652,777 B2 | 2/2014 | Kamalakaran et al. |
| 8,664,358 B2 | 3/2014 | Mansfield et al. |
| 8,682,591 B2 | 3/2014 | Chan et al. |
| 8,700,335 B2 | 4/2014 | Von Hoff et al. |
| 8,728,823 B2 | 5/2014 | Lam et al. |
| 8,741,587 B2 | 6/2014 | Roessler et al. |
| 8,741,641 B2 | 6/2014 | Inazawa et al. |
| 8,741,889 B2 | 6/2014 | Boylan et al. |
| 8,748,470 B2 | 6/2014 | Lengyel et al. |
| 8,768,629 B2 | 7/2014 | Von Hoff et al. |
| 8,828,657 B2 | 9/2014 | Rafnar et al. |
| 8,841,277 B2 | 9/2014 | Nguyen et al. |
| 8,911,940 B2 | 12/2014 | Weiss et al. |
| 8,920,799 B2 | 12/2014 | Graham et al. |
| 8,921,367 B2 | 12/2014 | Friberg et al. |
| 8,921,407 B2 | 12/2014 | Ying et al. |
| 8,921,414 B2 | 12/2014 | Reddell et al. |
| 8,921,522 B2 | 12/2014 | Grosveld et al. |
| 8,921,546 B2 | 12/2014 | Chao |
| 8,921,565 B2 | 12/2014 | Flynn et al. |
| 8,927,533 B2 | 1/2015 | Giannini et al. |
| 8,927,538 B2 | 1/2015 | Kamal et al. |
| 8,927,548 B2 | 1/2015 | Ying et al. |
| 8,927,560 B2 | 1/2015 | Ahmed et al. |
| 8,927,562 B2 | 1/2015 | Meng et al. |
| 8,927,580 B2 | 1/2015 | Richardson et al. |
| 8,927,711 B2 | 1/2015 | Abraham et al. |
| 8,927,717 B1 | 1/2015 | Huang et al. |
| 8,927,718 B2 | 1/2015 | Sasaki et al. |
| 8,933,053 B2 | 1/2015 | Mcguigan et al. |
| 8,933,080 B2 | 1/2015 | Singh et al. |
| 8,933,084 B2 | 1/2015 | Andrews et al. |
| 8,933,103 B2 | 1/2015 | Ohki et al. |
| 8,933,116 B2 | 1/2015 | Wu et al. |
| 8,933,212 B2 | 1/2015 | Fayard et al. |
| 8,937,094 B2 | 1/2015 | Burlison et al. |
| 8,937,095 B2 | 1/2015 | Zahn et al. |
| 8,937,193 B2 | 1/2015 | Pellecchia et al. |
| 8,940,302 B2 | 1/2015 | Amler et al. |
| 8,940,726 B2 | 1/2015 | Duncan et al. |
| 8,940,733 B2 | 1/2015 | Howard et al. |
| 8,940,737 B2 | 1/2015 | Wang et al. |
| 8,940,756 B2 | 1/2015 | Flynn et al. |
| 8,940,760 B2 | 1/2015 | Page et al. |
| 8,940,936 B2 | 1/2015 | Lee et al. |
| 8,946,213 B2 | 2/2015 | Crawford et al. |
| 8,946,216 B2 | 2/2015 | Deng et al. |
| 8,946,224 B2 | 2/2015 | Craighead et al. |
| 8,946,235 B2 | 2/2015 | Butterworth et al. |
| 8,946,239 B2 | 2/2015 | Gangjee |
| 8,946,246 B2 | 2/2015 | Magedov et al. |
| 8,946,275 B2 | 2/2015 | Curd et al. |
| 8,946,278 B2 | 2/2015 | Seefeld et al. |
| 8,946,289 B2 | 2/2015 | Hong et al. |
| 8,946,296 B2 | 2/2015 | Ortega Muñoz et al. |
| 8,946,409 B2 | 2/2015 | Becker et al. |
| 8,946,413 B2 | 2/2015 | Hughes et al. |
| 8,946,444 B2 | 2/2015 | Lennox et al. |
| 8,946,445 B2 | 2/2015 | Wang |
| 8,951,536 B2 | 2/2015 | Combs et al. |
| 8,951,987 B2 | 2/2015 | Hamilton et al. |
| 8,951,993 B2 | 2/2015 | Hu et al. |
| 8,952,043 B2 | 2/2015 | Blaquiere et al. |
| 8,952,054 B2 | 2/2015 | Kufe et al. |
| 8,952,151 B2 | 2/2015 | Chen et al. |
| 8,952,157 B2 | 2/2015 | Ding et al. |
| 8,952,161 B2 | 2/2015 | Beaton et al. |
| 8,952,163 B2 | 2/2015 | Blackburn et al. |
| 8,956,613 B2 | 2/2015 | Wu |
| 8,957,056 B2 | 2/2015 | Danishefsky et al. |
| 8,957,068 B2 | 2/2015 | Caferro et al. |
| 8,957,078 B2 | 2/2015 | Brenchley et al. |
| 8,957,102 B2 | 2/2015 | Kim et al. |
| 8,957,109 B2 | 2/2015 | Heaton et al. |
| 8,961,966 B2 | 2/2015 | Schoeberl et al. |
| 8,961,970 B2 | 2/2015 | Huang et al. |
| 8,962,602 B2 | 2/2015 | Fernández Rodríguez et al. |
| 8,962,608 B2 | 2/2015 | Brubaker et al. |
| 8,962,609 B2 | 2/2015 | Perrior et al. |
| 8,962,611 B2 | 2/2015 | Christopher et al. |
| 8,962,619 B2 | 2/2015 | Ashwell et al. |
| 8,962,620 B2 | 2/2015 | Kuntz et al. |
| 8,962,630 B2 | 2/2015 | Brain et al. |
| 8,962,637 B2 | 2/2015 | Mc Allister et al. |
| 8,962,642 B2 | 2/2015 | Mortimore et al. |
| 8,962,663 B2 | 2/2015 | Mahadevan et al. |
| 8,962,679 B2 | 2/2015 | Wang et al. |
| 8,962,855 B2 | 2/2015 | Chen et al. |
| 8,969,001 B2 | 3/2015 | Buckingham |
| 8,969,313 B2 | 3/2015 | Yu |
| 8,969,335 B2 | 3/2015 | Hoelzemann et al. |
| 8,969,360 B2 | 3/2015 | Charrier et al. |
| 8,969,366 B2 | 3/2015 | Marchionni et al. |
| 8,969,372 B2 | 3/2015 | Huesca et al. |
| 8,969,375 B2 | 3/2015 | Lai et al. |
| 8,969,379 B2 | 3/2015 | Furitsu et al. |
| 8,969,381 B2 | 3/2015 | Wilson et al. |
| 8,969,395 B2 | 3/2015 | Ribeiro Salvador et al. |
| 8,969,396 B2 | 3/2015 | Du et al. |

(56) References Cited

U.S. PATENT DOCUMENTS

| | | |
|---|---|---|
| 8,969,401 B2 | 3/2015 | Maier et al. |
| 8,969,587 B2 | 3/2015 | Abraham et al. |
| 8,974,781 B2 | 3/2015 | Bauer et al. |
| 8,975,248 B2 | 3/2015 | Zaknoen et al. |
| 8,975,260 B2 | 3/2015 | Currie et al. |
| 8,975,265 B2 | 3/2015 | Ince et al. |
| 8,975,267 B2 | 3/2015 | Caldarelli et al. |
| 8,975,287 B2 | 3/2015 | Karp et al. |
| 8,975,376 B2 | 3/2015 | Blein et al. |
| 8,975,398 B2 | 3/2015 | Hansen et al. |
| 8,975,401 B2 | 3/2015 | Qian et al. |
| 8,980,257 B2 | 3/2015 | Kaneda et al. |
| 8,980,268 B2 | 3/2015 | Lowy et al. |
| 8,980,824 B2 | 3/2015 | Cong et al. |
| 8,980,850 B2 | 3/2015 | Smith |
| 8,980,875 B2 | 3/2015 | Mailliet et al. |
| 8,980,879 B2 | 3/2015 | Liu et al. |
| 8,980,902 B2 | 3/2015 | Brown et al. |
| 8,980,909 B2 | 3/2015 | Chen et al. |
| 8,980,933 B2 | 3/2015 | Schobert et al. |
| 8,980,934 B2 | 3/2015 | Pauls et al. |
| 8,980,955 B2 | 3/2015 | Turchi et al. |
| 8,981,084 B2 | 3/2015 | Baloglu et al. |
| 8,981,085 B2 | 3/2015 | Le Huerou et al. |
| 8,981,094 B2 | 3/2015 | Bongartz et al. |
| 8,981,131 B2 | 3/2015 | Bhedi et al. |
| 8,987,257 B2 | 3/2015 | Radetich et al. |
| 8,987,260 B2 | 3/2015 | Chuckowree et al. |
| 8,987,267 B2 | 3/2015 | Reddy et al. |
| 8,987,280 B2 | 3/2015 | Dotson et al. |
| 8,987,281 B2 | 3/2015 | Reddy et al. |
| 8,987,412 B2 | 3/2015 | Arora et al. |
| 8,987,461 B2 | 3/2015 | Nie et al. |
| 2002/0037328 A1 | 3/2002 | Brown |
| 2004/0023290 A1 | 2/2004 | Griffin et al. |
| 2005/0085419 A1 | 4/2005 | Morrison et al. |
| 2005/0272766 A1 | 12/2005 | Koya |
| 2006/0058217 A1 | 3/2006 | White et al. |
| 2006/0094738 A1 | 5/2006 | Rabizadeh et al. |
| 2007/0032502 A1 | 2/2007 | Mallams et al. |
| 2007/0207952 A1 | 9/2007 | Silva et al. |
| 2007/0299020 A1 | 12/2007 | Zeldis |
| 2009/0099102 A1 | 4/2009 | Ye et al. |
| 2009/0118271 A1 | 5/2009 | Umeda et al. |
| 2010/0009930 A1 | 1/2010 | Sherman et al. |
| 2012/0183546 A1 | 7/2012 | Weinreich |
| 2012/0237502 A1 | 9/2012 | Darnowski |
| 2012/0269827 A1 | 10/2012 | Whiteman et al. |
| 2013/0178487 A1 | 7/2013 | Solca et al. |
| 2013/0203861 A1 | 8/2013 | Liu et al. |
| 2013/0210144 A1 | 8/2013 | Arora et al. |
| 2013/0231286 A1 | 9/2013 | Chen |
| 2014/0017703 A1 | 1/2014 | Lancaster et al. |
| 2014/0057798 A1 | 2/2014 | Gong et al. |
| 2014/0134169 A1 | 5/2014 | Kuhnert et al. |
| 2014/0275174 A1 | 9/2014 | Moore et al. |
| 2014/0302174 A1 | 10/2014 | Chan et al. |
| 2014/0309184 A1 | 10/2014 | Rocconi et al. |
| 2014/0315959 A1 | 10/2014 | Moore et al. |
| 2014/0336150 A1 | 11/2014 | Frederick |
| 2014/0350096 A1 | 11/2014 | Yang et al. |
| 2014/0357594 A1 | 12/2014 | Hendrickson et al. |
| 2014/0357605 A1 | 12/2014 | Gavai et al. |
| 2014/0364341 A1 | 12/2014 | Mansfield et al. |
| 2014/0371158 A1 | 12/2014 | Chadli et al. |
| 2014/0371254 A1 | 12/2014 | Leung et al. |
| 2014/0378466 A1 | 12/2014 | Maderna et al. |
| 2015/0005309 A1 | 1/2015 | Bärfacker et al. |
| 2015/0011461 A1 | 1/2015 | Crawford et al. |
| 2015/0011506 A1 | 1/2015 | Olhava et al. |
| 2015/0011561 A1 | 1/2015 | Allwein et al. |
| 2015/0031561 A1 | 1/2015 | Bertenshaw et al. |
| 2015/0031669 A1 | 1/2015 | Woodhead et al. |
| 2015/0038430 A1 | 2/2015 | Nash et al. |
| 2015/0038506 A1 | 2/2015 | Nacro et al. |
| 2015/0045324 A1 | 2/2015 | Cha et al. |
| 2015/0045386 A1 | 2/2015 | Bencherif et al. |
| 2015/0051209 A1 | 2/2015 | Bock et al. |
| 2015/0057286 A1 | 2/2015 | Reiser |
| 2015/0057293 A1 | 2/2015 | Angibaud et al. |
| 2015/0057295 A1 | 2/2015 | Reiser et al. |
| 2015/0057309 A1 | 2/2015 | Vakkalanka et al. |
| 2015/0065526 A1 | 3/2015 | Deng et al. |
| 2015/0073003 A1 | 3/2015 | Dagan et al. |
| 2015/0073054 A1 | 3/2015 | Strongin et al. |
| 2015/0079081 A1 | 3/2015 | Dotson et al. |
| 2015/0080249 A1 | 3/2015 | Lancaster et al. |
| 2015/0080392 A1 | 3/2015 | Wang et al. |
| 2015/0086551 A1 | 3/2015 | Chen et al. |
| 2015/0087600 A1 | 3/2015 | Popovici-Muller et al. |
| 2015/0087628 A1 | 3/2015 | Ostrem et al. |
| 2015/0087630 A1 | 3/2015 | Chen et al. |
| 2015/0087664 A1 | 3/2015 | Blake et al. |

FOREIGN PATENT DOCUMENTS

| | | |
|---|---|---|
| WO | 0196602 A2 | 12/2001 |
| WO | 03070823 A2 | 8/2003 |
| WO | 2012024367 A2 | 2/2012 |
| WO | WO 2013/096755 A1 | 6/2013 |
| WO | 2013110058 A2 | 7/2013 |
| WO | 2014004376 A2 | 1/2014 |

OTHER PUBLICATIONS

Mandziuk et al. "Expression of p53 gene in non-small cell lung cancer in stage IIIa in patitents after neoadiuvant chemotherapy", 2003, Annales Universitatis Marie Curie-Sklodowska, vol. LVIII, No. 1, 28, pp. 154-157. (Year: 2003).*

Eagan et al., A role of cis-dichlorodiamineplatinum(II) in Squamous Cell Lung Cancer, 1980, Cancer Treatment Reprots vol. 64, No. 1, pp. 87-91. (Year: 1980).*

Bacha et al., "VAL-083: NSCLC: Historical Review & Strategy for Product Differentiation", Rodman & Renshaw 14th Annual Global Investment Conference, Sep. 9-11, 2012, 26 Pages.

Mischler et al., "Dibromodulcitol", Cancer Treatment Reviews, Sep. 1979, vol. 6, No. 3, pp. 191-204.

Mialiepaard et al., "Overexpression of the BCRP/MXR/ABCP Gene in a Topotecan-selected Ovarian Tumor Cell Line", The Journal of Cancer Research, Sep. 15, 1999, vol. 59, No. 18, pp. 4559-4563.

Ng et al., "Antiangiogenic Activity of N-substituted and Tetrafluorinated Thalidomide Analogues", Cancer Research, Jun. 15, 2003, pp. 3189-3194.

Baraldi et al., "Design, Synthesis, and Biological Activity of Hybrid Compounds between Uramustine and DNA Minor Groove Binder Distamycin A", Journal of Medicinal Chemistry, Jul. 13, 2002, vol. 45, No. 17, pp. 3630-3638.

Fabrissin et al., "Synthesis and Anticancer Activity of 5-Diethylaminomethyl Derivatives and Nitrogen Mustards of Uracil and 2-Thiouracils", Journal of Medicinal Chemistry, May 1976, vol. 19, No. 5, pp. 639-642.

Mattes et al., "DNA Sequence Selectivity of Guanine-N7 Alkylation by Nitrogen Mustards", Nucleic Acids Research, Mar. 3, 1986, vol. 14, No. 7, pp. 2971-2987.

O' Connor et al., "Comparative Pharmacokinetics of DNA Lesion Formation and Removal Following Treatment of L1210 Cells with Nitrogen Mustards", Cancer Communications, 1990, vol. 2, No. 12, pp. 387-394.

Kennedy et al., "Uracil Mustard Revisited", American Cancer Society, May 15, 1999, vol. 85, No. 10, pp. 2265-2272.

Mertins et al., "In Vitro Evaluation of Dimethane Sulfonate Analogues with Potential Alkylating Activity and Selective Renal Cell Carcinoma Cytotoxicity", Molecular Cancer Therapeutics, Jul. 2004, vol. 3, No. 7, 13 Pages.

Shah et al., "Multiple BCR-ABL Kinase Domain Mutations Confer Polyclonal Resistance to the Tyrosine Kinase Inhibitor Imatinib (STI571) in Chronic Phase and Blast Crisis Chronic Myeloid Leukemia", Cancer Cell, Aug. 2002, vol. 2, pp. 117-125.

(56) References Cited

OTHER PUBLICATIONS

Gaurnier-Hausser et al., "NEMO-Binding Domain Peptide Inhibits Constitutive NF-κB Activity and Reduces Tumor Burden in a Canine Model of Relapsed, Refractory Diffuse Large B-Cell Lymphoma", American Association for Cancer Research, May 24, 2011, 12 Pages.
Rusch et al., "Overexpression of the Epidermal Growth Factor Receptor and Its Ligand Transforming Growth Factor alpha is Frequent in Resectable Non-Small Cell Lung Cancer but Does Not Predict Tumor Progression", Clinical Cancer Research, Apr. 1997, vol. 3, 9 Pages.
Ma et al., "Identification of the Binding Site for Gqα on its Effector Bruton's Tyrosine Kinase", Proceedings of the National Academy of Sciences, Oct. 1998, vol. 95, pp. 12197-12201.
Calabretta et al., "Altered Expression of G1-Specific Genes in Human Malignant Myeloid Cells", Proceedings of the National Academy of Sciences, Mar. 1986, vol. 83, pp. 1495-1498.
Yasuda et al., "Cb1-b Positively Regulates Btk-mediated Activation of Phospholipase C-γ2 in B Cells", The Journal of Experimental Medicine, Jun. 24, 2002, vol. 196, No. 1, pp. 51-63.
Akinleye et al., "Ibrutinib and Novel BTK Inhibitors in Clinical Development", Journal of Hematology & Oncology, 2013, 9 Pages.
Child et al., "High-Dose Chemotherapy with Hematopoietic Stem-Cell Rescue for Multiple Myeloma", The New England Journal of Medicine, May 8, 2003, pp. 1875-1883.
Hideshima et al., "The Proteasome Inhibitor PS-341 Inhibits Growth, Induces Apoptosis, and Overcomes Drug Resistance in Human Multiple Myeloma Cells", Cancer Research, Apr. 1, 2001, pp. 3071-3076.
Vuyyuri et al., "Evaluation of D-Methionine as a Novel Oral Radiation Protector for Prevention of Mucositis", Clinical Cancer Research, Apr. 1, 2008, vol. 14, No. 7, 11 Pages.
Hingorani et al., "Inhibition of Repair of Radiation-Induced DNA Damage Enhances Gene Expression from Replication-Defective Adenoviral Vectors", Cancer Research, Dec. 1, 2008, 9 Pages.
Seynhaeve et al., "Tumor Necrosis Factor alpha Mediates Homogeneous Distribution of Liposomes in Murine Melanoma that Contributes to a Better Tumor Response", Cancer Research, Oct. 1, 2007, vol. 67, No. 19, 9 Pages.
Aghajanian et al., "A Phase 1 Trial of the Novel Proteasome Inhibitor PS341 in Advanced Solid Tumor Malignancies", Clinical Cancer Research, Aug. 2002, vol. 8, 8 Pages.
Gao et al., "Differential and Antagonistic Effects of v-Jun and c-Jun", Cancer Research, Sep. 15, 1996, vol. 56, No. 18, received on Nov. 14, 2016 from http://cancerres.aacrjournals.org/content/canres/56/18/4229.full.pdf, 8 Pages.
Barranco, S.C., et al., "Enhanced Cell Killing Through the Use of Cell Kinetics-Directed Treatment Schedules for Two-Drug Combinations in Vitro," Cancer Research 42(7):2894-2898, Jul. 1982.
Gong, Z., et al., "LOC401317, a p53-Regulated Long Non-Coding RNA, Inhibits Proliferation and Induces Apoptosis in the Nasopharyngeal Carcinoma Cell Line HNE2," PLOS One 9(11):e110674, pp. 1-19, Nov. 2014.
Hermisson, M., et al., "O6-Methylguanine DNA Methyltransferase and p53 Status Predict Temozolomide Sensitivity in Human Malignant Glioma Cells," Journal of Neurochemistry 96(3):766-776, Feb. 2006.

Stehman, F.B., et al., "Phase II Trial of Galactitol 1,2:5,6-Dianhydro (NSC 132313) in the Treatment of Advanced Gynecologic Malignanciesi A Gynecological Oncology Group Study," Gynecologic Oncology 15(3):381-390, Jun. 1983.
International Search Report and Written Opinion dated Aug. 19, 2015, issued in International Application No. PCT/US2015/024462, filed Apr. 6, 2015, 11 pages.
International Preliminary Report on Patentability dated May 12, 2016, issued in International Application No. PCT/US2015/024462, filed Apr. 6, 2015, 11 pages.
International Search Report and Written Opinion dated Aug. 26, 2016, issued in International Application No. PCT/US2016/032120, filed May 12, 2016, 7 pages.
International Preliminary Report on Patentability dated Jul. 31, 2017, issued in International Application No. PCT/US2016/032120, filed May 12, 2016, 11 pages.
Search Report and Written Opinion dated Jan. 29, 2018, issued in Singapore Application No. 11201608303Q, filed Apr. 6, 2015, 11 pages.
Extended European Search Report dated Feb. 2, 2018, in European Application No. 15772413.9, filed Apr. 6, 2015, 18 pages.
Lastersky, "Therapy with Cisplatin and Etoposide for Non-Small-Cell Lung Cancer," Semin. Oncol. vol. 13, (1986) pp. 104-114.
Steino, A., et al., "Abstract B252: The Unique Mechanism of Action of VAL-083 May Provide a New Treatment Option for Some Chemo-Resistant Cancers," Molecular Cancer Therapeutics 12(11 Suppl):Abstract B252, Nov. 2013.
Lai, X.-J., et al., "Apoptosis of Hepatocarcinoma Cell Line HLE Induced by the Combination of Wild Type P53 Gene and 1,2:5,6-Dianhydro-3,4-diacetylgalactitol," Ai Zheng (Chinese Journal of Cancer) 23(10):1139-1143, Nov. 2004.
Notification of Reasons for Rejection dated Apr. 4, 2019, issued in JP Application No. 2017-503798, filed Apr. 6, 2015, 10 pages.
Eagan, R.T., et al., "Thoracic Radiation Therapy and Adriamycin/Cisplatin-Containing Chemotherapy for Locally Advanced Non-Small-Cell Lung Cancer," Cancer Clinical Trials 4(4):381-388, Jan. 1981.
Sculier, J-P and J. Klastersky, "Perspective and Commentaries: Progress in Chemotherapy of Non-Small Cell Lung Cancer," European Journal of Cancer and Clinical Oncology 20(11):1329-1333, Nov. 1984.
Steino, A., et al., "Abstract 2157: Enhanced in vitro Activity of Dianhydrogalactitol (VAL-083) in Combination With Platinum Drugs: Impact of p53 and Platinum-Resistance," Proceedings of the 107th Annual Meeting of the American Association for Cancer Research, New Orleans, Apr. 16-20, 2016, Cancer Research: Experimental and Molecular Therapeutics 76(14 Suppl), Jul. 2016.
Extended European Search Report dated Jan. 23, 2019, issued in EP 16793533.7, filed May 12, 2016, 9 pages.
Notice of Reasons for Refusal dated Jan. 31, 2019, issued in JP 2018-511343, filed May 12, 2016, 10 pages.
Grönroos, M., et al., "Steroid Receptors and Response of Ovarian Cancer to Cytostatic Drugs in Vitro," British Journal of Obstetrics and Gynaecology 91(5):479-482, May 1984.
Kojima, S., et al., "Protective Effect of N-Benzyl-D-glucamine Dithiocarbamate Against cis-Diamminedichloroplatinum-Induced Toxicity in Gastrointestinal Tract and Bone Marrow in Rats," Chemical & Pharmaceutical Bulletin (Tokyo) 38(11):3127-3129, Nov. 1990.
First Office Action dated Nov. 26, 2019, issued in Chinese Application No. 201580030033.3, filed Apr. 6, 2015, 17 pages.

* cited by examiner

USE OF DIANHYDROGALACTITOL AND ANALOGS OR DERIVATIVES THEREOF IN COMBINATION WITH PLATINUM-CONTAINING ANTINEOPLASTIC AGENTS TO TREAT NON-SMALL-CELL CARCINOMA OF THE LUNG AND BRAIN METASTASES

CROSS-REFERENCES TO RELATED APPLICATIONS

This application claims the benefit of U.S. Provisional Patent Application No. 61/975,587, filed Apr. 4, 2014, and claims the benefit of U.S. Provisional Patent Application No. 62/062,246, filed Oct. 10, 2014. The contents of both of these United States provisional patent applications are incorporated herein in their entirety by this reference.

FIELD OF THE INVENTION

The present invention relates to the general field of hyperproliferative diseases including oncology with a focus on novel methods and compositions for the improved utility of chemical agents, compounds, and dosage forms previously limited by suboptimal human therapeutic performance including substituted hexitols such as dianhydrogalactitol and diacetyldianhydrogalactitol, as well as other classes of chemical agents. In particular, the present invention relates to the treatment of non-small-cell carcinoma of the lung with dianhydrogalactitol, diacetyldianhydrogalactitol, or derivatives or analogs thereof. Other malignancies that can be treated by dianhydrogalactitol that are frequently treated with platinum-containing anti-neoplastic agents include: cervical cancer, frequently treated with cisplatin; colorectal cancer, frequently treated with oxaliplatin; fallopian tube cancer, frequently tube cancer, frequently treated with carboplatin; and bladder cancer, frequently treated with cisplatin.

BACKGROUND OF THE INVENTION

The search for and identification of cures for many life-threatening diseases that plague humans still remains an empirical and sometimes serendipitous process. While many advances have been made from basic scientific research to improvements in practical patient management, there still remains tremendous frustration in the rational and successful discovery of useful therapies particularly for life-threatening diseases such as cancer, inflammatory conditions, infection, and other conditions.

Since the "War on Cancer" began in the early 1970's by the United States National Cancer Institute (NCI) of the National Institutes of Health (NIH), a wide variety of strategies and programs have been created and implemented to prevent, diagnose, treat and cure cancer. One of the oldest and arguably most successful programs has been the synthesis and screening of small chemical entities (<1500 MW) for biological activity against cancer. This program was organized to improve and streamline the progression of events from chemical synthesis and biological screening to preclinical studies for the logical progression into human clinical trials with the hope of finding cures for the many types of life-threatening malignant tumors. The synthesis and screening of hundreds of thousands of chemical compounds from academic and industrial sources, in addition to the screening of natural products and extracts from prokaryotes, invertebrate animals, plant collections, and other sources from all over the world has been and continues to be a major approach for the identification of novel lead structures as potential new and useful medicines. This is in addition to other programs including biotherapeutics designed to stimulate the human immune system with vaccines, therapeutic antibodies, cytokines, lymphokines, inhibitors of tumor blood vessel development (angiogenesis) or gene and antisense therapies to alter the genetic make-up of cancer cells, and other biological response modifiers.

The work supported by the NCI, other governmental agencies both domestic and foreign in academic or industrial research and development laboratories has resulted in an extraordinary body of biological, chemical and clinical information. In addition, large chemical libraries have been created, as well as highly characterized in vitro and in vivo biological screening systems that have been successfully used. However, from the tens of billions of dollars spent over the past thirty years supporting these programs both preclinically and clinically, only a small number of compounds have been identified or discovered that have resulted in the successful development of useful therapeutic products. Nevertheless, the biological systems both in vitro and in vivo and the "decision trees" used to warrant further animal studies leading to clinical studies have been validated. These programs, biological models, clinical trial protocols, and other information developed by this work remain critical for the discovery and development of any new therapeutic agent.

Unfortunately, many of the compounds that have successfully met the preclinical testing and federal regulatory requirements for clinical evaluation were either unsuccessful or disappointing in human clinical trials. Many compounds were found to have untoward or idiosyncratic side-effects that were discovered during human clinical Phase I dose-escalation studies used to determine the maximum tolerated dose (MTD) and side-effect profile. In some cases, these toxicities or the magnitude of their toxicity were not identified or predicted in preclinical toxicology studies. In other cases, chemical agents where in vitro and in vivo studies suggested a potentially unique activity against a particular tumor type, molecular target or biological pathway were not successful in human Phase II clinical trials where specific examination of particular cancer indications/types were evaluated in government sanctioned (e.g., U.S. FDA), IRB approved clinical trials. In addition, there are those cases where potential new agents were evaluated in randomized Phase III clinical trials where a significant clinical benefit could not be demonstrated; such cases have also been the cause of great frustration and disappointment. Finally, a number of compounds have reached commercialization but their ultimate clinical utility has been limited by poor efficacy as monotherapy (<25% response rates) and untoward dose-limiting side-effects (Grade III and IV) (e.g., myelosuppression, neurotoxicity, cardiotoxicity, gastrointestinal toxicities, or other significant side effects).

In many cases, after the great time and expense of developing and moving an investigational compound into human clinical trials and where clinical failure has occurred, the tendency has been to return to the laboratory to create a better analog, look for agents with different structures but potentially related mechanisms of action, or try other modifications of the drug. In some cases, efforts have been made to try additional Phase I or II clinical trials in an attempt to make some improvement with the side-effect profile or therapeutic effect in selected patients or cancer indications. In many of those cases, the results did not realize a significant enough improvement to warrant further clinical development toward product registration. Even for commercialized products, their ultimate use is still limited by suboptimal performance.

With so few therapeutics approved for cancer patients and the realization that cancer is a collection of diseases with a multitude of etiologies and that a patient's response and survival from therapeutic intervention is complex with many factors playing a role in the success or failure of treatment including disease indication, stage of invasion and metastatic spread, patient gender, age, health conditions, previous therapies or other illnesses, genetic markers that can either promote or retard therapeutic efficacy, and other factors, the opportunity for cures in the near term remains elusive. Moreover, the incidence of cancer continues to rise with an approximate 4% increase predicted for 2003 in the United States by the American Cancer Society such that over 1.3 million new cancer cases are estimated. In addition, with advances in diagnosis such as mammography for breast cancer and PSA tests for prostate cancer, more patients are being diagnosed at a younger age. For difficult to treat cancers, a patient's treatment options are often exhausted quickly resulting in a desperate need for additional treatment regimens. Even for the most limited of patient populations, any additional treatment opportunities would be of considerable value. This invention focuses on inventive compositions and methods for improving therapeutic benefit of suboptimally administered chemical compounds including substituted hexitols such as dianhydrogalactitol.

Non-small-cell lung carcinoma (NSCLC) includes several types of lung cancer, including squamous cell carcinoma, large cell carcinoma, and adenocarcinoma, as well as other types of lung cancer. Although smoking is apparently the most frequent cause of squamous cell carcinoma, when lung cancer occurs in patients without any history of prior tobacco smoking, it is frequently adenocarcinoma. In many cases, NSCLC is refractory to chemotherapy, so surgical resection of the tumor mass is typically the treatment of choice, particularly if the malignancy is diagnosed early. However, chemotherapy and radiation therapy are frequently attempted, particularly if the diagnosis cannot be made at an early stage of the malignancy. Other treatments include radiofrequency ablation and chemoembolization. A wide variety of chemotherapeutic treatments has been tried for advanced or metastatic NSCLC. Some patients with particular mutations in the EGFR gene respond to EGFR tyrosine kinase inhibitors such as gefitinib (M. G. Kris, "How Today's Developments in the Treatment of Non-Small Cell Lung Cancer Will Change Tomorrow's Standards of Care," Oncologist 10 (Suppl. 2): 23-29 (2005), incorporated herein by this reference). Cisplatin has frequently been used as ancillary therapy together with surgery. Erlotinib, pemetrexed, About 7% of NSCLC have EML4-ALK translocations, and such patients may benefit from ALK inhibitors such as crizotinib. Other therapies, including the vaccine TG4010, motesanib diphosphate, tivantinib, belotecan, eribulin mesylate, ramucirumab, necitumumab, the vaccine GSK1572932A, custirsen sodium, the liposome-based vaccine BLP25, nivolumab, EMD531444, dacomitinib, and genetespib, are being evaluated, particularly for advanced or metastatic NSCLC.

However, there is still a need for effective therapies against NSCLC, especially against advanced or metastatic NSCLC. Preferably, such therapies should be well-tolerated and with side effects, if any, that could be easily controlled. Also, preferably, such therapies should be compatible with other chemotherapeutic approaches and with surgery or radiation. Additionally, and preferably, such therapies should be able to exert a synergistic effect on other treatment modalities.

SUMMARY OF THE INVENTION

The use of a substituted hexitol derivative to treat non-small-cell lung carcinoma (NSCLC) provides an improved therapy for NSCLC and ovarian cancer that yields increased survival and is substantially free of side effects. In general, the substituted hexitols usable in methods and compositions according to the present invention include galactitols, substituted galacitols, dulcitols, and substituted dulcitols. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. A particularly preferred substituted hexitol derivative is dianhydrogalactitol (DAG). The substituted hexitol derivative can be employed together with other therapeutic modalities for these malignancies. Dianhydrogalactitol is particularly suited for the treatment of these malignancies because it can suppress the growth of cancer stem cells (CSC), and because it is resistant to drug inactivation by $O^6$-methylguanine-DNA methyltransferase (MGMT). The substituted hexitol derivative yields increased response rates and improved quality of life for patients with NSCLC and ovarian cancer.

Dianhydrogalactitol is a novel alkylating agent that creates $N^7$-methylation in DNA. Specifically, the principal mechanism of action of dianhydrogalactitol is attributed to bi-functional $N^7$ DNA alkylation, via actual or derived epoxide groups, which cross-links across DNA strands.

Accordingly, one aspect of the present invention is a method to improve the efficacy and/or reduce the side effects of the administration of a substituted hexitol derivative for treatment of NSCLC or ovarian cancer comprising the steps of:

(1) identifying at least one factor or parameter associated with the efficacy and/or occurrence of side effects of the administration of the substituted hexitol derivative for treatment of NSCLC or ovarian cancer; and (2) modifying the factor or parameter to improve the efficacy and/or reduce the side effects of the administration of the substituted hexitol derivative for treatment of NSCLC or ovarian cancer.

Typically, the factor or parameter is selected from the group consisting of:

(1) dose modification;
(2) route of administration;
(3) schedule of administration;
(4) indications for use;
(5) selection of disease stage;
(6) other indications;
(7) patient selection;
(8) patient/disease phenotype;
(9) patient/disease genotype;
(10) pre/post-treatment preparation;
(11) toxicity management;
(12) pharmacokinetic/pharmacodynamic monitoring;
(13) drug combinations;
(14) chemosensitization;
(15) chemopotentiation;
(16) post-treatment patient management;
(17) alternative medicine/therapeutic support;
(18) bulk drug product improvements;
(19) diluent systems;

(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action;
(33) selective target cell population therapeutics;
(34) use with ionizing radiation;
(35) use with an agent that counteracts myelosuppression; and
(36) use with an agent that increases the ability of the substituted hexitol to pass through the blood-brain barrier to treat brain metastases of NSCLC or ovarian cancer.

As detailed above, typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

Another aspect of the present invention is a composition to improve the efficacy and/or reduce the side effects of suboptimally administered drug therapy employing a substituted hexitol derivative for the treatment of NSCLC or ovarian cancer comprising an alternative selected from the group consisting of:

(i) a therapeutically effective quantity of a modified substituted hexitol derivative or a derivative, analog, or prodrug of a substituted hexitol derivative or a modified substituted hexitol derivative, wherein the modified substituted hexitol derivative or the derivative, analog or prodrug of the substituted hexitol derivative or modified substituted hexitol derivative possesses increased therapeutic efficacy or reduced side effects for treatment of NSCLC as compared with an unmodified substituted hexitol derivative;

(ii) a composition comprising:
 (a) a therapeutically effective quantity of a substituted hexitol derivative, a modified substituted hexitol derivative, or a derivative, analog, or prodrug of a substituted hexitol derivative or a modified substituted hexitol derivative; and
 (b) at least one additional therapeutic agent, therapeutic agent subject to chemosensitization, therapeutic agent subject to chemopotentiation, diluent, excipient, solvent system, drug delivery system, or agent to counteract myelosuppression, wherein the composition possesses increased therapeutic efficacy or reduced side effects for treatment of NSCLC as compared with an unmodified substituted hexitol derivative;

(iii) a therapeutically effective quantity of a substituted hexitol derivative, a modified substituted hexitol derivative or a derivative, analog, or prodrug of a substituted hexitol derivative or a modified substituted hexitol derivative that is incorporated into a dosage form, wherein the substituted hexitol derivative, the modified substituted hexitol derivative or the derivative, analog, or prodrug of a substituted hexitol derivative or a modified substituted hexitol derivative incorporated into the dosage form possesses increased therapeutic efficacy or reduced side effects for treatment of NSCLC as compared with an unmodified substituted hexitol derivative;

(iv) a therapeutically effective quantity of a substituted hexitol derivative, a modified substituted hexitol derivative or a derivative, analog, or prodrug of a substituted hexitol derivative or a modified substituted hexitol derivative that is incorporated into a dosage kit and packaging, wherein the substituted hexitol derivative, the modified substituted hexitol derivative or the derivative, analog, or prodrug of a substituted hexitol derivative or a modified substituted hexitol derivative incorporated into the dosage kit and packaging possesses increased therapeutic efficacy or reduced side effects for treatment of NSCLC as compared with an unmodified substituted hexitol derivative; and (v) a therapeutically effective quantity of a substituted hexitol derivative, a modified substituted hexitol derivative or a derivative, analog, or prodrug of a substituted hexitol derivative or a modified substituted hexitol derivative that is subjected to a bulk drug product improvement, wherein substituted hexitol derivative, a modified substituted hexitol derivative or a derivative, analog, or prodrug of a substituted hexitol derivative or a modified substituted hexitol derivative subjected to the bulk drug product improvement possesses increased therapeutic efficacy or reduced side effects for treatment of NSCLC as compared with an unmodified substituted hexitol derivative.

As detailed above, typically the unmodified substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the unmodified substituted hexitol derivative is dianhydrogalactitol.

Another aspect of the present invention is a method of treating NSCLC comprising the step of administering a therapeutically effective quantity of a substituted hexitol derivative to a patient suffering from the malignancy. As detailed above, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol. The method can be used to treat patients who have developed resistance to tyrosine kinase inhibitors (TKI) or platinum-based chemotherapeutic agents such as cisplatin. The method can also be used together with TKI or platinum-based chemotherapeutic agents. Suitable platinum-based therapeutic chemotherapeutic agents include, but are not limited to, cisplatin and oxaliplatin.

Yet another aspect of the invention is a method of treating ovarian cancer comprising the step of administering a therapeutically effective quantity of a substituted hexitol derivative to a patient suffering from ovarian cancer. Suitable substituted hexitol derivatives are as described above; a particularly preferred substituted hexitol derivative is dianhydrogalactitol. In one alternative, the ovarian cancer is a cisplatin-resistant wild-type p53 cancer.

Yet another aspect of the invention is a method of treating a patient with a malignancy selected from the group consisting of Stage II non-small cell lung cancer (NSCLC), Stage III NSCLC, and Stage IV NSCLC comprising the steps of:
(a) administering a therapeutically effective quantity of dianhydrogalactitol to the patient to treat the malignancy; and (b) administering a therapeutically effective quantity of a platinum-based anti-neoplastic agent to the patient to treat the malignancy.

In this method, in one alternative, the dianhydrogalactitol and the platinum-based anti-neoplastic agent are administered subsequent to surgical resection of the NSCLC. In another alternative, the dianhydrogalactitol and the platinum-based anti-neoplastic agent are administered prior to surgical resection of the NSCLC to shrink the tumor prior to surgery.

The patient can have brain metastases. The method is particularly useful for patients with NSCLC wherein brain metastases have been confirmed or suspected.

In one alternative, the dianhydrogalactitol and the platinum-based anti-neoplastic agent are administered in a single pharmaceutical composition, wherein the pharmaceutical composition comprises: (i) dianhydrogalactitol; (ii) the platinum-based anti-neoplastic agent; and (iii) at least one pharmaceutically acceptable carrier. In another alternative, the dianhydrogalactitol and the platinum-based anti-neoplastic agent are administered in two pharmaceutical compositions: (i) a first pharmaceutical composition comprising dianhydrogalactitol and at least one pharmaceutically acceptable carrier; and (ii) a second pharmaceutical composition comprising the platinum-based anti-neoplastic agent and at least one pharmaceutically acceptable carrier.

The patient can have a wild-type p53 genotype. In another alternative, the patient can have a mutated p53 genotype; as shown in the examples, a mutation in p53 results in less resistance to dianhydrogalactitol than to temozolomide or platinum-containing anti-neoplastic drugs, so dianhydrogalactitol can be particularly useful in such patients. The role of p53 is addressed further below.

In another alternative, the patient can have a wild-type EGFR genotype.

In yet another alternative, the patient has at least one mutation in a gene encoding a protein that is a target of at least one tyrosine kinase inhibitor (TKI). In still another alternative, the patient is characterized by the presence of at least one additional gene in either a wild-type or mutated state encoding a product that confers resistance to therapeutic effects of at least one TKI. The additional gene in either a wild-type or mutated state encoding a product that confers resistance to therapeutic effects of at least one TKI can be AHI-1. The AHI-1 can be mutated as the result of a proviral insertion.

In yet another alternative, the patient is characterized by a mutation in the kinase domain of ABL1 protein that is part of a BCR-ABL fusion protein that is a target of TKIs.

In still another alternative, the patient is characterized by a germline deletion polymorphism conferring resistance to tyrosine kinase inhibitors (TKIs). Typically, the germline DNA deletion polymorphism is a germline DNA deletion polymorphism of 2903 bp located in the BIM gene, and the germline DNA deletion polymorphism causes a splicing variation that leads to expression of an isoform of BIM protein that lacks a BH3 domain and thus inhibits the induction of apoptosis.

Typically, the platinum-containing anti-neoplastic agent is selected from the group consisting of cisplatin, carboplatin, oxaliplatin, satraplatin, picoplatin, nedaplatin, triplatin, lobapatin, heptaplatin, and lipoplatin. Preferably, the platinum-containing anti-neoplastic agent is selected from the group consisting of cisplatin, carboplatin, and oxaliplatin. A particularly preferred platinum-containing anti-neoplastic agent is cisplatin.

In one alternative, the dosages of dianhydrogalactitol and the platinum-containing anti-neoplastic agent are such that the dianhydrogalactitol and the platinum-containing anti-neoplastic agent act synergistically.

Yet another aspect of the invention is a pharmaceutical composition comprising:
(1) a therapeutically effective quantity of dianhydrogalactitol;
(2) a therapeutically effective quantity of a platinum-containing anti-neoplastic agent; and
(3) optionally, at least one pharmaceutically acceptable carrier.

The pharmaceutical composition can be formulated for treatment of a malignancy selected from the group consisting of Stage II non-small cell lung cancer (NSCLC), Stage III NSCLC, and Stage IV NSCLC. The pharmaceutical composition can also be formulated for treatment of a malignancy selected from the group consisting of Stage II non-small cell lung cancer (NSCLC), Stage III NSCLC, and Stage IV NSCLC wherein metastasis to the brain has occurred.

In one alternative for the pharmaceutical composition, the dosages of dianhydrogalactitol and the platinum-containing anti-neoplastic agent are such that the dianhydrogalactitol and the platinum-containing anti-neoplastic agent act synergistically.

When the pharmaceutical composition comprises at least one pharmaceutically acceptable carrier, typically the pharmaceutically acceptable carrier is selected from the group consisting of aqueous and non-aqueous solvents, dispersion media, coatings, antibacterial and/or antifungal agents, and isotonic and/or absorption delaying agents.

The pharmaceutical composition can be formulated for parenteral administration; other routes of administration are possible.

In yet another alternative, the composition can comprise at least one p53 mimetic. Compounds that act as p53 mimetics are described below.

Yet another aspect of the invention is a method for treating a patient with a malignancy selected from the group consisting of Stage II non-small cell lung cancer (NSCLC), Stage III NSCLC, and Stage IV NSCLC wherein the patient has a mutated p53 gene comprising the steps of:
(1) determining the existence of a mutated p53 gene in the patient, wherein the mutated p53 gene affects the proliferation of the malignancy and/or the resistance of the malignancy to at least one anti-neoplastic agent;
(2) administering a therapeutically effective quantity of dianhydrogalactitol to the patient to treat the malignancy, wherein therapeutically effective quantity of dianhydrogalactitol is determined from results on cell lines with a mutated p53 gene;
(3) administering a therapeutically effective quantity of a platinum-based anti-neoplastic agent to the patient to treat the malignancy, wherein therapeutically effective quantity of the platinum-based anti-neoplastic agent is determined from results on cell lines with a mutated p53 gene; and
(4) optionally, administering a therapeutically effective quantity of a p53 mimetic to the patient to treat the malignancy.

Typically, the existence of the mutated p53 gene in the patient is determined by a method selected from the group consisting of gene sequencing, restriction fragment length polymorphism, and determining whether p53 in a cell sample from the patient binds to a pGL3 vector.

A number of p53 mimetics are known in the art and include, but are not limited, to the following:

(i) N'-[2-[2-(4-methoxyphenyl)ethenyl]-4-quinazolinyl]-N,N-dimethyl-1,3-propanediamine dihydrochloride hydrate) (CP-31398);

(ii) a compound of Formula (P-1):

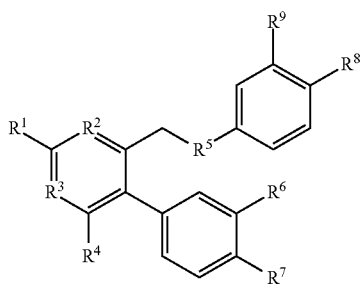

(P-1)

wherein:
(A) $R^1$ and $R^4$ are each independently selected from the group consisting of amino, cyano, nitro, carboxyl, halo, hydroxyl, $SO_2$, $C_1$-$C_6$ alkyl, $C_1$-$C_6$ haloalkyl, $C_1$-$C_8$ alkoxyl, $C_1$-$C_{11}$ alkoxyalkyl, $C_1$-$C_6$ alkylamino, and $C_1$-$C_6$ aminoalkyl;
(B) $R^2$ and $R^3$ are each independently selected from the group consisting of CH and N;
(C) $R^5$ is CH or O;
(D) $R^6$ is selected from the group consisting of halogen, cyano, nitro, $C_1$-$C_{10}$ branched or unbranched, saturated or unsaturated alkyl, $C_1$-$C_{10}$ branched or unbranched alkoxy, $C_1$-$C_{10}$ branched or unbranched acyl, $C_1$-$C_{10}$ branched or unbranched acyloxy, $C_1$-$C_{10}$ branched or unbranched alkylthio, aminosulfonyl, aryl, aroyl, aryloxy, arylsulfonyl, heteroaryl, and heteroaryloxy;
(E) $R^7$ is selected from the group consisting of hydrogen, halogen, cyano, nitro, $C_1$-$C_{10}$ branched or unbranched, saturated or unsaturated alkyl, $C_1$-$C_{10}$ branched or unbranched alkoxy, $C_1$-$C_{10}$ branched or unbranched acyl, $C_1$-$C_{10}$ branched or unbranched acyloxy, $C_1$-$C_{10}$ branched or unbranched alkylthio, aminosulfonyl, aryl, aroyl, aryloxy, arylsulfonyl, heteroaryl, and heteroaryloxy;
(F) $R^8$ is selected from the group consisting of nitro, hydroxy, and carboxyl; and
(G) $R^9$ is methyl; or
a pharmaceutically acceptable ester or salt thereof; and (iii) a compound having a stable, internally constrained protein secondary structure, wherein the compound is of Formula (P-2):

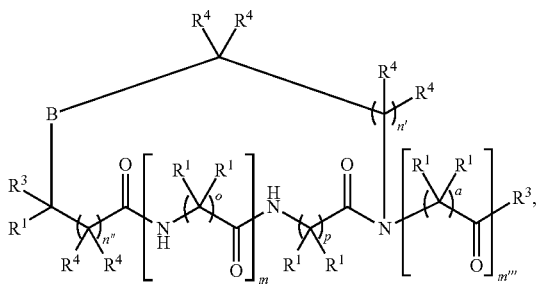

(P-2)

wherein:
(A) B is $C(R^1)_2$, O, S, or $NR^1$;
(B) each $R^1$ is independently hydrogen, an amino acid side chain, an alkyl, an alkenyl, an alkynyl, a cycloalkyl, a heterocyclyl, an aryl, a heteroaryl, or an arylalkyl;
(C) $R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$, wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula (P-2(a)):

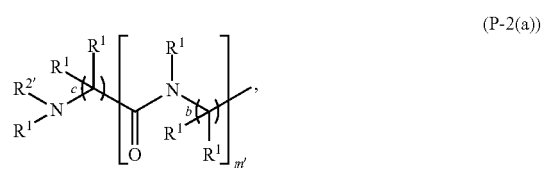

(P-2(a))

wherein:
(1) $R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen; an alkyl; an alkenyl; an alkynyl; a cycloalkyl; a heterocyclyl; an aryl; a heteroaryl; an arylalkyl; a targeting moiety; or a tag; or; —$(CH_2)_{0-1}N(R^5)_2$, wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
(2) m' is zero or any number;
(3) each b is independently 1 or 2; and
(4) c is 1 or 2;
(D) $R^3$ is hydrogen; an alkyl; an alkenyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula (P-2(b)):

(P-2(b))

wherein:
(1) $R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl; an aryl, a targeting moiety, or a tag; or —N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
(2) m" is zero or any number; and
(3) each d is 1 or 2;
(E) each R$^4$ is independently hydrogen, an alkyl, an alkenyl, an alkynyl, a cycloalkyl, a heterocyclyl, an aryl, a heteroaryl, or an arylalkyl;
(F) m, n', and n" are each independently 0, 1, 2, 3, or 4, wherein the sum of m, n', and n" is from 2 to 6;
(G) m'" is 0 or 1;
(H) a is 1 or 2;
(I) each o is independently 1 or 2; and
(J) p is 1 or 2;
wherein at least one of the following conditions is met: (i) m is 1, 2, 3, or 4 and at least one o is 2; (ii) p is 2; (iii) m'" is 1 and a is 2; (iv) R$^2$ is a beta amino acid; (v) R$^2$ is a moiety of Formula (P-2(a)) wherein m' is at least 1 and at least one b is 2; (vi) R$^2$ is a moiety of Formula (P-2(a)) wherein c is 2; (vii) R$^2$ is a moiety of Formula (P-2(a)) wherein R$^{2'}$ is a beta amino acid; (viii) R$^3$ is a beta amino acid; (ix) R$^3$ is a moiety of Formula (P-2(b)) wherein m" is at least 1 and at least one d is 2; and (x) R$^3$ is a moiety of Formula (P-2(b)) wherein R$^{3'}$ is a beta amino acid.

Suitable platinum-containing anti-neoplastic agents are as described above. In one alternative, the dosages of dianhydrogalactitol and the platinum-containing anti-neoplastic agent are such that the dianhydrogalactitol and the platinum-containing anti-neoplastic agent act synergistically.

BRIEF DESCRIPTION OF THE DRAWINGS

The following invention will become better understood with reference to the specification, appended claims, and accompanying drawings, where:

In FIGS. 1-2 of the Example, • is the untreated control; ■ is the cisplatin control at 5 mg/kg; ▲ is dianhydrogalactitol at 1.5 mg/kg; ▲ is dianhydrogalactitol at 3.0 mg/kg; and ♦ is dianhydrogalactitol at 6.0 mg/kg.

FIG. 2 is a graph that shows the tumor volume (means±S.E.M.) for the A549 NSCLC tumor-bearing female Rag2 mice with tumor volume on the y axis versus days post-inoculation on the x-axis for the results of the Example. The top panel of FIG. 2 represents all mice for the complete duration of the study. The bottom panel of FIG. 2 represents all mice until day 70 (last day for untreated control group).

FIG. 10 is a graph showing the cytotoxicity of cisplatin and relative resistance in a human NSCLC tumor panel in vitro. The cell lines used are H460, A549, H838, and H226, which have a wild-type p53; H1975, SkLU1, H2122, and H157, which have a mutated p53; and H1229, which has a null p53.

FIG. 18 is a graph showing the effect of dianhydrogalactitol (DAG) in combination with cisplatin (CDDP) or oxaliplatin (OXT) on cytotoxicity in H1975 NSCLC cells in vitro. The left panel shows the results of DAG in combination with cisplatin; the right panel shows the results of DAG in combination with oxaliplatin. With N=4 independent studies with H1975 cells, the combination of cisplatin+DAG is additive, whereas the combination of oxaliplatin+DAG approaches significance for super-additivity. Data are shown as Mean+/−SE.

DETAILED DESCRIPTION OF THE INVENTION

Figure 1:
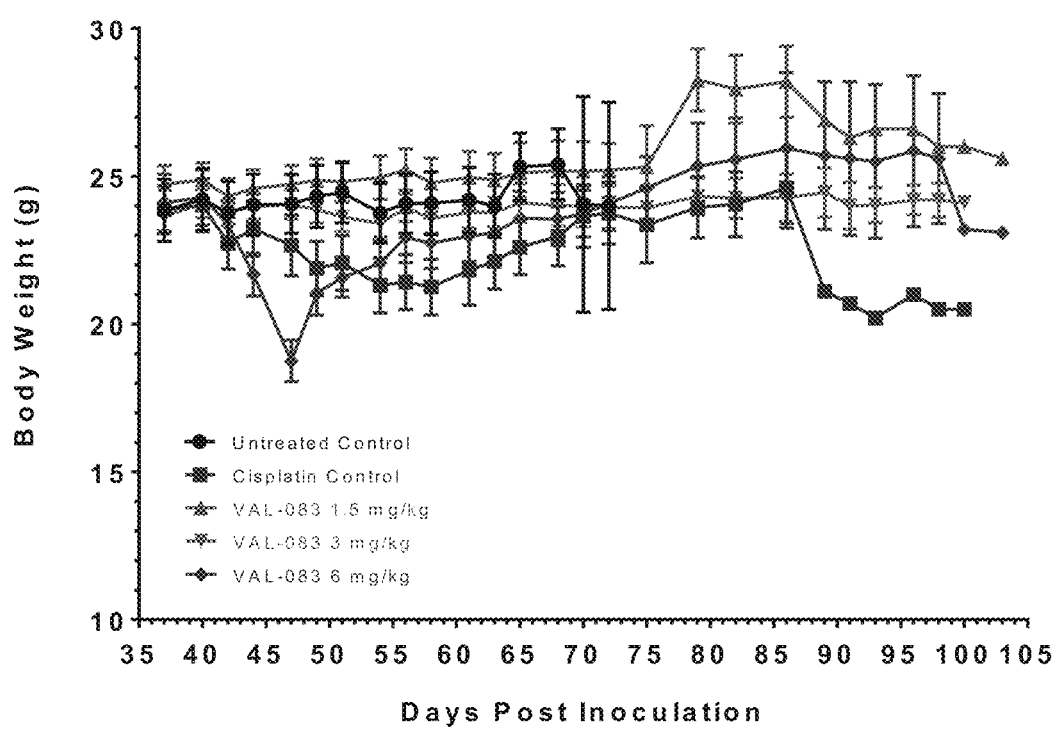
FIG. 1 is a graph that shows body weight of female Rag2 mice after subcutaneous inoculation with 5 million A549 NSCLC cells. Body weight is shown on the y-axis versus days post-inoculation on the x-axis for the results of the Example.

The compound dianhydrogalactitol (DAG) has been shown to have substantial efficacy in inhibiting the growth of non-small-cell lung carcinoma (NSCLC) cells. In the case of GBM, DAG has proven to be more effective in suppressing the growth of NSCLC cells in a mouse model than cisplatin, the current chemotherapy of choice for NSCLC. As detailed below, DAG can effectively suppress the growth of cancer stem cells (CSCs). DAG acts independently of the MGMT repair mechanism.

As detailed below, DAG also shows efficacy against ovarian tumor cells. Methods and compositions suitable for use against ovarian cancer are described below. Other malignancies that can be treated by dianhydrogalactitol that are frequently treated with platinum-containing anti-neoplastic agents include: cervical cancer, frequently treated with cisplatin; colorectal cancer, frequently treated with oxaliplatin; fallopian tube cancer, frequently tube cancer, frequently treated with carboplatin; and bladder cancer, frequently treated with cisplatin. Accordingly, methods and compositions according to the present invention can be used to treat these malignancies, including combinations of dianhydrogalactitol and a platinum-containing anti-neoplastic agent, and pharmaceutical compositions formulated for treating these malignancies.

The structure of dianhydrogalactitol (DAG) is shown in Formula (I), below.

As detailed below, other substituted hexitols can be used in methods and compositions according to the present invention. In general, the substituted hexitols usable in methods and compositions according to the present invention include galactitols, substituted galacitols, dulcitols, and substituted dulcitols, including dianhydrogalactitol, diacetyldianhydrogalactitol, dibromodulcitol, and derivatives and analogs thereof. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

These galactitols, substituted galacitols, dulcitols, and substituted dulcitols are either alkylating agents or prodrugs of alkylating agents, as discussed further below.

Also within the scope of the invention are derivatives of dianhydrogalactitol that, for example, have one or both hydrogens of the two hydroxyl groups of dianhydrogalactitol replaced with lower alkyl, have one or more of the hydrogens attached to the two epoxide rings replaced with lower alkyl, or have the methyl groups present in dianhydrogalactitol and that are attached to the same carbons that bear the hydroxyl groups replaced with $C_2$-$C_6$ lower alkyl or substituted with, for example, halo groups by replacing a hydrogen of the methyl group with, for example a halo group. As used herein, the term "halo group," without further limitation, refers to one of fluoro, chloro, bromo, or iodo. As used herein, the term "lower alkyl," without further limitation, refers to $C_1$-$C_6$ groups and includes methyl. The term "lower alkyl" can be further limited, such as "$C_2$-$C_6$ lower alkyl," which excludes methyl. The term "lower alkyl", unless further limited, refers to both straight-chain and branched alkyl groups. These groups can, optionally, be further substituted, as described below.

The structure of diacetyldianhydrogalactitol is shown in Formula (II), below.

Also within the scope of the invention are derivatives of diacetyldianhydrogalactitol that, for example, have one or both of the methyl groups that are part of the acetyl moieties replaced with $C_2$-$C_6$ lower alkyl, have one or both of the hydrogens attached to the epoxide ring replaced with lower alkyl, or have the methyl groups attached to the same carbons that bear the acetyl groups replaced with lower alkyl or substituted with, for example, halo groups by replacing a hydrogen with, for example, a halo group.

The structure of dibromodulcitol is shown in Formula (III), below. Dibromodulcitol can be produced by the reaction of dulcitol with hydrobromic acid at elevated temperatures, followed by crystallization of the dibromodulcitol. Some of the properties of dibromodulcitol are described in N. E. Mischler et al., "Dibromoducitol," *Cancer Treat. Rev.* 6: 191-204 (1979), incorporated herein by this reference. In particular, dibromodulcitol, as an α,ω-dibrominated hexitol, dibromodulcitol shares many of the biochemical and biological properties of similar drugs such as dibromomannitol and mannitol myleran. Activation of dibromodulcitol to the diepoxide dianhydrogalactitol occurs in vivo, and dianhydrogalactitol may represent a major active form of the drug; this means that dibromogalactitol has many of the properties of a prodrug. Absorption of dibromodulcitol by the oral route is rapid and fairly complete. Dibromodulcitol has known activity in melanoma, breast lymphoma (both Hodgkins and non-Hodgkins), colorectal cancer, acute lymphoblastic leukemia and has been shown to lower the incidence of central nervous system leukemia, non-small cell lung cancer, cervical carcinoma, bladder carcinoma, and metastatic hemangiopericytoma.

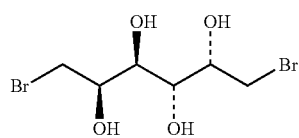

(III)

Also within the scope of the invention are derivatives of dibromodulcitol that, for example, have one or more hydrogens of the hydroxyl groups replaced with lower alkyl, or have one or both of the bromo groups replaced with another halo group such as chloro, fluoro, or iodo.

In general, for optional substituents at saturated carbon atoms such as those that are part of the structures of dianhydrogalactitol, derivatives of dianhydrogalactitol, diacetyldianhydrogalactitol, derivatives of diacetyldianhydrogalactitol, dibromodulcitol, and derivatives of dibromodulcitol, the following substituents can be employed: $C_6$-$C_{10}$ aryl, heteroaryl containing 1-4 heteroatoms selected from N, O, and S, $C_1$-$C_{10}$ alkyl, $C_1$-$C_{10}$ alkoxy, cycloalkyl, F, amino ($NR^1R^2$), nitro, —SR, —S(O)R, —S($O_2$)R, —S($O_2$)$NR^1R^2$, and —$CONR^1R^2$, which can in turn be optionally substituted. Further descriptions of potential optional substituents are provided below.

Optional substituents as described above that are within the scope of the present invention do not substantially affect the activity of the derivative or the stability of the derivative, particularly the stability of the derivative in aqueous solution. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl and naphthyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicylic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valiences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, =O, —$OZ^b$, —$SZ^b$, —$S^-$, —$NZ^cZ^c$, =$NZ^b$, =N—$OZ^b$, trihalomethyl, —$CF_3$, —CN, —OCN, —SCN, —NO, —$NO_2$, =$N_2$, —$N_3$, —$S(O)_2Z^b$, —$S(O)_2NZ^b$, —$S(O)_2O^-$, —$S(O)_2OZ^b$, —$OS(O)_2OZ^b$, —$OS(O)_2O^-$, —$OS(O)_2OZ^b$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)O^-$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)OZ^b$, —$NZ^bC(O)Z^b$, —$NZ^bC(S)Z^b$, —$NZ^bC(O)O^-$, —$NZ^bC(O)OZ^b$, —$NZ^bC(S)OZ^b$, —$NZ^bC(O)NZ^cZ^c$, —$NZ^bC(NZ^b)Z^b$, —$NZ^bC(NZ^b)NZ^cZ^c$, wherein $Z^a$ is selected from the group consisting of alkyl, cycloalkyl, heteroalkyl, cycloheteroalkyl, aryl, arylalkyl, heteroaryl and heteroarylalkyl; each $Z^b$ is independently hydrogen or $Z^a$; and each $Z^c$ is independently $Z^b$ or, alternatively, the two $Z^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —$NZ^cZ^c$ is meant to include —$NH_2$, —NH-alkyl, —N-pyrrolidinyl, and —N-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-C(O)$OZ^b$, -alkylene-C(O)$NZ^bZ^b$, and —$CH_2$—$CH_2$—C(O)—$CH_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —$Z^a$, halo, —$O^-$, —$OZ^b$, —$SZ^b$, —$S^-$, —$NZ^cZ^c$, trihalomethyl, —$CF_3$, —CN, —OCN, —SCN, —NO, —$NO_2$, —$N_3$, —$S(O)_2Z^b$, —$S(O)_2O^-$, —$S(O)_2OZ^b$, —$OS(O)_2OZ^b$, —$OS(O)_2O^-$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)O^-$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)OZ^b$, —$NZ^bC(O)OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

Similarly, substituent groups useful for substituting nitrogen atoms in heteroalkyl and cycloheteroalkyl groups include, but are not limited to, —$Z^a$, halo, —$O^-$, —$OZ^b$, —$SZ^b$, —$S^-$, —$NZ^cZ^c$, trihalomethyl, —$CF_3$, —CN, —OCN, —SCN, —NO, —$NO_2$, —$S(O)_2Z^b$, —$S(O)_2O^-$, —$S(O)_2OZ^b$, —$OS(O)_2OZ^b$, —$OS(O)_2O^-$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)OZ^b$, —$OC(S)OZ^b$, —$NZ^bC(O)Z^b$, —$NZ^bC(S)Z^b$, —$NZ^bC(O)OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers, unless a specific stereoisomer is specified. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolysable esters of the present compounds are the compounds whose carboxyls are present in the form of hydrolysable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —$NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

As used herein, the term "alkanoyl" refers to an alkyl group covalently linked to a carbonyl (C=O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Alk_2$ and -$Alk_1$-N($Alk_2$)($Alk_3$), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —$S(O)_2$—Ar wherein Ar refers to an aryl group as described above. The term "aryloxyalkylsulfonyl" refers to a group of the structure —$S(O)_2$-Alk-O—Ar, where Alk is an alkyl group as described above and Ar is an aryl group as described above. The term "arylalkylsulfonyl" refers to a group of the structure —$S(O)_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is $CH_3CH_2OC(O)$—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al., incorporated herein by this reference. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

For the aspects described below relating to improvement in therapeutic employment of a substituted hexitol derivative, typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol, unless otherwise specified. Preferably, the substituted hexitol derivative is dianhydrogalactitol, unless otherwise specified. In some cases, derivatives of dianhydrogalactitol such as compound analogs or prodrugs are preferred, as stated below.

One aspect of the present invention is an improvement in therapeutic employment of a substituted hexitol derivative such as dianhydrogalactitol for treatment of NSCLC or ovarian cancer made by alterations to the time that the compound is administered, the use of dose-modifying agents that control the rate of metabolism of the compound, normal tissue protective agents, and other alterations. General examples include: variations of infusion schedules (e.g., bolus i.v. versus continuous infusion), the use of lymphokines (e.g., G-CSF, GM-CSF, EPO) to increase leukocyte count for improved immune response or for preventing anemia caused by myelosuppressive agents, or the use of rescue agents such as leucovorin for 5-FU or thiosulfate for cisplatin treatment. Specific inventive examples for a substituted hexitol derivative such as dianhydrogalactitol for treatment of NSCLC or ovarian cancer include: continuous i.v. infusion for hours to days; biweekly administration; doses greater than 5 mg/m$^2$/day; progressive escalation of dosing from 1 mg/m$^2$/day based on patient tolerance; doses less than 1 mg/m$^2$ for greater than 14 days; use of caffeine to modulate metabolism; use of isoniazid to modulate metabolism; single and multiple doses escalating from 5 mg/m$^2$/day via bolus; oral doses below 30 or above 130 mg/m$^2$; oral dosages up to 40 mg/m$^2$ for 3 days and then a nadir/recovery period of 18-21 days; dosing at a lower level for an extended period (e.g., 21 days); dosing at a higher level; dosing with a nadir/recovery period longer than 21 days; the use of a substituted hexitol derivative such as dianhydrogalactitol as a single cytotoxic agent, typically at 30 mg/m$^2$/day×5 days, repeated monthly; dosing at 3 mg/kg; the use of a substituted hexitol derivative such as dianhydrogalactitol in combination therapy, typically at 30 mg/m$^2$/day×5 days; or dosing at 40 mg/day×5 days in adult patients, repeated every two weeks.

Another aspect of the invention is an improvement in therapeutic employment of a substituted hexitol derivative such as dianhydrogalactitol for treatment of NSCLC or ovarian cancer made by alterations in the route by which the compound is administered. General examples include: changing route from oral to intravenous administration and vice versa; or the use of specialized routes such as subcutaneous, intramuscular, intraarterial, intraperitoneal, intralesional, intralymphatic, intratumoral, intrathecal, intravesicular, intracranial. Specific inventive examples for a substituted hexitol derivative such as dianhydrogalactitol for treatment of NSCLC or ovarian cancer include: topical administration; oral administration; slow-release oral delivery; intrathecal administration; intraarterial administration; continuous infusion; intermittent infusion; intravenous administration; or administration through a longer infusion; or administration through IV push.

Yet another aspect of the invention is an improvement in therapeutic employment of a substituted hexitol derivative such as dianhydrogalactitol for treatment of NSCLC or ovarian cancer made by changes in the schedule of administration. General examples include: daily administration, biweekly administration, or weekly administration. Specific inventive examples for a substituted hexitol derivative such as dianhydrogalactitol for treatment of NSCLC or ovarian cancer include: daily administration; weekly administration; weekly administration for three weeks; biweekly administration; biweekly administration for three weeks with a 1-2 week rest period; intermittent boost dose administration; or daily administration for one week for multiple weeks.

Yet another aspect of the invention is an improvement in therapeutic employment of a substituted hexitol derivative such as dianhydrogalactitol for treatment of NSCLC or ovarian cancer made by alterations in the stage of disease at diagnosis/progression that the compound is administered. General examples include: the use of chemotherapy for non-resectable local disease, prophylactic use to prevent metastatic spread or inhibit disease progression or conversion to more malignant stages. Specific inventive examples for a substituted hexitol derivative such as dianhydrogalactitol for treatment of NSCLC or ovarian cancer include: use in an appropriate disease stage for NSCLC or ovarian cancer; use of the substituted hexitol derivative such as dianhydrogalactitol with angiogenesis inhibitors such as Avastin, a VEGF inhibitor, to prevent or limit metastatic spread; the use of a substituted hexitol derivative such as dianhydrogalactitol for newly diagnosed disease; the use of a substituted hexitol derivative such as dianhydrogalactitol for recurrent disease; or the use of a substituted hexitol derivative such as dianhydrogalactitol for resistant or refractory disease.

Yet another aspect of the invention is an improvement in therapeutic employment of a substituted hexitol derivative such as dianhydrogalactitol for treatment of NSCLC or ovarian cancer made by alterations to the type of patient that would best tolerate or benefit from the use of the compound. General examples include: use of pediatric doses for elderly patients, altered doses for obese patients; exploitation of co-morbid disease conditions such as diabetes, cirrhosis, or other conditions that may uniquely exploit a feature of the compound. Specific inventive examples for a substituted hexitol derivative such as dianhydrogalactitol for treatment of NSCLC or ovarian cancer include: patients with a disease condition characterized by a high level of a metabolic enzyme selected from the group consisting of histone deacetylase and ornithine decarboxylase; patients with a low or high susceptibility to a condition selected from the group consisting of thrombocytopenia and neutropenia; patients intolerant of GI toxicities; patients characterized by over- or under-expression of a gene selected from the group consisting of c-Jun, a GPCR, a signal transduction protein, VEGF, a prostate-specific gene, and a protein kinase; prostate-specific gene, and a protein kinase; patients characterized by a mutation in EGFR including, but not limited to, EGFR Variant III; patients being administered a platinum-based drug as combination therapy; patients who do not have EGFR mutations and thus are less likely to respond to tyrosine kinase inhibitors (TKI); patients who have become resistant to TKI treatment; patients who have the BIM co-deletion mutation and thus are less likely to respond to TKI treatment; patients who have become resistant to platinum-based drug treatment; or patients with brain metastases.

Yet another aspect of the invention is an improvement in therapeutic employment of a substituted hexitol derivative such as dianhydrogalactitol for treatment of NSCLC or ovarian cancer made by more precise identification of a patient's ability to tolerate, metabolize and exploit the use of the compound as associated with a particular phenotype of the patient. General examples include: use of diagnostic tools and kits to better characterize a patient's ability to process/metabolize a chemotherapeutic agent or the susceptibility of the patient to toxicity caused by potential specialized cellular, metabolic, or organ system phenotypes. Specific inventive examples for a substituted hexitol derivative such as dianhydrogalactitol for treatment of NSCLC or ovarian cancer include: use of a diagnostic tool, a diagnostic technique, a diagnostic kit, or a diagnostic assay to confirm a patient's particular phenotype; use of a method for measurement of a marker selected from the group consisting of histone deacetylase, ornithine decarboxylase, VEGF, a protein that is a gene product of jun, and a protein kinase; surrogate compound testing; or low dose pre-testing for enzymatic status.

Yet another aspect of the invention is an improvement in therapeutic employment of a substituted hexitol derivative such as dianhydrogalactitol for treatment of NSCLC or ovarian cancer made by more precise identification of a patient's ability to tolerate, metabolize and exploit the use of the compound as associated with a particular genotype of the patient. General examples include: biopsy samples of tumors or normal tissues (e.g., glial cells or other cells of the central nervous system) that may also be taken and analyzed to specifically tailor or monitor the use of a particular drug against a gene target; studies of unique tumor gene expression patterns; or analysis of SNP's (single nucleotide polymorphisms), to enhance efficacy or to avoid particular drug-sensitive normal tissue toxicities. Specific inventive examples for a substituted hexitol derivative such as dianhydrogalactitol for treatment of NSCLC or ovarian cancer include: diagnostic tools, techniques, kits and assays to confirm a patient's particular genotype; gene/protein expression chips and analysis; Single Nucleotide Polymorphisms (SNP's) assessment; SNP's for histone deacetylase, ornithine decarboxylase, GPCR's, protein kinases, telomerase, or jun; identification and measurement of metabolism enzymes and metabolites; determination of mutation of PDGFRA gene; determination of mutation of IDH1 gene; determination of mutation of NF1 gene; determination of copy number of the EGFR gene; determination of status of methylation of promoter of MGMT gene; use for disease characterized by an unmethylated promoter region of the MGMT gene; use for disease characterized by a methylated promoter region of the MGMT gene; use for disease characterized by high expression of MGMT; use for disease characterized by low expression of MGMT; or use for disease characterized by EML4-ALK translocations.

Yet another aspect of the invention is an improvement in therapeutic employment of a substituted hexitol derivative such as dianhydrogalactitol for treatment of NSCLC or ovarian cancer made by specialized preparation of a patient prior to or after the use of a chemotherapeutic agent. General examples include: induction or inhibition of metabolizing enzymes, specific protection of sensitive normal tissues or organ systems. Specific inventive examples for a substituted hexitol derivative such as dianhydrogalactitol for treatment of NSCLC or ovarian cancer include: the use of colchicine or analogs; use of diuretics such as probenecid; use of a uricosuric; use of uricase; non-oral use of nicotinamide; sustained release forms of nicotinamide; use of inhibitors of poly (ADP ribose) polymerase; use of caffeine; leucovorin rescue; infection control; antihypertensives.

Yet another aspect of the invention is an improvement in therapeutic employment of a substituted hexitol derivative such as dianhydrogalactitol for treatment of NSCLC or ovarian cancer made by use of additional drugs or procedures to prevent or reduce potential side-effects or toxicities. General examples include: the use of anti-emetics, anti-nausea, hematological support agents to limit or prevent neutropenia, anemia, thrombocytopenia, vitamins, antidepressants, treatments for sexual dysfunction, and other supportive techniques. Specific inventive examples for a substituted hexitol derivative such as dianhydrogalactitol for treatment of NSCLC or ovarian cancer include: the use of colchicine or analogs; use of diuretics such as probenecid; use of a uricosuric; use of uricase; non-oral use of nicotinamide; use of sustained release forms of nicotinamide; use of inhibitors of poly ADP-ribose polymerase; use of caffeine; leucovorin rescue; use of sustained release allopurinol; non-oral use of allopurinol; use of bone marrow transplants; use of a blood cell stimulant; use of blood or platelet infusions; use of filgrastim, G-CSF, or GM-CSF; use of pain management techniques; use of anti-inflammatories; use of fluids; use of corticosteroids; use of insulin control medications; use of antipyretics; use of anti-nausea treatments; use of anti-diarrheal treatment; use of N-acetylcysteine; or use of antihistamines.

Yet another aspect of the invention is an improvement in therapeutic employment of a substituted hexitol derivative such as dianhydrogalactitol for treatment of NSCLC or ovarian cancer made by the use of monitoring drug levels after dosing in an effort to maximize a patient's drug plasma level, to monitor the generation of toxic metabolites, monitoring of ancillary medicines that could be beneficial or harmful in terms of drug-drug interactions. General examples include: the monitoring of drug plasma protein binding, and monitoring of other pharmacokinetic or pharmacodynamic variables. Specific inventive examples for a substituted hexitol derivative such as dianhydrogalactitol for treatment of NSCLC or ovarian cancer include: multiple determinations of drug plasma levels; or multiple determinations of metabolites in the blood or urine.

Yet another aspect of the invention is an improvement in therapeutic employment of a substituted hexitol derivative such as dianhydrogalactitol for treatment of NSCLC or ovarian cancer made by exploiting unique drug combinations that may provide a more than additive or synergistic improvement in efficacy or side-effect management. Specific inventive examples for a substituted hexitol derivative such as dianhydrogalactitol for treatment of NSCLC or ovarian cancer include: use with topoisomerase inhibitors; use with fraudulent nucleosides; use with fraudulent nucleotides; use with thymidylate synthetase inhibitors; use with signal transduction inhibitors; use with cisplatin, oxaliplatin, or other platinum analogs; use with alkylating agents such as the nitrosoureas (BCNU, Gliadel wafers, CCNU, nimustine (ACNU), bendamustine (Treanda)); use with alkylating agents that damage DNA at a different place than does DAG (TMZ, BCNU, CCNU, and other alkylating agents all damage DNA at $O^6$ of guanine, whereas DAG cross-links at $N^7$); use with a monofunctional alkylating agent; use with a bifunctional alkylating agent; use with anti-tubulin agents; use with antimetabolites; use with berberine; use with apigenin; use with amonafide; use with colchicine or analogs; use with genistein; use with etoposide; use with cytarabine; use with camptothecins; use with vinca alkaloids; use with topoisomerase inhibitors; use with 5-fluorouracil; use with curcumin; use with NF-κB inhibitors; use with rosmarinic acid; use with mitoguazone; use with tetrandrine; use with temozolomide (TMZ); use with biological therapies such as antibodies such as Avastin (a VEGF inhibitor), Rituxan, Herceptin, Erbitux; use with epidermal growth factor receptor (EGFR) inhibitors; use with tyrosine kinase inhibitors; use with poly (ADP-ribose) polymerase (PARP) inhibitors; or use with cancer vaccine therapy. The ability to be more than additive or synergistic is particularly significant with respect to the combination of a substituted hexitol derivative such as dianhydrogalactitol with cisplatin, oxaliplatin, or other platinum-containing chemotherapeutic agents.

When methods according to the present invention are intended for treatment of ovarian cancer, drug combinations can include the use of a substituted hexitol derivative as described above together with an additional agent that possesses anti-neoplastic activity against ovarian tumors. Such additional agents include, but are not limited to, paclitaxel, docetaxel, cisplatin, carboplatin, topotecan, gemcitabine, bleomycin, etoposide, doxorubicin (which can be used in a pegylated liposomal form), tamoxifen, letrozole, olaparib, selumetinib, mTOR inhibitors, PI3 kinase inhibitors, and trichostatin A.

Additional agents that possess anti-neoplastic activity against NSCLC are known in the art. These additional agents can be included in drug combinations according to the present invention in a therapeutically effective quantity together with a therapeutically effective quantity of a substituted hexitol derivative as described above. One or more than one of these additional agents can be used. These additional agents can be used together with one or more of the agents as described above for activity against NSCLC in drug combinations including a substituted hexitol derivative such as dianhydrogalactitol or diacetyldianhydrogalactitol. Collectively, these agents are referred to herein as "Additional Secondary Agents with Activity Against NSCLC." These agents include the following: U.S. Pat. No. 8,841,277 to Nguyen et al. discloses the use of 5-azacytidine. U.S. Pat. No. 8,741,889 to Boylan et al. discloses the use of a γ-secretase inhibitor. U.S. Pat. No. 8,575,191 to Chen et al. discloses the use of a pyrroloquinolinyl-pyrrole-2,5-dione compound in combination with an EGFR inhibitor. U.S. Pat. No. 8,529,900 to Alifano et al. discloses the use of an inhibitor of the neurotensin activation of the neurotensin receptor 1 (NTSR1). U.S. Pat. No. 5,795,870 to Narita et al. discloses the use of 14- or 15-membered-ring macrolide compounds such as clarithromycin or erythromycin B. U.S. Pat. No. 5,756,512 to Johnson discloses the use of water-soluble camptothecin analogs. U.S. Pat. No. 4,853,221 to Elslager et al. discloses the use of 5-methyl-6-[[(3,4,5-trimethoxyphenyl)amino]-methyl]-2,4-quinazolinediamine (trimetrexate). U.S. Pat. No. 8,987,461 to Nie et al. discloses the use of substituted pyrazolylpyridine, pyrazolylpyridazine, and pyrazolylpyrimidine derivatives. U.S. Pat. No. 8,987,412 to Arora et al. discloses the use of hydrogen bond surrogate macrocyclic peptides. U.S. Pat. No. 8,987,281 to Reddy et al. discloses the use of folate-vinca conjugates. U.S. Pat. No. 8,987,280 to Dotson et al. discloses the use of pyrazolopyrimidine PIK3 inhibitors, including 4-(3,4-dimethoxyphenoxy)-6-(1H-indazol-4-yl)-1-methyl-1H-pyrazolo[3,4-d]pyrimidine; 6-(1H-indazol-4-yl)-1-methyl-4-(4-(methylsulfonyl)phenoxy)-1H-pyrazolo[3,4-d]pyrimidine; N-(3-(6-(1H-indazol-4-yl)-1-methyl-1H-pyrazolo[3,4-d]pyrimidin-4-yl)phenyl)methanesulfonamide; 6-(1H-indazol-4-yl)-4-(3-(methoxymethyl)phenyl)-1-methyl-1H-pyrazolo[3,4-d]pyrimidine; 3-(6-(1H-indazol-4-yl)-1-methyl-1H-pyrazolo[3,4-d]pyrimidin-4-yl) benzonitrile; 3-(6-(1H-indazol-4-yl)-1-methyl-1H-pyrazolo[3,4-d]pyrimidin-4-yl)-N-methylbenzamide; 6-(1H-indazol-4-yl)-4-(3-methoxyphenyl)-1-methyl-1H-pyrazolo[3,4-d]pyrimidine; N-(3-(6-(1H-indazol-4-yl)-1-methyl-1H-pyrazolo[3,4-d]pyrimidin-4-yl)phenyl)acetamide; 6-(1H-indazol-4-yl)-1-methyl-4-(4-(methylsulfonyl)phenyl)-1H-pyrazolo[3,4-d]pyrimidine; 6-(1H-indazol-4-yl)-4-(4-methoxyphenyl)-1-methyl-1H-pyrazolo[3,4-d]pyrimidine; 4-(3,4-dimethoxyphenyl)-6-(1H-indazol-4-yl)-1-methyl-1H-pyrazolo[3,4-d]pyrimidine; 6-(1H-indazol-4-yl)-1-methyl-4-(pyridin-3-yloxy)-1H-pyrazolo[3,4-d]pyrimidine; 6-(1H-indazol-4-yl)-4-(3-methoxyphenoxy)-1-methyl-1H-pyrazolo[3,4-d]pyrimidine; and 6-(1H-indazol-4-yl)-N-(3-methoxyphenyl)-1-methyl-1H-pyrazolo[3,4-d]pyrimidin-4-amine). U.S. Pat. No. 8,987,267 to Reddy et al. discloses the use of 2-substituted-8-alkyl-7-oxo-7,8-dihydropyrido[2,3-d] pyrimidine-6-carbonitriles including 8-cyclopentyl-2-((4-(4-methylpiperazin-1-yl)phenyl)amino)-7-oxo-7,8-dihydropyrido[2,3-d]pyrimidine-6-carbonitrile; 8-cyclohexyl-2-((4-(4-methylpiperazin-1-yl)phenyl)amino)-7-oxo-7,8-dihydropyrido[2,3-d]pyrimidine-6-carbonitrile; 8-cyclopentyl-2-((3,5-dimethoxyphenyl)amino)-7-oxo-7,8-dihydropyrido[2,3-d]pyrimidine-6-carbonitrile; 8-cyclopentyl-7-oxo-2-((3,4,5-trimethoxyphenyl)amino)-7,8-dihydropyrido[2,3-d] pyrimidine-6-carbonitrile; and 8-cyclopentyl-2-((4-morpholinopheny)amino)-7-oxo-7,8-dihydropyrido[2,3-d] pyrimidine-6-carbonitrile. U.S. Pat. No. 8,987,260 to Chuckowree et al. discloses the use of 2-(1H-indazol-4-yl)-6-(4-methanesulfonyl-piperazin-1-ylmethyl)-4-morpholin-4-yl-thieno[3,2-d]pyrimidine bismesylate. U.S. Pat. No. 8,987,257 to Radetich et al. discloses the use of morpholinylpurine derivatives including 3-[2-((2S,6R)-2,6-dimethyl-morpholin-4-yl)-6-morpholin-4-yl-9H-purin-8-yl]-phenol; 2,6-bis-((S)-3-methyl-morpholin-4-yl)-8-(1H-pyrrolo[2,3-b]pyridin-4-yl)-9H-purine; {2-fluoro-5-[6-((S)-3-methyl-morpholin-4-yl)-2-morpholin-4-yl-9H-purin-8-yl]-phenyl}-methanol; 2-(4,4-difluoro-piperidin-1-yl)-8-(1H-indol-4-yl)-6-((S)-3-methyl-morpholin-4-yl)-9H-purine; 5-[2,6-bis-((S)-3-methyl-morpholin-4-yl)-9H-purin-8-yl]-1,3-dihydro-benzoimidazol-2-one; {5-[2,6-bis-((S)-3-methyl-morpholin-4-yl)-9H-purin-8-yl]-2-methoxy-phenyl}-methanol; 8-(1H-indol-4-yl)-2-morpholin-4-yl-6-(8-oxa-3-aza-bicyclo[3.2.1]oct-3-yl)-9H-purine; 2-methoxy-5-[6-((S)-3-methyl-morpholin-4-yl)-2-morpholin-4-yl-9H-purin-8-yl]-benzoic acid; {4-chloro-3-[6-((S)-3-methyl-morpholin-4-yl)-2-morpholin-4-yl-9H-purin-8-yl]-phenyl}-methanol; 3-(2,6-di-morpholin-4-yl-9H-purin-8-yl)-benzylamine; 1-{3-[6-((S)-3-methyl-morpholin-4-yl)-2-morpholin-4-yl-9H-purin-8-yl]-phenyl}-ethanol; 2,6-di-morpholin-4-yl-8-(1H-pyrrolo[3,2-b]pyridin-6-yl)-9H-purine; 8-(1H-indol-6-yl)-2,6-bis-((S)-3-methyl-morpholin-4-yl)-9H-purine; 8-(1H-indol-4-yl)-2,6-bis-((R)-3-methyl-morpholin-4-yl)-9H-purine; 1-[8-(1H-indol-4-yl)-6-((S)-3-methyl-morpholin-4-yl)-9H-purin-2-yl]-piperidin-4-ol; {3-[2,6-bis-((S)-3-methyl-morpholin-4-yl)-9H-purin-8-yl]-5-methoxy-phenyl}-methanol; and 8-(1H-indol-4-yl)-2-((R)-3-methyl-morpholin-4-yl)-6-((S)-3-methyl-morpholin-4-yl)-9H-purine. U.S. Pat. No. 8,980,955 to Turchi et al. discloses the use of small molecule inhibitors of Replication Protein A including substituted haloester isoborneols. U.S. Pat. No. 8,980,824 to Cong et al. discloses the use of tubulysins as anti-mitotic agents. U.S. Pat. No. 8,975,401 to Qian et al. discloses the use of quinazoline-based EGFR inhibitors containing a zinc binding moiety. U.S. Pat. No. 8,975,265 to Ince et al. discloses the use of substituted imidazo[1,2-a]pyrimidines and substituted imidazo[1,2-a]pyridines. U.S. Pat. No. 8,975,260 to Currie et al. discloses the use of pyridazinones as Btk kinase inhibitors. U.S. Pat. No. 8,975,248 to Zaknoen et al. discloses the use of 7-t-butoxyiminomethylcamptothecin in combination with paclitaxel, epothilone B, cisplatin, carboplatin, {6-[4-(4-ethyl-piperazin-1-ylmethyl)-phenyl]-7H-pyrrolo[2,3-d]pyrimidin-4-yl}-((R)-1-phenyl-ethyl)-amine, everolimus, imatinib, or bortezomib. U.S. Pat. No. 8,969,401 to Maier et al. discloses the use of sulfonylpyrroles as HDAC inhibitors, including (E)-N-hydroxy-3-[1-(toluene-4-sulfonyl)-1-H-pyrrol-3-yl]-acrylamide; N-hydroxy-3-(1-phenylmethanesulfonyl-1H-pyrrol-3-yl)-acrylamide; (E)-3-[1-(4-dimethylamino-benzenesulfonyl)-1H-pyrrol-3-yl]-N-hydroxy-acrylamide; (E)-N-(2-amino-phenyl)-3-[1-(toluene-4-sulfonyl)-1H-pyrrol-3-yl]-acrylamide; (E)-N-(2-amino-phenyl)-3-(1-phenylmethanesulfonyl-1H-pyrrol-3-yl)-acrylamide; (E)-N-(2-amino-phenyl)-3-[1-(4-dimethylamino-benzenesulfonyl)-1H-pyrrol-3-yl]-acrylamide; (E)-N-hydroxy-3-(1-[4-(([2-(1H-indol-2-yl)-ethyl]-methyl-amino)-methyl)-benzenesulfonyl]-1H-pyrrol-3-yl)-acrylamide; (E)-3-[1-(4-dimethylaminomethyl-benzenesulfonyl)-1H-pyrrol-3-yl]-N-hydroxy-acrylamide; and (E)-N-hydroxy-3-[1-(4-{[(pyridin-3-ylmethyl)-amino]-methyl}-benzenesulfonyl)-1H-pyrrol-3-yl]-acrylamide. U.S. Pat. No. 8,969,379 to Furitsu et al. discloses the use of 4-(3-chloro-4-(cyclopropylaminocarbonyl)aminophenoxy)-7-methoxy-6-quinolinecarboxamide. U.S. Pat. No. 8,969,372 to Huesca et al. discloses the use of 2,4,5-trisubstituted arylimidazoles. U.S. Pat. No. 8,962,637 to McAllister et al. discloses the use of aromatic bicyclic compounds with pyrimidine and pyridine moieties that are dual c-SRC/JAK inhibitors, including N-(4-methyl-3-{2-[4-(4-methyl-piperazine-1-carbonyl)-phenylamino]-7,8-dihydro-5H-pyrido[4,3-d]pyrimidin-6-yl}-phenyl)-3-trifluoromethyl-benzamide; N-(4-methyl-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide; 5-{6-[2-methyl-5-(3-trifluoromethyl-benzoylamino)-phenyl]-5,6,7,8-tetrahydro-pyrido[4,3-d]pyrimidin-2-ylamino}-pyridine-2-carboxylic acid cyclopropylamide; N-{3-[2-(4-cyclopropylsulfamoyl-phenylamino)-7,8-dihydro-5H-pyrido[4,3-d]pyrimidin-6-yl]-4-methyl-phenyl}-3-trifluoromethyl-benzamide; N-(4-chloro-3-{2-[4-(4-methyl-piperazin-1-yl)-phenylamino]-5-oxo-7,8-dihydro-5H-pyrido[4,3-d]pyrimidin-6-yl}-phenyl)-3-trifluoromethyl-benzamide; 4-trifluoromethyl-pyridine-2-carboxylic acid {4-chloro-3-[2-(4-methylcarbamoyl-phenylamino)-7,8-dihydro-5H-pyrido[4,3-d]pyrimidin-6-yl]-phenyl}-amide; 4,4,4-trifluoro-3-methyl-N-[4-methyl-3-(2-{4-[2-(4-methyl-piperazin-1-yl)-ethoxy]-phenylamino}-7,8-dihydro-5H-pyrido[4,3-d]pyrimidin-6-yl)-phenyl]-butyramide; and 1-cyclopentyl-3-(4-methyl-3-{2-[4-(2-pyrrolidin-1-yl-ethoxy)-phenylamino]-7,8-dihydro-5H-pyrido[4,3-d]pyrimidin-6-yl}-phenyl)-urea. U.S. Pat. No. 8,962,620 to Kuntz et al. discloses the use of substituted 6,5-fused bicyclic heteroaryl compounds to prevent aberrant H3-K27 histone methylation, including N-((4,6-dimethyl-2-oxo-1,2-dihydropyridin-3-yl)methyl)-6-(2,5-dimethylthiophen-3-yl)-1-isopropyl-1H-pyrazolo[3,4-b]pyridine-4-carboxamide; 6-(2,3-dihydro-1,4-benzodioxin-6-yl)-N-[(1,2-dihydro-4,6-dimethyl-2-oxo-3-pyridinyl)methyl]-1-(1-methylethyl)-1H-pyrazolo[3,4-b]pyridine-4-carboxamide; 6-cyclopropyl-N-((4,6-dimethyl-2-oxo-1,2-dihydropyridin-3-yl)methyl)-1,3-dimethyl-1H-pyrazolo[3,4-b]pyridine-4-carboxamide; N-[(1,2-dihydro-4,6-dimethyl-2-oxo-3-pyridinyl)methyl]-1,3,6-trimethyl-1H-pyrazolo[3,4-b]pyridine-4-carboxamide; N-[(1,2-dihydro-4,6-dimethyl-2-oxo-3-pyridinyl)methyl]-6-methyl-1-(1-methylethyl)-1H-pyrazolo[3,4-b]pyridine-4-carboxamide; and 6-cyclopropyl-N-((4,6-dimethyl-2-oxo-1,2-dihydropyridin-3-yl)methyl)-1-isopropyl-1H-pyrazolo[3,4-b]pyridine-4-carboxamide. U.S. Pat. No. 8,962,619 to Ashwell et al. discloses the use of substituted imidazopyridinyl-aminopyridine compounds. U.S. Pat. No. 8,962,609 to Perrior et al. discloses the use of pyrimidine compounds as inhibitors of protein kinases IKKε and/or TBK-1, including 5-(2-phenylamino-pyrimidin-4-yl)-2-pyrrolidin-1-yl-benzonitrile; 5-[2-(pyridin-4-ylamino)-pyrimidin-4-yl]-2-pyrrolidin-1-yl-benzonitrile; 5-[2-(pyridin-2-ylamino)-pyrimidin-4-yl]-2-pyrrolidin-1-yl-benzonitrile; 2-pyrrolidin-1-yl-5-[2-(3-trifluoromethyl-phenylamino)-pyrimidin-4-yl]-benzonitrile; 2-[4-(3-cyano-4-pyrrolidin-1-yl-phenyl)-pyrimidin-2-ylamino]-oxazole-5-carboxylic acid amide; 5-[2-(5-methyl-isoxazol-3-ylamino)-pyrimidin-4-yl]-2-pyrrolidin-1-yl-benzonitrile; 2-[4-(3-cyano-4-pyrrolidin-1-yl-phenyl)-pyrimidin-2-ylamino]-oxazole-4-carboxylic acid amide; 5-[4-(3-cyano-4-pyrrolidin-1-yl-phenyl)-pyrimidin-2-ylamino]-2-methyl-2H-pyrazole-3-carboxylic acid amide; 5-[2-(5-methyl-thiazol-2-ylamino)-pyrimidin-4-yl]-2-pyrrolidin-1-yl-benzonitrile; 5-[2-(oxazol-2-ylamino)-pyrimidin-4-yl]-2-pyrrolidin-1-yl-benzonitrile; 5-[2-(4-methyl-thiazol-2-ylamino)-pyrimidin-4-yl]-2-pyrrolidin-1-yl-benzonitrile; 4-[4-(3-cyano-4-pyrrolidin-1-yl-phenyl)-pyrimidin-2-ylamino]-3-methyl-benzamide; 5-[2-(3-fluoro-phenylamino)-pyrimidin-4-yl]-2-pyrrolidin-1-yl-benzonitrile; 5-[2-(4-fluoro-phenylamino)-pyrimidin-4-yl]-2-pyrrolidin-1-yl-benzonitrile; 5-[2-(3-methoxy-phenylamino)-pyrimidin-4-yl]-2-pyrrolidin-1-yl-benzonitrile; 5-[2-(pyridin-3-ylamino)-pyrimidin-4-yl]-2-pyrrolidin-1-yl-benzonitrile; 5-[2-(3-methyl-isoxazol-5-ylamino)-pyrimidin-4-yl]-2-pyrrolidin-1-yl-benzonitrile; 5-[2-(2-methyl-2H-pyrazol-3-ylamino)-pyrimidin-4-yl]-2-pyrrolidin-1-yl-benzonitrile; and 5-[2-(1-methyl-1H-pyrazol-3-ylamino)-pyrimidin-4-yl]-2-pyrrolidin-1-yl-benzonitrile. U.S. Pat. No. 8,962,602 to Fernandez Rodriguez et al. discloses the use of unsaturated steroidal lactone derivatives related to bufadienolides. U.S. Pat. No. 8,961,970 to Huang et al. discloses the use of combinations with the MEK inhibitor 6-(4-bromo-2-fluorophenylamino)-7-fluoro-3-methyl-3H-benzoimidazole-5-carboxylic acid (2-hydroxyethoxy)-amide and an antibody that is an IGFR1 inhibitor. U.S. Pat. No. 8,952,151 to Chen et al. discloses the use of substituted amidopyridine or amidopyridazine derivatives that are histone demethylase inhibitors. U.S. Pat. No. 8,951,993 to Hu et al. discloses the use of phosphorus-substituted aryl compounds as ALK or c-Met kinase inhibitors, including 3-[1-(2,6-dichloro-3-fluoro-phenyl)ethoxy]-5-(4-dimethylphosphorylphenyl)pyridin-2-amine; 3-[1-(2,6-dichloro-3-fluoro-phenyl)ethoxy]-5-[1-[1-(dimethylphosphorylmethyl)-4-piperidyl]pyrazol-4-yl]pyridin-2-amine; 3-[1-(2,6-dichloro-3-fluoro-phenyl)ethoxy]-5-[1-(dimethylphosphorylmethyl)pyrazol-4-yl]pyridin-2-amine; 5-[4-[(bis(dimethylphosphorylmethyl)amino)methyl]phenyl]-3-[1-(2,6-dichloro-3-fluoro-phenyl)ethoxy]pyridin-2-amine; 3-[1-(2,6-dichloro-3-fluoro-phenyl)ethoxy]-5-[4-[(dimethylphosphorylmethylamino)methyl]phenyl]pyridin-2-amine; 3-[1-(2,6-dichloro-3-fluoro-phenyl)ethoxy]-5-(5-dimethylphosphoryl-3-pyridyl)pyridin-2-amine; 3-[1-(2,6-dichloro-3-fluoro-phenyl)ethoxy]-5-[4-(dimethylphosphoryloxymethyl)phenyl]pyridin-2-amine; 3-[1-(2,6-dichloro-3-fluoro-phenyl)ethoxy]-5-(4-dimethylphosphoryl-2-methoxy-phenyl)pyridin-2-amine; 3-[1-(2,6-dichloro-3-fluoro-phenyl)ethoxy]-5-(4-dimethylphosphoryl-1-naphthyl)pyridin-2-amine; 3-[1-(2,6-dichloro-3-fluoro-phenyl)ethoxy]-5-(4-dimethylphosphoryl-2-fluoro-5-methoxy-phenyl)pyridin-2-amine; 3-[1-(2,6-dichloro-3-fluoro-phenyl)ethoxy]-5-(4-dimethylphosphorylphenyl)pyrazin-2-amine; 3-[1-(2,6- dichloro-3-fluoro-phenyl)ethoxy]-5-(4-dimethylphosphoryl-3-methoxy-phenyl)pyridin-2-amine; 3-[1-(2,6-dichloro-3-fluoro-phenyl)ethoxy]-5-(4-dimethylphosphoryl-2-fluoro-phenyl)pyridin-2-amine; 3-[1-(2,6-dichloro-3-fluoro-phenyl)ethoxy]-5-(4-dimethylphosphoryl-3-fluoro-phenyl)pyridin-2-amine; and 3-[1-(2,6-dichloro-3-fluoro-phenyl)ethoxy]-5-[4-dimethylphosphoryl-2-(trifluoromethyl)phenyl]pyridin-2-amine. U.S. Pat. No. 8,946,444 to Lennox et al. discloses the use of tetrahydrocarbazoles as VEGF synthesis inhibitors. U.S. Pat. No. 8,946,296 to Ortega Munoz et al. discloses the use of substituted heteroaryl- and aryl-cyclopropylamine acetamides as lysine specific demethylase-1 inhibitors, including 2-((t)-2-(4-(4-cyanobenzyloxy)phenyl)cyclopropylamino)acetamide; 2-((t)-2-(4-(3-cyanobenzyloxy)phenyl)cyclopropylamino)acetamide; 2-((t)-2-(4-(benzyloxy)phenyl)cyclopropylamino)acetamide; 2-((t)-2-(4-(4(benzyloxy)phenyl)cyclopropylamino)acetamide; 2-((t)-2-(4-(3-fluorobenzyloxy)phenyl)cyclopropylamino)acetamide; 2-((t)-2-(4-(3-chlorobenzyloxy)phenyl)cyclopropylamino)acetamide; 2-((t)-2-(4-(4-chlorobenzyloxy)phenyl)cyclopropylamino)acetamide; 2-((t)-2-(4-(3-bromobenzyloxy)phenyl)cyclopropylamino)acetamide; 2-((t)-2-(4-(3,5-difluorobenzyloxy)phenyl)cyclopropylamino)acetamide; 2-((t)-2-(4-phenethoxyphenyl)cyclopropylarnino)acetamide; 2-((t)-2-(3'-(trifluoromethyl)biphenyl-4-yl)cyclopropylamino)acetamide; 2-((t)-2-(3'-chlorobiphenyl-4-yl)cyclopropylamino)acetamide; 2-((t)-2-(6-(4-chlorophenyl)pyridin-3-yl)cyclopropylamino)acetamide; (R)-2-((t)-2-(4-(3-fluorobenzyloxy)phenyl)cyclopropylamino)propanamide; (S)-2-((t)-2-(4-(4-fluorobenzyloxy)phenacyclopropylamino)propanamide; (R)-2-((t)-2-(4-(4-fluorobenzyloxy)phenyl)cyclopropylamino)propanamide; (S)-2-((t)-2-(4-(4-fluorobenzyloxy)phenyl)cyclopropylamino)propanamide; and (R)-2-((t)-2-(4-(benzyloxy)phenyl)cyclopropylamino)propanamide. U.S. Pat. No. 8,946,246 to Magedov et al. discloses the use of rigidin analogs. U.S. Pat. No. 8,946,235 to Butterworth et al. discloses the use of 2-(2,4,5-substituted-anilino)pyrimidine compounds as inhibitors of mutated EGFR. U.S. Pat. No. 8,946,213 to Crawford et al. discloses the use of alkylated piperazines as Btk inhibitors including (S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrido[3,4-b]indolizin-1(2H)-one; (S)-5-[5-fluoro-2-(hydroxymethyl)-3(1-methyl-5-(5-(2-methyl-4-(oxetan-3-yl)piperazin-1-yl)pyridin-2-ylamino)-6-oxo-1,6-dihydropyridin-3-yl)phenyl]-8-thia-4,5-diazatricyclo[7.4.0.02,7]trideca-[(9),2(7),3-trien-6-one; (2S)-10-[5-fluoro-2-(hydroxymethyl)-3-[1-methyl-5-({5-[2-methyl-4-(oxetan-3-yl)piperazin-1-yl]pyridine-2-yl}amino)-6-oxo-1,6-dihydropyridin-3-yl]phenyl]-4,4-dimethyl-1,10-diazatricyclo[6.4.0.02,6]dodeca-2(6),7-dien-9-one; 2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1 (2H)-one; (S)-2-(3-(5-(5-(2-ethyl-4-(oxetan-3-yl)piperazin-1-yl)pyridin-2-ylamino)-1-methyl-6-oxo-1,6-dihydropyridin-3-yl-5-fluoro-2-(hydroxymethyl)phenyl)-3,4,6,7,8,9-hexahydropyrazino[1,2-a]indol-1 (2H)-one; (S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one; (S)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1 (2H)-one; (R)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-c]indol-1(2H)-one; and (R)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one. U.S. Pat. No. 8,937,095 to Zahn et al. discloses the use of dual Aurora kinase/MEK inhibitors including 3-[3-[[4-(dimethyloxidoaminomethy)anilino]-phenylmethylidene]-2-oxo-1H-indol-6-yl]-N-ethylprop-2-ynamide. United States Patent Application Publication No. 2015/0087664 by Blake et al. discloses the use of quinazolines as serine/threonine kinase inhibitors, including N-((4-chloro-3-fluorophenyl)(1-methyl-1H-pyrazol-4-yl)methyl)-2-((S)-1-hydroxypropan-2-ylamino)quinazoline-7-carboxamide; 2-(tetrahydropyran-4-ylamino)-quinazoline-7-carboxylic acid [(4-chloro-3-fluoro-phenyl)-(1-methyl-1H-pyrazol-4-yl)-methyl]-amide; 2-(tetrahydropyran-4-ylamino)-quinazoline-7-carboxylic acid [(S)-(3-fluoro-4-trifluoromethyl-phenyl)-(S)-pyrrolidin-2-yl-methyl]-amide; 2-(tetrahydropyran-4-ylamino)-quinazoline-7-carboxylic acid [(4-chloro-3-fluoro-phenyl)-(1-methyl-1H-pyrazol-3-yl)-methyl]-amide; 2-isopropylamino-quinazoline-7-carboxylic acid [(S)-(3-fluoro-4-trifluoromethyl-phenyl)-(R)-pyrrolidin-2-yl-methyl]-amide; N-((4-chloro-3-fluorophenyl)(1-methyl-1H-pyrazol-3-yl)methyl)-2-((S)-1-hydroxypropan-2-ylamino)quinazoline-7-carboxamide; 2-(tetrahydropyran-4-ylamino)-quinazoline-7-carboxylic acid [(S)-(3-fluoro-4-trifluoromethyl-phenyl)-(R)-pyrrolidin-2-yl-methyl]-amide; 2-(tetrahydropyran-4-ylamino)-quinazoline-7-carboxylic acid [(R)-(3-chloro-4-fluoro-phenyl)-(R)-pyrrolidin-3-yl-methyl]-amide; 2-(tetrahydropyran-4-ylamino)-quinazoline-7-carboxylic acid [(R)-(3-chloro-4-fluoro-phenyl)-(S)-pyrrolidin-3-yl-methyl]-amide; 2-(tetrahydropyran-4-ylamino)-quinazoline-7-carboxylic acid [(S)-(3-chloro-4-fluoro-phenyl)-(S)-pyrrolidin-3-yl-methyl]-amide; 2-(tetrahydropyran-4-ylamino)-quinazoline-7-carboxylic acid [(S)-(3-chloro-4-fluoro-phenyl)-(R)-pyrrolidin-3-yl-methyl]-amide; 2-(tetrahydropyran-4-ylamino)-quinazoline-7-carboxylic acid [(S)-(4-chloro-3-fluoro-phenyl)-(1-methyl-1H-pyrazol-4-yl)-methyl]-amide; 2-(tetrahydropyran-4-ylamino)-quinazoline-7-carboxylic acid [(R)-(4-chloro-3-fluoro-phenyl)-(1-methyl-1H-pyrazol-4-yl)-methyl]-amide; and 2-((S)-2-hydroxy-1-methyl-ethylamino)-quinazoline-7-carboxylic acid. United States Patent Application Publication No. 2015/0087630 by Chen et al. discloses the use of diazacarbazoles. United States Patent Application Publication No. 2015/0087628 by Ostrem et al. discloses the use of modulators of K-Ras activity that include a Switch-2 binding pocket moiety and an electrophilic chemical moiety capable of forming a covalent bond with a K-Ras cysteine residue or a K-Ras aspartate residue. United States Patent Application Publication No. 2015/0087600 by Popovici-Muller et al. discloses the use of inhibitors of mutants of isocitrate dehydrogenase 1 or isocitrate dehydrogenase 2. United States Patent Application Publication No. 2015/0086551 by Chen et al. discloses the use of hydroxamic acid derivatives that inhibit the HDAC pathway. United States Patent Application Publication No. 2015/0080392 by Wang et al. discloses the use of quinazoline derivatives as kinase inhibitors including one or more of EGFR, VEGFR-2, c-erbB-2, c-erbB-4, c-met, tie-2, PDGFR, c-src, lck, Zap70 and fyn kinases, such as N-(3-chloro-4-((3-fluorobenzyl)oxy)phenyl)-6-(5-((4-hydroxybutyl)amino)methyl-2-furyl)-4-quinazolinamine; N-(3- chloro-4-((3-fluorobenzyl)oxy)phenyl)-6-(5-((3-phenylpropyl)amino)methyl)-2-furyl)-4-quinazolinamine; N-(3-chloro-4-((3-fluorobenzyl)oxy)phenyl)-6-(5-((n-hexylamino)methyl)-2-furyl)-4-quinazolinamine; N-(3-chloro-4-((3-fluorobenzyl)oxy)phenyl)-6-(5-((ethylamino)methyl)-2-furyl)-4-quinazolinamine; N-(3-chloro-4-((3-fluorobenzyl)oxy)phenyl)-6-(5-((N,N-diethyl)amino)methyl)-2-furyl)-4-quinazolinamine; N-(3-chloro-4-((3-fluorobenzyl)oxy)phenyl)-6-(5-(((2-butenyl)amino)methyl)-2-furyl)-4-quinazolinamine; N-(3-chloro-4-((3-fluorobenzyl)oxy)phenyl)-6-(5-((2-(1,3-dihydroxypropyl)amino)methyl)-2-furyl)-4-quinazolinamine; N-(3-chloro-4-((3-fluorobenzyl)oxy)phenyl)-6-((5-((cyclohexylmethyl)amino)methyl)-2-furyl)-4-quinazolinamine; N-(3-chloro-4-((3-fluorobenzyl)oxy)phenyl)-6-(5-(((2-(3-cyclohexenyl)ethyl)amino)methyl)-2-furyl)-4-quinazolinamine; N-(3-chloro-4-((3-fluorobenzyl)oxy)phenyl)-6-(5-((((3-chlorocyclohexyl)methyl)amino)methyl)-2-furyl)-4-quinazolinamine; N-(3-chloro-4-((3-fluorobenzyl)oxy)phenyl)-6-(5-(((4-methoxybutyl)amino)methyl)-2-furyl)-4-quinazolinamine; N-(3-chloro-4-((3-fluorobenzyl)oxy)phenyl)-6-(5-(((3-chlorobenzyl)amino)methyl)-2-furyl)-4-quinazolinamine; N-(3-chloro-4-((3-fluorobenzyl)oxy)phenyl)-6-(5-(((2-(4-nitrophenyl)ethyl)amino)methyl)-2-furyl)-4-quinazolinamine; N-(3-chloro-4-((3-fluorobenzyl)oxy)phenyl)-6-(5-(((2-(4-hydroxyphenyl)ethyl)amino)methyl)-2-furyl)-4-quinazolinamine; N-(3-chloro-4-((3-fluorobenzyl)oxy)phenyl)-6-(5-(((2-(3,5-dimethoxyphenyl)ethylamino)methyl)-2-furyl)-4-quinazolinamine; N-(3-chloro-4-((3-fluorobenzyl)oxy)phenyl)-6-(5-(((2-(3-hydroxy-5-fluorophenyl)ethyl)amino)methyl)-2-furyl)-4-quinazolinamine; N-(3-chloro-4-((3-fluorobenzyl)oxy)phenyl)-6-(5-(((2-(3-chloro-5-fluorophenyl)ethyl)amino)methyl)-2-furyl)-4-quinazolinamine; N-(3-chloro-4-((3-fluorobenzyl)oxy)phenyl)-6-(5-(((2-,6-dihydroxyhexyl)amino)methyl)-2-furyl)-4-quinazolinamine; and N-(3-chloro-4-((3-fluorobenzyl)oxy)phenyl)-6-(5-((bis(2-hydroxyethyl)amino)methyl)-2-furyl)-4-quinazolinamine. United States Patent Application Publication No. 2015/0079081 by Dotson et al. discloses the use of tricyclic PI3K inhibitors such as 1-[4-(3a,8-dimethyl-7-morpholin-4-yl-3,3a,8,8a-tetrahydro-2H-1-oxa-4,6,8-triaza-cyclopenta[a]inden-5-yl)-phenyl]-3-ethyl-urea; 5-(6,6-dimethyl-4-morpholino-8,9-dihydro-6H-[1,4]oxazino[3,4-e]purin-2-yl)-4-methylpyrimidin-2-amine; 5-(6,6-dimethyl-4-morpholino-8,9-dihydro-6H-[1,4]oxazino[3,4-e]purin-2-yl)pyrimidin-2-amine; 5-(6,6-dimethyl-4-morpholino-8,9-dihydro-6H-[1,4]oxazino[3,4-e]purin-2-yl)-4-(trifluoromethyl)pyridyl-2-amine; 5-(4-morpholino-8,9-dihydro-7H-[1,3]oxazino[2,3-e]purin-2-yl)pyrimidin-2-amine; 5-(4-morpholino-6,7,8,9-tetrahydropyrido[2,1-e]purin-2-yl)pyrimidin-2-amine; 5-(4-morpholino-6,7,8,9-tetrahydropyrido[2,1-e]purin-2-yl)pyridin-2-amine; 5-(4-morpholino-8,9-dihydro-6H-[1,4]oxazino[3,4-e]purin-2-yl)-4-(trifluoromethyl)pyridyl-2-amine; 5-(4-morpholino-7,8-dihydro-6H-pyrrolo[2,1-e]purin-2-yl)pyrimidin-2-amine; 6,6-dimethyl-4-morpholino-2-(1H-pyrrolo[2,3-b]pyridin-5-yl)-8,9-dihydro-6H-[1,4]oxazino[3,4-e]purine; 5-(6,6-dimethyl-4-morpholino-8,9-dihydro-6H-[1,4]oxazino[3,4-e]purin-2-yl)pyridin-2-amine; 5-(4-morpholino-8,9-dihydrospiro[[1,3]oxazino[2,3-e]purine-7,1'-cyclopropane]-2-yl)pyrimidin-2-amine; 5-(4-morpholino-8,9-dihydro-6H-[1,4]oxazino[3,4-e]purin-2-yl)pyrimidin-2-amine; 5-(4-morpholino-8,9-dihydrospiro[[1,4]oxazino[3,4-e]purine-6,3'-oxetane]-2-yl)pyrimidin-2-amine; 5-(7,7-dimethyl-4-morpholino-8,9-dihydro-7H-[1,3]oxazino[2,3-e]purin-2-yl)pyrimidin-2-amine; 5-(4-morpholino-6-(trifluoromethyl)-8,9-dihydro-6H-[1,4]oxazino[3,4-e]purin-2-yl)pyridin-2-amine; and 5-(6,6-(hexadeuterio)dimethyl-4-morpholino-8,9-dihydro-6H-[1,4]oxazino[3,4-e]purin-2-yl)pyrimidin-2-amine. United States Patent Application Publication No. 2015/0073054 by Strongin et al. discloses the use of furin inhibitors and inhibitors of other pro-protein convertases. United States Patent Application Publication No. 2015/0073003 by Dagan et al. discloses the use of sphingolipid analogs. United States Patent Application Publication No. 2015/065526 by Deng et al. discloses the use of Stat3 inhibitors including niclosamide. United States Patent Application Publication No. 2015/0057309 by Vakkalanka et al. discloses the use of 3,5-disubstituted-3h-imidazo[4,5-b]pyridine and 3,5-disubstituted-3H-[1,2,3]triazolo[4,5-b]pyridine compounds as c-Met modulators, including N-(2-amino-2-oxoethyl)-4-(3-(quinolin-7-ylmethyl)-3H-[1,2,3]-triazolo[4,5-b]pyridin-5-yl)benzamide: N-(2-(methylamino)-2-oxoethyl)-4-(3-(quinolin-6-ylmethyl)-3H-[1,2,3]-triazolo[4,5-b]pyridin-5-yl)benzamide: N-(3-amino-3-oxopropyl)-4-(3-(quinolin-6-ylmethyl)-3H-[1,2,3]-triazolo[4,5-b]pyridin-5-yl)benzamide: N-(3-(methylamino)-3-oxopropyl)-4-(3-(quinolin-6-ylmethyl)-3H-[1,2,3]-triazolo[4,5-b]pyridin-5-yl)benzamide 2-chloro-N-(2-(pyrrolidin-1-yl)ethyl)-4-(3-(quinolin-7-ylmethyl)-3H-[1,2,3]-triazolo[4,5-b]pyridin-5-yl)benzamide: 2-chloro-N-(2-hydroxyethoxy)-4-(3-(quinolin-6-ylmethyl)-3H-[1,2,3]-triazolo[4,5-b]pyridin-5-yl)benzamide: 2-chloro-N-(2-hydroxyethoxy)-4-(3-(quinolin-6-ylmethyl)-3H-[1,2,3]-triazolo[4,5-b]pyridin-5-yl)benzamide hydrochloride: 2-chloro-N-(2-hydroxyethoxy)-4-(3-(quinolin-6-ylmethyl)-3H-[1,2,3]-triazolo[4,5-b]pyridin-5-yl)benzamide 4-methylbenzenesulfonate 2-chloro-N-(2-hydroxyethoxy)-4-(3-(quinolin-6-ylmethyl)-3H-[1,2,3]-triazolo[4,5-b]pyridin-5-yl)benzamide hydrobromide; and sodium (2-chloro-4-(3-(quinolin-6-ylmethyl)-3H-[1,2,3]-triazolo[4,5-b]pyridin-5-yl)benzoyl)(2-hydroxyethoxy)amide. United States Patent Application Publication No. 2015/0057295 by Reiser et al. discloses the use of 6-alkynylpyridine derivatives as SMAC mimetics. United States Patent Application Publication No. 2015/0057293 by Angibaud et al. discloses the use of naphthyridine derivatives. United States Patent Application Publication No. 2015/0057286 by Reiser et al. discloses the use of bis-amidopyridines as SMAC mimetics. United States Patent Application Publication No. 2015/0051209 by Bock et al. discloses the use of MEK inhibitors with imidazoquinolone or imidazoquinoline moieties including 1-((3S,4S)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone; 1-((3R,4R)-4-(8-(2-chloro-4-(pyrimidin-2-yloxy)phenyl)-7-fluoro-2-methyl-1H-imidazo[4,5-c]quinolin-1-yl)-3-fluoropiperidin-1-yl)-2-hydroxyethanone; 8-(2-chloro-4-(pyrimidin-2-yloxy)phenyl)-7-fluoro-1-(1-(2-methoxyethyl)piperidin-4-yl)-2-methyl-1H-imidazo[4,5-c]quinolone; 2-(4-(8-(2-chloro-4-(pyrimidin-2-yloxy)phenyl)-7-fluoro-2-methyl-1H-imidazo[4,5-c]quinolin-1-yl)piperidin-1-yl)ethanol; 8-(2-chloro-4-(pyrimidin-2-yloxy)phenyl)-7-fluoro-2-methyl-1-(1-((3-methyloxetan-3-yl)methyl)piperidin-4-yl)-1H-imidazo[4,5-c]quinolone; 8-(2-chloro-4-(pyrimidin-2-yloxy)phenyl)-7-fluoro-2-methyl-1-(1-(methylsulfonyl)piperidin-4-yl)-1H-imidazo[4,5-c]quinolone; 1-(4-(8-(2-chloro-4-(pyrimidin-2-yloxy)phenyl)-7-fluoro-2-methyl-1H-imidazo[4,5-c]quinolin-1-yl)piperidin-1-yl)-2-hydroxypropan-1-one; 1-(4-(8-(2-chloro-4-(pyrimidin-2-yloxy)phenyl)-7-fluoro-2-methyl-1H-imidazo[4,5-c]quinolin-1-yl)piperidin-1-yl)propan-2-ol; 8-(2-chloro-4-(pyrimidin-2-yloxy)phenyl)-1-(1-(cyclopropylsulfonyl)piperidin-4-yl)-7-fluoro-2-methyl- 1H-imidazo[4,5-c]quinolone; 8-(2-chloro-4-(pyrimidin-2-yloxy)phenyl)-7-fluoro-1-(1-(isopropylsulfonyl)piperidin-4-yl)-2-methyl-1H-imidazo[4,5-c]quinolone; 4-(8-(2-chloro-4-(pyrimidin-2-yloxy)phenyl)-7-fluoro-2-methyl-1H-imidazo[4,5-c]quinolin-1-yl)-N,N-dimethylpiperidine-1-sulfonamide; 4-(8-(2-chloro-4-(pyrimidin-2-yloxy)phenyl)-7-fluoro-2-methyl-1H-imidazo[4,5-c]quinolin-1-yl)-N,N-dimethylpiperidine-1-carboxamide; and 1-(4-(8-(2-chloro-4-(pyrimidin-2-yloxy)phenyl)-7-fluoro-2-methyl-1H-imidazo[4,5-c]quinolin-1-yl)piperidin-1-yl)ethanone. United States Patent Application Publication No. 2015/0045386 by Bencherif et al. discloses the use of (2S,3R)—N-(2-((3-pyridinyl)methyl)-1-azabicyclo[2.2.2]oct-3-yl)benzofuran-2-carboxamide. United States Patent Application Publication No. 2015/0045324 by Cha et al. discloses the use of fused pyrimidine derivatives, including N-(3-((2-((4-(4-methylpiperazin-1-yl)phenyl)amino)furo[3,2-d]pyrimidin-4-yl)oxy)phenyl)acrylamide; N-(3-((2-((4-(4-isopropylpiperazin-1-yl)phenyl)amino)furo[3,2-d]pyrimidin-4-yl)oxy)phenyl)acrylamide; N-(3-((2-((4-morpholinophenyl)amino)furo[3,2-d]pyrimidin-4-yl)oxy)phenyl)acrylamide; N-(3-((2-((4-((dimethylamino)methyl)phenyl)amino)furo[3,2-d]pyrimidin-4-yl)oxy)phenyl)acrylamide; N-(3-((2-((4-((4-(dimethylamino)piperidin-1-yl)methyl)phenyl)amino)furo[3,2-d]pyrimidin-4-yl)oxy)phenyl)acrylamide; N-(3-((2-((3-fluoro-4-(1-methylpiperazin-4-yl)phenyl)amino)furo[3,2-d]pyrimidin-4-yl)oxy)phenyl)acrylamide; N-(3-((2-((4-(2-dimethylamino)ethyl)amino)-3-fluorophenyl)amino)furo[3,2-d]pyrimidin-4-yl)oxy)phenyl)acrylamide; N-(3-((2-((3-fluoro-4-((1-methylpiperidin-4-yl)amino)phenyl)amino)furo[3,2-d]pyrimidin-4-yl)oxy)phenyl)acrylamide; N-(3-(2-(3-methoxy-4-(4-methyl-piperazin-1-yl)-phenylamino)-furo[3,2-d]pyrimidin-4-yloxy)-phenyl)-acrylamide; and N-(3-((2-((4-sulfamoylphenyl)amino)furo[3,2-d]pyrimidin-4-yl)oxy)phenyl)acrylamide. United States Patent Application Publication No. 2015/0038506 by Nacro et al. discloses the use of imidazopyrazine, imidazopyridine, imidazopyridazine and imidazpyrimidine compounds as MNK1 or MNK2 inhibitors. United States Patent Application Publication No. 2015/0038430 by Nash et al. discloses the use of peptidomimetic macrocycles binding to MCL-1. United States Patent Application Publication No. 2015/0031669 by Woodhead et al. discloses the use of benzopyrazines as inhibitors of FGFR kinases. United States Patent Application Publication No. 2015/0011561 by Allwein et al. discloses the use of fused bicyclic 2,4-diaminopyridine derivatives as dual ALK and FAK inhibitors. United States Patent Application Publication No. 2015/0011506 by Olhava et al. discloses the use of boron-containing proteasome inhibitors such as [(1R)-1-({[(2,3-difluorobenzoyl)amino]acetyl}amino)-3-methylbutyl]boronic acid; [(1R)-1-({[(5-chloro-2-fluorobenzoyl)amino]acetyl}amino)-3-methylbutyl]boronic acid; [(1R)-1-({[(3,5-difluorobenzoyl)amino]acetyl}amino)-3-methylbutyl]boronic acid; [(1R)-1-({[(2,5-difluorobenzoyl)amino]acetyl}amino)-3-methylbutyl]boronic acid; [(1R)-1-({[(2-bromobenzoyl)amino]acetyl}amino)-3-methylbutyl]boronic acid; [(1R)-1-({[(2-fluorobenzoyl)amino]acetyl}amino)-3-methylbutyl]boronic acid; [(1R)-1-({[(2-chloro-5-fluorobenzoyl)amino]acetyl}amino)-3-methylbutyl]boronic acid; [(1R)-1-({[(4-fluorobenzoyl)amino]acetyl}amino)-3-methylbutyl]boronic acid; [(1R)-1-({[(3,4-difluorobenzoyl)amino]acetyl}amino)-3-methylbutyl]boronic acid; [(1R)-1-({[(3-chlorobenzoyl)amino]acetyl}amino)-3-methylbutyl]boronic acid; [(1R)-1-({[(2,5-dichlorobenzoyl)amino]acetyl}amino)-3-methylbutyl]boronic acid; [(1R)-1-({[(3,4-dichlorobenzoyl)amino]acetyl}amino)-3-methylbutyl]boronic acid; [(1R)-1-({[(3-fluorobenzoyl)amino]acetyl}amino)-3-methylbutyl]boronic acid; [(1R)-1-({[(2-chloro-4-fluorobenzoyl)amino]acetyl}amino)-3-methylbutyl]boronic acid; [(1R)-1-({[(2,3-dichlorobenzoyl)amino]acetyl}amino)-3-methylbutyl]boronic acid; [(1R)-1-({[(2-chlorobenzoyl)amino]acetyl}amino)-3-methylbutyl]boronic acid; [(1R)-1-({[(2,4-difluorobenzoyl)amino]acetyl}amino)-3-methylbutyl]boronic acid; [(1R)-1-({[(4-chloro-2-fluorobenzoyl)amino]acetyl}amino)-3-methylbutyl]boronic acid; [(1R)-1-({[(4-chlorobenzoyl)amino]acetyl}amino)-3-methylbutyl]boronic acid; [(1R)-1-({[(2,4-dichlorobenzoyl)amino]acetyl}amino)-3-methylbutyl]boronic acid; and [(1R)-1-({[(3,5-dichlorobenzoyl)amino]acetyl}amino)-3-methylbutyl]boronic acid. United States Patent Application Publication No. 2015/0011461 by Crawford et al. discloses the use of heteroaryl pyridone and aza-pyridone amide compounds as Btk inhibitors, including N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]cyclobutanecarboxamide; N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]cyclopropanecarboxamide; 2-cyclopropyl-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]acetamide; N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]oxetane-3-carboxamide; N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-morpholino-acetamide; N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methyl-cyclopropanecarboxamide; and N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]propanamide. United States Patent Application Publication No. 2015/0005309 by Barfacker et al. discloses the use of substituted imidazopyrazines as PI3K/Akt inhibitors, including 2-[4-(1-aminocyclobutyl)phenyl]-3-phenylimidazo[1,2-a]pyrazin-8-ol; 1-[4-(6,8-dimethyl-3-phenylimidazo[1,2-a]pyrazin-2-yl)phenyl]-cyclobutanamine; 1-[4-(6-bromo-8-methoxy-3-phenylimidazo[1,2-a]pyrazin-2-yl)phenyl]cyclobutanamine; 1-[4-(6-ethyl-8-methoxy-3-phenylimidazo[1,2-a]pyrazin-2-yl)phenyl]-cyclobutanamine; ethyl 2-[4-(1-aminocyclobutyl)phenyl]-3-phenylimidazo[1,2-a]pyrazine-6-carboxylate; 2-[4-(1-aminocyclobutyl)phenyl]-3-phenylimidazo[1,2-a]pyrazine-6-carboxamide; methyl 2-[4-(1-aminocyclobutyl)phenyl]-8-methoxy-3-phenylimidazo[1,2-a]-pyrazine-6-carboxylate; and 2-[4-(1-aminocyclobutyl)phenyl]-8-methoxy-3-phenylimidazo[1,2-a]pyrazine-6-carboxamide. United States Patent Application Publication No. 2014/0378466 by Maderna et al. discloses the use of derivatives of N-(arylamino) sulfonamides as MEK inhibitors. United States Patent Application Publication No. 2014/0371254 by Leung et al. discloses the use of isoquinoline alkaloids including sanguinarine. United States Patent Application Publication No. 2014/0371158 by Chadli et al. discloses the use of beauvericin and analogs and derivatives as Hsp90 chaperone pathway inhibitors. United States Patent Application Publication No. 2014/0357605 by Gavai et al. discloses the use of bis-(fluoroalkyl)-1,4-benzodiazapinone compounds as Notch receptor inhibitors, including (2R,3S)—N-((3S)-1-methyl-2-oxo-5-phenyl-2,3- dihydro-1H-1,4-benzodiazepin-3-yl)-2,3-bis(3,3,3-trifluoropropyl)succinamide; (2R,3S)—N-((3S)-2-oxo-5-phenyl-2,3-dihydro-1H-1,4-benzodiazepin-3-yl)-2,3-bis(3,3,3-trifluoropropyl)succinamide; (2R,3S)—N-((3S)-1-methyl-2-oxo-5-phenyl-2,3-dihydro-1H-1,4-benzodiazepin-3-yl)-2-(2,2,2-trifluoroethyl)-3-(3,3,3-trifluoropropyl)succinamide; (2R,3S)—N-((3S)-1-methyl-2-oxo-5-phenyl-2,3-dihydro-1H-1,4-benzodiazepin-3-yl)-3-(2,2,2-trifluoroethyl)-2-(3,3,3-trifluoropropyl)succinamide; (2R,3S)—N-((3S)-1-(2H$_3$)methyl-2-oxo-5-phenyl-2,3-dihydro-1H-1,4-benzodiazepin-3-yl)-2,3-bis(3,3,3-trifluoropropyl)succinamide; (2R,3S)—N-((3S)-7-chloro-1-methyl-2-oxo-5-phenyl-2,3-dihydro-1H-1,4-benzodiazepin-3-yl)-2,3-bis(3,3,3-trifluoropropyl)succinamide; (2R,3S)—N-((3S)-8-methoxy-1-methyl-2-oxo-5-phenyl-2,3-dihydro-1H-1,4-benzodiazepin-3-yl)-2,3-bis(3,3,3-trifluoropropyl)succinamide; (2R,3S)—N-((3S)-8-fluoro-1-methyl-2-oxo-5-phenyl-2,3-dihydro-1H-1,4-benzodiazepin-3-yl)-2,3-bis(3,3,3-trifluoropropyl)succinamide; and (2R,3S)—N-((3S)-7-methoxy-1-methyl-2-oxo-5-phenyl-2,3-dihydro-1H-1,4-benzodiazepin-3-yl)-2,3-bis(3,3,3-trifluoropropyl)succinamide. United States Patent Application Publication No. 2014/0357594 by Hendrickson et al. discloses the use of purinyl-containing heteroaryl compounds that inhibit DNA methyltransferase. United States Patent Application Publication No. 2014/0350096 by Yang et al. discloses the use of antrocin.

Additional agents that possess anti-neoplastic activity against ovarian cancer are known in the art. These additional agents can be included in drug combinations according to the present invention in a therapeutically effective quantity together with a therapeutically effective quantity of a substituted hexitol derivative as described above. One or more than one of these additional agents can be used. These additional agents can be used together with one or more of the agents as described above for activity against ovarian cancer in drug combinations including a substituted hexitol derivative such as dianhydrogalactitol or diacetyldianhydrogalactitol. Collectively, these agents are referred to herein as "Additional Secondary Agents with Activity Against Ovarian Cancer." These agents include the following: U.S. Pat. No. 8,981,131 to Bhedi et al., discloses the use of tricyclic compounds such as (5aR,9bS)-3a-hydroxy-5a,9-dimethyl-3-((4-methylpiperazin-1-yl)methyl)-3,3a,4,5,5a,6,7,8-octahydronaphtho[1,2-b]furan-2(9bH)-one hydrochloride; ethyl 4-(((5aR,9bS)-3a-hydroxy-5a,9-dimethyl-2-oxo-2,3,3a,4,5,5a,6,7,8,9b-decahydronaphtha[1,2-b]furan-3-yl)methyl)piperazine-1-carboxylate hydrochloride; (5aR,9bS)-3a-hydroxy-5a,9-dimethyl-3-((4-o-tolylpiperazin-1-yl)methyl)-3,3a,4,5,5a,6,7,8-octahydronaphtho[1,2-b]furan-2(9bH)-one hydrochloride; or (5aR,9bR)-3a-hydroxy-3-((((5aR,9bS)-3a-hydroxy-5a,9-dimethyl-2-oxo-2,3,3a,4,5,5a,6,7,8,9b-decahydronaphtho[1,2-b]furan-3-yl)methylamino)methyl)-5a,9-dimethyl-3,3a,4,5,5a,6,7,8-octahydronaphtho[1,2-b]furan-2(9bH)-one hydrochloride). U.S. Pat. No. 8,981,094 to Bongartz et al. discloses the use of piperidine/piperazine derivatives that are DGAT inhibitors, particularly DGAT1 inhibitors. U.S. Pat. No. 8,981,085 to Le Huerou et al. discloses the use of pyrrolopyrimidine CHK1 or CHK2 inhibitors. U.S. Pat. No. 8,981,084 to Balogu et al. discloses the use of oxadiazole HDAC inhibitors. U.S. Pat. No. 8,980,955 to Turchi et al. discloses the use of inhibitors of Replication Protein A that are haloester isoborneol derivatives. U.S. Pat. No. 8,980,934 to Pauls et al. discloses the use of indazole inhibitors of TTK protein kinase. U.S. Pat. No. 8,980,933 to Schobert et al. discloses the use of combretastatin analogs. U.S. Pat. No. 8,980,909 to Chen et al. discloses the use of HDAC inhibiting derivatives of camptothecin. U.S. Pat. No. 8,980,902 to Brown et al. discloses the use of piperazinylbenzamide PARP inhibitors. U.S. Pat. No. 8,980,879 to Liu et al. discloses the use of BET bromodomain inhibitors including 5-(cyclopropylmethyl)-11-methyl-8-((methylsulfonyl)methyl)-2,4,5,11-tetrahydro-1H-2,5,11-triazadibenzo[cd,h]azulen-1-one; 5-(4-fluorophenyl)-11-methyl-8-((methylsulfonyl)methyl)-2,4,5,11-tetrahydro-1H-2,5,11-triazadibenzo[cd,h]azulen-1-one; 5-(2,4-difluorophenyl)-11-methyl-8-((methylsulfonyl)methyl)-2,4,5,11-tetrahydro-1H-2,5,11-triazadibenzo[cd,h]azulen-1-one; 5-(cyclopropanecarbonyl)-11-methyl-8-((methylsulfonyl)methyl)-2,4,5,11-tetrahydro-1H-2,5,11-triazadibenzo[cd,h]azulen-1-one; 5-(4-fluorophenyl)-4-(2-methoxyethyl)-11-methyl-8-((methylsulfonyl)methyl)-2,4,5,11-tetrahydro-1H-2,5,11-triazadibenzo[cd,h]azulen-1-one; methyl 3-(5-(4-fluorophenyl)-11-methyl-8-((methylsulfonyl)methyl)-1-oxo-2,4,5,11-tetrahydro-1H-2,5,11-triazadibenzo[cd,h]azulen-4-yl)propanoate; N-(5-(4-fluorophenyl)-11-methyl-1-oxo-2,4,5,11-tetrahydro-1H-2,5,11-triazadibenzo[cd,h]azulen-8-yl)ethanesulfonamide; 8-fluoro-5-(4-fluorophenyl)-1-methyl-2,4,5,11-tetrahydro-1H-2,5,6,11-tetraazadibenzo[cd,h]azulen-1-one; N-(5-(4-fluorophenyl)-11-methyl-1-oxo-2,4,5,11-tetrahydro-1H-2,5,6,11-tetraazadibenzo[cd,h]azulen-8-yl)-2-(1-methyl-1H-pyrazol-4-yl)acetamide; 8-amino-5-(4-fluorophenyl)-1-methyl-2,4,5,11-tetrahydro-1H-2,5,11-triaza-dibenzo[cd,h]azulen-1-one; N-(5-(4-fluorophenyl)-11-methyl-1-oxo-2,4,5,11-tetrahydro-1H-2,5,11-triazadibenzo[cd,h]azulen-8-yl)benzenesulfonamide; N-(4-(N-(5-(4-fluorophenyl)-11-methyl-1-oxo-2,4,5,11-tetrahydro-1H-2,5,11-triazadibenzo[cd,h]azulen-8-yl)sulfamoyl)phenyl)acetamide. U.S. Pat. No. 8,980,875 to Mailliet et al. discloses the use of platinum N-heterocyclic carbene derivatives. U.S. Pat. No. 8,980,850 to Smith discloses the use of NEDD8-activating enzyme inhibitors such as ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or {(1 S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate. U.S. Pat. No. 8,980,838 to Wang et al. discloses the use of cyclic peptidomimetic inhibitors of the WDR5/MLL1 interaction. U.S. Pat. No. 8,980,268 to Lowy et al. discloses the use of anti-Ang-2 antibodies. U.S. Pat. No. 8,980,257 to Kaneda et al. discloses the use of anti-TGFα antibodies. U.S. Pat. No. 8,975,398 to Hansen et al. discloses the use of NAMPT inhibitors such as N-{4-[1-(2-methylpropanoyl)piperidin-4-yl]phenyl})-1-(pyridazin-3-yl)azetidine-3-carboxamide; N-(4-{[1-(2-chlorobenzoyl)piperidin-4-yl]oxy}phenyl)-1-(pyridazin-3-yl)azetidine-3-carboxamide; N-[4-({1-[(2S)-2-methylbutanoyl]piperidin-4-yl}oxy)phenyl]-1-(pyridazin-3-yl)azetidine-3-carboxamide; 1-(pyridazin-3-yl)-N-(4-{[1-(1,3-thiazol-2-ylcarbonyl)piperidin-4-yl]oxy}phenyl)azetidine-3-carboxamide; 1-(pyridazin-3-yl)-N-(4-{[1-(tetrahydro-2H-pyran-4-ylcarbonyl)piperidin-4-yl]oxy}phenyl)azetidine-3-carboxamide; N-[4-({1-[difluoro(phenyl)acetyl]piperidin-4-yl}oxy)phenyl]-1-(pyridazin-3-yl)azetidine-3-carboxamide; N-[4-({1-[(4,4-difluorocyclohexyl)carbonyl]piperidin-4-yl}oxy)phenyl]-1-(pyridazin-3-yl)azetidine-3-carboxamide; N-(4-{[1-(2-methyl-2-phenylpropanoyl)piperidin-4-yl]oxy}phenyl)-1-(pyridazin-3-yl)azetidine-3-carboxamide; 1-(pyridazin-3-yl)-N-(4-{[1-(1,3-thiazol-4-ylcarbonyl)piperidin-4-yl]oxy}phenyl)azetidine-3-carboxamide; N-[4-({1-[(5-methylthiophen-2-yl)carbonyl]piperidin-4-yl}oxy)phenyl]-1-(pyridazin-3-yl)azetidine-3-carboxamide; 1-(pyridazin-3-yl)-N-{4-[(1-{[4-(trifluoromethyl)phenyl]acetyl}piperidin-4-yl)oxy]phenyl}azetidine-3-carboxamide; 1-(pyridazin-3- yl)-N-(4-{[1-(tetrahydrofuran-2-ylcarbonyl)piperidin-4-yl]oxy}phenyl)azetidine-3-carboxamide; 1-(pyridazin-3-yl)-N-[4-({1-[3-(trifluoromethyl)benzoyl]piperidin-4-yl}oxy)phenyl]azetidine-3-carboxamide; 1-(pyridazin-3-yl)-N-(4-{[1-(thiophen-3-ylcarbonyl)piperidin-4-yl]oxy}phenyl)azetidine-3-carboxamide; 1-(pyridazin-3-yl)-N-[4-({1-[3-(trifluoromethoxy)benzoyl]piperidin-4-yl}oxy)phenyl]azetidine-3-carboxamide; N-(4-{[1-(3-methylbutanoyl)piperidin-4-yl]oxy}phenyl)-1-(pyridazin-3-yl)azetidine-3-carboxamide; 1-(pyridazin-3-yl)-N-(4-{[1-(tetrahydrofuran-3-ylcarbonyl)piperidin-4-yl]oxy}phenyl)azetidine-3-carboxamide; N-[4-({1-[(3-fluorophenyl)acetyl]piperidin-4-yl}oxy)phenyl]-1-(pyridazin-3-yl)azetidine-3-carboxamide; N-(4-{[1-(2-fluorobenzoyl)piperidin-4-yl]oxy}phenyl)-1-(pyridazin-3-yl)azetidine-3-carboxamide; N-(4-{[1-(2,4-difluorobenzoyl)piperidin-4-yl]oxy}phenyl)-1-(pyridazin-3-yl)azetidine-3-carboxamide; N-(4-{[1-(4-fluorobenzoyl)piperidin-4-yl]oxy}phenyl)-1-(pyridazin-3-yl)azetidine-3-carboxamide; and N-(4-{[1-(3-fluorobenzoyl)piperidin-4-yl]oxy}phenyl)-1-(pyridazin-3-yl)azetidine-3-carboxamide. U.S. Pat. No. 8,975,376 to Blein et al. discloses the use of anti-α$_2$-integrin antibodies. U.S. Pat. No. 8,975,287 to Karp et al. discloses the use of 1,2,4-oxadiazole benzoic acid compounds. U.S. Pat. No. 8,975,267 to Caldarelli et al. discloses the use of tricylic pyrrole derivatives such as N-(2,6-diethylphenyl)-9-(methoxymethyl)-2-{[2-methoxy-4-(4-methylpiperazin-1-yl)phenyl]amino}-8-methyl-6,9-dihydro-5H-pyrrolo[3,2-h]quinazoline-7-carboxamide, 2-[(4-bromo-2-methoxyphenyl)amino]-N-(2,6-diethylphenyl)-8,9-dimethyl-6,9-dihydro-5H-pyrrolo[3,2-h]quinazoline-7-carboxamide, N-(2,6-diethylphenyl)-2-({2-methoxy-4-[4-(pyrrolidin-1-yl)piperidin-1-yl]phenyl}amino)-8,9-dimethyl-6,9-dihydro-5H-pyrrolo[3,2-h]quinazoline-7-carboxamide, N-(2,6-diethylphenyl)-2-({4-[4-(dimethylamino)piperidin-1-yl]-2-methoxyphenyl}amino)-8,9-dimethyl-6,9-dihydro-5H-pyrrolo[3,2-h]quinazoline-7-carboxamide, N-(2,6-diethylphenyl)-2-{[2-methoxy-4-(4-methylpiperazin-1-yl)phenyl]amino}-8,9-dimethyl-6,9-dihydro-5H-pyrrolo[3,2-h]quinazoline-7-carboxamide, N-(2,6-diethylphenyl)-2-({4-[4-(2-hydroxyethyl)piperazin-1-yl]-2-methoxyphenyl}amino)-8,9-dimethyl-6,9-dihydro-5H-pyrrolo[3,2-h]quinazoline-7-carboxamide, 2-{[2-methoxy-4-(4-methylpiperazin-1-yl)phenyl]amino}-8,9-dimethyl-6,9-dihydro-5H-pyrrolo[3,2-h]quinazoline-7-carboxamide, and 2-[(4-bromo-2-methoxyphenyl)amino]-N-(2,6-diethylphenyl)-9-methyl-6,9-dihydro-5H-pyrrolo[3,2-h]quinazoline-7-carboxamide. U.S. Pat. No. 8,974,781 to Bauer et al. discloses the use of anti-P-cadherin antibodies. U.S. Pat. No. 8,969,587 to Abraham et al. discloses the use of BRAF kinase inhibitors, such as 1-(3-(6,7-dimethoxyquinazolin-4-yloxy)phenyl)-3-(5-(1,1,1-trifluoro-2-methylpropan-2-yl)isoxazol-3-yl)urea. U.S. Pat. No. 8,969,401 to Maier et al. discloses the use of sulfonylpyrroles as HDAC inhibitors. U.S. Pat. No. 8,969,396 to Du et al. discloses the use of BRAF inhibitors including Hsp90 inhibitors such as 3-(2,4-dihydroxy-5-isopropyl-phenyl)-4-(1-methyl-indol-5-yl)-5-hydroxy-[1,2,4]triazole. U.S. Pat. No. 8,969,395 to Ribeiro Salvador et al. discloses the use of triterpenoid derivatives. U.S. Pat. No. 8,969,381 to Wilson et al. discloses the use of chemokine CXCR4 modulators such as N$^1$—(((S)-1,2,3,4-tetrahydroisoquinolin-3-yl)methyl)-N$^1$—((S)-5,6,7,8-tetrahydroquinolin-8-yl)butane-1,4-diamine; N$^1$—(((R)-1,2,3,4-tetrahydroisoquinolin-3-yl)methyl)-N—((S)-5,6,7,8-tetrahydroquinolin-8-yl)butane-1,4-diamine; N$^1$—(((S)-4-benzylpiperazin-2-yl)methyl)-N$^1$—((S)-5,6,7,8-tetrahydroquinolin-8-yl)butane-1,4-diamine; and N—(((R)-4-benzylpiperazin-2-yl)methyl)-N$^1$—((S)-5,6,7,8-tetrahydroquinolin-8-yl)butane-1,4-diamine. U.S. Pat. No. 8,969,379 to Furitsu et al. discloses the use of 4-(3-chloro-4-(cyclopropylaminocarbonyl)aminophenoxy)-7-methoxy-6-quinolinecarboxamide. U.S. Pat. No. 8,969,375 to Lai et al. discloses the use of CDK9 kinase inhibitors such as 4-[1-(3-fluorobenzyl)-2,3-dihydro-1H-indol-6-yl]-2-(piperidin-4-yl)-1H-pyrrolo[2,3-b]pyridine; 1-(3-fluorobenzyl)-6-[2-(piperidin-4-yl)-1H-pyrrolo[2,3-b]pyridin-4-yl]-1H-benzimidazole; 1-benzyl-6-[2-(piperidin-4-yl)-1H-pyrrolo[2,3-b]pyridin-4-yl]-1H-indole-3-carbonitrile; 1-(3-fluorobenzyl)-6-{2-[1-(methylsulfonyl)piperidin-4-yl]-1H-pyrrolo[2,3-b]pyridin-4-yl}-1H-benzimidazole; 6-[2-(piperidin-4-yl)-1H-pyrrolo[2,3-b]pyridin-4-yl]-1-(tetrahydro-2H-pyran-4-ylmethyl)-1H-benzimidazole; 6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole; 5-[2-(piperidin-4-yl)-1H-pyrrolo[2,3-b]pyridin-4-yl]-3-(tetrahydro-2H-pyran-4-ylmethyl)-3H-imidazo[4,5-b]pyridine; 1-(3-fluorobenzyl)-6-[2-(piperidin-4-yl)-1H-pyrrolo[2,3-b]pyridin-4-yl]-1H-indole-3-carbonitrile; 4-[5-fluoro-1-(3-fluorobenzyl)-1H-indol-6-yl]-2-(piperidin-4-yl)-1H-pyrrolo[2,3-b]pyridine; 6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile; 1-(3-fluorobenzyl)-6-{2-[1-(methylsulfonyl)piperidin-4-yl]-1H-pyrrolo[2,3-b]pyridin-4-yl}-1H-indole-3-carbonitrile; and 1-[(5-fluoropyridin-3-yl)methyl]-6-[2-(piperidin-4-yl)-1H-pyrrolo[2,3-b]pyridin-4-yl]-1H-benzimidazole. U.S. Pat. No. 8,969,366 to Marchionni et al. discloses the use of substituted pyrimidinylpyrrolopyridinone derivatives. U.S. Pat. No. 8,969,360 to Charrier et al. discloses the use of inhibitors of ATR kinase. U.S. Pat. No. 8,969,335 to Hoelzemann et al. discloses the use of inhibitors of IKKε and TBK1 including benzonitrile derivatives. U.S. Pat. No. 8,969,313 to Yu discloses the use of DACT protein activators. U.S. Pat. No. 8,962,855 to Chen et al. discloses the use of nitrogen mustard derivatives. U.S. Pat. No. 8,962,679 to Wang et al. discloses the use of daidzein derivatives including alkoxychromenon-4-ones. U.S. Pat. No. 8,962,663 to Mahadevan et al. discloses the use of pleckstrin homology domain inhibitors. U.S. Pat. No. 8,962,642 to Mortimore et al. discloses the use of 5-cyano-4-(pyrrolo[2,3-b]pyridine-3-yl)pyrimidine derivatives. U.S. Pat. No. 8,962,637 to McAllister et al. discloses the use of substituted aromatic bicyclic compounds as c-SRC/JAK inhibitors. U.S. Pat. No. 8,962,630 to Brain et al. discloses the use of pyrrolopyrimidine compounds including 7-cyclopentyl-2-(5-piperazin-1-yl-pyridin-2-ylamino)-7H-pyrrolo[2,3-d]pyrimidine-6-carboxylic acid dimethylamide as CDK protein kinase inhibitors. U.S. Pat. No. 8,962,620 to Kuntz et al. discloses the use of substituted 6,5-fused bicyclic aryl compounds. U.S. Pat. No. 8,962,619 to Ashwell et al. discloses the use of substituted imidazopyridinyl-aminopyridine compounds. U.S. Pat. No. 8,962,611 to Christopher et al. discloses the use of substituted imidazopyridines as HDM2 inhibitors. U.S. Pat. No. 8,962,608 to Brubaker et al. discloses the use of cycloalkylnitrile pyrazole carboxamides as janus kinase inhibitors. U.S. Pat. No. 8,961,966 to Schoeberl et al. discloses the use of anti-ERBB3 antibodies. U.S. Pat. No. 8,957,109 to Heaton et al. discloses the use of chroman derivatives. U.S. Pat. No. 8,957,103 to Dannhardt et al. discloses the use of conjugated 3-(indolyl)- and 3-(azaindolyl)-4-arylmaleimide compounds. U.S. Pat. No. 8,957,102 to Kim et al. discloses the use of c-Met inhibitors including 1,5-dimethyl-3-oxo-2-phenyl-2,3-dihydro-1H-pyrazole-4-carboxylic acid [3-fluoro-4-(2-phenyl-1H-pyrrolo[2,3-b]pyridin-4-yloxy)-phenyl]-amide; 2-(4-fluoro-phenyl)-1,5- dimethyl-3-oxo-2,3-dihydro-1H-pyrazole-4-carboxylic acid [3-fluoro-4-(2-phenyl-1H-pyrrolo[2,3-b]pyridin-4-yloxy)-phenyl]-amide; 2-(4-fluoro-phenyl)-1,5-dimethyl-3-oxo-2,3-dihydro-1H-pyrazole-4-carboxylic acid [3-fluoro-4-(3-phenyl-1H-pyrrolo[2,3-b]pyridin-4-yloxy)-phenyl]-amide; N-(3-fluoro-4-(2-(thiophen-2-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide; and N-(3-fluoro-4-(2-(thiophen-3-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide. U.S. Pat. No. 8,957,078 to Brenchley et al. discloses the use of pyrazolopyrimidines as ATR kinase inhibitors. U.S. Pat. No. 8,957,068 to Caferro et al. discloses the use of 3-pyrimidin-4-yl-oxazolidin-2-ones as inhibitors of mutant IDH. U.S. Pat. No. 8,957,056 to Danishefsky et al. discloses the use of migrastatin analogs. U.S. Pat. No. 8,956,613 to Wu et al. discloses the use of gemcitabine prodrugs. U.S. Pat. No. 8,952,163 to Blackburn discloses the use of substituted hydroxamic acids as HDAC6 inhibitors. U.S. Pat. No. 8,952,161 to Beaton et al. discloses the use of gonadotrophin-releasing hormone receptor antagonists. U.S. Pat. No. 8,952,157 to Ding et al. discloses the use of inhibitors of anti-apoptotic Bcl-2 proteins such as 4-(4-{[2-(4-chlorophenyl)-4,4-dimethylcyclohex-1-en-1-yl]methyl}piperazin-1-yl)-2-(2,3-difluorophenoxy)-N-({4-[(3-morpholin-4-ylpropyl)amino]-3-nitrophenyl}sulfonyl)benzamide; 2-(4-amino-3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide; 4-(4-{[2-(4-chlorophenyl)-4,4-dimethylcyclohex-1-en-1-yl]methyl}piperazin-1-yl)-2-(2,5-dichlorophenoxy)-N-({4-[(3-morpholin-4-ylpropyl)amino]-3-nitrophenyl}sulfonyl)benzamide; N-(4-((4-aminotetrahydro-2H-pyran-4-yl)methylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide; 4-(4-{[2-(4-chlorophenyl)-4,4-dimethylcyclohex-1-en-1-yl]methyl}piperazin-1-yl)-2-(3-fluorophenoxy)-N-({4-[(3-morpholin-4-ylpropyl)amino]-3-nitrophenyl}sulfonyl)benzamide; 2-(2-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide; 2-(2-chloro-4-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide; 4-(4-{[2-(4-chlorophenyl)-4,4-dimethylcyclohex-1-en-1-yl]methyl}piperazin-1-yl)-2-(2-fluorophenoxy)-N-({4-[(3-morpholin-4-ylpropyl)amino]-3-nitrophenyl}sulfonyl)benzamide; 4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide; and 2-(3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide. U.S. Pat. No. 8,952,054 to Kufe et al. discloses the use of small molecule inhibitors of MUC1 oligomerization such as flavone derivatives. U.S. Pat. No. 8,952,043 to Blaquiere et al. discloses the use of benzoxepin PI3K inhibitors. U.S. Pat. No. 8,951,987 to Hamilton et al. discloses the use of tetrahydrouridine derivatives. U.S. Pat. No. 8,951,536 to Combs et al. discloses the use of N-hydroxyamidino heterocycles as modulators of indoleamine 2,3-dioxygenase. U.S. Pat. No. 8,946,445 to Wang discloses the use of heterocyclic apoptosis inhibitors such as (Z)-5-(2-((3,5-dimethyl-1H-pyrrol-2-yl)methylene)-3-methoxy-2H-pyrrol-5-yl)-4H-thieno[3,2-b]pyrrole (Z)-2-chloro-5-(2-((3,5-dimethyl-1H-pyrrol-2-yl)methylene)-3-methoxy-2H-pyrrol-5-yl)-4H-thieno[3,2-b]pyrrole; (Z)-5-(2-((3,5-dimethyl-1H-pyrrol-2-yl)methylene)-3-methoxy-2H-pyrrol-5-yl)-2-methyl-4H-thieno[3,2-b]pyrrole; (Z)-2-bromo-5-(2-((3,5-dimethyl-1H-pyrrol-2-yl)methylene)-3-methoxy-2H-pyrrol-5-yl)-4H-thieno[3,2-b]pyrrole; (Z)-5-(2-((3,5-dimethyl-1H-pyrrol-2-yl)methylene)-3-methoxy-2H-pyrrol-5-yl)-6H-thieno[2,3-b]pyrrole; and (Z)-5-(2-((3,5-dimethyl-1H-pyrrol-2-yl)methylene)-3-methoxy-2H-pyrrol-5-yl)-2-methyl-6H-thieno[2,3-b]pyrrole. U.S. Pat. No. 8,946,413 to Hughes et al. discloses the use of 3-aminocyclopentanecarboxamides as chemokine receptor antagonists. U.S. Pat. No. 8,946,409 to Becker et al. discloses the use of polycyclic β-lactam derivatives. U.S. Pat. No. 8,946,289 to Hong et al. discloses the use of manassatin compounds that block the HIF pathway. U.S. Pat. No. 8,946,278 to Seefeld et al. discloses the use of heterocyclic carboxamides as AKT inhibitors, such as N-((1S)-2-amino-1-{[2-(trifluoromethyl)phenyl]methyl}ethyl)-5-chloro-4-(1-methyl-1H-pyrazol-5-yl)-2-thiophenecarboxamide; N-((1S)-2-amino-1-{[2-(trifluoromethyl)phenyl]methyl}ethyl)-4-(4-bromo-1-methyl-1H-pyrazol-5-yl)-5-methyl-2-thiophenecarboxamide; N-((1S)-2-amino-1-{[2-(trifluoromethyl)phenyl]methyl}ethyl)-4-(4-chloro-1-methyl-1H-pyrazol-5-yl)-5-methyl-2-thiophenecarboxamide; N-((1S)-2-amino-1-{[2-(trifluoromethyl)phenyl]methyl}ethyl)-5-chloro-4-(4-chloro-1-methyl-1H-pyrazol-5-yl)-2-thiophenecarboxamide; N-((1S)-2-amino-1-{[2-(trifluoromethyl)phenyl]methyl}ethyl)-4-(4-bromo-1-methyl-1H-pyrazol-5-yl)-5-chloro-2-thiophenecarboxamide; N-((1S)-2-amino-1-{[2-(trifluoromethyl)phenyl]methyl}ethyl)-5-methyl-4-(1-methyl-1H-pyrazol-5-yl)-2-thiophenecarboxamide; N-((1S)-2-amino-1-{[2-(trifluoromethyl)phenyl]methyl}ethyl)-5-chloro-4-(1-ethyl-1H-pyrazol-5-yl)-2-thiophenecarboxamide; N-((1S)-2-amino-1-{[2-(trifluoromethyl)phenyl]methyl}ethyl)-5-chloro-4-(1,4-dimethyl-1H-pyrazol-5-yl)-2-thiophenecarboxamide; N-{(1S)-2-amino-1-[(3-fluorophenyl)methyl]ethyl}-5-chloro-4-(1-methyl-1H-pyrazol-5-yl)-2-thiophenecarboxamide; N-((1S)-2-amino-1-{[2-(trifluoromethyl)phenyl]methyl}ethyl)-5-ethyl-4-(1-methyl-1H-pyrazol-5-yl)-2-thiophenecarboxamide; and N-((1S)-2-amino-1-{[2-(trifluoromethyl)phenyl]methyl}ethyl)-4-(1,4-dimethyl-1H-pyrazol-5-yl)-5-methyl-2-thiophenecarboxamide. U.S. Pat. No. 8,946,205 to Curd et al. discloses the use of hypoxia activated prodrugs, including N,N'-bis(2-bromoethyl)phosphorodamidic acid (1-methyl-2-nitro-1H-imidazol-5-yl) methyl ester. U.S. Pat. No. 8,946,239 to Gangjee discloses the use of substituted pyrrolo-, furano-, and cyclopentylpyrimidine bicyclic compounds. U.S. Pat. No. 8,946,235 to Butterworth et al. discloses the use of 2-(2,4,5-substituted-anilino)pyrimidine compounds. U.S. Pat. No. 8,946,224 to Craighead et al. discloses the use of substituted [1,2,4]triazolo[4,3-a]pyrazines. U.S. Pat. No. 8,946,216 to Deng et al. discloses the use of indazole derivatives as ERK inhibitors, including N-[3-[6-(1-methylethoxy)-3-pyridinyl]-1H-indazol-5-yl]-4-(phenylmethyl)-2-morpholinecarboxamide; N-[3-[6-(1-methylethoxy)-3-pyridinyl]-1H-indazol-5-yl]-2-morpholinecarboxamide; N-[3-(4-pyridinyl)-1H-indazol-5-yl]-4-(4-thiazolylmethyl)-2-morpholinecarboxamide; N-[3-(4-pyridinyl)-1H-indazol-5-yl]-4-(3-thienylmethyl)-2-morpholinecarboxamide; 4-[(2-fluorophenyl)methyl]-N-[3-(4-pyridinyl)-1 h-indazol-5-yl]-2-morpholinecarboxamide; N-[3-(4-pyridinyl)-1H-indazol-5-yl]-4-(2-pyridinylmethyl)-2-morpholinecarboxamide; N-[3-(4-pyridinyl)-1H-indazol-5-yl]-4-(2-pyridinylmethyl)-2-morpholinecarboxamide; and 4-[(2-bromophenyl)methyl]-N-[3-(4-pyridinyl)-1H-indazol- 5-yl]-2-morpholinecarboxamide. U.S. Pat. No. 8,940,936 to Lee et al. discloses the use of aryloxy phenoxy acrylic compounds. U.S. Pat. No. 8,940,760 to Page et al. discloses the use of pyrazolopyridine derivatives as NADPH oxidase inhibitors. U.S. Pat. No. 8,940,756 to Flynn et al. discloses the use of dihydronaphthyridines as c-Kit inhibitors. U.S. Pat. No. 8,940,737 to Wang et al. discloses the use of apoptosis-inducing agents, such as 6-[8-(1,3-benzothiazol-2-ylcarbamoyl)-3,4-dihydroisoquinolin-2(1H)-yl]-3-(1-benzyl-1H-pyrazol-4-yl)pyridine-2-carboxylic acid; 6-[8-(1,3-benzothiazol-2-ylcarbamoyl)-3,4-dihydroisoquinolin-2(1H)-yl]-3-[1-(pyridin-4-ylmethyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-[1-(pyridin-3-ylmethyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-[1-(4-hydroxybenzyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-[1-(1-phenylethyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-(1-{4-[2-(dimethylamino)ethoxy]benzyl}-1H-pyrazol-4-yl)pyridine-2-carboxylic acid; 3-(1-benzyl-1H-pyrazol-4-yl)-6-{8-[(5,6-difluoro-1,3-benzothiazol-2-yl)carbamoyl]-3,4-dihydroisoquinolin-2(1H)-yl}pyridine-2-carboxylic acid; 6-[8-(1,3-benzothiazol-2-ylcarbamoyl)-3,4-dihydroisoquinolin-2(1H)-yl]-3-{1-[2-(4-fluorophenyl)ethyl]-1H-pyrazol-4-yl}pyridine-2-carboxylic acid; 6-[8-(1,3-benzothiazol-2-ylcarbamoyl)-3,4-dihydroisoquinolin-2(1H)-yl]-3-[1-(3-chlorobenzyl)-1H-pyrazol-4-yl]pyridine-2-carboxylic acid; and 3-(1-benzyl-1H-pyrazol-4-yl)-6-{8-[(6-fluoro-1,3-benzothiazol-2-yl)carbamoyl]-3,4-dihydroisoquinolin-2(1H)-yl}pyridine-2-carboxylic acid. U.S. Pat. No. 8,940,733 to Howard et al. discloses the use of unsymmetrical pyrrolobenzodiazepine dimers. U.S. Pat. No. 8,940,726 to Duncan et al. discloses the use of PRMT5 inhibitors. U.S. Pat. No. 8,937,193 to Pellecchia et al. discloses the use of apogossypolone derivatives. U.S. Pat. No. 8,937,094 to Burlison et al. discloses the use of Hsp90 modulators, including 5-(4-ethoxy-2-hydroxyphenyl)-4-(4-(morpholinomethyl)phenyl)-4H-1,2,4-triazole-3-carboxamide; 5-(2-hydroxy-4-methoxyphenyl)-4-(4-(morpholinomethyl)phenyl)-4H-1,2,4-triazole-3-carboxamide; 5-(2-hydroxy-4-propoxyphenyl)-4-(4-(morpholinomethyl)phenyl)-4H-1,2,4-triazole-3-carboxamide; 5-(2-hydroxy-4-isopropoxyphenyl)-4-(4-(morpholinomethyl)phenyl)-4H-1,2,4-triazole-3-carboxamide; 5-(2,4-dimethoxyphenyl)-4-(4-(morpholinomethyl)phenyl)-4H-1,2,4-triazole-3-carboxamide; 5-(2-hydroxy-4-isopropylphenyl)-4-(4-methoxyphenyl)-4H-1,2,4-triazole-3-carboxamide; 5-(2-hydroxy-4-methylphenyl)-4-(4-methoxyphenyl)-4H-1,2,4-triazole-3-carboxamide; 5-(4-hydroxy-3-isopropylphenyl)-4-(4-methoxyphenyl)-4H-1,2,4-triazole-3-carboxamide; 5-(3-tert-butyl-4-hydroxyphenyl)-4-(4-methoxyphenyl)-4H-1,2,4-triazole-3-carboxamide; and 5-(4-hydroxy-3-propylphenyl)-4-(4-methoxyphenyl)-4H-1,2,4-triazole-3-carboxamide. U.S. Pat. No. 8,937,068 to Seipelt et al. discloses the use of pyridopyrazine compounds. U.S. Pat. No. 8,933,212 to Fayard et al. discloses the use of protease nexin 1 inhibitors to reduce metastasis. U.S. Pat. No. 8,933,116 to Wu et al. discloses the use of γ-secretase inhibitors. U.S. Pat. No. 8,933,103 to Ohki et al. discloses the use of Axl inhibitors that are pyridone derivatives including N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride. U.S. Pat. No. 8,933,084 to Andrews et al. discloses the use of macrocyclic compounds as Trk inhibitors such as (6R)-9-fluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione. U.S. Pat. No. 8,933,080 to Singh et al. discloses the use of bridged bicyclic heteroaryl substituted triazoles as Axl inhibitors. U.S. Pat. No. 8,933,053 to McGuigan et al. discloses the use of phosphoramidate derivatives of 5-fluoro-2'-deoxyuridine. U.S. Pat. No. 8,927,718 to Sasaki et al. discloses the use of fused heterocyclic ring derivatives as Smo inhibitors, including 3,6-diethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide; 3-ethenyl-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide; and 6-Ethyl-3-(ethylamino)-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide. U.S. Pat. No. 8,927,717 to Huang et al. discloses the use of thiochromeno[2,3-c]quinolin-12-one derivatives including 3-((4-chlorophenyl)thio)-2-hydroxyquinoline-4-carboxylic acid, 6,9-dichloro-12H-thiochromeno[2,3-c]quinolin-12-one, 10-chloro-6-hydroxy-12H-thiochromeno[2,3-c]quinolin-12-one, 10-chloro-6-methoxy-12H-thiochromeno[2,3-c]quinolin-12-one 10-chloro-6-dimethylamino-12H-thiochromeno[2,3-c]quinolin-12-one, 10-chloro-6-(piperazin-1-yl)-12H-thiochromeno[2,3-c]quinolin-12-one, 10-chloro-6-(4-methylpiperazin-1-yl)-12H-thiochromeno[2,3-c]quinolin-12-one, 10-chloro-6-(4-ethylpiperazin-1-yl)-12H-thiochromeno[2,3-c]quinolin-12-one, 10-chloro-6-(4-(2-hydroxyethyl)piperazin-1-yl)-12H-thiochromeno[2,3-c]quinolin-12-one, and 6-(4-benzylpiperazin-1-yl)-10-chloro-12H-thiochromeno[2,3-c]quinolin-12-one. U.S. Pat. No. 8,927,711 to Abraham et al. discloses the use of quinazoline JAK inhibitors, including (3-fluorophenyl)(4-(5-methyl-1H-pyrazol-3-ylamino)quinazolin-2-yl)methanone; (4-(1H-pyrazol-3-ylamino)quinazolin-2-yl)(3-fluorophenyl)methanone; (4-fluorophenyl)(4-(5-methyl-1H-pyrazol-3-ylamino)quinazolin-2-yl)methanone; (4-(1H-pyrazol-3-ylamino)quinazolin-2-yl)(4-fluorophenyl)methanone; (4-(1H-pyrazol-3-ylamino)quinazolin-2-yl)(2-methoxyphenyl)methanone; (4-(1H-pyrazol-3-ylamino)quinazolin-2-yl)(4-fluorophenyl)methanol; 2-(fluoro(4-fluorophenyl)methyl)-N-(1H-pyrazol-3-yl)quinazolin-4-amine; 2-(difluoro(4-fluorophenyl)methyl)-N-(5-methyl-1H-pyrazol-3-yl)quinazolin-4-amine; 2-(difluoro(4-fluorophenyl)methyl)-N-(1H-pyrazol-3-yl)quinazolin-4-amine; N-(5-cyclopropyl-1H-pyrazol-3-yl)-2-(difluoro(4-fluorophenyl)methyl)quinazolin-4-amine; 3-(2-(4-fluorobenzoyl)quinazolin-4-ylamino)-1H-pyrazole-5-carbonitrile; (4-fluorophenyl)(4-(5-methyl-1H-pyrazol-3-ylamino)quinazolin-2-yl)methanol; 2-((4-fluorophenyl)(methoxy)methyl)-N-(5-methyl-1H-pyrazol-3-yl)quinazolin-4-amine; 2-(amino(4-fluorophenyl)methyl)-N-(5-methyl-1H-pyrazol-3-yl)quinazolin-4-amine; 3-(2-((4-fluorophenyl)(hydroxy)methyl)quinazolin-4-ylamino)-1H-pyrazole-5-carbonitrile; (5-fluoro-4-(5-methyl-1H-pyrazol-3-ylamino)quinazolin-2-yl)(4-fluorophenyl)methanol; (4-fluorophenyl)(4-(5-methyl-1H-pyrazol-3-ylamino)-7-(trifluoromethyl)quinazolin-2-yl)methanone; and (4-fluorophenyl)(4-(5-methyl-1H-pyrazol-3-ylamino)-7-(trifluoromethyl)quinazolin-2-yl)methanol. U.S. Pat. No. 8,927,580 to Richardson et al. discloses the use of dipyridyl thiosemicarbazones such as di-2-pyridylketone 4-ethyl-4-methyl-3-thiosemicarbazone. U.S. Pat. No. 8,927,562 to Meng et al. discloses the use of fused tricyclic inhibitors of mTOR. U.S. Pat. No. 8,927,560 to Ahmed et al. discloses the use of 4-aza-2,3-didehydropodophyllotoxin compounds. U.S. Pat. No. 8,927,548 to Ying et al. discloses the use of triazole compounds that are Hsp90 inhibitors. U.S. Pat. No. 8,927,538 to Kamal et al. discloses the use of carbazole linked pyrrolo[2,1-c][1,4]benzodiazepine hybrids as agents reacting with DNA to form an N2-guanine adduct that lies within the minor groove of duplex DNA via an acid-labile aminal bond to the electrophilic imine at the N10-C11 position. U.S. Pat. No. 8,927,533 to Giannini et al. discloses the use of lactam-substituted thio derivatives. U.S. Pat. No. 8,921,565 to Flynn et al. discloses the use of pyridone amides as c-Met kinase inhibitors, such as N-(4-((2-acetamidopyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-propionamidopyridin-4-yl)oxy)phenyl)-4-ethoxy-1-(4-fluorophenyl)-2-oxo-1,2-dihydropyridine-3-carboxamide, N-(4-(2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-pivalamidopyridin-4-yl)oxy)phenyl)-4-ethoxy-1-(4-fluorophenyl)-2-oxo-1,2-dihydropyridine-3-carboxamide, N-(2,5-difluoro-4-((2-isobutyramidopyridin-4-yl)oxy)phenyl)-4-ethoxy-1-(4-fluorophenyl)-2-oxo-1,2-dihydropyridine-3-carboxamide. U.S. Pat. No. 8,921,522 to Kamal et al. discloses the use of benzothiazole derivatives including olefins, chalcones, pyrazolines, pyrazole, isoxazolines, and isoxazoles linked to 2-phenylbenzothiazoles. U.S. Pat. No. 8,921,546 to Chao discloses the use of imidazothiazoles such as 7-(2-morpholin-4-yl-ethoxy)-2-(4-nitro-phenyl)imidazo[2,1-b][1,3]benzothiazole and 4-(7-(2-morpholinoethoxy)benzo[d]imidazo[2,1-b]thiazol-2-yl)aniline. U.S. Pat. No. 8,921,414 to Reddell et al. discloses the use of spiroketals. U.S. Pat. No. 8,921,407 to Ying et al. discloses the use of pyrazole compounds as Hsp90 modulators. U.S. Pat. No. 8,921,367 to Friberg et al. discloses the use of AMG 900 (N-(4-(3-(2-aminopyrimidin-4-yl)pyridin-2-yloxy)phenyl)-4-(4-methylthiophen-2-yl)phthalazin-1-amine) as Aurora kinase inhibitor. U.S. Pat. No. 8,920,799 to Graham et al. discloses the use of Axl ligand-binding portion of Axl tyrosine kinase receptor. U.S. Pat. No. 8,778,340 to Dupont et al. discloses the use of anti-angiogenesis agents including antibodies. U.S. Pat. No. 8,748,470 to Lengyel et al. discloses the use of fatty acid binding protein inhibitors including carbazole butanoic acids, aryl sulfonamides, sulfonyl-thiophenes, 4-hydroxypyrimidines, 2,3-dimethylindoles, benzoylbenzenes, biphenyl-alkanoic acids, 2-oxazole-alkanoic acids, tetrahydropyrimidones, pyridones, pyrazinones, aryl carboxylic acids, tetrazoles, triazolopyrimidinones, indoles, BMS480404 ((2S)-2-[2,3-bis[(2-chlorophenyl) methoxy]phenyl]-2-hydroxyacetic acid), or BMS309403 (2-[[2'-(5-ethyl-3,4-diphenyl-1H-pyrazol-1-yl)[1,1'-biphenyl]-3-yl]oxy]-acetic acid. U.S. Pat. No. 8,541,433 to Clozel et al. discloses the use of macitentan. U.S. Pat. No. 8,362,072 to Jensen et al. discloses the use of BRCA1 production enhancers. U.S. Pat. No. 8,268,889 to Kloog et al. discloses the use of farnesylthiosalicylic acid and analogs. U.S. Pat. No. 7,968,514 to Coelingh Bennink et al. discloses the use of immunogenic peptides. U.S. Pat. No. 7,323,164 to Chandrasekher et al. discloses the use of interleukin 24. U.S. Pat. No. 7,074,575 to Chandrasekher et al. discloses the use of interleukin 19. U.S. Pat. No. 6,237,307 to Miller et al. discloses the use of 2-phenyl-1-[4-(2-aminoethoxy)-benzyl]-indole derivatives. U.S. Pat. No. 5,597,798 to Howell et al. discloses the use of combinations with taxol and epidermal growth factor. United States Patent Application Publication No. 2014/0336150 by Frederick discloses the use of karenitecin (7-[(2'-trimethylsilyl)ethyl]-20(S) camptothecin). United States Patent Application Publication No. 2014/0315959 by Moore et al. discloses the use of benzylidinebenzohydrazides. United States Patent Application Publication No. 2014/0309184 by Rocconi et al. discloses the use of Smo inhibitors used in combination with other drugs, including platinum-containing agents. United States Patent Application Publication No. 2014/0302174 by Chan et al. discloses combination therapy with gemcitabine, cisplatin or carboplatin, and 5-[2-tert-butyl-5-(4-fluoro-phenyl)-1H-imidazol-4-yl]-3-(2,2-dimethyl-propyl)-3H-imidazo[4,5-b]pyridin-2-ylamine. United States Patent Application Publication No. 2014/0275174 by Moore et al. discloses the use of 2-amino-4H-naphtho[1,2-b]pyran-3-carbonitriles. United States Patent Application Publication No. 2014/0134169 by Kuhnert et al. discloses the use of DII4 antagonists. United States Patent Application Publication No. 2013/0231286 by Chen discloses the use of prolactin receptor antagonist. United States Patent Application Publication No. 2013/0203861 by Liu et al. discloses the use of cyclohexenone compounds. United States Patent Application Publication No. 2012/0269827 by Whiteman et al. discloses the use of conjugates with CD56. United States Patent Application Publication No. 2012/0237502 by Darnowski discloses the use of 17,20-lyase inhibitors such as 3β-acetoxy-17-(3-pyridyl)androsta-5,16-diene, 6-[(7S)-7-hydroxy-6,7-dihydro-5H-pyrrolo[1,2-c]imidazol-7-yl]-N-methyl-2-naphthalenecarboxamide, 3β-hydroxy-17-(1H-benzimidazol-1-yl)androsta-5,16-diene, or 6-[(7S)-7-hydroxy-6,7-dihydro-5H-pyrrolo[1,2-c]imidazol-7-yl]-N-methyl-2-naphthalenecarboxamide. United States Patent Application Publication No. 2012/0183546 by Weinreich discloses the use of angiopoietin-2 inhibitor. United States Patent Application Publication No. 2010/0009330 by Sherman et al. discloses the use of PARP inhibitors including 4-iodo-3-nitrobenzamide. United States Patent Application Publication No. 2009/0118271 by Umeda et al. discloses the use of water-soluble prodrugs such as (9S)-1-butyl-9-ethyl-9-hydroxy-1H,12H-pyrano[3',4":6',7']indolizino[1',2':6,5] pyrido[4,3,2-de]quinazoline-2,10,13(3H,9H,15H)-trione; (9S)-9-ethyl-9-hydroxy-1-[2-(4-morpholino)ethyl]-1H, 12H-pyrano[3",4":6',7']indolizino[1',2':6,5]pyrido[4,3,2-de] quinazoline-2,10,13(3H,9H,15H)-trione; (9S)-1-[3-(dimethylamino)propyl]-9-ethyl-9-hydroxy-1H,12H-pyrano[3",4": 6',7']indolizino[1',2':6,5]pyrido[4,3,2-de]quinazoline-2,10, 13(3H,9H,15H)-trione; (9S)-9-ethyl-9-hydroxy-1-phenethyl-1H,12H-pyrano[3",4":6',7']indolizino[1',2':6,5] pyrido[4,3,2-de]quinazoline-2,10,13(3H,9H,15H)-trione; (9S)-9-ethyl-9-hydroxy-1-[2-(pyridin-2-yl)ethyl]-1H,12H-pyrano[3",4":6',7']indolizino[1',2':6,5]pyrido[4,3,2-de]quinazoline-2,10,13(3H,9H,15H)-trione; (9S)-9-ethyl-1-heptyl-9-hydroxy-1H,12H-pyrano[3",4":6',7']indolizino[1',2':6, 5]pyrido[4,3,2-de]quinazoline-2,10,13(3H,9H,15H)-trione; and (9S)-9-ethyl-9-hydroxy-1-propyl-1H,12H-pyrano[3", 4":6',7']indolizino[1',2':6,5]pyrido[4,3,2-de]quinazoline-2, 10,13(3H,9H,15H)-trione. United States Patent Application Publication No. 2009/0099102 by Ye et al. discloses the use of ginkgolides, including ginkgolides A and B. United States Patent Application Publication No. 2007/0299020 by Zeldis discloses the use of 4-(amino)-2(2,6-dioxo(3-piperidyl))-isoindoline-1,3-dione. United States Patent Application Publication No. 2006/0058217 by White et al. discloses the use of antialamin. United States Patent Application No. 2005/0272766 by Koya et al. discloses the use of 1-glyoxylamide indolizines.

Yet another aspect of the invention is an improvement in therapeutic employment of a substituted hexitol derivative such as dianhydrogalactitol for treatment of NSCLC or ovarian cancer made by exploiting the substituted hexitol derivative such as dianhydrogalactitol as a chemosensitizer where no measureable activity is observed when used alone but in combination with other therapeutics a more than additive or synergistic improvement in efficacy is observed. Specific inventive examples for a substituted hexitol derivative such as dianhydrogalactitol for treatment of NSCLC or ovarian cancer include: as a chemosensitizer in combination with topoisomerase inhibitors; as a chemosensitizer in combination with fraudulent nucleosides; as a chemosensitizer in combination with fraudulent nucleotides; as a chemosensitizer in combination with thymidylate synthetase inhibitors; as a chemosensitizer in combination with signal transduction inhibitors; as a chemosensitizer in combination with cisplatin, oxaliplatin, or other platinum analogs; as a chemosensitizer in combination with alkylating agents such as BCNU, BCNU wafers, Gliadel, CCNU, bendamustine (Treanda), or Temozolomide (Temodar); as a chemosensitizer in combination with anti-tubulin agents; as a chemosensitizer in combination with antimetabolites; as a chemosensitizer in combination with berberine; as a chemosensitizer in combination with apigenin; as a chemosensitizer in combination with amonafide; as a chemosensitizer in combination with colchicine or analogs; as a chemosensitizer in combination with genistein; as a chemosensitizer in combination with etoposide; as a chemosensitizer in combination with cytarabine; as a chemosensitizer in combination with camptothecins; as a chemosensitizer in combination with vinca alkaloids; as a chemosensitizer in combination with topoisomerase inhibitors; as a chemosensitizer in combination with 5-fluorouracil; as a chemosensitizer in combination with curcumin; as a chemosensitizer in combination with NF-κB inhibitors; as a chemosensitizer in combination with rosmarinic acid; as a chemosensitizer in combination with mitoguazone; as a chemosensitizer in combination with tetrandrine; as a chemosensitizer in combination with a tyrosine kinase inhibitor; as a chemosensitizer in combination with an EGFR inhibitor; or as a chemosensitizer in combination with an inhibitor of poly (ADP-ribose) polymerase (PARP).

Yet another aspect of the invention is an improvement in therapeutic employment of a substituted hexitol derivative such as dianhydrogalactitol for treatment of NSCLC or ovarian cancer made by exploiting the substituted hexitol derivative such as dianhydrogalactitol as a chemopotentiator where minimal therapeutic activity is observed alone but in combination with other therapeutics a more than additive or synergistic improvement in efficacy is observed. Specific inventive examples for a substituted hexitol derivative such as dianhydrogalactitol for treatment of NSCLC or ovarian cancer include: as a chemopotentiator in combination with topoisomerase inhibitors; as a chemopotentiator in combination with fraudulent nucleosides; as a chemopotentiator in combination with thymidylate synthetase inhibitors; as a chemopotentiator in combination with signal transduction inhibitors; as a chemopotentiator in combination with cisplatin, oxaliplatin, or other platinum analogs; as a chemopotentiator in combination with use with alkylating agents such as BCNU, BCNU wafers, Gliadel, or bendamustine (Treanda); as a chemopotentiator in combination with anti-tubulin agents; as a chemopotentiator in combination with antimetabolites; as a chemopotentiator in combination with berberine; as a chemopotentiator in combination with apigenin; as a chemopotentiator in combination with amonafide; as a chemopotentiator in combination with colchicine or analogs; as a chemopotentiator in combination with genistein; as a chemopotentiator in combination with etoposide; as a chemopotentiator in combination with cytarabine; as a chemopotentiator in combination with camptothecins; as a chemopotentiator in combination with vinca alkaloids; as a chemopotentiator in combination with topoisomerase inhibitors; as a chemopotentiator in combination with 5-fluorouracil; as a chemopotentiator in combination with curcumin; as a chemopotentiator in combination with NF-κB inhibitors; as a chemopotentiator in combination with rosmarinic acid; as a chemopotentiator in combination with mitoguazone; as a chemopotentiator in combination with tetrandrine; as a chemopotentiator in combination with a tyrosine kinase inhibitor; as a chemopotentiator in combination with an EGFR inhibitor; or as a chemopotentiator in combination with an inhibitor of poly (ADP-ribose) polymerase (PARP).

Yet another aspect of the invention is an improvement in therapeutic employment of a substituted hexitol derivative such as dianhydrogalactitol for treatment of NSCLC or ovarian cancer made by drugs, treatments and diagnostics to allow for the maximum benefit to patients treated with a compound. General examples include: pain management, nutritional support, anti-emetics, anti-nausea therapies, anti-anemia therapy, anti-inflammatories. Specific inventive examples for a substituted hexitol derivative such as dianhydrogalactitol for treatment of NSCLC or ovarian cancer include: use with therapies associated with pain management; nutritional support; anti-emetics; anti-nausea therapies; anti-anemia therapy; anti-inflammatories: antipyretics; immune stimulants.

Yet another aspect of the invention is an improvement in therapeutic employment of a substituted hexitol derivative such as dianhydrogalactitol for treatment of NSCLC or ovarian cancer made by the use of complementary therapeutics or methods to enhance effectiveness or reduce side effects. Specific inventive examples for a substituted hexitol derivative such as dianhydrogalactitol for treatment of NSCLC or ovarian cancer include: hypnosis; acupuncture; meditation; herbal medications created either synthetically or through extraction including NF-κB inhibitors (such as parthenolide, curcumin, rosmarinic acid); natural anti-inflammatories (including rhein, parthenolide); immunostimulants (such as those found in *Echinacea*); antimicrobials (such as berberine); flavonoids, isoflavones, and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); applied kinesiology.

Yet another aspect of the invention is an improvement in therapeutic employment of a substituted hexitol derivative such as dianhydrogalactitol for treatment of NSCLC or ovarian cancer made by alterations in the pharmaceutical bulk substance. General examples include: salt formation, homogeneous crystalline structure, pure isomers. Specific inventive examples for a substituted hexitol derivative such as dianhydrogalactitol for treatment of NSCLC or ovarian cancer include: salt formation; homogeneous crystalline structure; pure isomers; increased purity; lower residual solvents; or lower heavy metals.

Yet another aspect of the invention is an improvement in therapeutic employment of a substituted hexitol derivative such as dianhydrogalactitol or ovarian cancer for treatment of NSCLC made by alterations in the diluents used to solubilize and deliver/present the compound for administration. General examples include: Cremophor-EL, cyclodextrins for poorly water soluble compounds. Specific inventive examples for a substituted hexitol derivative such as dianhydrogalactitol for treatment of NSCLC or ovarian cancer include: use of emulsions; dimethyl sulfoxide (DMSO); N-methylformamide (NMF); dimethylformamide (DMF); dimethylacetamide (DMA); ethanol; benzyl alcohol; dextrose containing water for injection; Cremophor; cyclodextrins; PEG.

Yet another aspect of the invention is an improvement in therapeutic employment of a substituted hexitol derivative such as dianhydrogalactitol for treatment of NSCLC made by alterations in the solvents used or required to solubilize a compound for administration or for further dilution. General examples include: ethanol, dimethylacetamide (DMA). Specific inventive examples for a substituted hexitol derivative such as dianhydrogalactitol for treatment of NSCLC or ovarian cancer include: the use of emulsions; DMSO; NMF; DMF; DMA; ethanol; benzyl alcohol; dextrose containing water for injection; Cremophor; cyclodextrin; or PEG.

Yet another aspect of the invention is an improvement in therapeutic employment of a substituted hexitol derivative such as dianhydrogalactitol for treatment of NSCLC or ovarian cancer made by alterations in the materials/excipients, buffering agents, or preservatives required to stabilize and present a chemical compound for proper administration. General examples include: mannitol, albumin, EDTA, sodium bisulfite, benzyl alcohol. Specific inventive examples for a substituted hexitol derivative such as dianhydrogalactitol for treatment of NSCLC or ovarian cancer include: the use of mannitol; albumin; EDTA; sodium bisulfite; benzyl alcohol; carbonate buffers; phosphate buffers.

Yet another aspect of the invention is an improvement in therapeutic employment of a substituted hexitol derivative such as dianhydrogalactitol for treatment of NSCLC or ovarian cancer made by alterations in the potential dosage forms of the compound dependent on the route of administration, duration of effect, plasma levels required, exposure to side-effect normal tissues and metabolizing enzymes. General examples include: tablets, capsules, topical gels, creams, patches, suppositories. Specific inventive examples for a substituted hexitol derivative such as dianhydrogalactitol for treatment of NSCLC or ovarian cancer include: the use of tablets; capsules; topical gels; topical creams; patches; suppositories; lyophilized dosage fills.

Yet another aspect of the invention is an improvement in therapeutic employment of a substituted hexitol derivative such as dianhydrogalactitol for treatment of NSCLC or ovarian cancer made by alterations in the dosage forms, container/closure systems, accuracy of mixing and dosage preparation and presentation. General examples include: amber vials to protect from light, stoppers with specialized coatings. Specific inventive examples for a substituted hexitol derivative such as dianhydrogalactitol for treatment of NSCLC or ovarian cancer include: the use of amber vials to protect from light; stoppers with specialized coatings to improve shelf-life stability.

Yet another aspect of the invention is an improvement in therapeutic employment of a substituted hexitol derivative such as dianhydrogalactitol for treatment of NSCLC or ovarian cancer made by the use of delivery systems to improve the potential attributes of a pharmaceutical product such as convenience, duration of effect, reduction of toxicities. General examples include: nanocrystals, bioerodible polymers, liposomes, slow release injectable gels, microspheres. Specific inventive examples for a substituted hexitol derivative such as dianhydrogalactitol for treatment of NSCLC or ovarian cancer include: the use of nanocrystals; bioerodible polymers; liposomes; slow release injectable gels; microspheres.

Yet another aspect of the invention is an improvement in therapeutic employment of a substituted hexitol derivative such as dianhydrogalactitol for treatment of NSCLC or ovarian cancer made by alterations to the parent molecule with covalent, ionic, or hydrogen bonded moieties to alter the efficacy, toxicity, pharmacokinetics, metabolism, or route of administration. General examples include: polymer systems such as polyethylene glycols, polylactides, polyglycolides, amino acids, peptides, or multivalent linkers. Specific inventive examples for a substituted hexitol derivative such as dianhydrogalactitol or ovarian cancer for treatment of NSCLC include: the use of polymer systems such as polyethylene glycols; polylactides; polyglycolides; amino acids; peptides; multivalent linkers.

Yet another aspect of the invention is an improvement in therapeutic employment of a substituted hexitol derivative such as dianhydrogalactitol for treatment of NSCLC or ovarian cancer made by alterations to the molecule such that improved pharmaceutical performance is gained with a variant of the active molecule in that after introduction into the body a portion of the molecule is cleaved to reveal the preferred active molecule. General examples include: enzyme sensitive esters, dimers, Schiff bases. Specific inventive examples for a substituted hexitol derivative such as dianhydrogalactitol for treatment of NSCLC or ovarian cancer include: the use of enzyme sensitive esters; dimers; Schiff bases; pyridoxal complexes; caffeine complexes.

Yet another aspect of the invention is an improvement in therapeutic employment of a substituted hexitol derivative such as dianhydrogalactitol for treatment of NSCLC or ovarian cancer made by the use of additional compounds, biological agents that, when administered in the proper fashion, a unique and beneficial effect can be realized. General examples include: inhibitors of multi-drug resistance, specific drug resistance inhibitors, specific inhibitors of selective enzymes, signal transduction inhibitors, repair inhibition. Specific inventive examples for a substituted hexitol derivative such as dianhydrogalactitol for treatment of NSCLC or ovarian cancer include: the use of inhibitors of multi-drug resistance; specific drug resistance inhibitors; specific inhibitors of selective enzymes; signal transduction inhibitors; repair inhibition; topoisomerase inhibitors with non-overlapping side effects.

Yet another aspect of the invention is an improvement in therapeutic employment of a substituted hexitol derivative such as dianhydrogalactitol for treatment of NSCLC or ovarian cancer made by the use of the substituted hexitol derivative such as dianhydrogalactitol in combination as sensitizers/potentiators with biological response modifiers. General examples include: use in combination as sensitizers/potentiators with biological response modifiers, cytokines, lymphokines, therapeutic antibodies, antisense therapies, gene therapies. Specific inventive examples for a substituted hexitol derivative such as dianhydrogalactitol for treatment of NSCLC or ovarian cancer include: use in combination as sensitizers/potentiators with biological response modifiers; cytokines; lymphokines; therapeutic antibodies such as Avastin, Herceptin, Rituxan, and Erbitux; antisense therapies; gene therapies; ribozymes; RNA interference; or vaccines.

Yet another aspect of the invention is an improvement in therapeutic employment of a substituted hexitol derivative such as dianhydrogalactitol for treatment of NSCLC or ovarian cancer made by exploiting the selective use of the substituted hexitol derivative such as dianhydrogalactitol to overcome developing or complete resistance to the efficient use of biotherapeutics. General examples include: tumors resistant to the effects of biological response modifiers, cytokines, lymphokines, therapeutic antibodies, antisense therapies, gene therapies. Specific inventive examples for a substituted hexitol derivative such as dianhydrogalactitol for treatment of NSCLC or ovarian cancer include: the use against tumors resistant to the effects of biological response modifiers; cytokines; lymphokines; therapeutic antibodies; antisense therapies; therapies such as Avastin, Rituxan, Herceptin, Erbitux; gene therapies; ribozymes; RNA interference; and vaccines.

Yet another aspect of the invention is an improvement in therapeutic employment of a substituted hexitol derivative such as dianhydrogalactitol for treatment of NSCLC or ovarian cancer made by exploiting their use in combination with ionizing radiation, phototherapies, heat therapies, or radio-frequency generated therapies. General examples include: hypoxic cell sensitizers, radiation sensitizers/protectors, photosensitizers, radiation repair inhibitors. Specific inventive examples for a substituted hexitol derivative such as dianhydrogalactitol for treatment of NSCLC or ovarian cancer include: use in combination with ionizing radiation; use in combination with hypoxic cell sensitizers; use in combination with radiation sensitizers/protectors; use in combination with photosensitizers; use in combination with radiation repair inhibitors; use in combination with thiol depletion; use in combination with vaso-targeted agents; use in combination with use with radioactive seeds; use in combination with radionuclides; use in combination with radiolabeled antibodies; use in combination with brachytherapy. This is useful because radiation therapy is frequently employed in the treatment of NSCLC or ovarian cancer, especially for advanced disease, and improvements in the efficacy of such radiation therapy or the ability to exert a synergistic effect by combining radiation therapy with the administration of a substituted hexitol derivative such as dianhydrogalactitol is significant.

Yet another aspect of the invention is an improvement in therapeutic employment of a substituted hexitol derivative such as dianhydrogalactitol for treatment of NSCLC or ovarian cancer made by optimizing its utility by determining the various mechanisms of action, biological targets of a compound for greater understanding and precision to better exploit the utility of the molecule. Specific inventive examples for a substituted hexitol derivative such as dianhydrogalactitol for treatment of NSCLC or ovarian cancer include: the use with inhibitors of poly-ADP ribose polymerase; agents that effect vasculature or vasodilation; oncogenic targeted agents; signal transduction inhibitors; EGFR inhibition; Protein Kinase C inhibition; Phospholipase C downregulation; Jun downregulation; histone genes; VEGF; ornithine decarboxylase; ubiquitin C; jun D; v-jun; GPCRs; protein kinase A; telomerase, prostate specific genes; protein kinases other than protein kinase A; histone deacetylase; and tyrosine kinase inhibitors.

Yet another aspect of the invention is an improvement in therapeutic employment of a substituted hexitol derivative such as dianhydrogalactitol for treatment of NSCLC or ovarian cancer made by more precise identification and exposure of the compound to those select cell populations where the compound's effect can be maximally exploited, particularly NSCLC tumor cells or ovarian tumor cells. Specific inventive examples for a substituted hexitol derivative such as dianhydrogalactitol for treatment of NSCLC or ovarian cancer include: use against radiation sensitive cells; use against radiation resistant cells; or use against energy depleted cells.

Yet another aspect of the invention is an improvement in therapeutic employment of a substituted hexitol derivative such as dianhydrogalactitol for treatment of NSCLC or ovarian cancer made by use of an agent that counteracts myelosuppression. Specific inventive examples for a substituted hexitol derivative such as dianhydrogalactitol for treatment of NSCLC or ovarian cancer include use of dithiocarbamates to counteract myelosuppression.

Yet another aspect of the invention is an improvement in therapeutic employment of a substituted hexitol derivative such as dianhydrogalactitol for treatment of brain metastases of NSCLC or ovarian cancer made by use of an agent that increases the ability of the substituted hexitol to pass through the blood-brain barrier. Specific examples for a substituted hexitol derivative such as dianhydrogalactitol for treatment of brain metastases of NSCLC or ovarian cancer include chimeric peptides; compositions comprising either avidin or an avidin fusion protein bonded to a biotinylated substituted hexitol derivative; neutral liposomes that are pegylated and that incorporate the substituted hexitol derivative and wherein the polyethylene glycol strands are conjugated to at least one transportable peptide or targeting agent; a humanized murine antibody that binds to the human insulin receptor linked to the substituted hexitol derivative through an avidin-biotin linkage; and a fusion protein linked to the hexitol through an avidin-biotin linkage.

Accordingly, one aspect of the present invention is a method to improve the efficacy and/or reduce the side effects of the administration of a substituted hexitol derivative such as dianhydrogalactitol for treatment of NSCLC or ovarian cancer comprising the steps of:

(1) identifying at least one factor or parameter associated with the efficacy and/or occurrence of side effects of the administration of the substituted hexitol derivative such as dianhydrogalactitol for treatment of NSCLC or ovarian cancer; and (2) modifying the factor or parameter to improve the efficacy and/or reduce the side effects of the administration of the substituted hexitol derivative such as dianhydrogalactitol for treatment of NSCLC or ovarian cancer.

In one alternative, the method improves the efficacy and/or reduces the side effects of the administration of the substituted hexitol derivative for treatment of NSCLC. In another alternative, the method improves the efficacy and/or reduces the side effects of the administration of the substituted hexitol derivative for treatment of ovarian cancer.

Typically, the factor or parameter is selected from the group consisting of:
   (1) dose modification;
   (2) route of administration;
   (3) schedule of administration;
   (4) indications for use;
   (5) selection of disease stage;
   (6) other indications;
   (7) patient selection;
   (8) patient/disease phenotype;
   (9) patient/disease genotype;
   (10) pre/post-treatment preparation
   (11) toxicity management;
   (12) pharmacokinetic/pharmacodynamic monitoring;
   (13) drug combinations;
   (14) chemosensitization;
   (15) chemopotentiation;
   (16) post-treatment patient management;

(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action;
(33) selective target cell population therapeutics;
(34) use with ionizing radiation;
(35) use of an agent that counteracts myelosuppression; and
(36) use with an agent that increases the ability of the substituted hexitol to pass through the blood-brain barrier to treat brain metastases of NSCLC or ovarian cancer.

As detailed above, in general, the substituted hexitol derivative usable in methods and compositions according to the present invention include galactitols, substituted galactitols, dulcitols, and substituted dulcitols, including dianhydrogalactitol, diacetyldianhydrogalactitol, dibromodulcitol, and derivatives and analogs thereof. Typically, the substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the substituted hexitol derivative is dianhydrogalactitol.

When the improvement made is by dose modification, the dose modification can be, but is not limited to, at least one dose modification selected from the group consisting of:
(a) continuous i.v. infusion for hours to days;
(b) biweekly administration;
(c) doses greater than 5 mg/m$^2$/day;
(d) progressive escalation of dosing from 1 mg/m$^2$/day based on patient tolerance;
(e) use of caffeine to modulate metabolism;
(f) use of isoniazid to modulate metabolism;
(g) selected and intermittent boosting of dosage administration;
(h) administration of single and multiple doses escalating from 5 mg/m$^2$/day via bolus;
(i) oral dosages of below 30 mg/m$^2$;
(j) oral dosages of above 130 mg/m$^2$;
(k) oral dosages up to 40 mg/m$^2$ for 3 days and then a nadir/recovery period of 18-21 days;
(l) dosing at a lower level for an extended period (e.g., 21 days);
(m) dosing at a higher level;
(n) dosing with a nadir/recovery period longer than 21 days;
(o) the use of a substituted hexitol derivative such as dianhydrogalactitol as a single cytotoxic agent, typically at 30 mg/m$^2$/day×5 days, repeated monthly;
(p) dosing at 3 mg/kg;
(q) the use of a substituted hexitol derivative such as dianhydrogalactitol in combination therapy, typically at 30 mg/m$^2$/day×5 days; and
(r) dosing at 40 mg/day×5 days in adult patients, repeated every two weeks.

When the improvement is made by route of administration, the route of administration can be, but is not limited to, at least one route of administration selected from the group consisting of:
(a) topical administration;
(b) oral administration;
(c) slow release oral delivery;
(d) intrathecal administration;
(e) intraarterial administration;
(f) continuous infusion;
(g) intermittent infusion;
(h) intravenous administration, such as intravenous administration for 30 minutes;
(i) administration through a longer infusion; and
(j) administration through IV push.

When the improvement is made by schedule of administration, the schedule of administration can be, but is not limited to, at least one schedule of administration selected from the group consisting of:
(a) daily administration;
(b) weekly administration;
(c) weekly administration for three weeks;
(d) biweekly administration;
(e) biweekly administration for three weeks with a 1-2 week rest period;
(f) intermittent boost dose administration; and
(g) daily administration for one week for multiple weeks.

When the improvement is made by selection of disease stage, the selection of disease stage can be, but is not limited to, at least one selection of disease stage selected from the group consisting of:
(a) use in an appropriate disease stage for NSCLC or ovarian cancer;
(b) use with an angiogenesis inhibitor to prevent or limit metastatic spread;
(c) use for newly diagnosed disease;
(d) use for recurrent disease; and
(e) use for resistant or refractory disease.

When the improvement is made by patient selection, the patient selection can be, but is not limited to, a patient selection carried out by a criterion selected from the group consisting of:
(a) selecting patients with a disease condition characterized by a high level of a metabolic enzyme selected from the group consisting of histone deacetylase and ornithine decarboxylase;
(b) selecting patients with a low or high susceptibility to a condition selected from the group consisting of thrombocytopenia and neutropenia; (c) selecting patients intolerant of GI toxicities;
(d) selecting patients characterized by over- or under-expression of a gene selected from the group consisting of c-Jun, a GPCR, a signal transduction protein, VEGF, a prostate-specific gene, and a protein kinase.
(e) selecting patients characterized by carrying extra copies of the EGFR gene for NSCLC;
(f) selecting patients characterized by methylation or lack of methylation of the promoter of the MGMT gene;
(g) selecting patients characterized by an unmethylated promoter region of MGMT (O$^6$-methylguanine methyltransferase);
(h) selecting patients characterized by a methylated promoter region of MGMT;
(i) selecting patients characterized by a high expression of MGMT;
(j) selecting patients characterized by a low expression of MGMT;

(k) selecting patients characterized by a mutation in EGFR, including, but not limited to EGFR Variant III;

(l) selecting patients being administered a platinum-based drug as combination therapy;

(m) selecting patients who do not have EGFR mutations and thus are less likely to respond to tyrosine kinase inhibitors (TKI);

(n) selecting patients who have become resistant to TKI treatment;

(o) selecting patients who have the BIM co-deletion mutation and thus are less likely to respond to TKI treatment;

(p) selecting patients who have become resistant to platinum-based drug treatment; and (q) selecting patients with brain metastases.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, 3-adrenergic receptors, $\beta_3$-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, folliclestimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

EGFR mutations can be associated with sensitivity to therapeutic agents such as gefitinib, as described in J. G. Paez et al., "EGFR Mutations in Lung Cancer: Correlation with Clinical Response to Gefitinib," *Science* 304: 1497-1500 (2004), incorporated herein by this reference. One specific mutation in EGFR that is associated with resistance to tyrosine kinase inhibitors is known as EGFR Variant III, which is described in C. A. Learn et al., "Resistance to Tyrosine Kinase Inhibition by Mutant Epidermal Growth Factor Variant III Contributes to the Neoplastic Phenotype of Glioblastoma Multiforme," *Clin. Cancer Res.* 10: 3216-3224 (2004), incorporated herein by this reference. EGFR Variant III is characterized by a consistent and tumor-specific in-frame deletion of 801 bp from the extracellular domain that splits a codon and produces a novel glycine at the fusion junction. This mutation encodes a protein with a constituently active tyrosine kinase that enhances the tumorigenicity of the cells carrying this mutation. This mutated protein sequence is absent from normal tissues.

Recent work has established that resistance to TKI (tyrosine kinase inhibitor) chemotherapy is at least partially due to genetic polymorphisms that affect the apoptotic response to TKI.

Specifically, these polymorphisms include, but are not necessarily limited to, polymorphisms in the gene BCL2L11 (also known as BIM), which encodes a BH3-only protein that is a BCL-2 family member. The BH3-only proteins activate cell death by either opposing the prosurvival members of the BCL2 family (BCL2, BCL2-like 1 (BCL-XL, also known as BCL2L1), myeloid cell leukemia sequence 1 (MCL1) and BCL2-related protein A1 (BCL2A1)) or by binding to the pro-apoptotic BCL2 family members (BCL2-associated X protein (BAX) and BCL2-antagonist/killer 1 (BAK1)) and directly activating their pro-apoptotic functions; the activation of pro-apoptotic functions would result in cell death (R. J. Youle & A. Strasser, "The BCL-2 Protein Family: Opposing Activities that Mediate Cell Death," *Nat. Rev. Mol. Cell. Biol.* 9: 47-59 (2008), incorporated herein by this reference.

It also has been previously shown that several kinase-driven cancers, such as CML and EGFR NSCLC, can maintain a survival advantage by suppressing BIM transcription and also by targeting BIM protein for proteasomal degradation through mitogen-activated protein kinase 1 (MAPK-1)-dependent phosphorylation. In all of these malignancies, BIM upregulation is required for TKIs to induce apoptosis of cancer cells, and suppression of BIM expression is sufficient to confer in vitro resistance to TKIs (J. Kuroda et al., "Bim and Bad Mediate Imatinib-Induced Killing of Bcr/Abl$^+$ Leukemic Cells, and Resistance Due to Their Loss is Overcome by a BH3 Mimetic," *Proc. Natl. Acad. Sci. USA* 103: 14907-14912 (2006); K. J. Aichberger et al., "Low-Level Expression of Proapoptotic Bcl-2-Interacting Mediator in Leukemic Cells in Patients with Chronic Myeloid Leukemia: Role of BCR/ABL, Characterization of Underlying Signaling Pathways, and Reexpression by Novel Pharmacologic Compounds," *Cancer Res.* 65: 9436-9444 (2005); R. Kuribara et al., "Roles of Bim in Apoptosis of Normal and Bcl-Abr-Expressing Hematopoietic Progenitors," *Mol. Cell. Biol.* 24: 6172-6183 (2004); M. S. Cragg et al., "Gefitinib-Induced Killing of NSCLC Cell Lines Expressing Mutant EGFR Requires BIM and Can Be Enhanced by BH3 Mimetics," *PLoS Med.* 4: 1681-1689 (2007); Y. Gong et al., "Induction of BIM Is Essential for Apoptosis Triggered by EGFR Kinase Inhibitors in Mutant EGFR-Dependent Lung Adenocarcinomas," *PLoS Med.* 4: e294 (2007); D. B. Costa et al., "BIM Mediates EGFR Tyrosine Kinase Inhibitor-Induced Apoptosis in Lung Cancers with Oncogenic EGFR Mutations," *PLoS Med.* 4: 1669-1679 (2007), all of which are incorporated herein by this reference).

One recent finding has been the discovery of a deletion polymorphism in the BIM gene that results in the generation of alternatively spliced isoforms of BIM that lack the crucial BH3 domain that is involved in the promotion of apoptosis. This polymorphism has a profound effect on the TKI sensitivity of CML and EGFR NSCLC cells, such that one copy of the deleted allele is sufficient to render cells intrinsically TKI resistant. This polymorphism therefore functions in a dominant manner to render such cells resistant to TKI chemotherapy. This finding also includes the result that individuals with the polymorphism have markedly inferior responses to TKI than do individuals without the polymorphism. In particular, the presence of the polymorphism was correlated with a lesser degree of response to imatinib, a TKI, in CML, as well as a shorter progression-free survival (PFS) with EGFR TKI therapy in EGFR NSCLC (K. P. Ng et al., "A Common BIM Deletion Polymorphism Mediates Intrinsic Resistance and Inferior Responses to Tyrosine Kinase Inhibitors in Cancer," Nature Med. doi 10.138/nm. 2713 (Mar. 18, 2012), incorporated herein by this reference).

When the method is intended to treat NSCLC, other biomarkers are known that are specific for the prognosis or staging of NSCLC and that can be used. Predictive biomarkers for NSCLC are disclosed in F. R. Hirsch et al., "Molecular Predictors of Outcome With Gefitinib in a Phase III Placebo-Controlled Study in Advanced Non-Small-Cell Lung Cancer," J. Clin. Oncol. 24: 5034-5042 (2006), incorporated herein by this reference. These biomarkers include: (i) EGFR gene copy number; (ii) the presence of EGFR mutations, including Exon 18 G719A; Exon 19 deletion; Exon 19 A743S; and Exon 21 L858R/L861Q; (iii) EGFR protein expression; (iv) p-Akt protein expression; (v) the presence of KRAS mutations; and (vi) the presence of BRAF mutations. Other biomarkers are described in M. Cobo et al., "Customizing Cisplatin Based on Quantitative Excision Repair Cross-Complementing 1 mRNA Expression: A Phase III Trial in Non-Small-Cell Lung Cancer," J. Clin. Oncol. 25: 2747-2754 (2006), incorporated herein by this reference, including mRNA levels for ERCC1.

Still other biomarkers for NSCLC are known in the art. U.S. Pat. No. 8,969,001 to Buckingham discloses DNA methylation as a biomarker for NSCLC. U.S. Pat. No. 8,940,302 to Amler et al. discloses the existence of low HER3 as a biomarker for NSCLC. U.S. Pat. No. 8,911,940 to Weiss et al. discloses miRNA expression as a biomarker for NSCLC. U.S. Pat. No. 8,828,657 to Rafnar et al. discloses genetic variants as biomarkers for NSCLC, including the alleles rs1051730 allele T, rs16969968 allele A, ss107794645 allele C, and rs8034191 allele C. U.S. Pat. No. 8,768,629 to Von Hoff et al. discloses TOP1, TYMS, MGMT, PTEN, ERBB2, and SPARC as biomarkers for NSCLC. U.S. Pat. No. 8,741,587 to Roessler et al. discloses a protein known as arginine-rich metastasized in early tumors protein (ARMET) as a biomarker for NSCLC. U.S. Pat. No. 8,728,823 to Lam et al. discloses CTAP-III related biomarkers as biomarkers for NSCLC. U.S. Pat. No. 8,700,335 to Von Hoff et al. discloses ERBB2, ESR1, PGR, KIT, EGFR, PTGS2 and AR as biomarkers for NSCLC. U.S. Pat. No. 8,632,592 to Schoeberl discloses pErbB3 as a biomarker for NSCLC; pErbB3 is determined by indirect measurement that includes: measuring total protein in the sample and levels of (i) at least one receptor selected from ErbB1, ErbB2, and ErbB3 and (ii) at least one of heregulin and betacellulin. U.S. Pat. No. 8,476,420 to Showe et al. discloses gene expression profiles as biomarkers for NSCLC. U.S. Pat. No. 8,377,888 to Costa et al. discloses the methylation state of nucleic acid encoding 14-3-3 sigma as a biomarker for NSCLC. U.S. Pat. No. 8,211,643 to Tsao et al. discloses a multigene signature as a biomarker for NSCLC. U.S. Pat. No. 8,133,692 to Jove et al. discloses phosphorylated Stat and expression of survivin as biomarkers for NSCLC. U.S. Pat. No. 7,655,414 to Brennscheidt et al. discloses overexpression of a phosphorylated AKT protein and/or a phosphorylated MAPK protein as biomarkers for NSCLC. These biomarkers, and others known in the art, can be used for patient selection.

When the method is intended to treat ovarian cancer, other biomarkers are known that are specific for the prognosis or staging of ovarian cancer and that can be used. Biomarkers for ovarian cancer are disclosed in B. Zhang et al., "An Overview of Biomarkers for the Ovarian Cancer Diagnosis," Eur. J. Obstet. Gynecol. Reprod. Biol. 2: 119-123 (2011), incorporated herein by this reference. These biomarkers include mutations in BRCA1 or BRCA2; hypermethylation of BRCA1, RASSF1A, APC, p14ARF, p16INK4a, or DAP-kinase; gene expression profiles specific for ovarian cancer; profiles derived from serial analysis of gene expression (SAGE) for CLDN3, HE4, FOLR1, COL18A1, CCND1, or FLJ12988; cleavage fragment of inter-α-trypsin inhibitor heavy chain H4; transferrin; afamin; apolipoprotein A-IV; and miRNA expression profiles. Another biomarker that has been used frequently for ovarian cancer is the protein CA125. CA125 is a heavily glycosylated protein of 1890 amino acids that is typically assayed in serum. Still another biomarker that has been used for ovarian cancer is the protein DF3; this protein is also typically assayed in serum.

Still other biomarkers for ovarian cancer are known in the art. U.S. Pat. No. 8,741,641 to Inazawa et al. discloses alterations of a gene existing in a chromosomal region 2q14.2, 3p24.1, 3q26.2, 3q29, 4q34.2, 6q23, 9p213, 11q13.3, 13q22.1, 13q33.1, 13q33.3, 15q12, 15q15.1, 17p12, 17p13.1, 17p13.3, 18q21.1, 18q21.2, 18q21.31, 18q21.32, 18q21.33, 18q23, 20q13.13, 20q13.2, 20q13.31, 20q13.33, Xp11.23, Xp13.1, Xp13.3, Xp26.2, Xp26.3, or Xq28 as biomarkers for ovarian cancer. U.S. Pat. No. 8,682,591 to Chan et al. discloses biomarkers for ovarian cancer including modified ApoA1 and one or more modified transthyretin selected from the group consisting of cysteinylated transthyretin, sulfonated transthyretin, CysGly modified transthyretin, and glutathionylated transthyretin. U.S. Pat. No. 8,664,358 to Mansfield et al. discloses a number of biomarkers for ovarian cancer, including CA-125, CRP, EGF-R, CA-19-9, Apo-AI, Apo-CIII, IL-6, IL-18, MIP-1a, tenascin C and myoglobin, and fragments thereof. U.S. Pat. No. 8,652,777 to Kamalakaran et al. discloses the methylation status of CpG dinucleotides as a biomarker for ovarian cancer. U.S. Pat. No. 8,642,347 to Ye et al. discloses peptides derived from the degradation of CA125 present in the urine as biomarkers for ovarian cancer. U.S. Pat. No. 8,476,026 to Alex et al. discloses that antibodies for a number of antigens are biomarkers for ovarian cancer; the antigens include casein kinase 1. U.S. Pat. No. 8,465,929 to Fung et al. discloses a number of biomarkers for ovarian cancer, including calcyclin, calgranulin C, hepcidin, ApoC1, ApoAII, ApoCII, calgranulin A, and transthyretin. U.S. Pat. No. 8,404,829 to Gray et al. discloses elevated expression of PVT1 as a biomarker for ovarian cancer. U.S. Pat. No. 8,323,906 to Veiby et al. discloses the use of LIV-1 as a biomarker for ovarian cancer. U.S. Pat. No. 8,192,935 to Al-Murrani discloses the expression level of MetAP2 as a biomarker for cisplatin resistance in ovarian cancer. U.S. Pat. No. 8,030,060 to Guo discloses gene signatures as biomarkers for prediction of recurrence and metastasis in ovarian cancer, including a 15-gene signature, a 23-gene signature, and a 28-gene signature. U.S. Pat. No. 7,910,314 to Frackelton, Jr. et al. discloses p66-Shc and phosphorylated Shc as biomarkers for ovarian cancer. U.S. Pat. No. 7,700,280 to Al-Murrani discloses the expression level of S100A10 and S100A11 as biomarkers for cisplatin resistance in ovarian cancer. U.S. Pat. No. 7,507,800 to van Ommen et al. discloses germline deletions of BRCA1 as biomarkers for ovarian cancer. U.S. Pat. No. 7,507,536 to Van Kriekinge et al. discloses epigenetic silencing of a number of genes as biomarkers for ovarian cancer, including the genes encoding plasmolipin, TNFRSF10B tumor necrosis factor receptor superfamily (member 10b), RUNX3 runt-related transcription factor 3, ACTN1 actinin (alpha 1), and FANCG Fanconi anemia (complementation group G). United States Patent Application Publication No. 2015/0080249 by Lancaster et al. discloses the use of an elevated expression level of a number of genes involved in the O-glycan pathway as biomarkers for ovarian cancer; these genes include B3GALT1, B3GALT2, B3GALT4, B3GALT5, B3GNT6, B4GALT1, B4GALT2, B4GALT3, C1GALT1, GALNT1, GALNT10, GALNT11, GALNT12, GALNT13, GALNT14, GALNT2, GALNT3, GALNT4, GALNT5, GALNT6, GALNT7, GALNT8, GALNT9, GALNTL1, GALNTL2, GALNTL4, GALNTL5, GCNT1, GCNT2, GCNT3, ST3GAL1, ST3GAL2, ST6GALN, and WBSCR17. United States Patent Application Publication No. 2015/0031561 by Bertenshaw et al. discloses a number of biomarkers for ovarian cancer, including CA125, HE4, IL-2Rα, α-1-antitrypsin, C-reactive protein, YKL-40, cellular fibronectin, prostasin, TIMP-1, IL-8, IL-6, VEGF-B, MMP-7, calprotectin, IGFBP-2, LOX-1, neuropilin-1, TNFR2, MPIF-1, and CA-72-4. United States Patent Application Publication No. 2014/0364341 by Bertenshaw et al. discloses a number of biomarkers for ovarian cancer including CA 15-3 (MUC-1), Her2/Neu (erbB-2), kallikrein-5, Macrophage Inhibitory Factor (MIF), osteopontin, TAG-72, IGF-II, HE4, IL6-R, IL18-R, IL-18BP, VCAM-1, IP-10 (interferon-gamma inducible 10 kD protein), SMRP, TgII (tissue transglutaminase), exotaxin-1, Cyfra 21-1 (cytokeratin 19 fragment), IGF2BP3, TIMP-1, alpha-1 antitrypsin, MMP7, IL-8, IL-6, sortillin, CD40, Alpha 1-Antichymotrypsin, VEGF, and haptoglobin. United States Patent Application Publication No. 2014/0017703 by Lancaster et al. discloses that the phosphorylation level of a BCL2 antagonist of cell death pathway protein can be used as a biomarker for predicting clinical outcome of platinum-based cancer treatment, taxane cancer treatment, or cyclophosphamide treatment, wherein the BCL2 antagonist of cell death pathway protein is BAD, Bax, BcL-XL, PP2C/PPM1A, AKT, EGFR, IRS-1, Shc, H-Ras, CDK1, G-protein alpha-s, G-protein beta/gamma, PI3K cat class 1A, c-Raf-1, p90Rsk, MEK2 (MAP2K2), PKA-cat, or PKA-reg.

When the improvement is made by analysis of patient or disease phenotype, the analysis of patient or disease phenotype can be, but is not limited to, a method of analysis of patient or disease phenotype carried out by a method selected from the group consisting of:

(a) use of a diagnostic tool, a diagnostic technique, a diagnostic kit, or a diagnostic assay to confirm a patient's particular phenotype;
(b) use of a method for measurement of a marker selected from the group consisting of histone deacetylase, ornithine decarboxylase, VEGF, a protein that is a gene product of jun, and a protein kinase;
(c) surrogate compound dosing; and
(d) low dose pre-testing for enzymatic status.

When the improvement is made by analysis of patient or disease genotype, the analysis of patient or disease genotype can be, but is not limited to, a method of analysis of patient or disease genotype carried out by a method selected from the group consisting of:

(a) use of a diagnostic tool, a diagnostic technique, a diagnostic kit, or a diagnostic assay to confirm a patient's particular genotype;
(b) use of a gene chip;
(c) use of gene expression analysis;
(d) use of single nucleotide polymorphism (SNP) analysis;
(e) measurement of the level of a metabolite or a metabolic enzyme;
(f) determination of copy number of the EGFR gene;
(g) determination of status of methylation of promoter of MGMT gene;
(h) determination of the existence of an unmethylated promoter region of the MGMT gene;
(i) determination of the existence of a methylated promoter region of the MGMT gene;
(j) determination of the existence of high expression of MGMT;
(k) determination of the existence of low expression of MGMT;
and
(l) for ovarian cancer, determination of the genotype status of p53.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference. This is particularly significant for NSCLC in that the prognosis for NSCLC can vary with the degree of methylation of the promoter of the MGMT gene because of the role of the MGMT gene in promoting drug resistance.

When the improvement is made by pre/post-treatment preparation, the pre/post-treatment preparation can be, but is not limited to, a method of pre/post treatment preparation selected from the group consisting of:

(a) the use of colchicine or an analog thereof;
(b) the use of a diuretic;
(c) the use of a uricosuric;
(d) the use of uricase;
(e) the non-oral use of nicotinamide;
(f) the use of a sustained-release form of nicotinamide;

(g) the use of an inhibitor of poly-ADP ribose polymerase;
(h) the use of caffeine;
(i) the use of leucovorin rescue;
(j) infection control; and
(k) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity. Other diuretics are well known in the art, and include, but are not limited to, hydrochlorothiazide, carbonic anhydrase inhibitors, furosemide, ethacrynic acid, amiloride, and spironolactone.

Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1 (2H)-ones and isoquinolin-1 (2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

When the improvement is made by toxicity management, the toxicity management can be, but is not limited to, a method of toxicity management selected from the group consisting of:
(a) the use of colchicine or an analog thereof;
(b) the use of a diuretic;
(c) the use of a uricosuric;
(d) the use of uricase;
(e) the non-oral use of nicotinamide;
(f) the use of a sustained-release form of nicotinamide;
(g) the use of an inhibitor of poly-ADP ribose polymerase;
(h) the use of caffeine;
(i) the use of leucovorin rescue;
(j) the use of sustained-release allopurinol;
(k) the non-oral use of allopurinol;
(l) the use of bone marrow transplants;
(m) the use of a blood cell stimulant;
(n) the use of blood or platelet infusions;
(o) the administration of an agent selected from the group consisting of filgrastim, G-CSF, and GM-CSF;
(p) the application of a pain management technique;
(q) the administration of an anti-inflammatory agent;
(r) the administration of fluids;
(s) the administration of a corticosteroid;
(t) the administration of an insulin control medication;
(u) the administration of an antipyretic;
(v) the administration of an anti-nausea treatment;
(w) the administration of an anti-diarrheal treatment;
(x) the administration of N-acetylcysteine; and
(y) the administration of an antihistamine.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumiracoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" in *Goodman & Gilman's The Pharmacological Basis of Therapeutics* (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

Poly-ADP ribose polymerase (PARP) inhibitors include, but are not limited to: (1) derivatives of tetracycline as described in U.S. Pat. No. 8,338,477 to Duncan et al.; (2) 3,4-dihydro-5-methyl-1(2H)-isoquinoline, 3-aminobenzamide, 6-aminonicotinamide, and 8-hydroxy-2-methyl-4 (3H)-quinazolinone, as described in U.S. Pat. No. 8,324,282 by Gerson et al.; (3) 6-(5H)-phenanthridinone and 1,5-isoquinolinediol, as described in U.S. Pat. No. 8,324,262 by Yuan et al.; (4) (R)-3-[2-(2-hydroxymethylpyrrolidin-1-yl)ethyl]-5-methyl-2H-isoquinolin-1-one, as described in U.S. Pat. No. 8,309,573 to Fujio et al.; (5) 6-alkenyl-substituted 2-quinolinones, 6-phenylalkyl-substituted quinolinones, 6-alkenyl-substituted 2-quinoxalinones, 6-phenylalkyl-substituted 2-quinoxalinones, substituted 6-cyclohexylalkyl substituted 2-quinolinones, 6-cyclohexylalkyl substituted 2-quinoxalinones, substituted pyridones, quinazolinone derivatives, phthalazine derivatives, quinazolinedione derivatives, and substituted 2-alkyl quinazolinone derivatives, as described in U.S. Pat. No. 8,299,256 to Vialard et al.; (6) 5-bromoisoquinoline, as described in U.S. Pat. No. 8,299,088 to Mateucci et al.; (7) 5-bis-(2-chloroethyl)amino]-1-methyl-2-benzimidazolebutyric acid, 4-iodo-3-nitrobenzamide, 8-fluoro-5-(4-((methylamino)methyl)phenyl)-3,4-dihydro-2H-azepino[5,4,3-cd]indol-1 (6H)-one phosphoric acid, and N-[3-(3,4-dihydro-4-oxo-1-phthalazinyl)phenyl]-4-morpholinebutanamide methanesulfonate, as described in U.S. Pat. No. 8,227,807 to Gallagher et al.; (8) pyridazinone derivatives, as described in U.S. Pat. No. 8,268,827 to Branca et al.; (9) 4-[3-(4-cyclopropanecarbonyl-piperazine-1-carbonyl)-4-fluorobenzyl]-2H-phthalazin-1-one, as described in U.S. Pat. No. 8,247,416 to Menear et al.; (10) tetraaza phenalen-3-one compounds, as described in U.S. Pat. No. 8,236,802 to Xu et al.; (11) 2-substituted-1H-benzimidazole-4-carboxamides, as described in U.S. Pat. No. 8,217,070 to Zhu et al.; (12) substituted 2-alkyl quinazolinones, as described in U.S. Pat. No. 8,188,103 to Van der Aa et al.; (13) 1H-benzimidazole-4-carboxamides, as described in U.S. Pat. No. 8,183,250 to Penning et al.; (14) indenoisoquinolinone analogs, as described in U.S. Pat. No. 8,119,654 to Jagtap et al.; (15) benzoxazole carboxamides, described in U.S. Pat. No. 8,088,760 to Chu et al; (16) diazabenzo[de]anthracen-3-one compounds, described in U.S. Pat. No. 8,058,075 to Xu et al.; (17) dihydropyridophthalazinones, described in U.S. Pat. No. 8,012,976 to Wang et al., (18) substituted azaindoles, described in U.S. Pat. No. 8,008,491 to Jiang et al.; (19) fused tricyclic compounds, described in U.S. Pat. No. 7,956,064 to Chua et al.; (20) substituted 6a,7,8,9-tetrahydropyrido[3,2-e]pyrrolo[1,2-a]pyrazin-6(5H)-ones, described in U.S. Pat. No. 7,928,105 to Gangloff et al.; and (21) thieno[2,3-c]isoquinolines, described in U.S. Pat. No. 7,825,129, all of which patents are incorporated herein by this reference. Other PARP inhibitors are known in the art.

When the improvement is made by pharmacokinetic/pharmacodynamic monitoring, the pharmacokinetic/pharmacodynamic monitoring can be, but is not limited to a method selected from the group consisting of:
  (a) multiple determinations of blood plasma levels; and
  (b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

When the improvement is made by drug combination, the drug combination can be, but is not limited to, a drug combination selected from the group consisting of:
  (a) use with topoisomerase inhibitors;
  (b) use with fraudulent nucleosides;
  (c) use with fraudulent nucleotides;
  (d) use with thymidylate synthetase inhibitors;
  (e) use with signal transduction inhibitors;
  (f) use with cisplatin, oxaliplatin, or other platinum analogs;
  (g) use with monofunctional alkylating agents;
  (h) use with bifunctional alkylating agents;
  (i) use with alkylating agents that damage DNA at a different place than does dianhydrogalactitol;
  (j) use with anti-tubulin agents;
  (k) use with antimetabolites;
  (l) use with berberine;
  (m) use with apigenin;
  (n) use with amonafide;
  (o) use with colchicine or analogs;
  (p) use with genistein;
  (q) use with etoposide;
  (r) use with cytarabine;
  (s) use with camptothecins;
  (t) use with vinca alkaloids;
  (u) use with 5-fluorouracil;
  (v) use with curcumin;
  (w) use with NF-κB inhibitors;
  (x) use with rosmarinic acid;
  (y) use with mitoguazone;
  (z) use with tetrandrine;
  (aa) use with temozolomide;
  (ab) use with VEGF inhibitors;
  (ac) use with cancer vaccines;
  (ad) use with EGFR inhibitors;
  (ae) use with tyrosine kinase inhibitors;
  (af) use with poly (ADP-ribose) polymerase (PARP) inhibitors; and
  (ag) use with ALK inhibitors.

Topoisomerase inhibitors include, but are not limited to, irinotecan, topotecan, camptothecin, lamellarin D, amsacrine, etoposide, etoposide phosphate, teniposide, doxorubicin, and ICRF-193.

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine (BCNU), Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine (CCNU), mafosfamide, melphalan, mitolactol, nimustine (ACNU), Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al., incorporated herein by this reference. Temozolomide, BCNU, CCNU, and ACNU all damage DNA at $O^6$ of guanine, whereas DAG cross-links at $N^7$); one alternative is therefore to use DAG in combination with an alkylating agent that damages DNA at a different place than DAG. The alkylating agent can be a monofunctional alkylating agent or a bifunctional alkylating agent. Monofunctional alkylating agents include, but are not limited to, carmustine lomustine, temozolomide, and dacarbazine, as described in N. Kondo et al., "DNA Damage Induced by Alkylating Agents and Repair Pathways," *J. Nucl. Acids* doi:10.4061/2010/543531 (2010), incorporated herein by this reference; monofunctional alkylating agents also include such agents as methyl methanesulfonate, ethylmethanesulfonate, and N-methyl-N-nitrosoguanidine, as described in J. M. Walling & I. J. Stratford, "Chemosensitization by Monofunctional Alkylating Agents," *Int. J. Radiat. Oncol. Biol. Phys.* 12: 1397-1400 (1986), incorporated herein by this reference. Bifunctional alkylating agents include, but are not limited to, mechlorethamine, chlorambucil, cyclophosphamide, busulfan, nimustine, carmustine, lomustine, fotemustine, and bis-(2-chloroethyl) sulfide (N. Kondo et al. (2010), supra). One significant class of bifunctional alkylating agents includes alkylating agents that target $O^6$ of guanine in DNA. Another significant class of alkylating agents comprises cisplatin and other platinum-containing agents, including, but not limited to, cisplatin, carboplatin, iproplatin, oxaliplatin, tetraplatin, satraplatin, picoplatin, nedaplatin, and triplatin. These agents cause cross-linking of DNA, which then induces apoptosis. The combination with cisplatin, oxaliplatin, or other platinum-containing agents is a potential component of standard platinum doublet therapy. Additionally, the ability to be more than additive or synergistic is particularly significant with respect to the combination of a substituted hexitol derivative such as dianhydrogalactitol with cisplatin, oxaliplatin, or other platinum-containing chemotherapeutic agents, as well as other chemotherapeutic agents recited herein.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Amonafide is a topoisomerase inhibitor and DNA intercalator that has anti-neoplastic activity.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to, bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Tetrandrine has the chemical structure 6,6',7,12-tetramethoxy-2,2'-dimethyl-1β-berbaman and is a calcium channel blocker that has anti-inflammatory, immunologic, and anti-allergenic effects, as well as an anti-arrhythmic effect similar to that of quinidine. It has been isolated from *Stephania tetranda* and other Asian herbs.

VEGF inhibitors include bevacizumab (Avastin), which is a monoclonal antibody against VEGF, itraconazole, and suramin, as well as batimastat and marimastat, which are matrix metalloproteinase inhibitors, and cannabinoids and derivatives thereof.

Cancer vaccines are being developed. Typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn, "Cancer Vaccines: Accomplishments and Challenges," *Crit. Rev. Oncol. Hematol.* 67: 93-102 (2008), incorporated herein by this reference.

The epidermal growth factor receptor (EGFR) exists on the cell surface of mammalian cells and is activated by binding of the receptor to its specific ligands, including, but not limited to epidermal growth factor and transforming growth factor α. Upon activation by binding to its growth factor ligands, EGFR undergoes a transition from an inactive monomeric form to an active homodimer, although preformed active dimers may exist before ligand binding. In addition to forming active homodimers after ligand binding, EGFR may pair with another member of the ErbB receptor family, such as ErbB2/Her2/neu, to create an activated heterodimer. There is also evidence that clusters of activated EGFRs form, although it is uncertain whether such clustering is important for activation itself or occurs subsequent to activation of individual dimers. EGFR dimerization stimulates its intracellular intrinsic protein-tyrosine kinase activity. As a result, autophosphorylation of several tyrosine residues in the carboxyl-terminal domain of EGFR occurs. These residues include Y992, Y1045, Y1068, Y1148, and Y1171. Such autophosphorylation elicits downstream activation and signaling by several other proteins that associate with the phosphorylated tyrosine residues through their own phosphotyrosine-binding SH2 domains. The signaling of these proteins that associate with the phosphorylated tyrosine residues through their own phosphotyrosine-binding SH2 domains can then initiate several signal transduction cascades and lead to DNA synthesis and cell proliferation. The kinase domain of EGFR can also cross-phosphorylate tyrosine residues of other receptors that it is aggregated with, and can itself be activated in that manner. EGFR is encoded by the c-erbB1 proto-oncogene and has a molecular mass of 170 kDa. It is a transmembrane glycoprotein with a cysteine-rich extracellular region, an intracellular domain containing an uninterrupted tyrosine kinase site, and multiple autophosphorylation sites clustered at the carboxyl-terminal tail as described above. The extracellular portion has been subdivided into four domains: domains I and III, which have 37% sequence identity, are cysteine-poor and conformationally contain the site for ligand (EGF and transforming growing factor α (TGFα) binding. Cysteine-rich domains II and IV contain N-linked glycosylation sites and disulfide bonds, which determine the tertiary conformation of the external domain of the protein molecule. In many human cell lines, TGFα expression has a strong correlation with EGFR overexpression, and therefore TGFα was considered to act in an autocrine manner, stimulating proliferation of the cells in which it is produced via activation of EGFR. Binding of a stimulatory ligand to the EGFR extracellular domain results in receptor dimerization and initiation of intracellular signal transduction, the first step of which is activation of the tyrosine kinase. The earliest consequence of kinase activation is the phosphorylation of its own tyrosine residues (autophosphorylation) as described above. This is followed by association with activation of signal transducers leading to mitogenesis. Mutations that lead to EGFR expression or overactivity have been associated with a number of malignancies, including glioblastoma multiforme. A specific mutation of EGFR known as EGFR Variant III has frequently been observed in glioblastoma (C. T. Kuan et al., "EGF Mutant Receptor VIII as a Molecular Target in Cancer Therapy," *Endocr. Relat. Cancer* 8: 83-96 (2001), incorporated herein by this reference). EGFR is considered an oncogene. Inhibitors of EGFR include, but are not limited to, erlotinib, gefitinib, lapatinib, lapatinib ditosylate, afatinib, canertinib, neratinib, CP-724714, WHI-P154, TAK-285, AST-1306, ARRY-334543, ARRY-380, AG-1478, tyrphostin 9, dacomitinib, desmethylerlotinib, OSI-420, AZD8931, AEE788, pelitinib, CUDC-101, WZ8040, WZ4002, WZ3146, AG-490, XL647, PD153035 HCl, BMS-599626, BIBW 2992, CI 1033, CP 724714, OSI 420, and vandetinib. Particularly preferred EGFR inhibitors include erlotinib, afatinib, and lapatinib.

Tyrosine kinase inhibitors include, but are not limited to, imatinib, gefitinib, erlotinib, sunitinib, sorafenib, foretinib, cederinib, axitinib, carbozantinib, BIBF1120, golvatinib, dovitinib, ZM 306416, ZM 323881 HCl, SAR 131675, semaxinib, telatinib, pazopanib, ponatinib, crenolanib, tivanitib, mubritinib, danusertib, brivanib, fingolimod, saracatinib, rebastinib, quizartinib, tandutinib, amuvatinib, ibrutinib, fostamatinib, crizotinib, and linsitinib. Such tyrosine kinase inhibitors can inhibit tyrosine kinases associated with one or more of the following receptors: VEGFR, EGFR, PDGFR, c-Kit, c-Met, Her-2, FGFR, FLT-3, IGF-1R, ALK, c-RET, and Tie-2. As the activity of epidermal growth factor receptor (EGFR) involves the activity of a tyrosine kinase, the category of tyrosine kinase inhibitors overlaps with the category of EGFR inhibitors. A number of tyrosine kinase inhibitors inhibit the activity of both EGFR and at least one other tyrosine kinase. In general, tyrosine kinase inhibitors can operate by four different mechanisms: competition with adenosine triphosphate (ATP), used by the tyrosine kinase to carry out the phosphorylation reaction; competition with the substrate; competition with both ATP and the substrate; or allosteric inhibition. The activity of these inhibitors is disclosed in P. Yaish et al., "Blocking of EGF-Dependent Cell Proliferation by EGF Receptor Kinase Inhibitors," *Science* 242: 933-935 (1988); A. Gazit et al., "Tyrphostins. 2. Heterocyclic and α-Substituted Benzylidenemalononitrile Tyrphostins as Potent Inhibitors of EGF Receptor and ErbB2/neu Tyrosine Kinases," *J. Med. Chem.* 34: 1896-1907 (1991); N. Osherov et al., "Selective Inhibition of the Epidermal Growth Factor and HER2/neu Receptors by Tyrphostins," *J. Biol. Chem.* 268: 11134-11142 (1993); and A. Levitzki & E. Mishani, "Tyrphostins and Other Tyrosine Kinase Inhibitors," *Annu. Rev. Biochem.* 75: 93-109 (2006), all of which are incorporated herein by this reference.

ALK inhibitors act on tumors with variations of anaplastic lymphoma kinase (ALK) such as an EML4-ALK translocation. ALK inhibitors include, but are not limited to: crizotinib (3-[(1R)-1-(2,6-dichloro-3-fluorophenyl)ethoxy]-5-(1-piperidin-4-ylpyrazol-4-yl)pyridin-2-amine); AP26113 ((2-((5-chloro-2-((4-(4-(dimethylamino)piperidin-1-yl)-2-methoxyphenyl)amino)pyrimidin-4-yl)amino)phenyl)dimethylphosphine oxide); ASP-3026 (N2-[2-methoxy-4-[4-(4-methyl-1-piperazinyl)-1-piperidinyl]phenyl]-N4-[2-[(1-methylethyl)sulfonyl]phenyl]-1,3,5-triazine-2,4-diamine); alectinib (9-ethyl-6,6-dimethyl-8-(4-morpholin-4-ylpiperidin-1-yl)-11-oxo-5H-benzo[b]carbazole-3-carbonitrile); NMS-E628 (N-(5-(3,5-difluorobenzyl)-1H-indazol-3-yl)-4-(4-methylpiperazin-1-yl)-2-((tetrahydro-2H-pyran-4-yl)amino)benzamide); ceritinib; PF-06363922; TSR-011; CEP-37440 (2-[[5-Chloro-2-[[(6S)-6-[4-(2-hydroxyethyl)piperazin-1-yl]-1-methoxy-6,7,8,9-tetrahydro-5H-benzo[7]annulen-2-yl]amino]pyrimidin-4-yl]amino]-N-methyl-benzamide); and X-396 (R)-6-amino-5-(1-(2,6-dichloro-3-fluorophenyl)ethoxy)-N-(4-(4-methylpiperazine-1-carbonyl)phenyl)pyridazine-3-carboxamide).

These additional agents described above can be used in drug combinations together with the substituted hexitol derivative for treatment of either NSCLC or ovarian cancer. The additional agent to be included is one that is either known to possess activity against the type of cancer being treated (NSCLC or ovarian cancer), is structurally related to a compound or a class of compounds known to possess activity against the type of cancer being treated, or is known to modulate a pathway for which modulation has been shown to be effective against the type of cancer being treated. As used herein, the term "modulation" can include either activation or inhibition of the pathway involved, but typically refers to inhibition of the pathway.

When methods according to the present invention are intended for treatment of ovarian cancer, drug combinations can include the use of a substituted hexitol derivative as described above together with an additional agent that possesses anti-neoplastic activity against ovarian tumors. Such additional agents include, but are not limited to, paclitaxel, docetaxel, cisplatin, carboplatin, topotecan, gemcitabine, bleomycin, etoposide, doxorubicin (which can be used in a pegylated liposomal form), tamoxifen, letrozole, olaparib, selumetinib, mTOR inhibitors, PI3 kinase inhibitors, and trichostatin A.

Additional agents that possess anti-neoplastic activity against NSCLC are known in the art. These additional agents can be included in drug combinations according to the present invention in a therapeutically effective quantity together with a therapeutically effective quantity of a substituted hexitol derivative as described above. One or more than one of these additional agents can be used. These additional agents can be used together with one or more of the agents as described above for activity against NSCLC in drug combinations including a substituted hexitol derivative such as dianhydrogalactitol or diacetyldianhydrogalactitol. The agents are those collectively referred to herein as "Additional Secondary Agents with Activity Against NSCLC."

Additional agents that possess anti-neoplastic activity against ovarian cancer are known in the art. These additional agents can be included in drug combinations according to the present invention in a therapeutically effective quantity together with a therapeutically effective quantity of a substituted hexitol derivative as described above. One or more than one of these additional agents can be used. These additional agents can be used together with one or more of the agents as described above for activity against ovarian cancer in drug combinations including a substituted hexitol derivative such as dianhydrogalactitol or diacetyldianhydrogalactitol. The agents are those collectively referred to herein as "Additional Secondary Agents with Activity Against Ovarian Cancer."

When the improvement is made by chemosensitization, the chemosensitization can comprise, but is not limited to, the use of a substituted hexitol derivative as a chemosensitizer in combination with an agent selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin, oxaliplatin, or another platinum analog;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) topoisomerase inhibitors;
(t) 5-fluorouracil;
(u) curcumin;
(v) NF-κB inhibitors;
(w) rosmarinic acid;
(x) mitoguazone;
(y) tetrandrine;
(z) a tyrosine kinase inhibitor;
(aa) an inhibitor of EGFR; and
(ab) an inhibitor of PARP.

When the improvement is made by chemopotentiation, the chemopotentiation can comprise, but is not limited to, the use of a substituted hexitol derivative as a chemopotentiator in combination with an agent selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin, oxaliplatin, or another platinum analog;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) 5-fluorouracil;
(t) curcumin;
(u) NF-κB inhibitors;
(v) rosmarinic acid;
(w) mitoguazone;
(x) tetrandrine;
(y) a tyrosine kinase inhibitor;
(z) an inhibitor of EGFR; and
(aa) an inhibitor of PARP.

When the improvement is made by post-treatment management, the post-treatment management can be, but is not limited to, a method selected from the group consisting of:
(a) a therapy associated with pain management;
(b) administration of an anti-emetic;
(c) an anti-nausea therapy;
(d) administration of an anti-inflammatory agent;
(e) administration of an anti-pyretic agent; and
(f) administration of an immune stimulant.

When the improvement is made by alternative medicine/post-treatment support, the alternative medicine/post-treatment support can be, but is not limited to, a method selected from the group consisting of:
(a) hypnosis;
(b) acupuncture;
(c) meditation;
(d) a herbal medication created either synthetically or through extraction; and
(e) applied kinesiology.

In one alternative, when the method is a herbal medication created either synthetically or through extraction, the herbal medication created either synthetically or through extraction can be selected from the group consisting of:
(a) a NF-κB inhibitor;
(b) a natural anti-inflammatory;
(c) an immunostimulant;
(d) an antimicrobial; and
(e) a flavonoid, isoflavone, or flavone.

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an anti-microbial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

When the improvement is made by a bulk drug product improvement, the bulk drug product improvement can be, but is not limited to, a bulk drug product improvement selected from the group consisting of:
 (a) salt formation;
 (b) preparation as a homogeneous crystal structure;
 (c) preparation as a pure isomer;
 (d) increased purity;
 (e) preparation with lower residual solvent content; and
 (f) preparation with lower residual heavy metal content.

When the improvement is made by use of a diluent, the diluent can be, but is not limited to, a diluent selected from the group consisting of:
 (a) an emulsion;
 (b) dimethylsulfoxide (DMSO);
 (c) N-methylformamide (NMF)
 (d) DMF;
 (e) ethanol;
 (f) benzyl alcohol;
 (g) dextrose-containing water for injection;
 (h) Cremophor;
 (i) cyclodextrin; and
 (j) PEG.

When the improvement is made by use of a solvent system, the solvent system can be, but is not limited to, a solvent system selected from the group consisting of:
 (a) an emulsion;
 (b) dimethylsulfoxide (DMSO);
 (c) N-methylformamide (NMF)
 (d) DMF;
 (e) ethanol;
 (f) benzyl alcohol;
 (g) dextrose-containing water for injection;
 (h) Cremophor;
 (i) cyclodextrin; and
 (j) PEG.

When the improvement is made by use of an excipient, the excipient can be, but is not limited to, an excipient selected from the group consisting of:
 (a) mannitol;
 (b) albumin;
 (c) EDTA;
 (d) sodium bisulfite;
 (e) benzyl alcohol;
 (f) a carbonate buffer; and
 (g) a phosphate buffer.

When the improvement is made by use of a dosage form, the dosage form can be, but is not limited to, a dosage form selected from the group consisting of:
 (a) tablets;
 (b) capsules;
 (c) topical gels;
 (d) topical creams;
 (e) patches;
 (f) suppositories; and
 (g) lyophilized dosage fills.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to dianhydrogalactitol and derivatives thereof and to diacetyldianhydrogalactitol and derivatives thereof, comprises the following steps:

(1) Dissolve the drug in water for injection precooled to below 10° C. Dilute to final volume with cold water for injection to yield a 40 mg/mL solution.

(2) Filter the bulk solution through an 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability.

When the improvement is made by use of a drug delivery system, the drug delivery system can be, but is not limited to, a drug delivery system selected from the group consisting of:
 (a) nanocrystals;
 (b) bioerodible polymers;
 (c) liposomes;
 (d) slow release injectable gels; and
 (e) microspheres.

Nanocrystals are described in U.S. Pat. No. 7,101,576 to Hovey et al., incorporated herein by this reference.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutryate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000), incorporated herein by this reference.

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

When the improvement is made by use of a drug conjugate form, the drug conjugate form can be, but is not limited to, a drug conjugate form selected from the group consisting of:
 (a) a polymer system;
 (b) polylactides;
 (c) polyglycolides;
 (d) amino acids;
 (e) peptides; and
 (f) multivalent linkers.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the ε-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonydlimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques" (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

When the improvement is made by use of a compound analog, the compound analog can be, but is not limited to, a compound analog selected from the group consisting of:
 (a) alteration of side chains to increase or decrease lipophilicity;
 (b) addition of an additional chemical functionality to alter a property selected from the group consisting of reactivity, electron affinity, and binding capacity; and
 (c) alteration of salt form.

When the improvement is made by use of a prodrug system, the prodrug system can be, but is not limited to, a prodrug system selected from the group consisting of:
 (a) the use of enzyme sensitive esters;
 (b) the use of dimers;
 (c) the use of Schiff bases;
 (d) the use of pyridoxal complexes; and
 (e) the use of caffeine complexes.

The use of prodrug systems is described in T. Järvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference.

When the improvement is made by use of a multiple drug system, the multiple drug system can be, but is not limited to, a multiple drug system selected from the group consisting of:
 (a) use of multi-drug resistance inhibitors;
 (b) use of specific drug resistance inhibitors;
 (c) use of specific inhibitors of selective enzymes;
 (d) use of signal transduction inhibitors;
 (e) use of repair inhibition; and
 (f) use of topoisomerase inhibitors with non-overlapping side effects.

Multi-drug resistance inhibitors are described in U.S. Pat. No. 6,011,069 to Inomata et al., incorporated herein by this reference.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference.

Repair inhibition is described in N. M. Martin, "DNA Repair Inhibition and Cancer Therapy," *J. Photochem. Photobiol. B* 63: 162-170 (2001), incorporated herein by this reference.

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:
 (a) cytokines;
 (b) lymphokines;
 (c) therapeutic antibodies;
 (d) antisense therapies;
 (e) gene therapies;
 (f) ribozymes;
 (g) RNA interference; and
 (h) vaccines.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" in *Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" in *Drug Discovery Handbook* (S. C. Gad, ed., Wiley-Interscience, Hoboken, N.J., 2005), ch. 27, pp. 1278-1283, incorporated herein by this reference.

As described above, typically, cancer vaccines are based on an immune response to a protein or proteins occurring in cancer cells that does not occur in normal cells. Cancer vaccines include Provenge for metastatic hormone-refractory prostate cancer, Oncophage for kidney cancer, CimaVax-EGF for lung cancer, MOBILAN, Neuvenge for Her2/neu expressing cancers such as breast cancer, colon cancer, bladder cancer, and ovarian cancer, Stimuvax for breast cancer, and others. Cancer vaccines are described in S. Pejawar-Gaddy & O. Finn (2008), supra.

When the biotherapeutic enhancement is use in combination as sensitizers/potentiators with a therapeutic antibody, therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by use of biotherapeutic resistance modulation, the biotherapeutic resistance modulation can be, but is not limited to, use against NSCLC resistant to a therapeutic agent or technique selected from the group consisting of:
 (a) biological response modifiers;
 (b) cytokines;
 (c) lymphokines;
 (d) therapeutic antibodies;
 (e) antisense therapies;
 (f) gene therapies;
 (g) ribozymes;
 (h) RNA interference; and
 (i) vaccines.

When the biotherapeutic resistance modulation is use against tumors resistant to therapeutic antibodies, therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:
 (a) hypoxic cell sensitizers;
 (b) radiation sensitizers/protectors;
 (c) photosensitizers;
 (d) radiation repair inhibitors;
 (e) thiol depleters;
 (f) vaso-targeted agents;
 (g) DNA repair inhibitors;

(h) radioactive seeds;
(i) radionuclides;
(j) radiolabeled antibodies; and
(k) brachytherapy.

A substituted hexitol derivative such as dianhydrogalactitol can be used in combination with radiation for the treatment of NSCLC or for the treatment of ovarian cancer.

Hypoxic cell sensitizers are described in C. C. Ling et al., "The Effect of Hypoxic Cell Sensitizers at Different Irradiation Dose Rates," Radiation Res. 109: 396-406 (1987), incorporated herein by this reference. Radiation sensitizers are described in T. S. Lawrence, "Radiation Sensitizers and Targeted Therapies," Oncology 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," Clin. Cancer Res. 14: 2161-2170 (2008), incorporated herein by this reference. Photosensitizers are described in R. R. Allison & C. H. Sibata, "Oncologic Photodynamic Therapy Photosensitizers: A Clinical Review," Photodiagnosis Photodynamic Ther. 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," Cancer Res. 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," Radiation Res. 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," Cancer Res. 67: 9455-9462 (2007). As described above, radiation therapy is employed for the treatment of NSCLC, so radiation therapy enhancement is significant for this malignancy.

When the improvement is by use of a novel mechanism of action, the novel mechanism of action can be, but is not limited to, a novel mechanism of action that is a therapeutic interaction with a target or mechanism selected from the group consisting of:
  (a) inhibitors of poly-ADP ribose polymerase;
  (b) agents that affect vasculature or vasodilation;
  (c) oncogenic targeted agents;
  (d) signal transduction inhibitors;
  (e) EGFR inhibition;
  (f) protein kinase C inhibition;
  (g) phospholipase C downregulation;
  (h) Jun downregulation;
  (i) histone genes;
  (j) VEGF;
  (k) ornithine decarboxylase;
  (l) ubiquitin C;
  (m) Jun D;
  (n) v-Jun;
  (o) GPCRs;
  (p) protein kinase A;
  (q) protein kinases other than protein kinase A;
  (r) prostate specific genes;
  (s) telomerase;
  (t) histone deacetylase; and
  (u) tyrosine kinase inhibitors.

EGFR inhibition is described in G. Giaccone & J. A. Rodriguez, "EGFR Inhibitors: What Have We Learned from the Treatment of Lung Cancer," Nat. Clin. Pract. Oncol. 11: 554-561 (2005), incorporated herein by this reference. Protein kinase C inhibition is described in H. C. Swannie & S. B. Kaye, "Protein Kinase C Inhibitors," Curr. Oncol. Rep. 4: 37-46 (2002), incorporated herein by this reference. Phospholipase C downregulation is described in A. M. Martelli et al., "Phosphoinositide Signaling in Nuclei of Friend Cells: Phospholipase C β Downregulation Is Related to Cell Differentiation," Cancer Res. 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," Oncogene 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," Proc. Natl. Acad. Sci. USA 83: 1495-1498 (1986). The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," Surgery 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," Cancer Cell 7: 433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," Clin. Cancer Res. 8: 2505-2511 (2002), incorporated herein by this reference. The role of Jun D as a target for therapeutic intervention is described in M. M. Caffarel et al., "JunD Is Involved in the Antiproliferative Effect of $\Delta^9$-Tetrahydrocannibinol on Human Breast Cancer Cells," Oncogene 27: 5033-5044 (2008), incorporated herein by this reference. The role of v-Jun as a target for therapeutic intervention is described in M. Gao et al., "Differential and Antagonistic Effects of v-Jun and c-Jun," Cancer Res. 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," Eur. J. Cancer 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," Ann. Med. 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," Curr. Opin. Hematol. 9: 322-332 (2002), incorporated herein by this reference.

When the improvement is made by use of selective target cell population therapeutics, the use of selective target cell population therapeutics can be, but is not limited to, a use selected from the group consisting of:
  (a) use against radiation sensitive cells;
  (b) use against radiation resistant cells; and
  (c) use against energy depleted cells.

The improvement can also be made by use of a substituted hexitol derivative in combination with ionizing radiation.

When the improvement is made by use of an agent that counteracts myelosuppression, the agent that counteracts myelosuppression can be, but is not limited to, a dithiocarbamate.

U.S. Pat. No. 5,035,878 to Borch et al., incorporated herein by this reference, discloses dithiocarbamates for treatment of myelosuppression; the dithiocarbamates are compounds of the formula $R^1R^2NCS(S)M$ or $R^1R^2NCSS$—$SC(S)NR^3R^4$, wherein $R^1$, $R^2$, $R^3$, and $R^4$ are the same or different, and $R^1$, $R^2$, $R^3$, and $R^4$ are aliphatic, cycloaliphatic, or heterocycloaliphatic groups that are unsubstituted or substituted by hydroxyl; or wherein one of $R^1$ and $R^2$ and one of $R^3$ and $R^4$ can be hydrogen; or wherein $R^1$, $R^2$, $R^3$, and $R^4$ taken together with the nitrogen atom upon which the pair of R groups is substituted, can be a 5-membered or 6-membered N-heterocyclic ring which is aliphatic or aliphatic interrupted by a ring oxygen or a second ring nitrogen, and M is hydrogen or one equivalent or a pharmaceutically acceptable cation, in which case the rest of the molecule is negatively charged.

U.S. Pat. No. 5,294,430 to Borch et al., incorporated herein by this reference, discloses additional dithiocarbamates for treatment of myelosuppression. In general, these are compounds of Formula (D-I):

(D-I)

wherein:

(i) $R^1$ and $R^2$ are the same or different $C_1$-$C_6$ alkyl groups, $C_3$-$C_6$ cycloalkyl groups, or $C_5$-$C_6$ heterocycloalkyl groups; or (ii) one of $R^1$ and $R^2$, but not both, can be H; or (iii) $R^1$ and $R^2$ taken together with the nitrogen atom can be a 5-membered or 6-membered N-heterocyclic ring which is aliphatic or aliphatic interrupted by a ring oxygen or a second ring nitrogen; and (iv) M is hydrogen or one equivalent of a pharmaceutically acceptable cation, in which case the rest of the molecule is negatively charged; or (v) M is a moiety of Formula (D-II):

(D-II)

wherein $R^3$ and $R^4$ are defined in the same manner as $R^1$ and $R^2$. Where the group defined by Formula (D-I) is an anion, the cation can be an ammonium cation or can be derived from a monovalent or divalent metal such as an alkali metal or an alkaline earth metal, such as $Na^+$, $K^+$, or $Zn^{+2}$. In the case of the dithiocarbamic acids, the group defined by Formula (D-I) is linked to an ionizable hydrogen atom; typically, the hydrogen atom will dissociate at a pH above about 5.0. Among dithiocarbamates that can be used are: N-methyl,N-ethyldithiocarbamates, hexamethylenedithiocarbamic acid, sodium di(β-hydroxyethyl)dithiocarbamate, various dipropyl, dibutyl and diamyl dithiocarbamates, sodium N-methyl,N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, α-furfuryl dithiocarbamates and imidazoline dithiocarbamates. Another alternative is a compound where $R^1$ of Formula (D-I) is a hydroxy-substituted or, preferably, a (bis to penta) polyhydroxy-substituted lower alkyl group having up to 6 carbon atoms. For example, $R^1$ can be $HO-CH_2-CHOH-CHOH-CHOH-CHOH-CH_2-$. In such compounds, $R^2$ can be H or lower alkyl (unsubstituted or substituted with one or more hydroxyl groups). Steric problems can be minimized when $R^2$ is H, methyl, or ethyl. Accordingly, a particularly preferred compound of this type is an N-methyl-glucamine dithiocarbamate salt, the most preferred cations of these salts being sodium or potassium. Other preferred dithiocarbamates include the alkali or alkaline earth metal salts wherein the anion is di-n-butyldithiocarbamate, di-n-propyldithiocarbamate, pentamethylenedithiocarbamate, or tetramethylene dithiocarbamate.

When the improvement is made by use with an agent that increases the ability of the substituted hexitol to pass through the blood-brain barrier to treat brain metastases of NSCLC or ovarian cancer, the agent that increases the ability of the substituted hexitol to pass through the blood-brain barrier can be, but is not limited to, an agent selected from the group consisting of:

(a) a chimeric peptide of the structure of Formula (D-III):

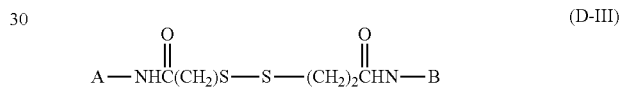

(D-III)

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

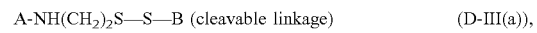

A-NH(CH$_2$)$_2$S—S—B (cleavable linkage)          (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

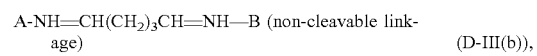

A-NH=CH(CH$_2$)$_3$CH=NH—B (non-cleavable linkage)          (D-III(b)), wherein the bridge is formed using glutaraldehyde as the bridge reagent;

(b) a composition comprising either avidin or an avidin fusion protein bonded to a biotinylated substituted hexitol derivative to form an avidin-biotin-agent complex including therein a protein selected from the group consisting of insulin, transferrin, an anti-receptor monoclonal antibody, a cationized protein, and a lectin;

(c) a neutral liposome that is pegylated and incorporates the substituted hexitol derivative, wherein the polyethylene glycol strands are conjugated to at least one transportable peptide or targeting agent;

(d) a humanized murine antibody that binds to the human insulin receptor linked to the substituted hexitol derivative through an avidin-biotin linkage; and (e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the substituted hexitol by a covalent link to biotin.

Agents that improve penetration of the blood-brain barrier are disclosed in W. M. Pardridge, "The Blood-Brain Barrier: Bottleneck in Brain Drug Development," *NeuroRx* 2: 3-14 (2005), incorporated herein by this reference.

One class of these agents is disclosed in U.S. Pat. No. 4,801,575 to Pardridge, incorporated herein by this reference, which discloses chimeric peptides for delivery of agents across the blood-brain barrier. These chimeric peptides include peptides of the general structure of Formula (D-IV):

(D-IV)

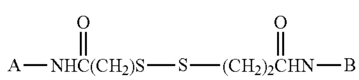

wherein:

(i) A is somatostatin, thyrotropin releasing hormone (TRH), vasopressin, alpha interferon, endorphin, muramyl dipeptide or ACTH 4-9 analogue; and (ii) B is insulin, IGF-I, IGF-II, transferrin, cationized (basic) albumin or prolactin.

In another alternative, the disulfide conjugating bridge between A and B is replaced with a bridge of Subformula (D-IV(a)):

$A\text{-}NH(CH_2)_2S—S—B$ (cleavable linkage) (D-IV(a));

the bridge of Subformula (D-III(a)) is formed when cysteamine and EDAC are employed as the bridge reagents. In yet another alternative, the disulfide conjugating bridge between A and B is replaced with a bridge of Subformula (D-IV(b)):

$A\text{-}NH{=}CH(CH_2)_3CH{=}NH—B$ (non-cleavable linkage) (D-IV(b));

the bridge of Subformula (D-III(b)) is formed when glutaraldehyde is employed as the bridge reagent.

U.S. Pat. No. 6,287,792 to Pardridge et al., incorporated herein by this reference, discloses methods and compositions for delivery of agents across the blood-brain barrier comprising either avidin or an avidin fusion protein bonded to a biotinylated agent to form an avidin-biotin-agent complex. The avidin fusion protein can include the amino acid sequences of proteins such as insulin or transferrin, an anti-receptor monoclonal antibody, a cationized protein, or a lectin.

U.S. Pat. No. 6,372,250 to Pardridge, incorporated herein by this reference, discloses methods and compositions for delivery of agents across the blood-brain barrier employing liposomes. The liposomes are neutral liposomes. The surface of the neutral liposomes is pegylated. The polyethylene glycol strands are conjugated to transportable peptides or other targeting agents. Suitable targeting agents include insulin, transferrin, insulin-like growth factor, or leptin. Alternatively, the surface of the liposome could be conjugated with 2 different transportable peptides, one peptide targeting an endogenous BBB receptor and the other targeting an endogenous BCM (brain cell plasma membrane) peptide. The latter could be specific for particular cells within the brain, such as neurons, glial cells, pericytes, smooth muscle cells, or microglia. Targeting peptides may be endogenous peptide ligands of the receptors, analogues of the endogenous ligand, or peptidomimetic MAbs that bind the same receptor of the endogenous ligand. Transferrin receptor-specific peptidomimetic monoclonal antibodies can be used as transportable peptides. Monoclonal antibodies to the human insulin receptor can be used as transportable peptides. The conjugation agents which are used to conjugate the blood-barrier targeting agents to the surface of the liposome can be any of the well-known polymeric conjugation agents such as sphingomyelin, polyethylene glycol (PEG) or other organic polymers, with PEG preferred. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol. The transportable peptide is linked to the liposome as follows: A transportable peptide such as insulin or an HIRMAb is thiolated and conjugated to a maleimide group on the tip of a small fraction of the PEG strands; or, surface carboxyl groups on a transportable peptide such as transferrin or a TfRMAb are conjugated to a hydrazide (Hz) moiety on the tip of the PEG strand with a carboxyl activator group such as N-methyl-N'-3(dimethylaminopropyl)carbodiimide hydrochloride (EDAC); a transportable peptide is thiolated and conjugated via a disulfide linker to the liposome that has been reacted with N-succinimidyl 3-(2-pyridylthio)propionate (SPDP); or a transportable peptide is conjugated to the surface of the liposome with avidin-biotin technology, e.g., the transportable peptide is mono-biotinylated and is bound to avidin or streptavidin (SA), which is attached to the surface of the PEG strand.

U.S. Pat. No. 7,388,079 to Pardridge et al., incorporated herein by this reference, discloses the use of a humanized murine antibody that binds to the human insulin receptor; the humanized murine antibody can be linked to the agent to be delivered through an avidin-biotin linkage.

U.S. Pat. No. 8,124,095 to Pardridge et al., incorporated herein by this reference, discloses monoclonal antibodies that are capable of binding to an endogenous blood-brain barrier receptor-mediated transport system and are thus capable of serving as a vector for transport of a therapeutic agent across the BBB. The monoclonal antibody can be, for example, an antibody specifically binding the human insulin receptor on the human BBB.

United States Patent Application Publication No. 2005/0085419 by Morrison et al., incorporated herein by this reference, discloses a fusion protein for delivery of a wide variety of agents to a cell via antibody-receptor-mediated endocytosis comprises a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative. Typically, the antigen is a protein. Typically, the protein antigen on the surface of the cell is a receptor such as a transferrin receptor—or an insulin receptor. The invention also includes an antibody construct incorporating the fusion protein that is either a heavy chain or a light chain together with a complementary light chain or heavy chain to form an intact antibody molecule. Therapeutic agent can be a non-protein molecule and can be linked covalently to biotin.

Another aspect of the present invention is a composition to improve the efficacy and/or reduce the side effects of suboptimally administered drug therapy employing a substituted hexitol derivative for the treatment of NSCLC or ovarian cancer comprising an alternative selected from the group consisting of:

(i) a therapeutically effective quantity of a modified substituted hexitol derivative or a derivative, analog, or prodrug of a substituted hexitol derivative or a modified substituted hexitol derivative, wherein the modified substituted hexitol derivative or the derivative, analog or prodrug of the substituted hexitol derivative or modified substituted hexitol derivative possesses increased therapeutic efficacy or reduced side effects for treatment of NSCLC or ovarian cancer as compared with an unmodified substituted hexitol derivative;

(ii) a composition comprising:
 (a) a therapeutically effective quantity of a substituted hexitol derivative, a modified substituted hexitol derivative, or a derivative, analog, or prodrug of a substituted hexitol derivative or a modified substituted hexitol derivative; and
 (b) at least one additional therapeutic agent, therapeutic agent subject to chemosensitization, therapeutic agent subject to chemopotentiation, diluent, excipient, solvent system, drug delivery system, agent to counteract myelosuppression, or agent that increases the ability of the substituted hexitol to pass through the blood-brain barrier, wherein the composition possesses increased therapeutic efficacy or reduced side effects for treatment of NSCLC or ovarian cancer as compared with an unmodified substituted hexitol derivative;

(iii) a therapeutically effective quantity of a substituted hexitol derivative, a modified substituted hexitol derivative or a derivative, analog, or prodrug of a substituted hexitol derivative or a modified substituted hexitol derivative that is incorporated into a dosage form, wherein the substituted hexitol derivative, the modified substituted hexitol derivative or the derivative, analog, or prodrug of a substituted hexitol derivative or a modified substituted hexitol derivative incorporated into the dosage form possesses increased therapeutic efficacy or reduced side effects for treatment of NSCLC or ovarian cancer as compared with an unmodified substituted hexitol derivative;

(iv) a therapeutically effective quantity of a substituted hexitol derivative, a modified substituted hexitol derivative or a derivative, analog, or prodrug of a substituted hexitol derivative or a modified substituted hexitol derivative that is incorporated into a dosage kit and packaging, wherein the substituted hexitol derivative, the modified substituted hexitol derivative or the derivative, analog, or prodrug of a substituted hexitol derivative or a modified substituted hexitol derivative incorporated into the dosage kit and packaging possesses increased therapeutic efficacy or reduced side effects for treatment of NSCLC or ovarian cancer as compared with an unmodified substituted hexitol derivative; and (v) a therapeutically effective quantity of a substituted hexitol derivative, a modified substituted hexitol derivative or a derivative, analog, or prodrug of a substituted hexitol derivative or a modified substituted hexitol derivative that is subjected to a bulk drug product improvement, wherein substituted hexitol derivative, a modified substituted hexitol derivative or a derivative, analog, or prodrug of a substituted hexitol derivative or a modified substituted hexitol derivative subjected to the bulk drug product improvement possesses increased therapeutic efficacy or reduced side effects for treatment of NSCLC or ovarian cancer as compared with an unmodified substituted hexitol derivative.

As detailed above, typically the unmodified substituted hexitol derivative is selected from the group consisting of dianhydrogalactitol, derivatives of dianhydrogalactitol, diacetyldianhydrogalactitol, derivatives of diacetyldianhydrogalactitol, dibromodulcitol, and derivatives of dibromodulcitol. Preferably, the unmodified substituted hexitol derivative is dianhydrogalactitol.

In one alternative, a composition according to the present invention possesses increased therapeutic efficacy or reduced side effects for treatment of both NSCLC and ovarian cancer. In another alternative, a composition according to the present invention possesses increased therapeutic efficacy or reduced side effects for treatment of NSCLC. In yet another alternative, a composition according to the present invention possesses increased therapeutic efficacy or reduced side effects for treatment of ovarian cancer.

In one alternative, the composition comprises a drug combination comprising:
 (i) a substituted hexitol derivative; and
 (ii) an additional therapeutic agent selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin, oxaliplatin, or another platinum analog;
  (g) monofunctional alkylating agents;
  (h) bifunctional alkylating agents;
  (i) alkylating agents that damage DNA at a different place than does dianhydrogalactitol;
  (j) anti-tubulin agents;
  (k) antimetabolites;
  (l) berberine;
  (m) apigenin;
  (n) amonafide;
  (o) colchicine or analogs;
  (p) genistein;
  (q) etoposide;
  (r) cytarabine;
  (s) camptothecins;
  (t) vinca alkaloids;
  (u) 5-fluorouracil;
  (v) curcumin;
  (w) NF-κB inhibitors;
  (x) rosmarinic acid;
  (y) mitoguazone;
  (z) tetrandrine;
  (aa) temozolomide;
  (ab) VEGF inhibitors;
  (ac) cancer vaccines;
  (ad) EGFR inhibitors;
  (ae) tyrosine kinase inhibitors;

(af) poly (ADP-ribose) polymerase (PARP) inhibitors; and
(ag) ALK inhibitors.

These additional agents described above can be used in compositions including drug combinations together with the substituted hexitol derivative for treatment of either NSCLC or ovarian cancer. The additional agent to be included is one that is either known to possess activity against the type of cancer being treated (NSCLC or ovarian cancer), is structurally related to a compound or a class of compounds known to possess activity against the type of cancer being treated, or is known to modulate a pathway for which modulation has been shown to be effective against the type of cancer being treated. As used herein, the term "modulation" can include either activation or inhibition of the pathway involved, but typically refers to inhibition of the pathway.

When compositions according to the present invention are intended for treatment of ovarian cancer, drug combinations included in the compositions can include a substituted hexitol derivative as described above together with an additional agent that possesses anti-neoplastic activity against ovarian tumors. Such additional agents include, but are not limited to, paclitaxel, docetaxel, cisplatin, carboplatin, topotecan, gemcitabine, bleomycin, etoposide, doxorubicin (which can be used in a pegylated liposomal form), tamoxifen, letrozole, olaparib, selumetinib, mTOR inhibitors, PI3 kinase inhibitors, and trichostatin A.

Additional agents that possess anti-neoplastic activity against NSCLC are known in the art. These additional agents can be included in compositions that include drug combinations according to the present invention in a therapeutically effective quantity together with a therapeutically effective quantity of a substituted hexitol derivative as described above. One or more than one of these additional agents can be included in the composition in the drug combination. These additional agents can be included in the composition together with one or more of the agents as described above for activity against NSCLC in drug combinations including a substituted hexitol derivative such as dianhydrogalactitol or diacetyldianhydrogalactitol. The agents are those collectively referred to herein as "Additional Secondary Agents with Activity Against NSCLC."

Additional agents that possess anti-neoplastic activity against ovarian cancer are known in the art. These additional agents can be included in compositions that include drug combinations according to the present invention in a therapeutically effective quantity together with a therapeutically effective quantity of a substituted hexitol derivative as described above. One or more than one of these additional agents can be included in the composition in the drug combination. These additional agents can be included in the composition together with one or more of the agents as described above for activity against ovarian cancer in drug combinations including a substituted hexitol derivative such as dianhydrogalactitol or diacetyldianhydrogalactitol. The agents are those collectively referred to herein as "Additional Secondary Agents with Activity Against Ovarian Cancer."

In another alternative, the composition comprises:
(i) a substituted hexitol derivative; and
(ii) a therapeutic agent subject to chemosensitization selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin, oxaliplatin, or another platinum analog;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) topoisomerase inhibitors;
(t) 5-fluorouracil;
(u) curcumin;
(v) NF-κB inhibitors;
(w) rosmarinic acid;
(x) mitoguazone;
(y) tetrandrine;
(z) a tyrosine kinase inhibitor;
(aa) an inhibitor of EGFR; and
(ab) an inhibitor of PARP;
wherein the substituted hexitol derivative acts as a chemosensitizer.

In still another alternative, the composition comprises:
(i) a substituted hexitol derivative; and
(ii) a therapeutic agent subject to chemopotentiation selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin, oxaliplatin, or another platinum analog;
(g) alkylating agents;
(h) anti-tubulin agents;
(i) antimetabolites;
(j) berberine;
(k) apigenin;
(l) amonafide;
(m) colchicine or analogs;
(n) genistein;
(o) etoposide;
(p) cytarabine;
(q) camptothecins;
(r) vinca alkaloids;
(s) 5-fluorouracil;
(t) curcumin;
(u) NF-κB inhibitors;
(v) rosmarinic acid;
(w) mitoguazone;
(x) tetrandrine;
(y) a tyrosine kinase inhibitor;
(z) an inhibitor of EGFR; and
(aa) an inhibitor of PARP;
wherein the substituted hexitol derivative acts as a chemopotentiator.

In yet another alternative, the substituted hexitol derivative is subjected to a bulk drug product improvement, wherein the bulk drug product improvement is selected from the group consisting of:
(a) salt formation;
(b) preparation as a homogeneous crystal structure;
(c) preparation as a pure isomer;
(d) increased purity;

(e) preparation with lower residual solvent content; and
(f) preparation with lower residual heavy metal content.

In still another alternative, the composition comprises a substituted hexitol derivative and a diluent, wherein the diluent is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In still another alternative, the composition comprises a substituted hexitol derivative and a solvent system, wherein the solvent system is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In yet another alternative, the composition comprises a substituted hexitol derivative and an excipient, wherein the excipient is selected from the group consisting of:
(a) mannitol;
(b) albumin;
(c) EDTA;
(d) sodium bisulfite;
(e) benzyl alcohol;
(f) a carbonate buffer; and
(g) a phosphate buffer.

In still another alternative, the substituted hexitol derivative is incorporated into a dosage form selected from the group consisting of:
(a) tablets;
(b) capsules;
(c) topical gels;
(d) topical creams;
(e) patches;
(f) suppositories; and
(g) lyophilized dosage fills.

In yet another alternative, the substituted hexitol derivative is incorporated into a dosage kit and packaging selected from the group consisting of amber vials to protect from light and stoppers with specialized coatings to improve shelf-life stability.

In still another alternative, the composition comprises a substituted hexitol derivative and a drug delivery system selected from the group consisting of:
(a) nanocrystals;
(b) bioerodible polymers;
(c) liposomes;
(d) slow release injectable gels; and
(e) microspheres.

In still another alternative, the substituted hexitol derivative is present in the composition in a drug conjugate form selected from the group consisting of:
(a) a polymer system;
(b) polylactides;
(c) polyglycolides;
(d) amino acids;
(e) peptides; and
(f) multivalent linkers.

In yet another alternative, therapeutic agent is a modified substituted hexitol derivative and the modification is selected from the group consisting of:
(a) alteration of side chains to increase or decrease lipophilicity;
(b) addition of an additional chemical functionality to alter a property selected from the group consisting of reactivity, electron affinity, and binding capacity; and
(c) alteration of salt form.

In still another alternative, the substituted hexitol derivative is in the form of a prodrug system, wherein the prodrug system is selected from the group consisting of:
(a) the use of enzyme sensitive esters;
(b) the use of dimers;
(c) the use of Schiff bases;
(d) the use of pyridoxal complexes; and
(e) the use of caffeine complexes.

In yet another alternative, the composition comprises a substituted hexitol derivative and at least one additional therapeutic agent to form a multiple drug system, wherein the at least one additional therapeutic agent is selected from the group consisting of:
(a) an inhibitor of multi-drug resistance;
(b) a specific drug resistance inhibitor;
(c) a specific inhibitor of a selective enzyme;
(d) a signal transduction inhibitor;
(e) an inhibitor of a repair enzyme; and
(f) a topoisomerase inhibitor with non-overlapping side effects.

In yet another alternative, the composition comprises a substituted hexitol derivative and an agent to counteract myelosuppression as described above. Typically, the agent to counteract myelosuppression is a dithiocarbamate.

In yet another alternative, the composition comprises a substituted hexitol derivative and an agent that increases the ability of the substituted hexitol to pass through the blood-brain barrier as described above. Typically, the agent that increases the ability of the substituted hexitol to pass through the blood-brain barrier is an agent selected from the group consisting of:
(a) a chimeric peptide of the structure of Formula (D-III):

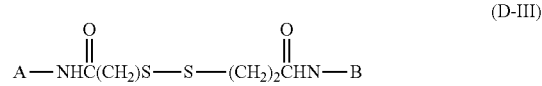

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

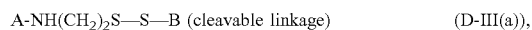

wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

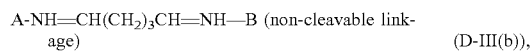

wherein the bridge is formed using glutaraldehyde as the bridge reagent;
  (b) a composition comprising either avidin or an avidin fusion protein bonded to a biotinylated substituted hexitol derivative to form an avidin-biotin-agent complex including therein a protein selected from the group consisting of insulin, transferrin, an anti-receptor monoclonal antibody, a cationized protein, and a lectin;
  (c) a neutral liposome that is pegylated and incorporates the substituted hexitol derivative, wherein the polyethylene glycol strands are conjugated to at least one transportable peptide or targeting agent;
  (d) a humanized murine antibody that binds to the human insulin receptor linked to the substituted hexitol derivative through an avidin-biotin linkage; and
  (e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the substituted hexitol by a covalent link to biotin.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent, such as a substituted hexitol derivative such as dianhydrogalactitol or an analog or derivative of dianhydrogalactitol as described above, that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., $20^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight. Other dosages are as described above.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg. Typically, doses are from about 1 mg/m$^2$ to about 40 mg/m$^2$. Preferably, doses are from about 5 mg/m$^2$ to about 25 mg/m$^2$. Additional alternatives for dosages are as described above with respect to schedules of administration and dose modification. Dosages can be varied according to therapeutic response. As described further below, when dianhydrogalactitol and a platinum-containing anti-neoplastic agent are administered at the same time or close together in time, the dosages of the dianhydrogalactitol and the platinum-containing anti-neoplastic agent can be selected to provide a synergistic or superadditive effect.

Plasma concentrations in the subjects may be between about 100 μM to about 1000 μM. In some embodiments, the plasma concentration may be between about 200 μM to about 800 μM. In other embodiments, the concentration is about 300 μM to about 600 μM. In still other embodiments the plasma concentration may be between about 400 to about 800 μM. In another alternative, the plasma concentration can be between about 0.5 μM to about 20 μM, typically 1 μM to about 10 μM. Administration of prodrugs is typically dosed at weight levels, which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-α-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing therapeutic agent. Various sustained-release materials have been established and are known by those skilled in the art. Sustained-release capsules may, depending on their chemical nature, release the compounds for a few weeks up to over 100 days; in other alternatives, depending on therapeutic agent and the formulation employed, release may occur over hours, days, weeks, or months. Depending on the chemical nature and the biological stability of therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated. In the case of NSCLC, the clinical parameters can include, but are not limited to, reduction in tumor burden, reduction in pain, improvement in lung function, improvement in Karnofsky Performance Score, and reduction in occurrence of tumor spread or metastasis. In the case of ovarian cancer, the similar clinical parameters can be applied, such as reduction in tumor burden, reduction in pain, reduction in abdominal symptoms, reduction in urinary tract symptoms, improvement in Karnofsky Performance Score, and reduction in occurrence of tumor spread or metastasis. As used herein, the terms "treatment," "treating," or equivalent terminology are not intended to imply a permanent cure for the disease, disorder, or condition being treated. Compositions and methods according to the present invention are not limited to treatment of humans, but are applicable to treatment of socially or economically important animals, such as dogs, cats, horses, cows, sheep, goats, pigs, and other animal species of social or economic importance. Unless specifically stated, compositions and methods according to the present invention are not limited to the treatment of humans.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining therapeutic effectiveness of such pharmacologically active agents and pharmaceutical compositions, are all incorporated herein by this reference.

In view of the results reported in the Examples below, another aspect of the present invention is a method of treating NSCLC comprising the step of administering a therapeutically effective quantity of a substituted hexitol derivative such as dianhydrogalactitol to a patient suffering from the malignancy.

Typically, when the substituted hexitol derivative is dianhydrogalactitol, therapeutically effective quantity of dianhydrogalactitol is from about 1 mg/m$^2$ to about 40 mg/m$^2$. Preferably, therapeutically effective quantity of dianhydrogalactitol is from about 5 mg/m$^2$ to about 25 mg/m$^2$. Therapeutically active quantities of substituted hexitol derivatives other than dianhydrogalactitol can be determined by one of ordinary skill in the art by using the molecular weight of the particular substituted hexitol derivative and the activity of the particular substituted hexitol derivative, such as the in vitro activity of the substituted hexitol derivative against a standard cell line. Other suitable dosages are described above with respect to dose modification and schedule of administration and also in the Examples.

Typically, the substituted hexitol derivative such as dianhydrogalactitol is administered by a route selected from the group consisting of intravenous and oral. Preferably, the substituted hexitol derivative such as dianhydrogalactitol is administered intravenously.

The method can further comprise the step of administering a therapeutically effective dose of ionizing radiation. The method can further comprise the step of administering a therapeutically effective dose of an additional chemotherapeutic agent selected from the group consisting of cisplatin, carboplatin, oxaliplatin, bevacizumab, paclitaxel, Abraxane (paclitaxel bound to albumin as a delivery vehicle), docetaxel, etoposide, gemcitabine, vinorelbine tartrate, and pemetrexed. Suitable methods for administration of these agents and suitable dosages are well known in the art.

Typically, the substituted hexitol derivative such as dianhydrogalactitol substantially suppresses the growth of cancer stem cells (CSCs). Typically, the suppression of the growth of cancer stem cells is at least 50%. Preferably, the suppression of the growth of cancer stem cells is at least 99%.

Typically, the substituted hexitol derivative such as dianhydrogalactitol is effective in suppressing the growth of cancer cells possessing O$^6$-methylguanine-DNA methyltransferase (MGMT)-driven drug resistance. Typically, the substituted hexitol derivative such as dianhydrogalactitol is also effective in suppressing the growth of cancer cells resistant to temozolomide.

The method can further comprise the administration of a therapeutically effective quantity of a tyrosine kinase inhibitor as described above.

The method can further comprise the administration of a therapeutically effective quantity of an epidermal growth factor receptor (EGFR) inhibitor as described above. The EGFR inhibitor can affect either wild-type binding sites or mutated binding sites, including EGFR Variant III, as described above.

Additionally, to treat brain metastases of NSCLC, the method can further comprise administering to the patient a therapeutically effective quantity of an agent that increases the ability of the substituted hexitol to pass through the blood-brain barrier. Alternatively, the method can further comprise administering to the patient a therapeutically effective quantity of an agent to counteract myelosuppression.

In view of the results reported in the Examples below, another aspect of the present invention is a method of treating ovarian cancer comprising the step of administering a therapeutically effective quantity of a substituted hexitol derivative such as dianhydrogalactitol to a patient suffering from the malignancy.

Typically, when the substituted hexitol derivative is dianhydrogalactitol, therapeutically effective quantity of dianhydrogalactitol is from about 1 mg/m$^2$ to about 40 mg/m$^2$. Preferably, therapeutically effective quantity of dianhydrogalactitol is from about 5 mg/m$^2$ to about 25 mg/m$^2$. Therapeutically active quantities of substituted hexitol derivatives other than dianhydrogalactitol can be determined by one of ordinary skill in the art by using the molecular weight of the particular substituted hexitol derivative and the activity of the particular substituted hexitol derivative, such as the in vitro activity of the substituted hexitol derivative against a standard cell line. Other suitable dosages are described above with respect to dose modification and schedule of administration and also in the Examples.

Typically, the substituted hexitol derivative such as dianhydrogalactitol is administered by a route selected from the group consisting of intravenous and oral. Preferably, the substituted hexitol derivative such as dianhydrogalactitol is administered intravenously.

The method can further comprise the step of administering a therapeutically effective dose of ionizing radiation. The method can further comprise the step of administering a therapeutically effective dose of an additional chemotherapeutic agent selected from the group consisting of cisplatin, carboplatin, oxaliplatin, bevacizumab, paclitaxel, Abraxane (paclitaxel bound to albumin as a delivery vehicle), docetaxel, etoposide, gemcitabine, vinorelbine tartrate, and pemetrexed. Suitable methods for administration of these agents and suitable dosages are well known in the art. When ovarian cancer is treated, additional therapeutic agents that are or may be effective against ovarian cancer can also be administered; these agents are described in further detail below.

Typically, the substituted hexitol derivative such as dianhydrogalactitol substantially suppresses the growth of cancer stem cells (CSCs). Typically, the suppression of the growth of cancer stem cells is at least 50%. Preferably, the suppression of the growth of cancer stem cells is at least 99%.

Typically, the substituted hexitol derivative such as dianhydrogalactitol is effective in suppressing the growth of cancer cells possessing $O^6$-methylguanine-DNA methyltransferase (MGMT)-driven drug resistance. Typically, the substituted hexitol derivative such as dianhydrogalactitol is also effective in suppressing the growth of cancer cells resistant to temozolomide.

The method can further comprise the administration of a therapeutically effective quantity of a tyrosine kinase inhibitor as described above.

Typically, the effect of administration of dianhydrogalactitol and a platinum-containing agent selected from the group consisting of cisplatin and oxaliplatin is at least additive. In some cases, the effect of administration of both of these agents is super-additive.

As stated above and as provided below in the Examples, substituted hexitol derivatives such as dianhydrogalactitol can also be used to treat ovarian cancer.

The risk of ovarian cancer increases with the frequency and duration of ovulation. Other risk factors include postmenopausal hormone therapy, fertility medication, and obesity. About 10% of the cases are related to increased genetic risk; women with the genetic mutations BRCA1 or BRCA2 can have up to a 50% risk of developing ovarian cancer. Such mutations occur more frequently in individuals with certain particular ethnic backgrounds, such as Ashkenazi Jews (Jews who can trace their ancestry to regions such as Germany, Austria, Poland, Hungary, Romania, the Czech Republic, Slovakia, Ukraine, Belarus, Lithuania, Latvia, or Russia), although they can occur in individuals with any ethnic background.

The most common type of ovarian cancer, comprising more than 95% of cases, is ovarian carcinoma. There are five main subtypes of ovarian carcinoma, of which high-grade serous is most common. These tumors are believed to start in the cells covering the ovaries, though some may form at the Fallopian tubes. Less common types include germ cell tumors and sex cord stromal tumors. As symptoms of ovarian cancer are frequently absent in early stages of the disease and, if present, are typically generic and not clearly attributable to ovarian cancer, confirmation requires a biopsy.

Current treatment modalities include some combination of surgery, radiotherapy, and chemotherapy. However, the overall five-year survival rate in the United States is only about 45%. Current chemotherapies used for ovarian cancer include paclitaxel, docetaxel, cisplatin, carboplatin, gemcitabine, topotecan, etoposide, and doxorubicin. Other platinum-containing drugs, such as oxaliplatin, satraplatin, picoplatin, nedaplatin, triplatin, and lipoplatin can also be used.

Olaparib, a PARP inhibitor, has been recently developed for ovarian cancer chemotherapy. However, in a substantial fraction of the cases, the tumor develops resistance to platinum-containing drugs. In cases of recurrent malignancy, carboplatin can also be combined with gemcitabine or paclitaxel. Tamoxifen or letrozole can be used, but are generally ineffective. Still other drugs such as selumetinib, mTOR inhibitors, and PI3 kinase inhibitors have been proposed. Additionally, histone deacetylase (HDAC) inhibitors such as trichostatin A have also been proposed as anti-ovarian cancer agents.

For most ovarian cancers, monitoring is performed by assessing the level of an antigen known as CA-125, also known as mucin 16, encoded by MUC16. This antigen is a protein antigen that is a membrane associated mucin that contains a single transmembrane domain.

Accordingly, one aspect of the present invention is a method of treating ovarian cancer comprising the step of administering a therapeutically effective quantity of a substituted hexitol derivative to a patient suffering from ovarian cancer. Suitable substituted hexitol derivatives are as described above; a particularly preferred substituted hexitol derivative is dianhydrogalactitol. Typically, therapeutically effective quantity of dianhydrogalactitol is a quantity of dianhydrogalactitol that results in a dosage of from about 1 mg/m² to about 40 mg/m². Preferably, therapeutically effective quantity of dianhydrogalactitol is a quantity of dianhydrogalactitol that results in a dosage of from about 5 mg/m² to about 25 mg/m². Typically, the dianhydrogalactitol is administered by a route selected from the group consisting of intravenous and oral.

In one alternative, the ovarian cancer is a cisplatin-resistant wild-type p53 cancer.

In methods according to the present invention, a substituted hexitol as described above can be employed in a therapeutically effective quantity together with a therapeutically effective quantity of one or more antineoplastic agents for the treatment of ovarian cancer. Typically, as described above, the substituted hexitol is dianhydrogalactitol. Suitable agents that possess anti-neoplastic activity against ovarian tumors include, but are not limited to: paclitaxel, docetaxel, cisplatin, carboplatin, topotecan, gemcitabine, bleomycin, etoposide, doxorubicin (which can be used in a pegylated liposomal form), tamoxifen, letrozole, olaparib, selumetinib, mTOR inhibitors, PI3 kinase inhibitors, and trichostatin A.

Typically, the substituted hexitol derivative suppresses the growth of cancer stem cells. Typically, the substituted hexitol derivative suppresses the growth of cancer cells possessing $O^6$-methylguanine-DNA methyltransferase (MGMT)-driven drug resistance.

In another alternative, the method further comprises the step of administering a therapeutically effective quantity of a platinum-containing chemotherapeutic agent and wherein the platinum-containing chemotherapeutic agent is selected from the group consisting of cisplatin, carboplatin, iproplatin, oxaliplatin, tetraplatin, satraplatin, picoplatin, nedaplatin, and triplatin.

Additional agents that possess anti-neoplastic activity against ovarian tumors are known in the art. U.S. Pat. No. 8,981,131 to Bhedi et al., discloses the use of tricyclic compounds such as (5aR,9bS)-3a-hydroxy-5a,9-dimethyl-3-((4-methylpiperazin-1-yl)methyl)-3,3a,4,5,5a,6,7,8-octahydronaphtho[1,2-b]furan-2(9bH)-one hydrochloride; ethyl 4-(((5aR,9bS)-3a-hydroxy-5a,9-dimethyl-2-oxo-2,3,3a,4,5, 5a,6,7,8,9b-decahydronaphtha[1,2-b]furan-3-yl)methyl)piperazine-1-carboxylate hydrochloride; (5aR,9bS)-3a-hydroxy-5a,9-dimethyl-3-((4-o-tolylpiperazin-1-yl)methyl)-3,3a,4,5,5a,6,7,8-octahydronaphtho[1,2-b]furan-2(9bH)-one hydrochloride; or (5aR,9bR)-3a-hydroxy-3-((((5aR,9bS)-3a-hydroxy-5a,9-dimethyl-2-oxo-2,3,3a,4,5,5a,6,7,8,9b-decahydronaphtho[1,2-b]furan-3-yl)methylamino)methyl)-5a,9-dimethyl-3,3a,4,5,5a,6,7,8-octahydronaphtho[1,2-b]furan-2(9bH)-one hydrochloride). U.S. Pat. No. 8,981,094 to Bongartz et al. discloses the use of piperidine/piperazine derivatives that are DGAT inhibitors, particularly DGAT1 inhibitors. U.S. Pat. No. 8,981,085 to Le Huerou et al. discloses the use of pyrrolopyrimidine CHK1 or CHK2 inhibitors. U.S. Pat. No. 8,981,084 to Balogu et al. discloses the use of oxadiazole HDAC inhibitors. U.S. Pat. No. 8,980,955 to Turchi et al. discloses the use of inhibitors of Replication Protein A that are haloester isoborneol derivatives. U.S. Pat. No. 8,980,934 to Pauls et al. discloses the use of indazole inhibitors of TTK protein kinase. U.S. Pat. No. 8,980,933 to Schobert et al. discloses the use of combretastatin analogs. U.S. Pat. No. 8,980,909 to Chen et al. discloses the use of HDAC inhibiting derivatives of camptothecin. U.S. Pat. No. 8,980,902 to Brown et al. discloses the use of piperazinylbenzamide PARP inhibitors. U.S. Pat. No. 8,980,879 to Liu et al. discloses the use of BET bromodomain inhibitors including 5-(cyclopropylmethyl)-11-methyl-8-((methylsulfonyl)methyl)-2,4,5,11-tetrahydro-1H-2,5,11-triazadibenzo[cd,h]azulen-1-one; 5-(4-fluorophenyl)-11-methyl-8-((methylsulfonyl)methyl)-2,4,5,11-tetrahydro-1H-2,5,11-triazadibenzo[cd,h]azulen-1-one; 5-(2,4-difluorophenyl)-11-methyl-8-((methylsulfonyl)methyl)-2,4,5,11-tetrahydro-1H-2,5,11-triazadibenzo[cd,h]azulen-1-one; 5-(cyclopropanecarbonyl)-11-methyl-8-((methylsulfonyl)methyl)-2,4,5,11-tetrahydro-1H-2,5,11-triazadibenzo[cd,h]azulen-1-one; 5-(4-fluorophenyl)-4-(2-methoxyethyl)-11-methyl-8-((methylsulfonyl)methyl)-2,4,5,11-tetrahydro-1H-2,5,11-triazadibenzo[cd,h]azulen-1-one; methyl 3-(5-(4-fluorophenyl)-11-methyl-8-((methylsulfonyl)methyl)-1-oxo-2,4,5,11-tetrahydro-1H-2,5,11-triazadibenzo[cd,h]azulen-4-yl)propanoate; N-(5-(4-fluorophenyl)-11-methyl-1-oxo-2,4,5,11-tetrahydro-1H-2,5,11-triazadibenzo[cd,h]azulen-8-yl)ethanesulfonamide; 8-fluoro-5-(4-fluorophenyl)-1-methyl-2,4,5,11-tetrahydro-1H-2,5,6,11-tetraazadibenzo[cd,h]azulen-1-one; N-(5-(4-fluorophenyl)-11-methyl-1-oxo-2,4,5,11-tetrahydro-1H-2,5,6,11-tetraazadibenzo[cd,h]azulen-8-yl)-2-(1-methyl-1H-pyrazol-4-yl)acetamide; 8-amino-5-(4-fluorophenyl)-1-methyl-2,4,5,11-tetrahydro-1H-2,5,11-triaza-dibenzo[cd,h]azulen-1-one; N-(5-(4-fluorophenyl)-11-methyl-1-oxo-2,4,5,11-tetrahydro-1H-2,5,11-triazadibenzo[cd,h]azulen-8-yl)benzenesulfonamide; N-(4-(N-(5-(4-fluorophenyl)-11-methyl-1-oxo-2,4,5,11-tetrahydro-1H-2,5,11-triazadibenzo[cd,h]azulen-8-yl)sulfamoyl)phenyl)acetamide. U.S. Pat. No. 8,980,875 to Mailliet et al. discloses the use of platinum N-heterocyclic carbene derivatives. U.S. Pat. No. 8,980,850 to Smith discloses the use of NEDD8-activating enzyme inhibitors such as ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or {(1 S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate. U.S. Pat. No. 8,980,838 to Wang et al. discloses the use of cyclic peptidomimetic inhibitors of the WDR5/MLL1 interaction. U.S. Pat. No. 8,980,268 to Lowy et al. discloses the use of anti-Ang-2 antibodies. U.S. Pat. No. 8,980,257 to Kaneda et al. discloses the use of anti-TGFα antibodies. U.S. Pat. No. 8,975,398 to Hansen et al. discloses the use of NAMPT inhibitors such as N-{4-[1-(2-methylpropanoyl)piperidin-4-yl]phenyl})-1-(pyridazin-3-yl)azetidine-3-carboxamide; N-(4-{[1-(2-chlorobenzoyl)piperidin-4-yl]oxy}phenyl)-1-(pyridazin-3-yl)azetidine-3-carboxamide; N-[4-({1-[(2S)-2-methylbutanoyl]piperidin-4-yl}oxy)phenyl]-1-(pyridazin-3-yl)azetidine-3-carboxamide; 1-(pyridazin-3-yl)-N-(4-{[1-(1,3-thiazol-2-ylcarbonyl)piperidin-4-yl]oxy}phenyl)azetidine-3-carboxamide; 1-(pyridazin-3-yl)-N-(4-{[1-(tetrahydro-2H-pyran-4-ylcarbonyl)piperidin-4-yl]oxy}phenyl)azetidine-3-carboxamide; N-[4-({1-[difluoro(phenyl)acetyl]piperidin-4-yl}oxy)phenyl]-1-(pyridazin-3-yl)azetidine-3-carboxamide; N-[4-({1-[(4,4-difluorocyclohexyl)carbonyl]piperidin-4-yl}oxy)phenyl]-1-(pyridazin-3-yl)azetidine-3-carboxamide; N-(4-{[1-(2-methyl-2-phenylpropanoyl)piperidin-4-yl]oxy}phenyl)-1-(pyridazin-3-yl)azetidine-3-carboxamide; 1-(pyridazin-3-yl)-N-(4-{[1-(1,3-thiazol-4-ylcarbonyl)piperidin-4-yl]oxy}phenyl)azetidine-3-carboxamide; N-[4-({1-[(5-methylthiophen-2-yl)carbonyl]piperidin-4-yl}oxy)phenyl]-1-(pyridazin-3-yl)azetidine-3-carboxamide; 1-(pyridazin-3-yl)-N-{4-[(1-{[4-(trifluoromethyl)phenyl]acetyl}piperidin-4-yl)oxy]phenyl}azetidine-3-carboxamide; 1-(pyridazin-3-yl)-N-(4-{[1-(tetrahydrofuran-2-ylcarbonyl)piperidin-4-yl]oxy}phenyl)azetidine-3-carboxamide; 1-(pyridazin-3-yl)-N-[4-({1-[3-(trifluoromethyl)benzoyl]piperidin-4-yl}oxy)phenyl]azetidine-3-carboxamide; 1-(pyridazin-3-yl)-N-(4-{[1-(thiophen-3-ylcarbonyl)piperidin-4-yl]oxy}phenyl)azetidine-3-carboxamide; 1-(pyridazin-3-yl)-N-[4-({1-[3-(trifluoromethoxy)benzoyl]piperidin-4-yl}oxy)phenyl]azetidine-3-carboxamide; N-(4-{[1-(3-methylbutanoyl)piperidin-4-yl]oxy}phenyl)-1-(pyridazin-3-yl)azetidine-3-carboxamide; 1-(pyridazin-3-yl)-N-(4-{[1-(tetrahydrofuran-3-ylcarbonyl)piperidin-4-yl]oxy}phenyl)azetidine-3-carboxamide; N-[4-({1-[(3-fluorophenyl)acetyl]piperidin-4-yl}oxy)phenyl]-1-(pyridazin-3-yl)azetidine-3-carboxamide; N-(4-{[1-(2-fluorobenzoyl)piperidin-4-yl]oxy}phenyl)-1-(pyridazin-3-yl)azetidine-3-carboxamide; N-(4-{[1-(2,4-difluorobenzoyl)piperidin-4-yl]oxy}phenyl)-1-(pyridazin-3-yl)azetidine-3-carboxamide; N-(4-{[1-(4-fluorobenzoyl)piperidin-4-yl]oxy}phenyl)-1-(pyridazin-3-yl)azetidine-3-carboxamide; and N-(4-{[1-(3-fluorobenzoyl)piperidin-4-yl]oxy}phenyl)-1-(pyridazin-3-yl)azetidine-3-carboxamide. U.S. Pat. No. 8,975,376 to Blein et al. discloses the use of anti-α$_2$-integrin antibodies. U.S. Pat. No. 8,975,287 to Karp et al. discloses the use of 1,2,4-oxadiazole benzoic acid compounds. U.S. Pat. No. 8,975,267 to Caldarelli et al. discloses the use of tricylic pyrrole derivatives such as N-(2,6-diethylphenyl)-9-(methoxymethyl)-2-{[2-methoxy-4-(4-methylpiperazin-1-yl)phenyl]amino}-8-methyl-6,9-dihydro-5H-pyrrolo[3,2-h]quinazoline-7-carboxamide, 2-[(4-bromo-2-methoxyphenyl)amino]-N-(2,6-diethylphenyl)-8,9-dimethyl-6,9-dihydro-5H-pyrrolo[3,2-h]quinazoline-7-carboxamide, N-(2,6-diethylphenyl)-2-({2-methoxy-4-[4-(pyrrolidin-1-yl)piperidin-1-yl]phenyl}amino)-8,9-dimethyl-6,9-dihydro-5H-pyrrolo[3,2-h]quinazoline-7-carboxamide, N-(2,6-diethylphenyl)-2-({4-[4-(dimethylamino)piperidin-1-yl]-2-methoxyphenyl}amino)-8,9-dimethyl-6,9-dihydro-5H-pyrrolo[3,2-h]quinazoline-7-carboxamide, N-(2,6-diethylphenyl)-2-{[2-methoxy-4-(4-methylpiperazin-1-yl)phenyl]amino}-8,9-dimethyl-6,9-dihydro-5H-pyrrolo[3,2-h]quinazoline-7-carboxamide, N-(2,6-diethylphenyl)-2-({4-[4-(2-hydroxyethyl)piperazin-1-yl]-2-methoxyphenyl}amino)-8,9-dimethyl-6,9-dihydro-5H-pyrrolo[3,2-h]quinazoline-7-carboxamide, 2-{[2-methoxy-4-(4-methylpiperazin-1-yl)phenyl]amino}-8,9-dimethyl-6,9-dihydro-5H-pyrrolo[3,2-h]quinazoline-7-carboxamide, and 2-[(4-bromo-2-methoxyphenyl)amino]-N-(2,6-diethylphenyl)-9-methyl-6,9-dihydro-5H-pyrrolo[3, 2-h]quinazoline-7-carboxamide. U.S. Pat. No. 8,974,781 to Bauer et al. discloses the use of anti-P-cadherin antibodies. U.S. Pat. No. 8,969,587 to Abraham et al. discloses the use of BRAF kinase inhibitors, such as 1-(3-(6,7-dimethoxyquinazolin-4-yloxy)phenyl)-3-(5-(1,1,1-trifluoro-2-methylpropan-2-yl)isoxazol-3-yl)urea. U.S. Pat. No. 8,969,401 to Maier et al. discloses the use of sulfonylpyrroles as HDAC inhibitors. U.S. Pat. No. 8,969,396 to Du et al. discloses the use of BRAF inhibitors including Hsp90 inhibitors such as 3-(2,4-dihydroxy-5-isopropyl-phenyl)-4-(1-methyl-indol-5-yl)-5-hydroxy-[1,2,4]triazole. U.S. Pat. No. 8,969,395 to Ribeiro Salvador et al. discloses the use of triterpenoid derivatives. U.S. Pat. No. 8,969,381 to Wilson et al. discloses the use of chemokine CXCR4 modulators such as $N^1$—(((S)-1,2,3,4-tetrahydroisoquinolin-3-yl)methyl)-$N^1$—((S)-5,6,7,8-tetrahydroquinolin-8-yl)butane-1,4-diamine; $N^1$—(((R)-1,2,3,4-tetrahydroisoquinolin-3-yl)methyl)-$N^1$—((S)-5,6,7,8-tetrahydroquinolin-8-yl)butane-1,4-diamine; $N^1$—(((S)-4-benzylpiperazin-2-yl)methyl)-$N^1$—((S)-5,6,7,8-tetrahydroquinolin-8-yl)butane-1,4-diamine; and N—(((R)-4-benzylpiperazin-2-yl)methyl)-$N^1$—((S)-5,6,7,8-tetrahydroquinolin-8-yl)butane-1,4-diamine. U.S. Pat. No. 8,969,379 to Furitsu et al. discloses the use of 4-(3-chloro-4-(cyclopropylaminocarbonyl)aminophenoxy)-7-methoxy-6-quinolinecarboxamide. U.S. Pat. No. 8,969,375 to Lai et al. discloses the use of CDK9 kinase inhibitors such as 4-[1-(3-fluorobenzyl)-2,3-dihydro-1H-indol-6-yl]-2-(piperidin-4-yl)-1H-pyrrolo[2,3-b]pyridine; 1-(3-fluorobenzyl)-6-[2-(piperidin-4-yl)-1H-pyrrolo[2,3-b]pyridin-4-yl]-1H-benzimidazole; 1-benzyl-6-[2-(piperidin-4-yl)-1H-pyrrolo[2,3-b]pyridin-4-yl]-1H-indole-3-carbonitrile; 1-(3-fluorobenzyl)-6-{2-[1-(methylsulfonyl)piperidin-4-yl]-1H-pyrrolo[2,3-b]pyridin-4-yl}-1H-benzimidazole; 6-[2-(piperidin-4-yl)-1H-pyrrolo[2,3-b]pyridin-4-yl]-1-(tetrahydro-2H-pyran-4-ylmethyl)-1H-benzimidazole; 6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole; 5-[2-(piperidin-4-yl)-1H-pyrrolo[2,3-b]pyridin-4-yl]-3-(tetrahydro-2H-pyran-4-ylmethyl)-3H-imidazo[4,5-b]pyridine; 1-(3-fluorobenzyl)-6-[2-(piperidin-4-yl)-1H-pyrrolo[2,3-b]pyridin-4-yl]-1H-indole-3-carbonitrile; 4-[5-fluoro-1-(3-fluorobenzyl)-1H-indol-6-yl]-2-(piperidin-4-yl)-1H-pyrrolo[2,3-b]pyridine; 6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile; 1-(3-fluorobenzyl)-6-{2-[1-(methylsulfonyl)piperidin-4-yl]-1H-pyrrolo[2,3-b]pyridin-4-yl}-1H-indole-3-carbonitrile; and 1-[(5-fluoropyridin-3-yl)methyl]-6-[2-(piperidin-4-yl)-1H-pyrrolo[2,3-b]pyridin-4-yl]-1H-benzimidazole. U.S. Pat. No. 8,969,366 to Marchionni et al. discloses the use of substituted pyrimidinylpyrrolopyridinone derivatives. U.S. Pat. No. 8,969,360 to Charrier et al. discloses the use of inhibitors of ATR kinase. U.S. Pat. No. 8,969,335 to Hoelzemann et al. discloses the use of inhibitors of IKKε and TBK1 including benzonitrile derivatives. U.S. Pat. No. 8,969,313 to Yu discloses the use of DACT protein activators. U.S. Pat. No. 8,962,855 to Chen et al. discloses the use of nitrogen mustard derivatives. U.S. Pat. No. 8,962,679 to Wang et al. discloses the use of daidzein derivatives including alkoxychromenon-4-ones. U.S. Pat. No. 8,962,663 to Mahadevan et al. discloses the use of pleckstrin homology domain inhibitors. U.S. Pat. No. 8,962,642 to Mortimore et al. discloses the use of 5-cyano-4-(pyrrolo[2,3-b]pyridine-3-yl)pyrimidine derivatives. U.S. Pat. No. 8,962,637 to McAllister et al. discloses the use of substituted aromatic bicyclic compounds as c-SRC/JAK inhibitors. U.S. Pat. No. 8,962,630 to Brain et al. discloses the use of pyrrolopyrimidine compounds including 7-cyclopentyl-2-(5-piperazin-1-yl-pyridin-2-ylamino)-7H-pyrrolo[2,3-d]pyrimidine-6-carboxylic acid dimethylamide as CDK protein kinase inhibitors. U.S. Pat. No. 8,962,620 to Kuntz et al. discloses the use of substituted 6,5-fused bicyclic aryl compounds. U.S. Pat. No. 8,962,619 to Ashwell et al. discloses the use of substituted imidazopyridinyl-aminopyridine compounds. U.S. Pat. No. 8,962,611 to Christopher et al. discloses the use of substituted imidazopyridines as HDM2 inhibitors. U.S. Pat. No. 8,962,608 to Brubaker et al. discloses the use of cycloalkylnitrile pyrazole carboxamides as janus kinase inhibitors. U.S. Pat. No. 8,961,966 to Schoeberl et al. discloses the use of anti-ERBB3 antibodies. U.S. Pat. No. 8,957,109 to Heaton et al. discloses the use of chroman derivatives. U.S. Pat. No. 8,957,103 to Dannhardt et al. discloses the use of conjugated 3-(indolyl)- and 3-(azaindolyl)-4-arylmaleimide compounds. U.S. Pat. No. 8,957,102 to Kim et al. discloses the use of c-Met inhibitors including 1,5-dimethyl-3-oxo-2-phenyl-2,3-dihydro-1H-pyrazole-4-carboxylic acid [3-fluoro-4-(2-phenyl-1H-pyrrolo[2,3-b]pyridin-4-yloxy)-phenyl]-amide; 2-(4-fluoro-phenyl)-1,5-dimethyl-3-oxo-2,3-dihydro-1H-pyrazole-4-carboxylic acid [3-fluoro-4-(2-phenyl-1H-pyrrolo[2,3-b]pyridin-4-yloxy)-phenyl]-amide; 2-(4-fluoro-phenyl)-1,5-dimethyl-3-oxo-2,3-dihydro-1H-pyrazole-4-carboxylic acid [3-fluoro-4-(3-phenyl-1H-pyrrolo[2,3-b]pyridin-4-yloxy)-phenyl]-amide; N-(3-fluoro-4-(2-(thiophen-2-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide; and N-(3-fluoro-4-(2-(thiophen-3-yl)-1H-pyrrolo[2,3-b]pyridin-4-yloxy)phenyl)-2-(4-fluorophenyl)-1,5-dimethyl-3-oxo-2,3-dihydro-1H-pyrazole-4-carboxamide. U.S. Pat. No. 8,957,078 to Brenchley et al. discloses the use of pyrazolopyrimidines as ATR kinase inhibitors. U.S. Pat. No. 8,957,068 to Caferro et al. discloses the use of 3-pyrimidin-4-yl-oxazolidin-2-ones as inhibitors of mutant IDH. U.S. Pat. No. 8,957,056 to Danishefsky et al. discloses the use of migrastatin analogs. U.S. Pat. No. 8,956,613 to Wu et al. discloses the use of gemcitabine prodrugs. U.S. Pat. No. 8,952,163 to Blackburn discloses the use of substituted hydroxamic acids as HDAC6 inhibitors. U.S. Pat. No. 8,952,161 to Beaton et al. discloses the use of gonadotrophin-releasing hormone receptor antagonists. U.S. Pat. No. 8,952,157 to Ding et al. discloses the use of inhibitors of anti-apoptotic Bcl-2 proteins such as 4-(4-{[2-(4-chlorophenyl)-4,4-dimethylcyclohex-1-en-1-yl]methyl}piperazin-1-yl)-2-(2,3-difluorophenoxy)-N-({4-[(3-morpholin-4-ylpropyl)amino]-3-nitrophenyl}sulfonyl)benzamide; 2-(4-amino-3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide; 4-(4-{[2-(4-chlorophenyl)-4,4-dimethylcyclohex-1-en-1-yl]methyl}piperazin-1-yl)-2-(2,5-dichlorophenoxy)-N-({4-[(3-morpholin-4-ylpropyl)amino]-3-nitrophenyl}sulfonyl)benzamide; N-(4-((4-aminotetrahydro-2H-pyran-4-yl)methylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide; 4-(4-{[2-(4-chlorophenyl)-4,4-dimethylcyclohex-1-en-1-yl]methyl}piperazin-1-yl)-2-(3-fluorophenoxy)-N-({4-[(3-morpholin-4-ylpropyl)amino]-3-nitrophenyl}sulfonyl)benzamide; 2-(2-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide; 2-(2-chloro-4-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)

amino]-3-nitrophenyl}sulfonyl)benzamide; 4-(4-{[2-(4-chlorophenyl)-4,4-dimethylcyclohex-1-en-1-yl]methyl}piperazin-1-yl)-2-(2-fluorophenoxy)-N-({4-[(3-morpholin-4-ylpropyl)amino]-3-nitrophenyl}sulfonyl)benzamide; 4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide; and 2-(3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide. U.S. Pat. No. 8,952,054 to Kufe et al. discloses the use of small molecule inhibitors of MUC1 oligomerization such as flavone derivatives. U.S. Pat. No. 8,952,043 to Blaquiere et al. discloses the use of benzoxepin PI3K inhibitors. U.S. Pat. No. 8,951,987 to Hamilton et al. discloses the use of tetrahydrouridine derivatives. U.S. Pat. No. 8,951,536 to Combs et al. discloses the use of N-hydroxyamidino heterocycles as modulators of indoleamine 2,3-dioxygenase. U.S. Pat. No. 8,946,445 to Wang discloses the use of heterocyclic apoptosis inhibitors such as (Z)-5-(2-((3,5-dimethyl-1H-pyrrol-2-yl)methylene)-3-methoxy-2H-pyrrol-5-yl)-4H-thieno[3,2-b]pyrrole (Z)-2-chloro-5-(2-((3,5-dimethyl-1H-pyrrol-2-yl)methylene)-3-methoxy-2H-pyrrol-5-yl)-4H-thieno[3,2-b]pyrrole; (Z)-5-(2-((3,5-dimethyl-1H-pyrrol-2-yl)methylene)-3-methoxy-2H-pyrrol-5-yl)-2-methyl-4H-thieno[3,2-b]pyrrole; (Z)-2-bromo-5-(2-((3,5-dimethyl-1H-pyrrol-2-yl)methylene)-3-methoxy-2H-pyrrol-5-yl)-4H-thieno[3,2-b]pyrrole; (Z)-5-(2-((3,5-dimethyl-1H-pyrrol-2-yl)methylene)-3-methoxy-2H-pyrrol-5-yl)-6H-thieno[2,3-b]pyrrole; and (Z)-5-(2-((3,5-dimethyl-1H-pyrrol-2-yl)methylene)-3-methoxy-2H-pyrrol-5-yl)-2-methyl-6H-thieno[2,3-b]pyrrole. U.S. Pat. No. 8,946,413 to Hughes et al. discloses the use of 3-aminocyclopentanecarboxamides as chemokine receptor antagonists. U.S. Pat. No. 8,946,409 to Becker et al. discloses the use of polycyclic β-lactam derivatives. U.S. Pat. No. 8,946,289 to Hong et al. discloses the use of manassatin compounds that block the HIF pathway. U.S. Pat. No. 8,946,278 to Seefeld et al. discloses the use of heterocyclic carboxamides as AkT inhibitors, such as N-((1S)-2-amino-1-{[2-(trifluoromethyl)phenyl]methyl}ethyl)-5-chloro-4-(1-methyl-1H-pyrazol-5-yl)-2-thiophenecarboxamide; N-((1S)-2-amino-1-{[2-(trifluoromethyl)phenyl]methyl}ethyl)-4-(4-bromo-1-methyl-1H-pyrazol-5-yl)-5-methyl-2-thiophenecarboxamide; N-((1S)-2-amino-1-{[2-(trifluoromethyl)phenyl]methyl}ethyl)-4-(4-chloro-1-methyl-1H-pyrazol-5-yl)-5-methyl-2-thiophenecarboxamide; N-((1S)-2-amino-1-{[2-(trifluoromethyl)phenyl]methyl}ethyl)-5-chloro-4-(4-chloro-1-methyl-1H-pyrazol-5-yl)-2-thiophenecarboxamide; N-((1S)-2-amino-1-{[2-(trifluoromethyl)phenyl]methyl}ethyl)-4-(4-bromo-1-methyl-1H-pyrazol-5-yl)-5-chloro-2-thiophenecarboxamide; N-((1S)-2-amino-1-{[2-(trifluoromethyl)phenyl]methyl}ethyl)-5-methyl-4-(1-methyl-1H-pyrazol-5-yl)-2-thiophenecarboxamide; N-((1S)-2-amino-1-{[2-(trifluoromethyl)phenyl]methyl}ethyl)-5-chloro-4-(1-ethyl-1H-pyrazol-5-yl)-2-thiophenecarboxamide; N-((1S)-2-amino-1-{[2-(trifluoromethyl)phenyl]methyl}ethyl)-5-chloro-4-(1,4-dimethyl-1H-pyrazol-5-yl)-2-thiophenecarboxamide; N-{(1S)-2-amino-1-[(3-fluorophenyl)methyl]ethyl}-5-chloro-4-(1-methyl-1H-pyrazol-5-yl)-2-thiophenecarboxamide; N-((1S)-2-amino-1-{[2-(trifluoromethyl)phenyl]methyl}ethyl)-5-ethyl-4-(1-methyl-1H-pyrazol-5-yl)-2-thiophenecarboxamide; and N-((1S)-2-amino-1-{[2-(trifluoromethyl)phenyl]methyl}ethyl)-4-(1,4-dimethyl-1H-pyrazol-5-yl)-5-methyl-2-thiophenecarboxamide. U.S. Pat. No. 8,946,205 to Curd et al. discloses the use of hypoxia activated prodrugs, including N,N'-bis(2-bromoethyl)phosphorodamidic acid (1-methyl-2-nitro-1H-imidazol-5-yl)methyl ester. U.S. Pat. No. 8,946,239 to Gangjee discloses the use of substituted pyrrolo-, furano-, and cyclopentylpyrimidine bicyclic compounds. U.S. Pat. No. 8,946,235 to Butterworth et al. discloses the use of 2-(2,4,5-substituted-anilino)pyrimidine compounds. U.S. Pat. No. 8,946,224 to Craighead et al. discloses the use of substituted [1,2,4]triazolo[4,3-a]pyrazines. U.S. Pat. No. 8,946,216 to Deng et al. discloses the use of indazole derivatives as ERK inhibitors, including N-[3-[6-(1-methylethoxy)-3-pyridinyl]-1H-indazol-5-yl]-4-(phenylmethyl)-2-morpholinecarboxamide; N-[3-[6-(1-methylethoxy)-3-pyridinyl]-1H-indazol-5-yl]-2-morpholinecarboxamide; N-[3-(4-pyridinyl)-1H-indazol-5-yl]-4-(4-thiazolylmethyl)-2-morpholinecarboxamide; N-[3-(4-pyridinyl)-1H-indazol-5-yl]-4-(3-thienylmethyl)-2-morpholinecarboxamide; 4-[(2-fluorophenyl)methyl]-N-[3-(4-pyridinyl)-1 h-indazol-5-yl]-2-morpholinecarboxamide; N-[3-(4-pyridinyl)-1H-indazol-5-yl]-4-(2-pyridinylmethyl)-2-morpholinecarboxamide; N-[3-(4-pyridinyl)-1H-indazol-5-yl]-4-(2-pyridinylmethyl)-2-morpholinecarboxamide; and 4-[(2-bromophenyl)methyl]-N-[3-(4-pyridinyl)-1H-indazol-5-yl]-2-morpholinecarboxamide. U.S. Pat. No. 8,940,936 to Lee et al. discloses the use of aryloxy phenoxy acrylic compounds. U.S. Pat. No. 8,940,760 to Page et al. discloses the use of pyrazolopyridine derivatives as NADPH oxidase inhibitors. U.S. Pat. No. 8,940,756 to Flynn et al. discloses the use of dihydronaphthyridines as c-Kit inhibitors. U.S. Pat. No. 8,940,737 to Wang et al. discloses the use of apoptosis-inducing agents, such as 6-[8-(1,3-benzothiazol-2-ylcarbamoyl)-3,4-dihydroisoquinolin-2(1H)-yl]-3-(1-benzyl-1H-pyrazol-4-yl)pyridine-2-carboxylic acid; 6-[8-(1,3-benzothiazol-2-ylcarbamoyl)-3,4-dihydroisoquinolin-2(1H)-yl]-3-[1-(pyridin-4-ylmethyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-[1-(pyridin-3-ylmethyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-[1-(4-hydroxybenzyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-[1-(1-phenylethyl)-1H-pyrazol-4-yl]pyridine-2-carboxylic acid; 6-[8-(1,3-benzothiazol-2-ylcarbamoyl)-3,4-dihydroisoquinolin-2(1H)-yl]-3-(1-{4-[2-(dimethylamino)ethoxy]benzyl}-1H-pyrazol-4-yl)pyridine-2-carboxylic acid; 3-(1-benzyl-1H-pyrazol-4-yl)-6-{8-[(5,6-difluoro-1,3-benzothiazol-2-yl)carbamoyl]-3,4-dihydroisoquinolin-2(1H)-yl}pyridine-2-carboxylic acid; 6-[8-(1,3-benzothiazol-2-ylcarbamoyl)-3,4-dihydroisoquinolin-2(1H)-yl]-3-{1-[2-(4-fluorophenyl)ethyl]-1H-pyrazol-4-yl}pyridine-2-carboxylic acid; 6-[8-(1,3-benzothiazol-2-ylcarbamoyl)-3,4-dihydroisoquinolin-2(1H)-yl]-3-[1-(3-chlorobenzyl)-1H-pyrazol-4-yl]pyridine-2-carboxylic acid; and 3-(1-benzyl-1H-pyrazol-4-yl)-6-{8-[(6-fluoro-1,3-benzothiazol-2-yl)carbamoyl]-3,4-dihydroisoquinolin-2(1H)-yl}pyridine-2-carboxylic acid. U.S. Pat. No. 8,940,733 to Howard et al. discloses the use of unsymmetrical pyrrolobenzodiazepine dimers. U.S. Pat. No. 8,940,726 to Duncan et al. discloses the use of PRMT5 inhibitors. U.S. Pat. No. 8,937,193 to Pellecchia et al. discloses the use of apogossypolone derivatives. U.S. Pat. No. 8,937,094 to Burlison et al. discloses the use of Hsp90 modulators, including 5-(4-ethoxy-2-hydroxyphenyl)-4-(4-(morpholinomethyl)phenyl)-4H-1,2,4-triazole-3-carboxamide; 5-(2-hydroxy-4-methoxyphenyl)-4-(4-(morpholinomethyl)phenyl)-4H-1,2,4-triazole-3- carboxamide; 5-(2-hydroxy-4-propoxyphenyl)-4-(4-(morpholinomethyl)phenyl)-4H-1,2,4-triazole-3-carboxamide; 5-(2-hydroxy-4-isopropoxyphenyl)-4-(4-(morpholinomethyl)phenyl)-4H-1,2,4-triazole-3-carboxamide; 5-(2,4-dimethoxyphenyl)-4-(4-(morpholinomethyl)phenyl)-4H-1,2, 4-triazole-3-carboxamide; 5-(2-hydroxy-4-isopropylphenyl)-4-(4-methoxyphenyl)-4H-1,2,4-triazole-3-carboxamide; 5-(2-hydroxy-4-methylphenyl)-4-(4-methoxyphenyl)-4H-1,2,4-triazole-3-carboxamide; 5-(4-hydroxy-3-isopropylphenyl)-4-(4-methoxyphenyl)-4H-1,2,4-triazole-3-carboxamide; 5-(3-tert-butyl-4-hydroxyphenyl)-4-(4-methoxyphenyl)-4H-1,2,4-triazole-3-carboxamide; and 5-(4-hydroxy-3-propylphenyl)-4-(4-methoxyphenyl)-4H-1, 2,4-triazole-3-carboxamide. U.S. Pat. No. 8,937,068 to Seipelt et al. discloses the use of pyridopyrazine compounds. U.S. Pat. No. 8,933,212 to Fayard et al. discloses the use of protease nexin 1 inhibitors to reduce metastasis. U.S. Pat. No. 8,933,116 to Wu et al. discloses the use of γ-secretase inhibitors. U.S. Pat. No. 8,933,103 to Ohki et al. discloses the use of Axl inhibitors that are pyridone derivatives including N-{4-[2-amino-5-(3,4-dimethoxyphenyl)pyridin-3-yl]phenyl}-5-(4-fluorophenyl)-4-oxo-1-(2,2,2-trifluoroethyl)-1,4-dihydropyridine-3-carboxamide hydrochloride. U.S. Pat. No. 8,933,084 to Andrews et al. discloses the use of macrocyclic compounds as Trk inhibitors such as (6R)-9-fluoro-2,11,15,19,20,23-hexaazapentacyclo[15.5.2.1$^{7,}$ 11.0$^{2,6}$.0$^{20,24}$]pentacosa-1(23),7,9,17(24),18,21-hexaene-16, 25-dione. U.S. Pat. No. 8,933,080 to Singh et al. discloses the use of bridged bicyclic heteroaryl substituted triazoles as Axl inhibitors. U.S. Pat. No. 8,933,053 to McGuigan et al. discloses the use of phosphoramidate derivatives of 5-fluoro-2'-deoxyuridine. U.S. Pat. No. 8,927,718 to Sasaki et al. discloses the use of fused heterocyclic ring derivatives as Smo inhibitors, including 3,6-diethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide; 3-ethenyl-6-ethyl-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide; and 6-Ethyl-3-(ethylamino)-N-[1-(hydroxyacetyl)piperidin-4-yl]-1-methyl-4-oxo-5-(2-oxo-2-phenylethyl)-4,5-dihydro-1H-pyrrolo[3,2-c]pyridine-2-carboxamide. U.S. Pat. No. 8,927, 717 to Huang et al. discloses the use of thiochromeno[2,3-c]quinolin-12-one derivatives including 3-((4-chlorophenyl) thio)-2-hydroxyquinoline-4-carboxylic acid, 6,9-dichloro-12H-thiochromeno[2,3-c]quinolin-12-one, 10-chloro-6-hydroxy-12H-thiochromeno[2,3-c]quinolin-12-one, 10-chloro-6-methoxy-12H-thiochromeno[2,3-c]quinolin-12-one 10-chloro-6-dimethylamino-12H-thiochromeno[2,3-c]quinolin-12-one, 10-chloro-6-(piperazin-1-yl)-12H-thiochromeno[2,3-c]quinolin-12-one, 10-chloro-6-(4-methylpiperazin-1-yl)-12H-thiochromeno[2,3-c]quinolin-12-one, 10-chloro-6-(4-ethylpiperazin-1-yl)-12H-thiochromeno[2, 3-c]quinolin-12-one, 10-chloro-6-(4-(2-hydroxyethyl)piperazin-1-yl)-12H-thiochromeno[2,3-c]quinolin-12-one, and 6-(4-benzylpiperazin-1-yl)-10-chloro-12H-thiochromeno[2, 3-c]quinolin-12-one. U.S. Pat. No. 8,927,711 to Abraham et al. discloses the use of quinazoline JAK inhibitors, including (3-fluorophenyl)(4-(5-methyl-1H-pyrazol-3-ylamino)quinazolin-2-yl)methanone; (4-(1H-pyrazol-3-ylamino)quinazolin-2-yl)(3-fluorophenyl)methanone; (4-fluorophenyl) (4-(5-methyl-1H-pyrazol-3-ylamino)quinazolin-2-yl) methanone; (4-(1H-pyrazol-3-ylamino)quinazolin-2-yl)(4-fluorophenyl)methanone; (4-(1H-pyrazol-3-ylamino) quinazolin-2-yl)(2-methoxyphenyl)methanone; (4-(1H-pyrazol-3-ylamino)quinazolin-2-yl)(4-fluorophenyl) methanol; 2-(fluoro(4-fluorophenyl)methyl)-N-(1H-pyrazol-3-yl)quinazolin-4-amine; 2-(difluoro(4-fluorophenyl)methyl)-N-(5-methyl-1H-pyrazol-3-yl)quinazolin-4-amine; 2-(difluoro(4-fluorophenyl)methyl)-N-(1H-pyrazol-3-yl)quinazolin-4-amine; N-(5-cyclopropyl-1H-pyrazol-3-yl)-2-(difluoro(4-fluorophenyl)methyl)quinazolin-4-amine; 3-(2-(4-fluorobenzoyl)quinazolin-4-ylamino)-1H-pyrazole-5-carbonitrile; (4-fluorophenyl)(4-(5-methyl-1H-pyrazol-3-ylamino)quinazolin-2-yl)methanol; 2-((4-fluorophenyl) (methoxy)methyl)-N-(5-methyl-1H-pyrazol-3-yl) quinazolin-4-amine; 2-(amino(4-fluorophenyl)methyl)-N-(5-methyl-1H-pyrazol-3-yl)quinazolin-4-amine; 3-(2-((4-fluorophenyl)(hydroxy)methyl)quinazolin-4-ylamino)-1H-pyrazole-5-carbonitrile; (5-fluoro-4-(5-methyl-1H-pyrazol-3-ylamino)quinazolin-2-yl)(4-fluorophenyl)methanol; (4-fluorophenyl)(4-(5-methyl-1H-pyrazol-3-ylamino)-7-(trifluoromethyl)quinazolin-2-yl)methanone; and (4-fluorophenyl)(4-(5-methyl-1H-pyrazol-3-ylamino)-7-(trifluoromethyl)quinazolin-2-yl)methanol. U.S. Pat. No. 8,927,580 to Richardson et al. discloses the use of dipyridyl thiosemicarbazones such as di-2-pyridylketone 4-ethyl-4-methyl-3-thiosemicarbazone. U.S. Pat. No. 8,927,562 to Meng et al. discloses the use of fused tricyclic inhibitors of mTOR. U.S. Pat. No. 8,927,560 to Ahmed et al. discloses the use of 4-aza-2,3-didehydropodophyllotoxin compounds. U.S. Pat. No. 8,927,548 to Ying et al. discloses the use of triazole compounds that are Hsp90 inhibitors. U.S. Pat. No. 8,927, 538 to Kamal et al. discloses the use of carbazole linked pyrrolo[2,1-c][1,4]benzodiazepine hybrids as agents reacting with DNA to form an N2-guanine adduct that lies within the minor groove of duplex DNA via an acid-labile aminal bond to the electrophilic imine at the N10-C11 position. U.S. Pat. No. 8,927,533 to Giannini et al. discloses the use of lactam-substituted thio derivatives. U.S. Pat. No. 8,921,565 to Flynn et al. discloses the use of pyridone amides as c-Met kinase inhibitors, such as N-(4-((2-acetamidopyridin-4-yl) oxy)-2,5-difluorophenyl)-4-ethoxy-1-(4-fluorophenyl)-2-oxo-1,2-dihydropyridine-3-carboxamide, N-(2,5-difluoro-4-((2-propionamidopyridin-4-yl)oxy)phenyl)-4-ethoxy-1-(4-fluorophenyl)-2-oxo-1,2-dihydropyridine-3-carboxamide, N-(4-(2-(cyclopropanecarboxamido)pyridin-4-yl)oxy)-2,5-difluorophenyl)-4-ethoxy-1-(4-fluorophenyl)-2-oxo-1,2-dihydropyridine-3-carboxamide, N-(2,5-difluoro-4-((2-pivalamidopyridin-4-yl)oxy)phenyl)-4-ethoxy-1-(4-fluorophenyl)-2-oxo-1,2-dihydropyridine-3-carboxamide, N-(2,5-difluoro-4-((2-isobutyramidopyridin-4-yl)oxy)phenyl)-4-ethoxy-1-(4-fluorophenyl)-2-oxo-1,2-dihydropyridine-3-carboxamide. U.S. Pat. No. 8,921,522 to Kamal et al. discloses the use of benzothiazole derivatives including olefins, chalcones, pyrazolines, pyrazole, isoxazolines, and isoxazoles linked to 2-phenylbenzothiazoles. U.S. Pat. No. 8,921,546 to Chao discloses the use of imidazothiazoles such as 7-(2-morpholin-4-yl-ethoxy)-2-(4-nitro-phenyl)imidazo[2,1-b][1,3]benzothiazole and 4-(7-(2-morpholinoethoxy)benzo[d]imidazo[2,1-b]thiazol-2-yl)aniline. U.S. Pat. No. 8,921,414 to Reddell et al. discloses the use of spiroketals. U.S. Pat. No. 8,921,407 to Ying et al. discloses the use of pyrazole compounds as Hsp90 modulators. U.S. Pat. No. 8,921,367 to Friberg et al. discloses the use of AMG 900 (N-(4-(3-(2-aminopyrimidin-4-yl)pyridin-2-yloxy)phenyl)-4-(4-methylthiophen-2-yl)phthalazin-1-amine) as Aurora kinase inhibitor. U.S. Pat. No. 8,920,799 to Graham et al. discloses the use of Axl ligand-binding portion of Axl tyrosine kinase receptor. U.S. Pat. No. 8,778,340 to Dupont et al. discloses the use of anti-angiogenesis agents including antibodies. U.S. Pat. No. 8,748,470 to Lengyel et al. (fatty acid binding protein inhibitors including carbazole butanoic acids, aryl sulfonamides, sulfonylthiophenes, 4-hydroxypyrimidines, 2,3-dimethylindoles, benzoylbenzenes, biphenylalkanoic acids, 2-oxazole-alkanoic acids, tetrahydropyrimidones, pyridones, pyrazinones, aryl carboxylic acids, tetrazoles, triazolopyrimidinones, indoles, BMS480404 ((2S)-2-[2,3-bis[(2-chlorophenyl)methoxy]phenyl]-2-hydroxyacetic acid), or BMS309403 (2-[[2'-(5-ethyl-3,4-diphenyl-1H-pyrazol-1-yl)[1,1'-biphenyl]-3-yl]oxy]-acetic acid. U.S. Pat. No. 8,541,433 to Clozel et al. discloses the use of macitentan. U.S. Pat. No. 8,362,072 to Jensen et al. discloses the use of BRCA1 production enhancers. U.S. Pat. No. 8,268,889 to Kloog et al. discloses the use of farnesylthiosalicylic acid and analogs. U.S. Pat. No. 7,968,514 to Coelingh Bennink et al. discloses the use of immunogenic peptides. U.S. Pat. No. 7,323,164 to Chandrasekher et al. discloses the use of interleukin 24. U.S. Pat. No. 7,074,575 to Chandrasekher et al. discloses the use of interleukin 19. U.S. Pat. No. 6,237,307 to Miller et al. discloses the use of 2-phenyl-1-[4-(2-aminoethoxy)-benzyl]-indole derivatives. U.S. Pat. No. 5,597,798 to Howell et al. discloses the use of combinations with taxol and epidermal growth factor. United States Patent Application Publication No. 2014/0336150 by Frederick discloses the use of karenitecin (7-[(2'-trimethylsilyl)ethyl]-20(S) camptothecin). United States Patent Application Publication No. 2014/0315959 by Moore et al. discloses the use of benzylidinebenzohydrazides. United States Patent Application Publication No. 2014/0309184 by Rocconi et al. discloses the use of Smo inhibitors used in combination with other drugs, including platinum-containing agents. United States Patent Application Publication No. 2014/0302174 by Chan et al. discloses combination therapy with gemcitabine, cisplatin or carboplatin, and 5-[2-tert-butyl-5-(4-fluoro-phenyl)-1H-imidazol-4-yl]-3-(2,2-dimethyl-propyl)-3H-imidazo[4,5-b]pyridin-2-ylamine. United States Patent Application Publication No. 2014/0275174 by Moore et al. discloses the use of 2-amino-4H-naphtho[1,2-b]pyran-3-carbonitriles. United States Patent Application Publication No. 2014/0134169 by Kuhnert et al. discloses the use of Dll4 antagonists. United States Patent Application Publication No. 2013/0231286 by Chen discloses the use of prolactin receptor antagonist. United States Patent Application Publication No. 2013/0203861 by Liu et al. discloses the use of cyclohexenone compounds. United States Patent Application Publication No. 2012/0269827 by Whiteman et al. discloses the use of conjugates with CD56. United States Patent Application Publication No. 2012/0237502 by Darnowski discloses the use of 17,20-lyase inhibitors such as 3β-acetoxy-17-(3-pyridyl)androsta-5,16-diene, 6-[(7S)-7-hydroxy-6,7-dihydro-5H-pyrrolo[1,2-c]imidazol-7-yl]-N-methyl-2-naphthalenecarboxamide, 3β-hydroxy-17-(1H-benzimidazol-1-yl)androsta-5,16-diene, or 6-[(7S)-7-hydroxy-6,7-dihydro-5H-pyrrolo[1,2-c]imidazol-7-yl]-N-methyl-2-naphthalenecarboxamide. United States Patent Application Publication No. 2012/0183546 by Weinreich discloses the use of angiopoietin-2 inhibitor. United States Patent Application Publication No. 2010/0009330 by Sherman et al. discloses the use of PARP inhibitors including 4-iodo-3-nitrobenzamide. United States Patent Application Publication No. 2009/0118271 by Umeda et al. discloses the use of water-soluble prodrugs such as (9S)-1-butyl-9-ethyl-9-hydroxy-1H,12H-pyrano[3',4'':6',7']indolizino[1',2':6,5]pyrido[4,3,2-de]quinazoline-2,10,13(3H,9H,15H)-trione; (9S)-9-ethyl-9-hydroxy-1-[2-(4-morpholino)ethyl]-1H,12H-pyrano[3'',4'':6',7']indolizino[1',2':6,5]pyrido[4,3,2-de]quinazoline-2,10,13(3H,9H,15H)-trione; (9S)-1-[3-(dimethylamino)propyl]-9-ethyl-9-hydroxy-1H,12H-pyrano[3'',4'':6',7']indolizino[1',2':6,5]pyrido[4,3,2-de]quinazoline-2,10,13(3H,9H,15H)-trione; (9S)-9-ethyl-9-hydroxy-1-phenethyl-1H,12H-pyrano[3'',4'':6',7']indolizino[1',2':6,5]pyrido[4,3,2-de]quinazoline-2,10,13(3H,9H,15H)-trione; (9S)-9-ethyl-9-hydroxy-1-[2-(pyridin-2-yl)ethyl]-1H,12H-pyrano[3'',4'':6',7']indolizino[1',2':6,5]pyrido[4,3,2-de]quinazoline-2,10,13(3H,9H,15H)-trione; (9S)-9-ethyl-1-heptyl-9-hydroxy-1H,12H-pyrano[3'',4'':6',7']indolizino[1',2':6,5]pyrido[4,3,2-de]quinazoline-2,10,13(3H,9H,15H)-trione; and (9S)-9-ethyl-9-hydroxy-1-propyl-1H,12H-pyrano[3'',4'':6',7']indolizino[1',2':6,5]pyrido[4,3,2-de]quinazoline-2,10,13(3H,9H,15H)-trione. United States Patent Application Publication No. 2009/0099102 by Ye et al. discloses the use of ginkgolides, including ginkgolides A and B. United States Patent Application Publication No. 2007/0299020 by Zeldis discloses the use of 4-(amino)-2(2,6-dioxo(3-piperidyl)-isoindoline-1,3-dione. United States Patent Application Publication No. 2006/0058217 by White et al. discloses the use of antialamin. United States Patent Application No. 2005/0272766 by Koya et al. discloses the use of 1-glyoxylamide indolizines. These patents and patent application publications are incorporated herein in their entirety by this reference.

Yet another aspect of the present invention is a method of treating a patient with a malignancy selected from the group consisting of Stage II non-small cell lung cancer (NSCLC), Stage III NSCLC, and Stage IV NSCLC comprising the steps of:

(1) administering a therapeutically effective quantity of dianhydrogalactitol to the patient to treat the malignancy; and (2) administering a therapeutically effective quantity of a platinum-based anti-neoplastic agent to the patient to treat the malignancy.

In this method, in one alternative, the dianhydrogalactitol and the platinum-based anti-neoplastic agent are administered subsequent to surgical resection of the NSCLC. In another alternative, the dianhydrogalactitol and the platinum-based anti-neoplastic agent are administered prior to surgical resection of the NSCLC to shrink the tumor prior to surgery.

The patient can have brain metastases. The method is particularly useful for patients with NSCLC wherein brain metastases have been confirmed or suspected.

In one alternative, the dianhydrogalactitol and the platinum-based anti-neoplastic agent are administered in a single pharmaceutical composition, wherein the pharmaceutical composition comprises: (i) dianhydrogalactitol; (ii) the platinum-based anti-neoplastic agent; and (iii) at least one pharmaceutically acceptable carrier. In another alternative, the dianhydrogalactitol and the platinum-based anti-neoplastic agent are administered in two pharmaceutical compositions: (i) a first pharmaceutical composition comprising dianhydrogalactitol and at least one pharmaceutically acceptable carrier; and (ii) a second pharmaceutical composition comprising the platinum-based anti-neoplastic agent and at least one pharmaceutically acceptable carrier.

The patient can have a wild-type p53 genotype. In another alternative, the patient can have a mutated p53 genotype; as shown in the examples, a mutation in p53 results in less resistance to dianhydrogalactitol than to temozolomide or platinum-containing anti-neoplastic drugs, so dianhydrogalactitol can be particularly useful in such patients. The role of p53 is addressed further below.

In another alternative, the patient can have a wild-type EGFR genotype.

In yet another alternative, the patient has at least one mutation in a gene encoding a protein that is a target of at least one tyrosine kinase inhibitor (TKI). In still another alternative, the patient is characterized by the presence of at least one additional gene in either a wild-type or mutated state encoding a product that confers resistance to therapeutic effects of at least one TKI. The additional gene in either a wild-type or mutated state encoding a product that confers resistance to therapeutic effects of at least one TKI can be AHI-1. The AHI-1 can be mutated as the result of a proviral insertion.

In yet another alternative, the patient is characterized by a mutation in the kinase domain of ABL1 protein that is part of a BCR-ABL fusion protein that is a target of TKIs.

In still another alternative, the patient is characterized by a germline deletion polymorphism conferring resistance to tyrosine kinase inhibitors (TKIs). Typically, the germline DNA deletion polymorphism is a germline DNA deletion polymorphism of 2903 bp located in the BIM gene, and the germline DNA deletion polymorphism causes a splicing variation that leads to expression of an isoform of BIM protein that lacks a BH3 domain and thus inhibits the induction of apoptosis.

Typically, the platinum-containing anti-neoplastic agent is selected from the group consisting of cisplatin, carboplatin, oxaliplatin, satraplatin, picoplatin, nedaplatin, triplatin, lobapatin, heptaplatin, and lipoplatin. Preferably, the platinum-containing anti-neoplastic agent is selected from the group consisting of cisplatin, carboplatin, and oxaliplatin. A particularly preferred platinum-containing anti-neoplastic agent is cisplatin.

In one alternative, the dosages of dianhydrogalactitol and the platinum-containing anti-neoplastic agent are such that the dianhydrogalactitol and the platinum-containing anti-neoplastic agent act synergistically.

Yet another aspect of the invention is a pharmaceutical composition comprising:

(1) a therapeutically effective quantity of dianhydrogalactitol;

(2) a therapeutically effective quantity of a platinum-containing anti-neoplastic agent; and (3) optionally, at least one pharmaceutically acceptable carrier.

The pharmaceutical composition can be formulated for treatment of a malignancy selected from the group consisting of Stage II non-small cell lung cancer (NSCLC), Stage III NSCLC, and Stage IV NSCLC. The pharmaceutical composition can also be formulated for treatment of a malignancy selected from the group consisting of Stage II non-small cell lung cancer (NSCLC), Stage III NSCLC, and Stage IV NSCLC wherein metastasis to the brain has occurred.

In one alternative for the pharmaceutical composition, the dosages of dianhydrogalactitol and the platinum-containing anti-neoplastic agent are such that the dianhydrogalactitol and the platinum-containing anti-neoplastic agent act synergistically.

When the pharmaceutical composition comprises at least one pharmaceutically acceptable carrier, typically the pharmaceutically acceptable carrier is selected from the group consisting of aqueous and non-aqueous solvents, dispersion media, coatings, antibacterial and/or antifungal agents, and isotonic and/or absorption delaying agents.

The pharmaceutical composition can be formulated for parenteral administration such as intravenous administration; other routes of administration are possible, as described above.

In yet another alternative, the composition can comprise at least one p53 mimetic. Compounds that act as p53 mimetics are described below.

Yet another aspect of the invention is a method for treating a patient with a malignancy selected from the group consisting of Stage II non-small cell lung cancer (NSCLC), Stage III NSCLC, and Stage IV NSCLC wherein the patient has a mutated p53 gene comprising the steps of:

(1) determining the existence of a mutated p53 gene in the patient, wherein the mutated p53 gene affects the proliferation of the malignancy and/or the resistance of the malignancy to at least one anti-neoplastic agent;

(2) administering a therapeutically effective quantity of dianhydrogalactitol to the patient to treat the malignancy, wherein therapeutically effective quantity of dianhydrogalactitol is determined from results on cell lines with a mutated p53 gene;

(3) administering a therapeutically effective quantity of a platinum-based anti-neoplastic agent to the patient to treat the malignancy, wherein therapeutically effective quantity of the platinum-based anti-neoplastic agent is determined from results on cell lines with a mutated p53 gene; and (4) optionally, administering a therapeutically effective quantity of a p53 mimetic to the patient to treat the malignancy.

The p53 gene, also known as TP53 in humans, prevents genome mutation and acts as a tumor suppressor. In humans, mutations in p53 are commonly associated with increased risk of cancer development. The gene acts as a transcription factor activator. The structure of the p53 protein includes: (1) n acidic amino-terminal transcription-activation domain, also known as activation domain 1 (AD1), which activates transcription factors (residues 1-42); the N-terminus contains two complementary transcriptional activation domains, with a major one at residues 1-42 and a minor one at residues 55-75, specifically involved in the regulation of several pro-apoptotic genes; (2) activation domain 2 (AD2) important for apoptotic activity (residues 43-63); (3) a proline-rich domain important for the apoptotic activity of p53 by nuclear exportation via MAPK (residues 64-92); (4) a central DNA-binding core domain (DBD), which contains one zinc atom and several arginine residues (residues 102-292); this domain is responsible for binding the p53 co-repressor LMO3; (5) a nuclear localization signaling domain (residues 316-325); (6) a homo-oligomerization domain (OD) (residues 307-355); tetramerization is essential for the activity of p53 in vivo; and (7) a C-terminal region involved in down-regulation of DNA binding of the central domain (residues 356-393). A tandem of nine-amino-acid transactivation domains (9aaTAD) was identified in the AD1 and AD2 regions of transcription factor p53. Many knockout mutations for p53 are known. The structure and activity of the p53 protein is described in Y. Cho et al., "Crystal Structure of a p53 Tumor Suppressor-DNA Complex: Understanding Tumorigenic Mutations," *Science* 265: 346-355 (1994), incorporated herein by this reference. There are also splice variants known (S. Surget et al., "Uncovering the Role of p53 Splice Variants in Human Malignancy: A Clinical Perspective," *OncoTarqets Ther.* 7: 57-68 (2013), incorporated herein by this reference). A large number of interactions are known for p53; the protein is multifunctional. One particular interaction is with checkpoint kinases (D. M. Goudelock et al., "Regulatory Interactions Between the Checkpoint Kinase Chk1 and the Proteins of the DNA-Dependent Protein Kinase Complex," *J. Biol. Chem.* 278: 29940-29947 (2003), incorporated herein by this reference).

Typically, the existence of the mutated p53 gene in the patient is determined by a method selected from the group consisting of gene sequencing, restriction fragment length polymorphism, and determining whether p53 in a cell sample from the patient binds to a pGL3 vector. The use of pGL3 vectors is described in PCT Patent Application Publication No. WO 01/96602 by Yang et al., incorporated herein by this reference. Other methods for determining p53 status are disclosed in A. L. Gartel et al., "A New Method for Determining the Status of p53 in Tumor Cell Lines of Different Origin," Oncol. Res. 13: 405-408 (2003), incorporated by this reference. Assays for p53 function are also disclosed in U.S. Pat. No. 6,740,523 to Hermeking et al. and U.S. Pat. No. 6,335,156 to Hermeking et al., both incorporated herein by this reference.

A number of p53 mimetics are known in the art and are described in U.S. Pat. No. 7,994,184 to Rabizadeh et al. and in United States Patent Application Publication No. 2013/0210144 by Arora et al.

These p53 mimetics include, but are not limited to, the following:

(i) N'-[2-[2-(4-methoxyphenyl)ethenyl]-4-quinazolinyl]-N,N-dimethyl-1,3-propanediamine dihydrochloride hydrate) (CP-31398);

(ii) a compound of Formula (P-1):

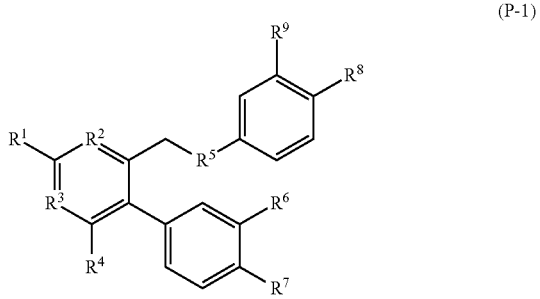

(P-1)

wherein:
(A) $R^1$ and $R^4$ are each independently selected from the group consisting of amino, cyano, nitro, carboxyl, halo, hydroxyl, $SO_2$, $C_1$-$C_6$ alkyl, $C_1$-$C_6$ haloalkyl, $C_1$-$C_8$ alkoxyl, $C_1$-$C_{11}$ alkoxyalkyl, $C_1$-$C_6$ alkylamino, and $C_1$-$C_6$ aminoalkyl;
(B) $R^2$ and $R^3$ are each independently selected from the group consisting of CH and N;
(C) $R^5$ is CH or O;
(D) $R^6$ is selected from the group consisting of halogen, cyano, nitro, $C_1$-$C_{10}$ branched or unbranched, saturated or unsaturated alkyl, $C_1$-$C_{10}$ branched or unbranched alkoxy, $C_1$-$C_{10}$ branched or unbranched acyl, $C_1$-$C_{10}$ branched or unbranched acyloxy, $C_1$-$C_{10}$ branched or unbranched alkylthio, aminosulfonyl, aryl, aroyl, aryloxy, arylsulfonyl, heteroaryl, and heteroaryloxy;
(E) $R^7$ is selected from the group consisting of hydrogen, halogen, cyano, nitro, $C_1$-$C_{10}$ branched or unbranched, saturated or unsaturated alkyl, $C_1$-$C_{10}$ branched or unbranched alkoxy, $C_1$-$C_{10}$ branched or unbranched acyl, $C_1$-$C_{10}$ branched or unbranched acyloxy, $C_1$-$C_{10}$ branched or unbranched alkylthio, aminosulfonyl, aryl, aroyl, aryloxy, arylsulfonyl, heteroaryl, and heteroaryloxy;
(F) $R^8$ is selected from the group consisting of nitro, hydroxy, and carboxyl; and
(G) $R^9$ is methyl; or a pharmaceutically acceptable ester or salt thereof; and (iii) a compound having a stable, internally constrained protein secondary structure, wherein the compound is of Formula (P-2):

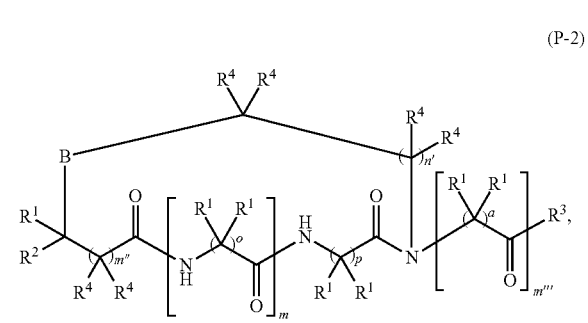

(P-2)

wherein:
(A) B is $C(R^1)_2$, O, S, or $NR^1$;
(B) each $R^1$ is independently hydrogen, an amino acid side chain, an alkyl, an alkenyl, an alkynyl, a cycloalkyl, a heterocyclyl, an aryl, a heteroaryl, or an arylalkyl;
(C) $R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$, wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula (P-2(a)):

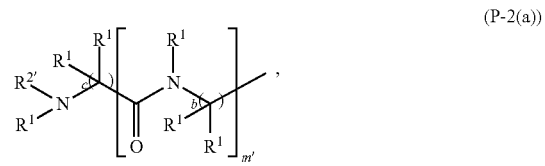

(P-2(a))

wherein:
(1) $R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen; an alkyl; an alkenyl; an alkynyl; a cycloalkyl; a heterocyclyl; an aryl; a heteroaryl; an arylalkyl; a targeting moiety; or a tag; or; —$(CH_2)_{0-1}N(R^5)_2$, wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
(2) m' is zero or any number;
(3) each b is independently 1 or 2; and
(4) c is 1 or 2;
(D) $R^3$ is hydrogen; an alkyl; an alkenyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula (P-2(b)):

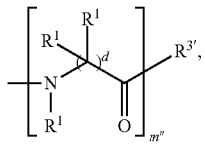

(P-2(b))

wherein:
(1) R³' is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl; an aryl, a targeting moiety, or a tag; or —N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
(2) m''' is zero or any number; and
(3) each d is 1 or 2;
(E) each R⁴ is independently hydrogen, an alkyl, an alkenyl, an alkynyl, a cycloalkyl, a heterocyclyl, an aryl, a heteroaryl, or an arylalkyl;
(F) m, n', and n'' are each independently 0, 1, 2, 3, or 4, wherein the sum of m, n', and n'' is from 2 to 6;
(G) m''' is 0 or 1;
(H) a is 1 or 2;
(I) each o is independently 1 or 2; and
(J) p is 1 or 2;
wherein at least one of the following conditions is met: (i) m is 1, 2, 3, or 4 and at least one o is 2; (ii) p is 2; (iii) m''' is 1 and a is 2; (iv) R² is a beta amino acid; (v) R² is a moiety of Formula (P-2(a)) wherein m''' is at least 1 and at least one b is 2; (vi) R² is a moiety of Formula (P-2(a)) wherein c is 2; (vii) R² is a moiety of Formula (P-2(a)) wherein R²' is a beta amino acid; (viii) R³ is a beta amino acid; (ix) R³ is a moiety of Formula (P-2(b)) wherein m'' is at least 1 and at least one d is 2; and (x) R³ is a moiety of Formula (P-2(b)) wherein R³' is a beta amino acid.

Suitable platinum-containing anti-neoplastic agents are as described above. In one alternative, the dosages of dianhydrogalactitol and the platinum-containing anti-neoplastic agent are such that the dianhydrogalactitol and the platinum-containing anti-neoplastic agent act synergistically.

The invention is illustrated by the following Examples. These Examples are included for illustrative purposes only, and are not intended to limit the invention.

Example 1

In Vivo Efficacy of Dianhydrogalactitol in the Treatment of Non-Small-Cell Lung Cancer Employing a Mouse Xenograft Model Background The median overall survival time for patients with stage IV non-small cell lung cancer (NSCLC) is 4 months, and 1- and 5-year survival is less than 16% and 2%, respectively. NSCLC is usually treated with surgery followed by treatment with either Tyrosine Kinase Inhibitors (TKIs) (e.g., erlotinib, gefitinib) or platinum-based regimens (e.g. cisplatin). TKIs have resulted in vastly improved outcomes for patients with EGFR mutations; however, TKI resistance has emerged as a significant unmet medical need, and long-term prognosis with platinum-based therapies is poor. Additionally, the incidence of brain metastases is high in patients with NSCLC with a poor prognosis.

Dianhydrogalactitol is a structurally unique bi-functional alkylating agent mediating interstrand DNA crosslinks at targeting N⁷ of guanine, thus differing in mechanism of action from TKIs and cisplatin. Dianhydrogalactitol further crosses the blood-brain barrier and accumulates in tumor tissue. Dianhydrogalactitol has demonstrated activity against NSCLC in preclinical and clinical trials, both as a single agent and in combination with other treatment regimens, suggesting dianhydrogalactitol may be a therapeutic option for drug-resistant NSCLC and NSCLC patients with brain metastasis.

The purpose of the study reported in this Example is to evaluate the activity of dianhydrogalactitol in in vivo models of drug-resistant NSCLC in comparison to other drugs, including cisplatin. Rag2 mice bearing subcutaneous human lung adenocarcinoma xenograft tumors of either TKI-resistant (H1975) or TKI-sensitive (A549) origin were treated.

Cell Lines and Animals

Two human NSCLC cell lines, A549 (TKI-sensitive) and H1975 (TKI-resistant), were used as xenograft tumor models in female Rag2 mice. The mice were 6 to 8 weeks of age and weighed 18-23 grams. 10 mice were used per group. The results reported below are for the A549 NSCLC cell line.

Drugs

Cisplatin was used in normal saline at a dose of 5 mg/kg. Administration was intravenous.

Dianhydrogalactitol was used in 0.9% sodium chloride for injection at 1.5 mg/kg to 6 mg/kg. Administration was intraperitoneal.

The study grouping was as shown in Table 1, below ("VAL-083" is dianhydrogalactitol).

TABLE 1

Study Grouping

| Gp # | Group Name | No. Mice | TA/CA* Dose (mg/kg) | Admin. Route | Volume (uL/20 g) | Timepoint/ Schedule |
|---|---|---|---|---|---|---|
| 1 | Untreated control | 10 | — | | | |
| 2 | Cisplatin control | 10 | 5 | i.v. | 200 | Q7D × 3 |
| 3 | VAL-083 dose 1 | 10 | 1.5 | i.p. | 200 | M, W, F × 3 |
| 4 | VAL-083 dose 2 | 10 | 3 | i.p. | 200 | M, W, F × 3 |
| 5 | VAL-083 dose 3 | 10 | 6 | i.p. | 200 | M, W, F × 3 |

*TA: Test Article; CA: Control Article

Treatment was initiated at a tumor volume of 100 mm³ to 150 mm³.

Experimental Design

Cell Preparation and Tissue Culture.

The A549 human lung carcinoma cell line had been obtained from the American Type Culture Collection (Cat. #CCL-185). The cells were started from a frozen vial of lab stock that were frozen down from the ATCC original vial and kept in liquid nitrogen. Cell cultures with a passage number of 3 to 10 and a confluence of 80%-90% were used. Cells were grown in RPMI 1640 supplemented with 10% fetal bovine serum and 2 mL L-glutamine at 37° C. in 5% $CO_2$ environment. Cells were subcultured once weekly with a split ratio 1:3 to 1:8 and expanded.

For cell preparation and harvesting for subcutaneous (s.c.) inoculation, the cells were rinsed briefly once with Hanks Balanced Salt Solution without calcium or magnesium. Fresh trypsin/EDTA solution (0.25% trypsin with tetrasodium EDTA) was added, the flask was laid horizontally to ensure that the cells were covered by trypsin/EDTA, and the extra trypsin/EDTA was aspirated. The cells were allowed to sit at 37° C. for a few minutes. The cells were observed under an inverted microscope until the cell layer was dispersed, fresh medium was added, 50 µL of cell suspension was taken and mixed with trypan blue (1:1), and the cells were counted and cell viability assessed by using Cellometer Auto T4. The cells were centrifuged at 200×g for 7 minutes and the supernatant was aspirated. The cells were resuspended in growth medium to obtain a concentration of $100×10^6$ cells/mL. For inoculation, $5×10^6$ cells were used in an injection volume of 50 µL per mouse in 1:1 Matrigel.

Tumor Cell Implantation

On day 0, tumor cells were implanted subcutaneously into mice in a volume of 50 µL in Matrigel using a 28-gauge needle; injection of the tumor cells was in the back of the mice. Mice were randomly assigned to groups based on tumor volume. The means of the tumor volumes prior at the time of randomization were 89.15 $mm^3$, 86.08 $mm^3$, 95.49 $mm^3$, 87.15 $mm^3$ and 81.76 $mm^3$ for groups 1-5, respectively.

Dose Administration

Dianhydrogalactitol (DAG) was provided as a lyophilized product at 40 mg of DAG per vial. For administration, 5 mL of 0.9% sodium chloride for injection, USP (saline) was added to yield a DAG solution with a concentration of 8 mg/mL. This stock solution was stable for 4 hours at room temperature or for 24 hours at 4° C. Further dilutions were made to prepare solutions of injection of 0.9 mg/mL (for administration of 0.18 mg/mouse in 0.2 mL; diluted from the 8 mg/mL reconstituted solution); of 0.45 mg/mL (for administration of 0.09 mg/mouse in 0.2 mL; a 1 to 2 dilution of the 0.9 mg/mL solution); and of 0.225 mg/mL (for administration of 0.045 mg/mouse in 0.2 mL; a 1 to 2 dilution of the 0.45 mg/mL solution).

Intravenous Injections

Mice were injected with the required volume to administer the prescribed dose (mg/kg) to the animals based on individual mouse weights using a 28-gauge needle. The injection volume was 200 µL for a 20-g mouse. The mice were briefly (less than 30 seconds) restrained during intravenous injections. Dilation of the vein for intravenous injections was achieved by holding the animals under a heat lamp for a period of between 1-2 minutes.

Intraperitoneal Injections

Mice were individually weighed and injected intraperitoneally according to body weight at the specified injection concentration (see Table 1). The injection volume was based on 200 µL per 20-g mouse. The abdominal surface was wiped down with 70% isopropyl alcohol to clean the injection site.

Data Collection

Tumor Monitoring

Tumor growth was monitored by measuring tumor dimensions with calipers beginning on the first day of treatment. Tumor length and width measurements were obtained each Monday, Wednesday, and Friday. Tumor volumes were calculated according to the equation $L×W^2/2$ with the length (in mm) being defined as the longer axis of the tumor. Animals were weighed at the time of tumor measurement. Tumors were allowed to grow to a maximum of 800 $mm^3$ before termination.

All animals had blood collected by cardiac puncture at termination for CBC (complete blood count) with differentiation. Statistical significance ($p<0.05$) between untreated control and groups 4 or 5 (dianhydrogalactitol-treated groups) was found for hemoglobin (g/L) for CBC analysis. Differential analysis was performed; however, it is noted that even in control mice there are low white blood cell (WBC) numbers (due to the fact that the strain is immunocompromised, which would affect WBC production). For WBC, statistical significance ($p<0.05$) was observed for lymphocytes and eosinophils. There were no differences between control non-tumor bearing animals (mouse ID # control 1 and control 2) and untreated control tumor-bearing animals (group 1; mouse ID #1-10) for CBC/differential analyses.

Observations of Animals

Clinical Observations

All animals were observed post-administration, and at least once per day, more frequently if deemed necessary, during the pre-treatment and treatment periods for morbidity and mortality. In particular, signs of ill-health were based on body weight loss, change in appetite, and behavioral signs such as altered gait, lethargy, and gross manifestations of stress. If signs of severe toxicity or tumor-related illness were seen, the animals were terminated by isoflurane overdose followed by $CO_2$ asphyxiation, and a necropsy was performed to assess other signs of toxicity. The following organs were examined: liver, gall bladder, spleen, lung, kidney, heart, intestine, lymph nodes, and bladder. Any unusual findings were noted.

The methodology was reviewed and approved by the Institutional Animal Care Committee (IACC) at the University of British Columbia. The housing and use of animals were performed in accordance with the Canadian Council on Animal Care Guidelines.

Summaries for the administration of dianhydrogalactitol ("VAL-083") and cisplatin are shown in Tables 2-3, below:

TABLE 2

Administration of Dianhydrogalactitol

| GROUP # | TREATMENT | DOSE mg/kg | MICE/group | AVR. WT. g | CONC. mg/ml | INJECTED ml/20 g | TOTAL ml | TOTAL mg | STOCK ml | Saline ml |
|---|---|---|---|---|---|---|---|---|---|---|
| 3 | VAL-083 | 1.5 | 10 | 20.0 | 0.150 | 0.200 | 3.00 | 0.450 | 0.583 | 2.438 |
| 4 | VAL-083 | 3.0 | 10 | 20.0 | 0.300 | 0.200 | 3.00 | 0.900 | 1.125 | 1.875 |
| 5 | VAL-083 | 6.0 | 10 | 20.0 | 0.800 | 0.200 | 3.00 | 1.800 | 2.250 | 0.750 |
| | | | | | | | 9.00 | 3.150 | 3.938 | |

VAL-083 Stock conc 0.80 mg/ml

TABLE 3

Administration of Cisplatin

| Group # | Treatment | Dose, mg/kg | Mice/ Group | Average Weight, g | Conc., mg/mL | Injected, ml/20 g | Total, mL | Total, mg | Stock. mL | Saline, mL |
|---|---|---|---|---|---|---|---|---|---|---|
| Cisplatin Control | Cisplatin | 5.0 | 10 | 20.0 | 0.500 | 0.200 | 3.00 | 1.500 | 1.500 | 1.500 |

Results and Conclusion

Figure 2:
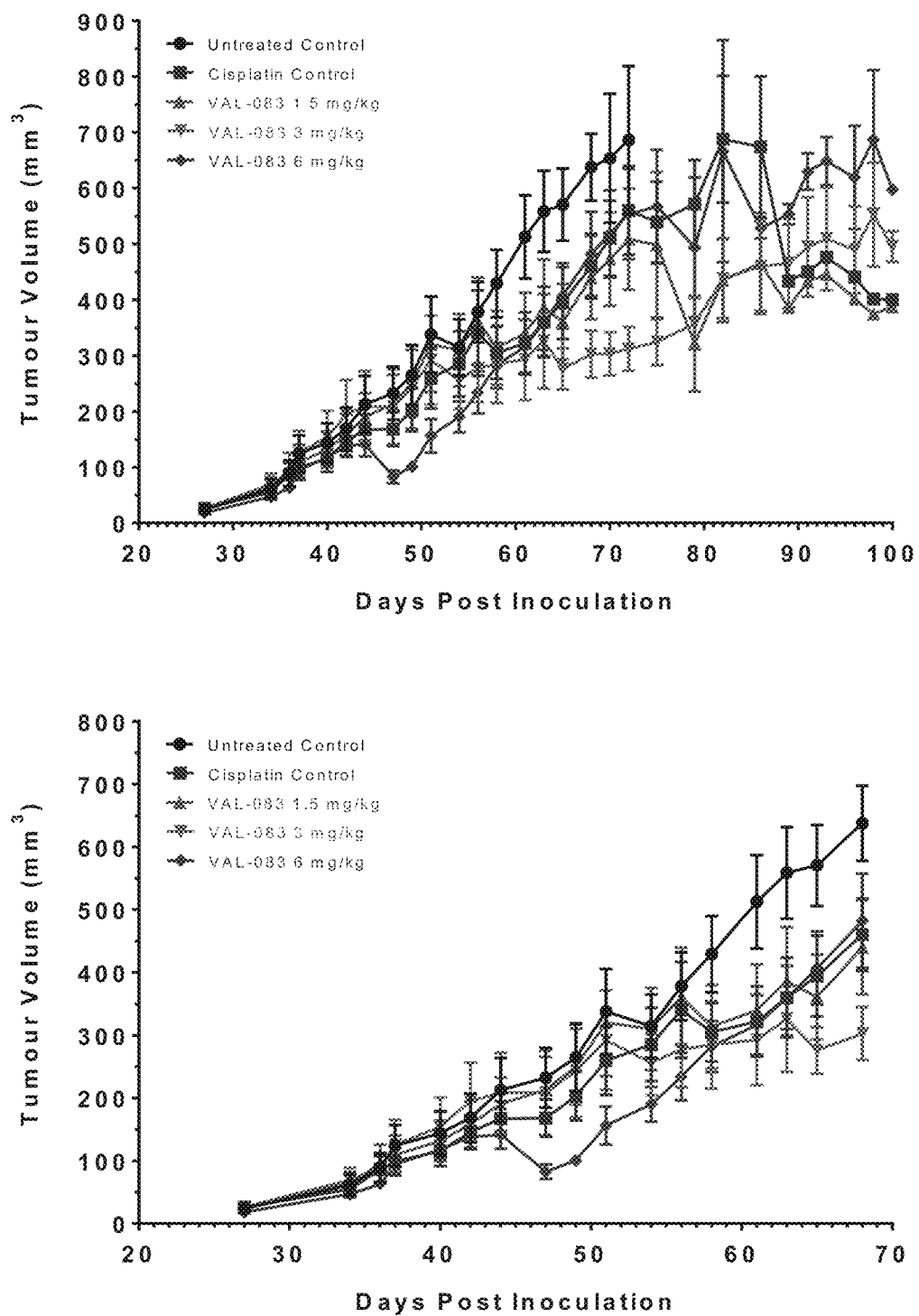

The results are shown in FIGS. 1-2.

FIG. 1 is a graph that shows body weight of female Rag2 mice after subcutaneous inoculation with 5 million A549 cells. Body weight is shown on the y-axis versus days post-inoculation on the x-axis for the results of the Example. In FIGS. 1-2 of the Example, • is the untreated control; ■ is the cisplatin control; ▲ is dianhydrogalactitol at 1.5 mg/kg; ▲ is dianhydrogalactitol at 3.0 mg/kg; and ♦ is dianhydrogalactitol at 6.0 mg/kg.

According to the results of FIG. 1, body weight loss was observed in mice treated with 5 mg/kg cisplatin (group 2) and 6 mg/kg dianhydrogalactitol (group 5). Group 5 treatment was stopped after 3 doses due to significant body weight loss. Body weights are shown as means±S.D.

FIG. 2 is a graph that shows the tumor volume (means±S.E.M.) for the A549 tumor-bearing female Rag2 mice with tumor volume on the y axis versus days post-inoculation on the x-axis for the results of the Example. The top panel of FIG. 2 represents all mice for the complete duration of the study. The bottom panel of FIG. 2 represents all mice until day 70 (last day for untreated control group).

To summarize the results, mice were administered with untreated control (group 1), cisplatin at 5 mg/kg Q7Dx3 i.v. (group 2) or dianhydrogalactitol at 1.5 mg/kg i.p. (group 3), 3 mg/kg (group 4), and 6 mg/kg (group 5) Monday, Wednesday, Friday for 3 weeks and tumor volume was measured 3× weekly and summarized in FIG. 2. The top panel indicates tumor volume for all animals and the bottom panel shows results for animal until day 70. Note that the number of animals remaining on study on day 70 was 2/10 (group 1), 6/10 (group 2), 7/10 (group 3), 6/10 (group 4) and 8/10 (group 5). For groups 1-5, a mean tumor volume of 200 mm$^3$ was observed on days 43, 49, 45, 42 and 54, respectively. For groups 1-4, a mean tumor volume of 400 mm$^3$ was reached on days 56, 66, 67 and 81 respectively. The doubling times for groups 1-4 were 13, 17, 22 and 39, respectively. A tumor growth delay of 26 days was observed in animals administered 3 mg/kg dianhydrogalactitol compared to untreated controls. The positive control of 5 mg/kg cisplatin had a tumor growth delay of only 4 days in comparison.

In terms of the tolerability of the dosages, dianhydrogalactitol at 6 mg/kg resulted in significant weight loss and morbidity of the mice and only 3 of the 9 scheduled doses were administered. The 5 mg/kg dose of cisplatin may also be near the MTD as 1 mouse was unable to receive the last dose.

In conclusion, administration of dianhydrogalactitol at a dose of 3 mg/kg resulted in a significant tumor growth delay as compared to cisplatin at 5 mg/kg.

Example 2

Use of Dianhydrogalactitol as a Novel Treatment Option for Chemo-Resistant Non-Small-Cell Lung Cancer The WHO predicts that the incidence of lung cancer may exceed 1 million cases per year by 2025 with non-small cell lung cancer (NSCLC) representing up to 90% of newly diagnosed cases. The median overall survival time for patients with stage IV NSCLC is 4 months, while 1- and 5-year survival is less than 16% and 2%, respectively. Metastatic NSCLC is usually treated with either Tyrosine Kinase Inhibitors (TKIs) (e.g. gefitinib) or platinum-based regimens (e.g. cisplatin). TKIs have resulted in vastly improved outcomes for patients with EGFR mutations; however, TKI resistance has emerged as a significant unmet medical need, and long-term prognosis with platinum-based therapies is poor. Additionally, the incidence of brain metastases is high in patients with NSCLC with a poor prognosis. In particular, NSCLC represents approximately 90% of the lung cancer cases diagnosed in China.

Dianhydrogalactitol is a structurally unique bi-functional alkylating agent mediating interstrand DNA crosslinks targeting N7 of guanine, thus differing in mechanism from TKIs and cisplatin. Dianhydrogalactitol is approved for treatment of lung cancer in China and has documented activity against NSCLC in historical NCI-sponsored clinical trials in the United States; however, specific questions regarding the efficacy of dianhydrogalactitol in comparison to cisplatin and in TKI-resistant NSCLC have to our knowledge not been addressed before. Further, dianhydrogalactitol crosses the blood-brain barrier and accumulates in tumor tissue. Dianhydrogalactitol has demonstrated activity against NSCLC in preclinical and clinical trials, suggesting dianhydrogalactitol may be a therapeutic option for drug-resistant NSCLC and NSCLC patients with brain metastasis. When tested side-by-side in a standard syngeneic mouse fibrosarcoma model (RIF-1 cell-line in C3H mice), dianhydrogalactitol demonstrated superiority to cisplatin in tumor growth delay. For mice treated with a single IP injection of dianhydrogalactitol (10 mg/kg) tumor growth was delayed by 5.6 days compared to control, versus 1.5 days for mice treated with single dose cisplatin (4 mg/kg). Combination treatment of dianhydrogalactitol and cisplatin produced a more than additive effect by delaying growth 8.7 days.

Previous clinical studies showing dianhydrogalactitol activity in NSCLC combined with the new data on synergy with cisplatin, makes dianhydrogalactitol a promising alternative for NSCLC with brain metastases as well as chemoresistant NSCLC.

In vitro, the cytotoxic effect of dianhydrogalactitol in combination with cisplatin or oxaliplatin was tested in NSCLC cell-lines A549 and H1975. The results show additive and more than additive effects of combining dianhydrogalactitol with cisplatin or oxaliplatin in both cell-lines.

In vivo, in two separate studies we evaluated the activity of dianhydrogalactitol in in vivo models of EGFR-TKI-resistant NSCLC in comparison to cisplatin. Rag2 mice bearing subcutaneous human lung adenocarcinoma xenograft tumors of either TKI-sensitive (A549) or TKI-resistant (H1975) origin were treated. Dianhydrogalactitol was given i.p. 3 times/week for 3 weeks, and the in vivo efficacy of dianhydrogalactitol in controlling tumor growth compared to cisplatin (5 mg/kg). Saline was used as control treatment. Disease progression was evaluated by tumor volume, clinical observations and body weight measurements. Blood samples were analyzed for CBC/differential analyses to assess myelosuppression or other changes in blood chemistry.

For A549 cells, tumor growth delay of 26 days was observed in animals treated with 3 mg/kg dianhydrogalactitol compared to controls, versus a 4-day delay for mice treated with cisplatin. Mean tumor volume on day 68 was significantly reduced in animals treated with 3 mg/kg dianhydrogalactitol compared to controls (p=0.001).

For H1975 cells, treatment was stopped after 6 doses of dianhydrogalactitol in the 4 mg/kg group due to significant body weight loss and the mice quickly recovered. Median survival time in mice treated with 4 mg/kg dianhydrogalactitol was 41 days compared to 31 days for all other treatment and control groups. Mean tumor volume on day 31 was significantly reduced in animals treated with 4 mg/kg dianhydrogalactitol compared to control (p=0.004).

Methods

In Vivo Models

Cell number for inoculation was $5 \times 10^6$ cells for A549 cells in an injection volume of 50 µL per animal. For H1975 cells, cell number for inoculation was $2 \times 10^6$ cells in an injection volume of 50 µL per animal.

Treatment was initiated at average tumor volume of 100-150 mm$^3$.

TABLE 4

Treatment Protocol for Testing Efficacy of Dianhydrogalactitol

| Group Name | Dosage (mg/kg), A549 | Dosage (mg/kg), H1975 | No. Mice | Admin. Route | Volume (µL/20 g) | Timepoint Schedule |
|---|---|---|---|---|---|---|
| 1. Untreated | | | 10 | n/a | n/a | n/a |
| 2. Cisplatin | 5.0 | 5.0 | 10 | i.v. | 200 | Q7D × 3 |
| 3. Dianhydrogalactitol | 1.5 | 2.0 | 10 | i.p. | 200 | M, W, F × 3 |
| 4. Dianhydrogalactitol | 3.0 | 3.0 | 10 | i.p. | 200 | M, W, F × 3 |
| 5. Dianhydrogalactitol | 6.0 | 4.0 | 10 | i.p | 200 | M, W, F × 3 |

Body weight loss was observed in mice treated with 5 mg/kg cisplatin (group 2) and 4 mg/kg dianhydrogalactitol (group 5). Treatment was stopped after 6 doses of dianhydrogalactitol in the 4 mg/kg group due to significant body weight loss, and the mice then quickly recovered.

In Vitro Models

The in vitro activity of dianhydrogalactitol in combination with cisplatin was tested in NSCLC cell-lines A549 and H1975. Cells were treated with dianhydrogalactitol and cisplatin or oxaliplatin, simultaneously, using IC10-30 concentrations of the individual agents, and cytotoxicity was monitored on day 5 with the colorimetric MTT assay. P-values were calculated by Student's t-test analysis of experimental values vs. predicted additive values for the treatment combinations Tumor growth inhibition (TGI) was calculated according to Equation (1):

$$TGI = \frac{(TVtxDDay68 - TVtx, int) \times 100\%}{(TVcontrolDay68 - TVcontrol, int.)}. \quad (1)$$

$(TVcontrolDay68 - TVcontrol, int) -$

Tumor growth delay (TGD) was calculated according to Equation (2):

$$TGD = DTtx - DTcontrol \quad (2).$$

For these calculations, TV is tumor volume, tx is treatment, int is initial, DT is doubling time for mean tumor volume from 200 mm$^3$ to 400 mm$^3$ for A549 or from 300 mm$^3$ to 600 mm$^3$ for H1975. MTV is mean tumor volume in mm$^3$ and TCR is tumor control ratio.

Results

Figure 3:
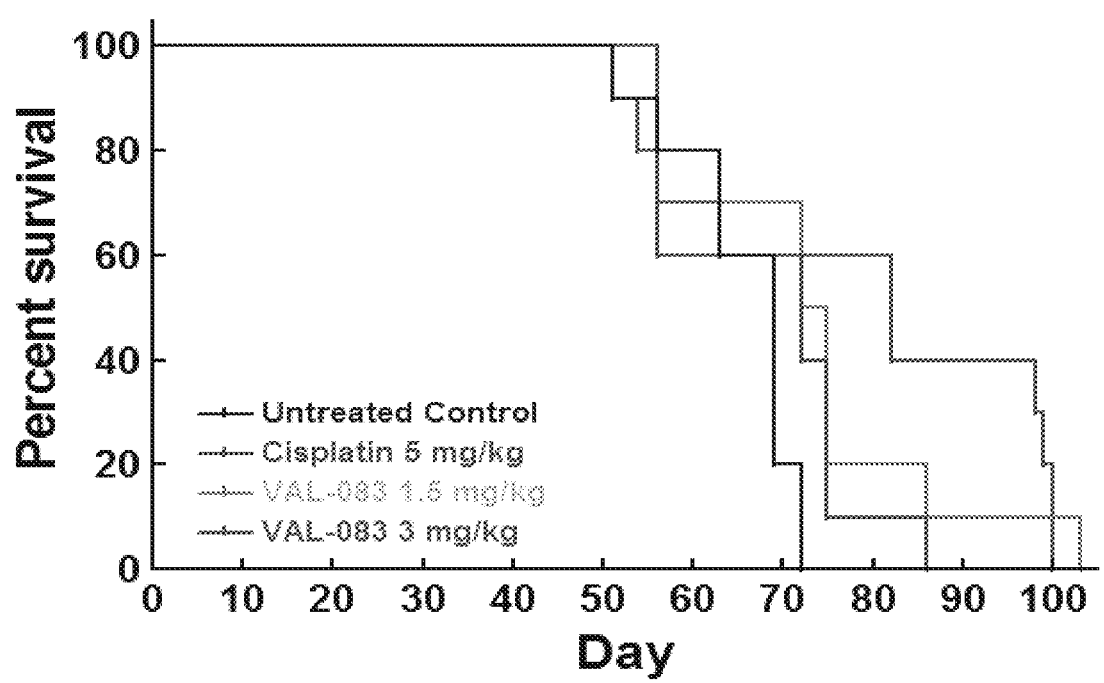
FIG. 3 is a Kaplan-Meier survival plot in an in vivo model of A549 (TKI-sensitive) cells in female Rag2 mice comparing the effect of cisplatin at 5 mg/kg and dianhydrogalactitol at 1.5 mg/kg and 3.0 mg/kg for A549 (TKI-sensitive) NSCLC cells.

The results for A549, which are TKI-sensitive cells, are shown in Table 5 and FIG. 3. A significant survival benefit was observed with dianhydrogalactitol at 3 mg/kg as shown in FIG. 3 and Table 5. FIG. 3 is a Kaplan-Meier survival plot in an in vivo model of A549 (TKI-sensitive) cells in female Rag2 mice comparing the effect of cisplatin at 5 mg/kg and dianhydrogalactitol at 1.5 mg/kg and 3.0 mg/kg for A549 (TKI-sensitive) cells. A log-rank statistical test (Mantel-Cox) was performed indicating p value of 0.0446 indicating a significant difference between the survival curves. A tumor growth delay of 26 days was observed in animals treated with 3 mg/kg dianhydrogalactitol compared to untreated controls, versus positive control, 5 mg/kg cisplatin, which resulted in a tumour growth delay of 4 days compared to untreated controls. Mean tumor volume on day 68 was significantly reduced in animals treated with 3 mg/kg dianhydrogalactitol (p=0.001) compared to untreated control. These observations suggest that dianhydrogalactitol maintains activity where cisplatin fails to gain a statistically significant benefit.

TABLE 5

Analysis Parameters for Groups 1-4 in A549 Model

| Treatment | MTV* at Day 68 | TCR* at Day 68 | TGD (Days) | TGI (%) | P value** | Median survival (days) |
|---|---|---|---|---|---|---|
| Control | 638 | 1 | 0 | 0 | n/a | 69 |
| Cisplatin, 5 mg/kg | 460 | 0.72 | 4 | 29% | 0.059 | 72 |
| Dianhydrogalactitol, 1.5 mg/kg | 440 | 0.69 | 9 | 32% | 0.069 | 73.5 |
| Dianhydrogalactitol, 3 mg/kg | 303 | 0.47 | 26 | 55% | 0.001 | 82 |

**shows the results for the unpaired t-test of tumor volume on day 68, treatment compared to untreated control.

Figure 4:
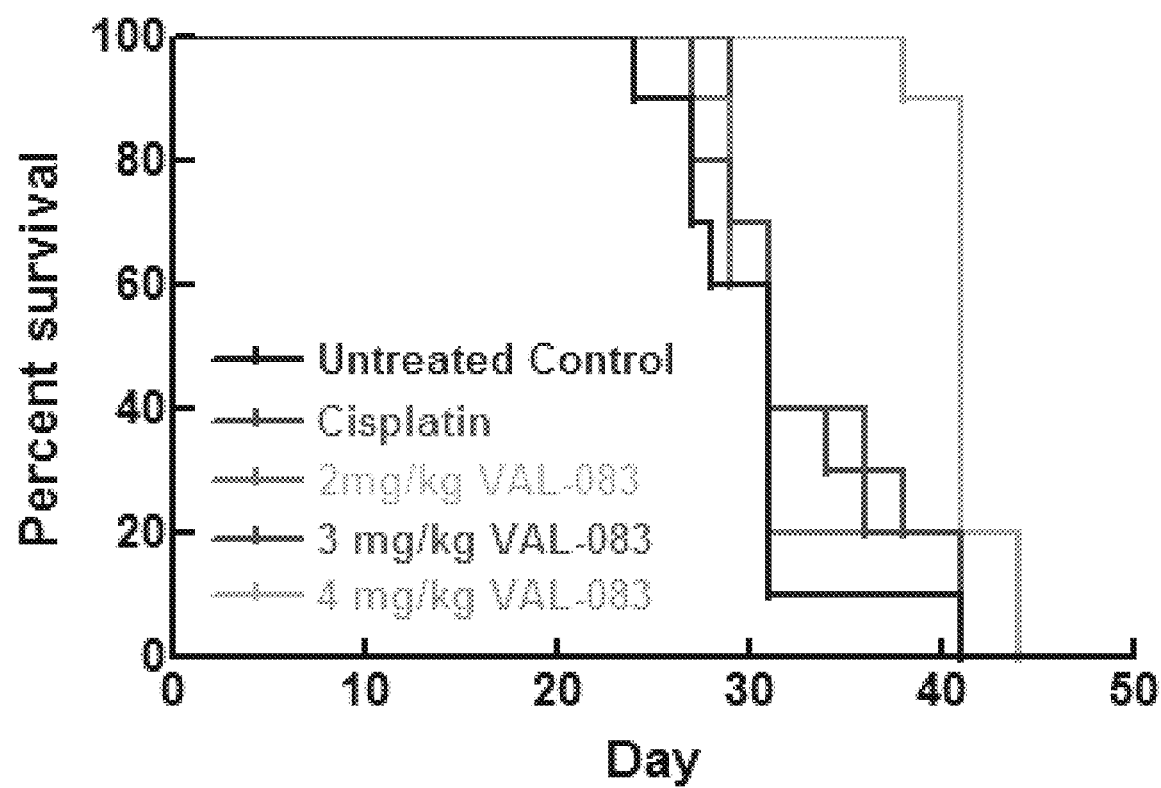
FIG. 4 is a Kaplan-Meier survival plot in an in vivo model of H1975 (TKI-resistant) NSCLC cells in female Rag2 mice comparing the effect of cisplatin at 5 mg/kg and dianhydrogalactitol at 2 mg/kg, 3 mg/kg, and 4 mg/kg for H1975 (TKI-resistant) cells.

The results for H1975, which are TKI-resistant cells, are shown in Table 6 and FIG. 4. A significant survival benefit was observed with dianhydrogalactitol at 4 mg/kg as shown in FIG. 4 and Table 6. FIG. 4 is a Kaplan-Meier survival plot in an in vivo model of H1975 (TKI-resistant) cells in female Rag2 mice comparing the effect of cisplatin at 5 mg/kg and dianhydrogalactitol at 2 mg/kg, 3 mg/kg, and 4 mg/kg for H1975 (TKI-resistant) cells. The median survival time for mice treated with 4 mg/kg dianhydrogalactitol was 41 days compared to 31 days for all other treatment and control groups. A log-rank statistical test (Mantel-Cox) was performed indicating p value of 0.0009 indicating a significant difference between the survival curves. Mean tumor volume on day 31 was significantly reduced in animals treated with 4 mg/kg dianhydrogalactitol compared to control (p=0.004). These observations suggest that dianhydrogalactitol maintains activity where cisplatin fails to gain a statistically significant benefit, even in a TKI-resistant setting.

TABLE 6

Analysis Parameters for Groups 1-5 in H1975 Model

| Treatment | MTV* at Day 31 | TCR* at Day 31 | P value** | Median survival (days) |
|---|---|---|---|---|
| Control | 459 | 1 | n/a | 31 |
| Cisplatin, 5 mg/kg | 381 | 0.83 | 0.102 | 31 |
| Dianhydrogalactitol, 2 mg/kg | 396 | 0.87 | 0.490 | 31 |
| Dianhydrogalactitol, 3 mg/kg | 383 | 0.84 | 0.769 | 31 |
| Dianhydrogalactitol, 4 mg/kg | 262 | 0.57 | 0.404 | 41 |

**shows the results for the unpaired t-test of tumor volume on day 31, treatment compared to untreated control.

In a separate, standard in vivo model of anti-cancer activity, VAL-083 was superior to cisplatin in tumor growth delay. Mice were treated with a single IP injection of either cisplatin, dianhydrogalactitol, or dianhydrogalactitol followed immediately by cisplatin. Interestingly, combination treatment of dianhydrogalactitol with cisplatin produced a more than additive effect by delaying growth 8.65 days, when tested side-by-side in a standard syngeneic mouse fibrosarcoma model (RIF-1 cell-line in C3H mice). The results are shown in Table 7.

TABLE 7

| Treatment | Dose (mg/kg) | Days to 4 × Median Tumor Size | Tumor Delay (days) |
|---|---|---|---|
| Untreated | n/a | 6.29 | 0.00 |
| Cisplatin | 4 | 7.75 | 1.45 |
| Dianhydrogalactitol | 10 | 11.45 | 5.16 |
| Dianhydrogalactitol + Cisplatin | 10 + 4 | 14.94 | 8.65 |

Figure 5A:
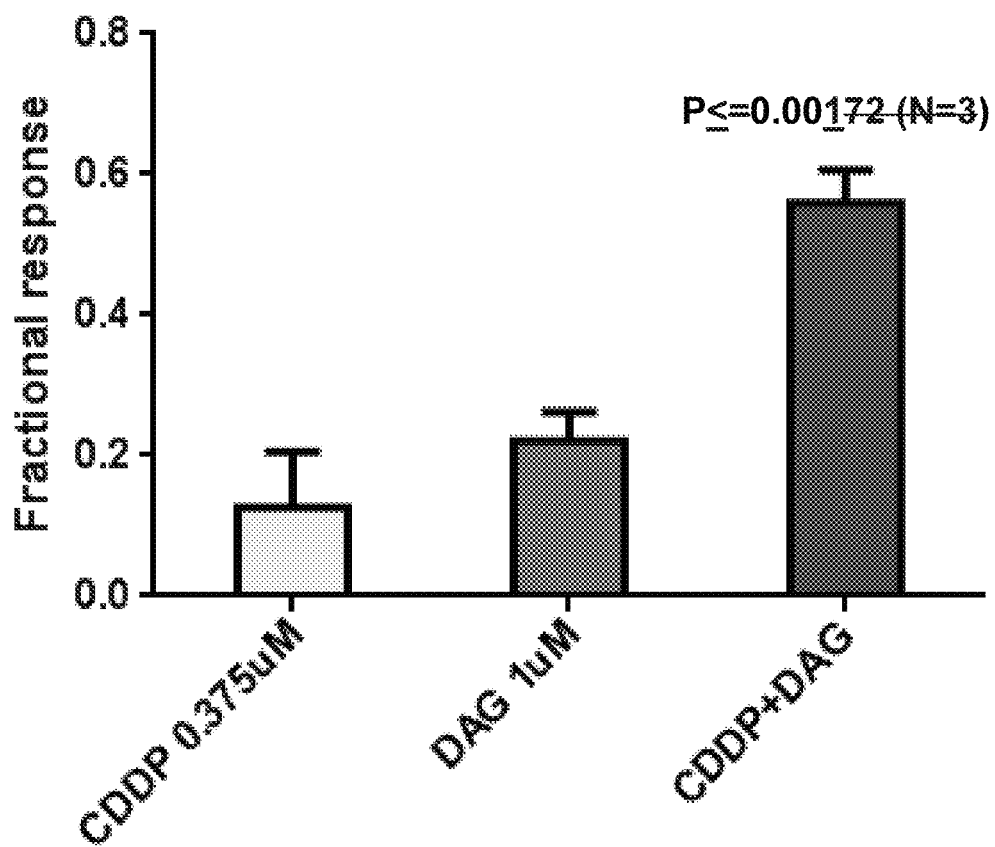
FIG. 5A is a graph showing the effect of dianhydrogalactitol (DAG) alone or with cisplatin (CDDP) on A549 (TKI-sensitive) NSCLC cells in vitro. Data are shown as mean±SE, N=7.
Figure 5B:
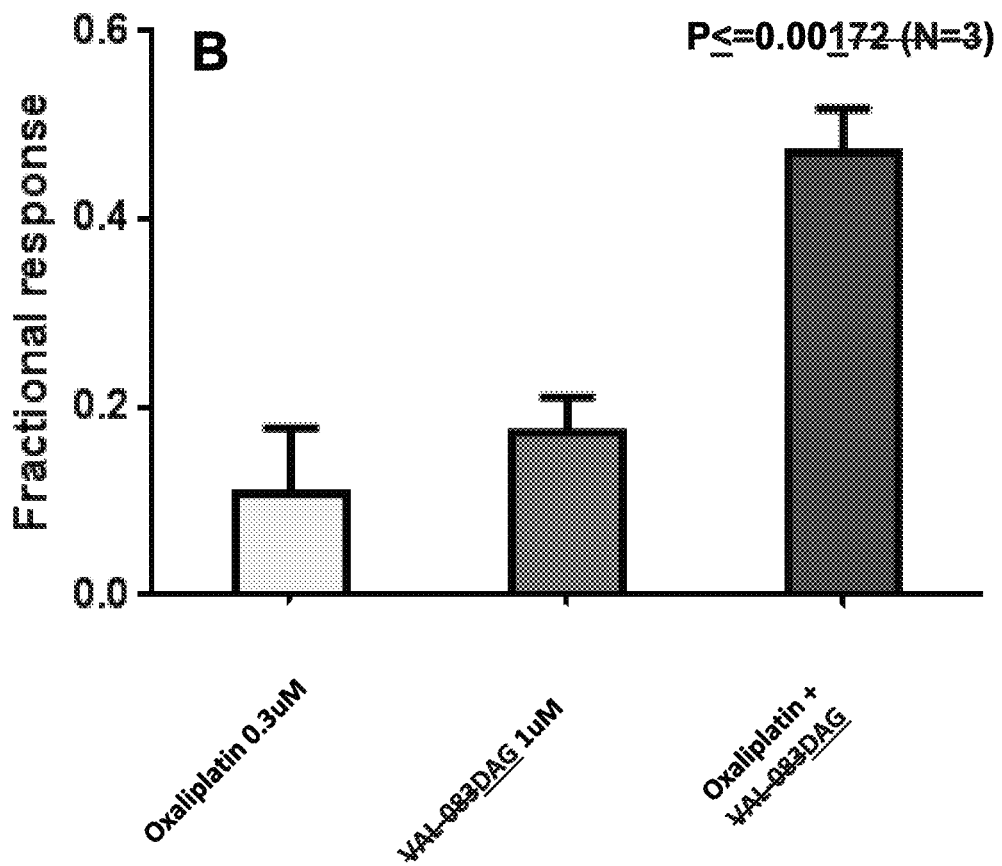
FIG. 5B is a graph showing the effect of dianhydrogalactitol (DAG) alone or with oxaliplatin on A549 (TKI-sensitive) NSCLC cells in vitro. Data are shown as mean±SE, N=7.
Figure 6:
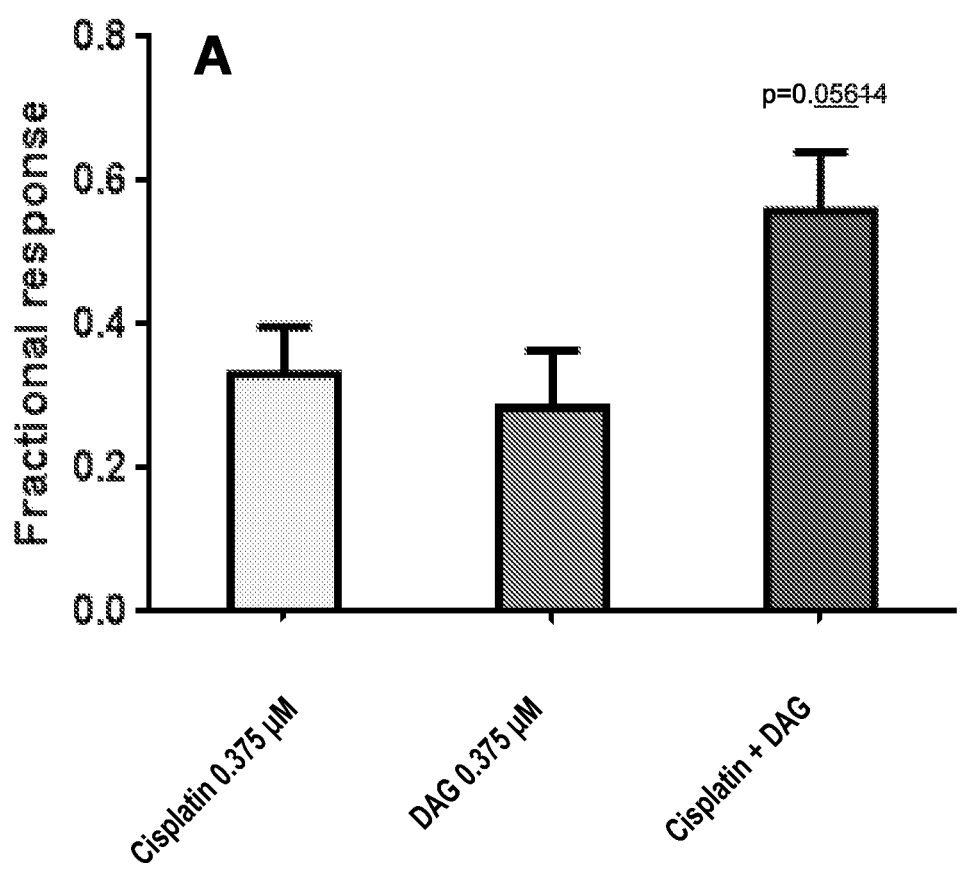
FIG. 6 is a graph showing the effect of dianhydrogalactitol alone or with cisplatin on H1975 (TKI-resistant) NSCLC cells in vitro. Data are shown as mean±SE, N=4.

Additional in vitro studies were performed to investigate the cytotoxic effect of dianhydrogalactitol alone or in combination with cisplatin (A) or oxaliplatin (B). FIG. 5A is a graph showing the effect of dianhydrogalactitol (DAG) alone or with cisplatin (CDDP) on A549 (TKI-sensitive) NSCLC cells in vitro. Data are shown as mean±SE, N=7. FIG. 5B is a graph showing the effect of dianhydrogalactitol (DAG) alone or with oxaliplatin on A549 (TKI-sensitive) NSCLC cells in vitro. Data are shown as mean±SE, N=7. FIG. 6 shows the cytotoxic effect of dianhydrogalactitol alone or in combination with cisplatin on H1975 NSCLC cells in vitro. Data are shown as mean±SE.

Dianhydrogalactitol in combination with either cisplatin or oxaliplatin has a more than additive cytotoxic effect on both TKI-resistant (H1975) and TKI-sensitive (A549) NSCLC cells. These results support the potential for synergistic benefit for a combination of dianhydrogalactitol and platinum-based therapies, similar to those results observed in vivo.

Taken together, the results suggest that dianhydrogalactitol is superior to cisplatin in both TKI-sensitive and TKI-resistant tumor models, has synergistic effect in combination with cisplatin, and suggest clinical potential in TKI-resistant NSCLC. In particular, dianhydrogalactitol maintains activity under conditions where platinum-based regimens have little or effect. Additionally, dianhydrogalactitol has a super-additive effect when combined with cisplatin or oxaliplatin in both TKI-sensitive (A549) and TKI-resistant (H1975) NSCLC cell-lines in vitro. Moreover, dianhydrogalactitol with cisplatin is better than additive in vivo.

Taken together, these results support dianhydrogalactitol as a viable treatment option for NSCLC patients failing platinum-based and TKI-based therapy, and support the potential benefit as part of a platinum-based combination therapy in newly diagnosed patients.

Example 3

Further Results on Cell Lines

Background

The median overall survival time for patients with stage IV non-small cell lung cancer (NSCLC) is 4 months, and 1- and 5-year survival is less than 16% and 2%, respectively. NSCLC is usually treated with surgery followed by treatment with either Tyrosine Kinase Inhibitors (TKIs) or platinum-based regimens (e.g. cisplatin). TKIs have resulted in vastly improved outcomes for patients with EGFR mutations; however, TKI resistance has emerged as a significant unmet medical need, and long-term prognosis with platinum-based therapies is poor. Dianhydrogalactitol is a structurally unique bifunctional alkylating agent mediating interstrand DNA crosslinks at $N^7$ of guanine, thus differing in mechanism of action from TKIs and cisplatin. Dianhydrogalactitol has demonstrated activity against NSCLC in preclinical and clinical trials, suggesting dianhydrogalactitol may be a therapeutic option for drug-resistant NSCLC. Dianhydrogalactitol is approved for treatment of lung cancer in China; however, specific questions regarding the efficacy of dianhydrogalactitol in comparison to—and combination with—cisplatin and in TKI-resistant NSCLC have to our knowledge not yet been investigated. The purpose of this study was to investigate dianhydrogalactitol activity in comparison to—and in combination with—cisplatin in TKI-resistant and TKI-sensitive NSCLC.

Methods

The in vitro activity of dianhydrogalactitol in combination with cisplatin was tested in NSCLC cell line H460. Cells were treated with dianhydrogalactitol and cisplatin, simultaneously, in a range of concentrations according to the Compusyn constant-ratio protocol and cytotoxicty was monitored on day 5 with the colorimetric MTT assay. The in vivo activity of dianhydrogalactitol compared to cisplatin was tested in Rag2 mice bearing xenograft tumors of either TKI-sensitive (A549) or TKI-resistant (H1975) origin.

Two human NSCLC cell lines, A549 and H1975, were used for subcutaneous human lung adenocarcinoma tumors and dianhydrogalactitol was given i.p. 3 times/week for 3 weeks. Disease progression was evaluated by tumor volume, clinical observations and body weight measurements.

Results

For H460, preliminary results indicate that the cytotoxic activity was more than additive for combinations of dianhydrogalactitol+cisplatin (Combination Index<0.7).

For A549, mean tumor volume on day 68 was significantly reduced in animals treated with 3 mg/kg dianhydrogalactitol (p=0.001) compared to untreated control. A tumor growth delay of 26 days was observed in animals treated with 3 mg/kg dianhydrogalactitol compared to untreated controls. Positive control, 5 mg/kg cisplatin, resulted in a tumor growth delay of 4 days compared to untreated controls.

For H1975, mean tumor volume on day 31 was significantly reduced in animals treated with 4 mg/kg dianhydrogalactitol (p=0.004) compared to untreated control. Median survival time for mice treated with 4 mg/kg dianhydrogalactitol was 41 days compared to 31 days for both 5 mg/kg cisplatin and for the untreated controls.

Conclusions

In conclusion, dianhydrogalactitol is highly efficacious in the NSCLC xenograft models, and preliminary in vitro studies suggest that dianhydrogalactitol in combination with cisplatin has synergistic activity.

Example 4

Dianhydrogalactitol Possesses Cytotoxic Activity Against Ovarian Cancer Lines

Dianhydrogalactitol possesses substantial cytotoxic activity against ovarian cancer cell lines.

Figure 7:
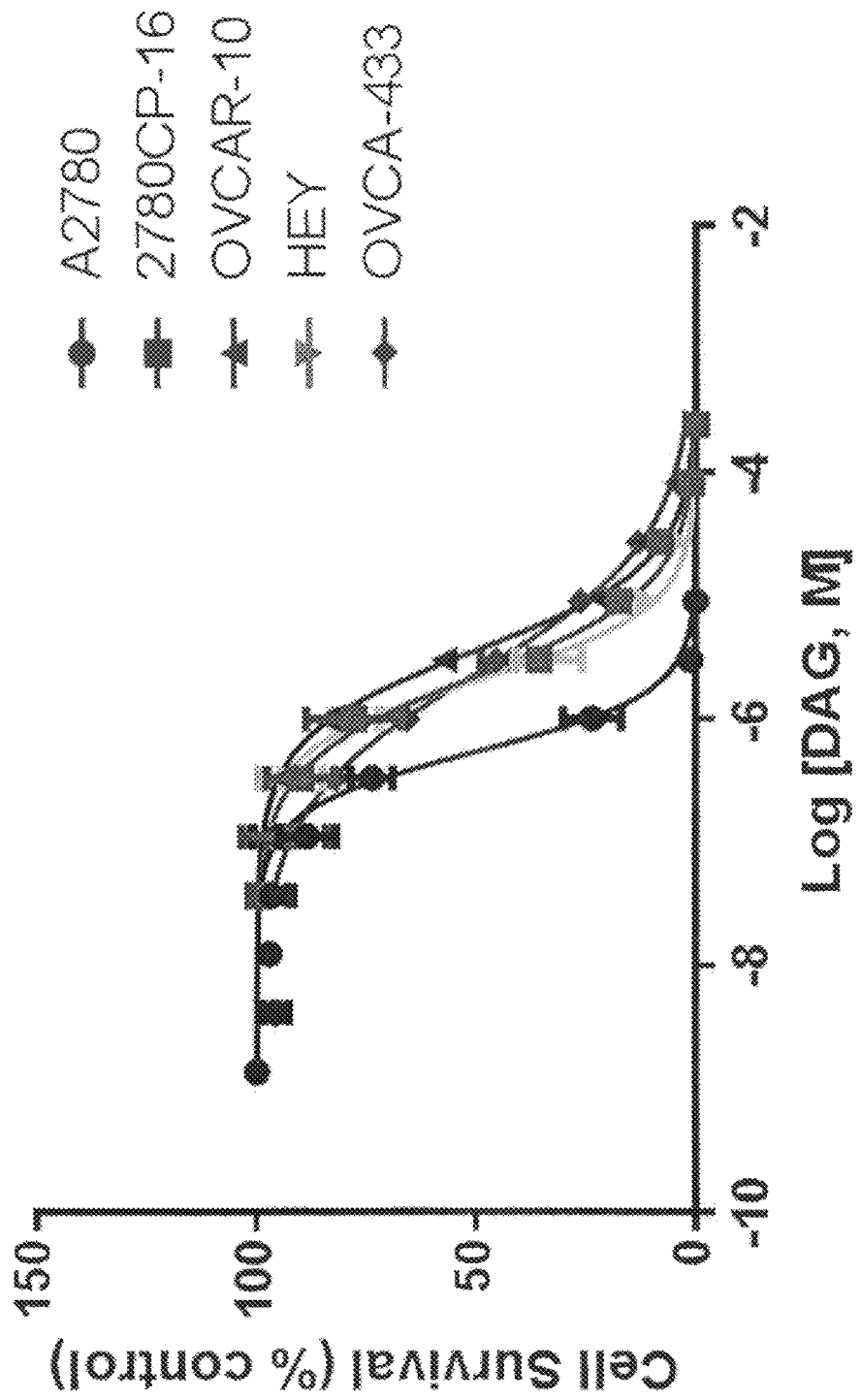
FIG. 7 is a graph showing a dose-response curve in an ovarian tumor cell line panel treated with dianhydrogalactitol (DAG) in vitro, showing cell survival on the y-axis and DAG concentration on the x-axis. The ovarian tumor panel lines are as follows: • is A2780; ■ is 2780-CP16; ▲ is OVCAR-10; ▼ is HEY; and ♦ is OVCA-433. Dose-response curves were undertaken using a 5-day MTT assay to determine cell viability. The A2780 represents a cisplatin-sensitive model, whereas the other four cell lines are cisplatin-resistant.

FIG. 7 is a graph showing a dose-response curve in an ovarian tumor cell line panel treated with dianhydrogalactitol in vitro. The ovarian tumor panel lines are as follows: • is A2780; ■ is 2780-CP16; ▲ is OVCAR-10; ▼ is HEY; and ♦ is OVCA-433. Dose-response curves were undertaken using a 5-day MTT assay to determine cell viability. The A2780 represents a cisplatin-sensitive model, whereas the other four cell lines are cisplatin-resistant. The cell line 2780-CP16 was derived for cisplatin resistance from A2780. The properties of some of these cell lines are disclosed in G. S. Hagopian et al., "Expression of p53 in Cisplatin-Resistant Ovarian Cell Lines: Modulation with the Novel Platinum Analog (1R,2R-Diaminocyclohexane) (trans-diacetato)(dichloro)-platinum(IV)," *Clin. Cancer Res.* 5: 655-663 (1999), and in Z. H. Siddik et al., "Independent Pathways of p53 Induction by Cisplatin and X-Rays in a Cisplatin-Resistant Cell Line," *Cancer Res.* 58: 698-703 (1998), both incorporated herein by this reference.

The data of FIG. 7 are shown in Table 8 in terms of the $IC_{50}$ of dianhdrogalactitol in the wild-type p53 human ovarian tumor panel.

TABLE 8

$IC_{50}$ of Dianhydrogalactitol in a Wild-Type p53 Human Ovarian Tumor Panel
Ovarian Tumor Models

| wt-p53 Cell Line | DAG $IC_{50}$ Mean | (µM) SE |
|---|---|---|
| A2780 | 0.54 | 0.046 |
| 2780-CP | 2.2 | 0.289 |
| Ovcar-10 | 3.6 | 0.173 |
| Hey | 2.1 | 0.289 |
| OVCA-433 | 2.3 | 0.058 |

N = 3

Figure 8:
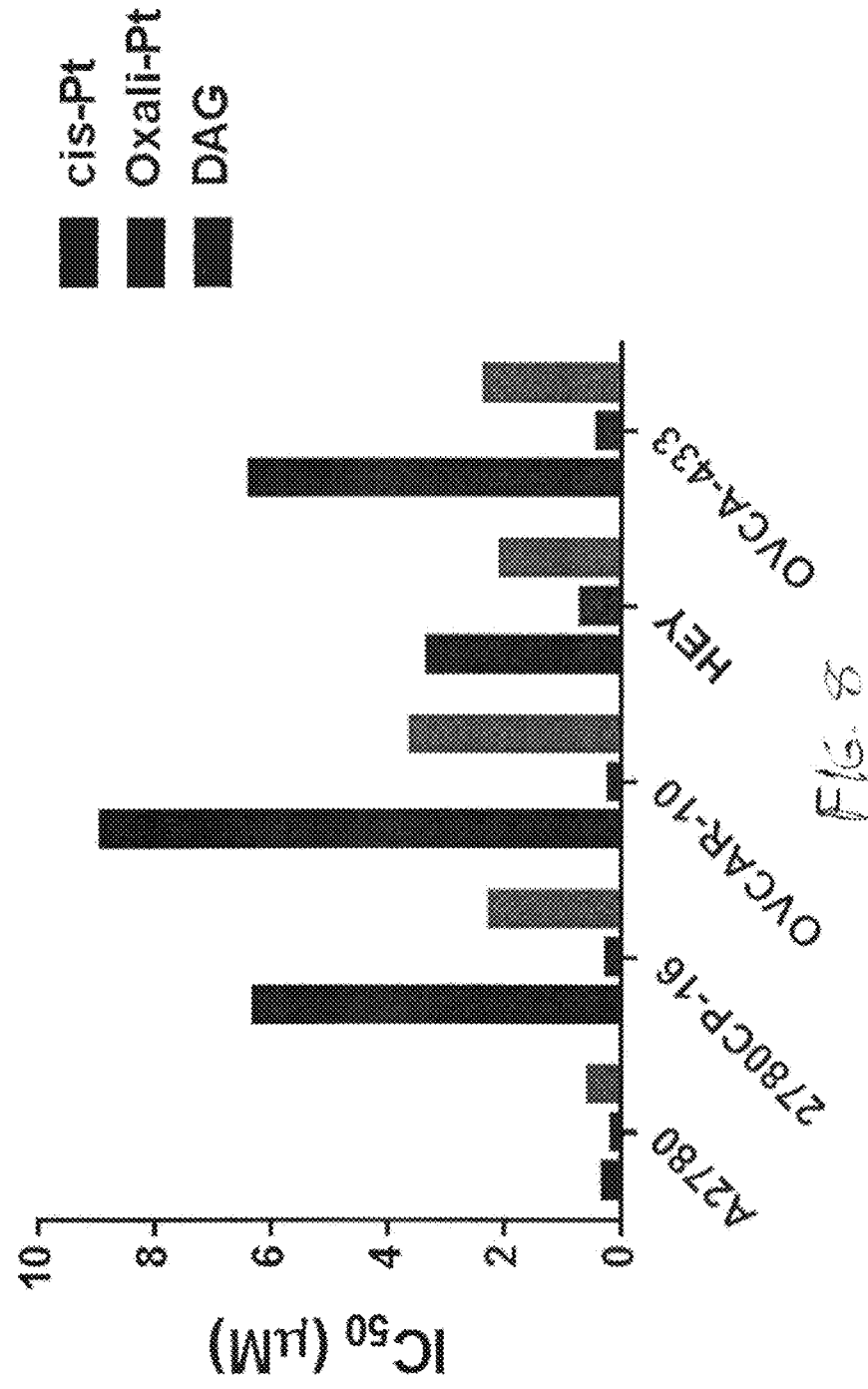
FIG. 8 is a graph showing the in vitro cytotoxicity of dianhydrogalactitol ("DAG"), cisplatin ("cis-Pt") and oxaliplatin ("Oxali-Pt") in a wild-type p53 human ovarian tumor panel. The relative activity (IC50) of dianhydrogalactitol, cisplatin, and oxaliplatin against wild-type p53 ovarian tumor cells is shown.

FIG. 8 is a graph showing the cytotoxicity of dianhydrogalactitol ("DAG"), cisplatin ("cis-Pt") and oxaliplatin ("Oxali-Pt") in a wild-type p53 human ovarian tumor panel in vitro. The relative activity ($IC_{50}$) of dianhydrogalactitol, cisplatin, and oxaliplatin against wild-type p53 ovarian tumor cells is shown.

Figure 9:
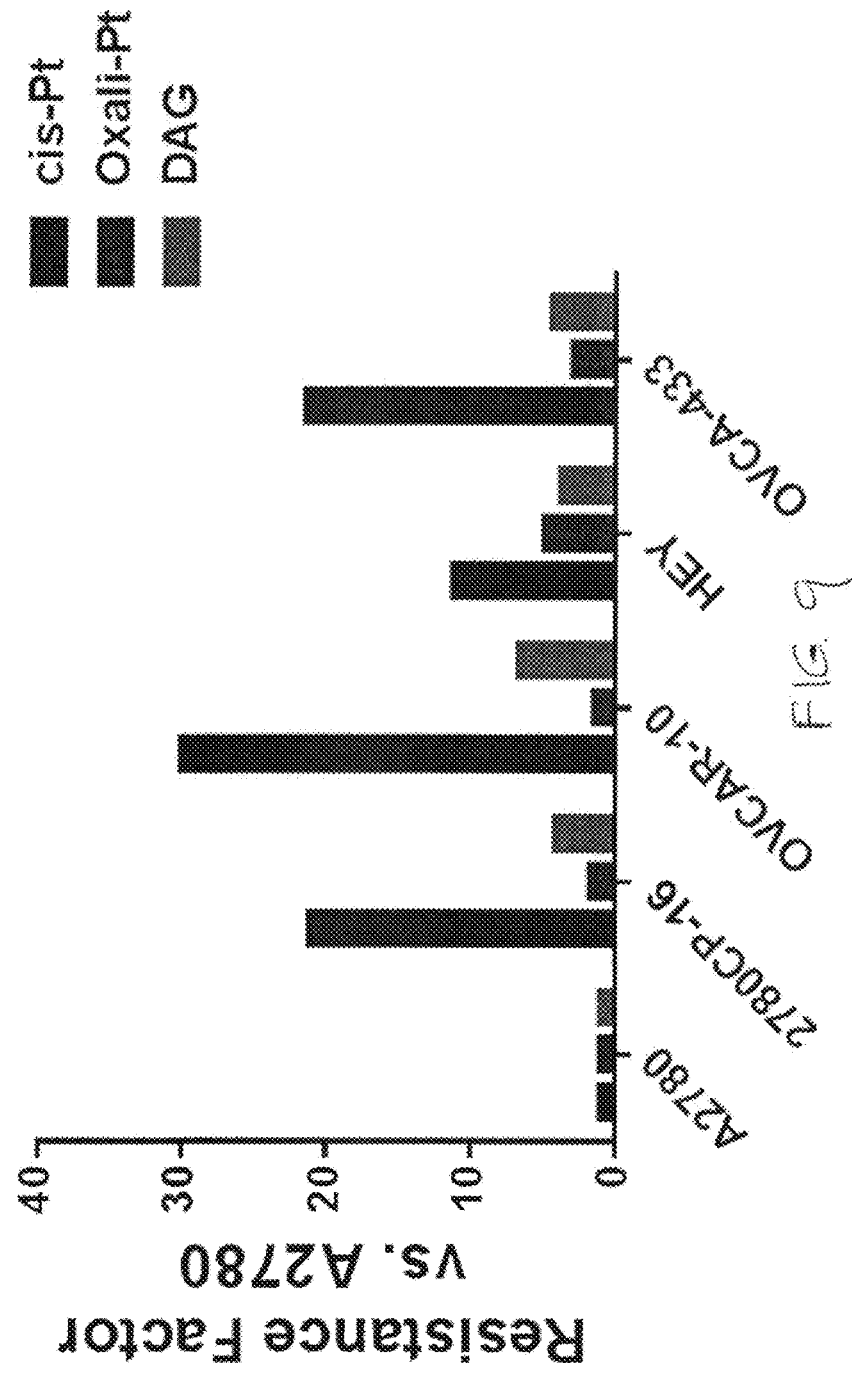
FIG. 9 is a graph showing the resistance factors of dianhydrogalactitol and the platinum drugs cisplatin and oxaliplatin in a wild-type p53 human ovarian tumor panel in vitro; the resistance factors are shown versus A2780 (cisplatin-sensitive). The activity of dianhydrogalactitol and the platinum drugs was normalized relative to the sensitive A2780 model. The graph indicates that the resistant tumor models are 10- to 30-fold resistant to cisplatin, 2- to 5-fold resistant to oxaliplatin, and 4- to 7-fold resistant to dianhydrogalactitol. Thus, cisplatin-resistant wild-type p53 ovarian tumor models demonstrate only partial cross-resistance to oxaliplatin and dianhydrogalactitol.
Figure 6:
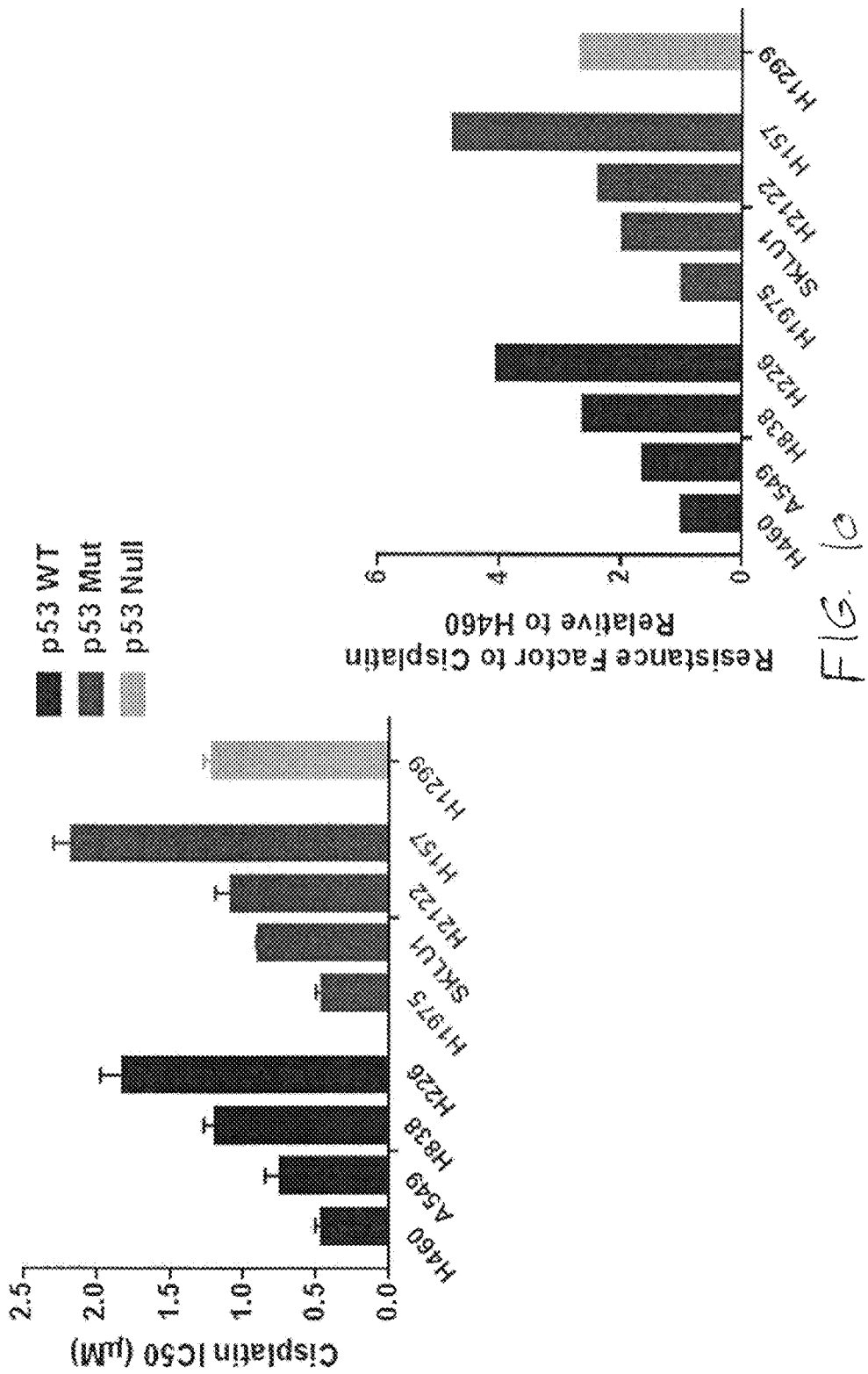

FIG. 9 is a graph showing the resistance factors of dianhydrogalactitol and the platinum drugs cisplatin and oxaliplatin in a wild-type p53 human ovarian tumor panel in vitro; the resistance factors are shown versus A2780. The activity of dianhydrogalactitol and the platinum drugs was normalized relative to the sensitive A2780 model. The graph indicates that the resistant tumor models are 10- to 30-fold resistant to cisplatin, 2- to 5-fold resistant to oxaliplatin, and 4- to 7-fold resistant to dianhydrogalactitol. Thus, cisplatin-resistant wild-type p53 ovarian tumor models demonstrate only partial cross-resistance to oxaliplatin and dianhydrogalactitol.

Therefore, the conclusion of this Example is that, even in ovarian tumors that demonstrate substantial resistance to cisplatin, dianhydrogalactitol exhibits a significant cytotoxic effect.

Example 5

Cytotoxicity Studies on NSCLC Tumor Models

Table 9 shows the cytotoxicity of dianhydrogalactitol (DAG) and the platinum drugs cisplatin and oxaliplatin in a number of cell lines for human NSCLC. The cell lines include cell lines with wild-type p53, cell lines with mutant p53, and cell lines in which p53 has been knocked out ("null"). The properties of these cell lines are described in F. Bunz et al., "Requirement for p53 and p21 to Sustain $G_2$ Arrest After DNA Damage," *Science* 282: 1497-1501 (1998), incorporated herein by this reference.

TABLE 9

NSCLC Tumor Models

| | | $IC_{50}$ (uM) | | | | |
|---|---|---|---|---|---|---|
| | p53 | Cisplatin | | Oxaliplatin | | DAG |
| Cell Line | Status | Mean | SE | Mean | SE | Mean | SE |
| H460 | wt | 0.45 | 0.052 | 0.36 | 0.014 | 0.49 | 0.050 |
| A549 | wt | 0.74 | 0.106 | 0.57 | 0.059 | 1.75 | 0.314 |
| H838 | wt | 1.18 | 0.092 | 2.63 | 0.041 | 4.52 | 0.421 |
| H226 | wt | 1.82 | 0.156 | 0.82 | 0.023 | 6.11 | 0.984 |
| H1975 | mu | 0.45 | 0.048 | 0.51 | 0.031 | 0.90 | 0.152 |
| SkLU1 | mu | 0.89 | 0.019 | 2.02 | 0.473 | 2.72 | 0.022 |
| H2122 | mu | 1.07 | 0.123 | 1.42 | 0.066 | 2.84 | 0.304 |
| H157 | mu | 2.16 | 0.135 | 2.04 | 0.128 | 4.48 | 0.415 |
| H1299 | null | 1.20 | 0.073 | 0.64 | 0.037 | 2.37 | 0.120 |

N = 3

FIG. 10 is a graph showing the cytotoxicity of cisplatin and relative resistance in a human NSCLC tumor panel in vitro. The cell lines used are H460, A549, H838, and H226, which have a wild-type p53; H1975, SkLU1, H2122, and H157, which have a mutated p53; and H1229, which has a null p53. H460 is considered sensitive to cisplatin; the other cell lines are considered resistant to cisplatin, with the exception of H1975. Some are relatively more sensitive to oxaliplatin.

Figure 11:
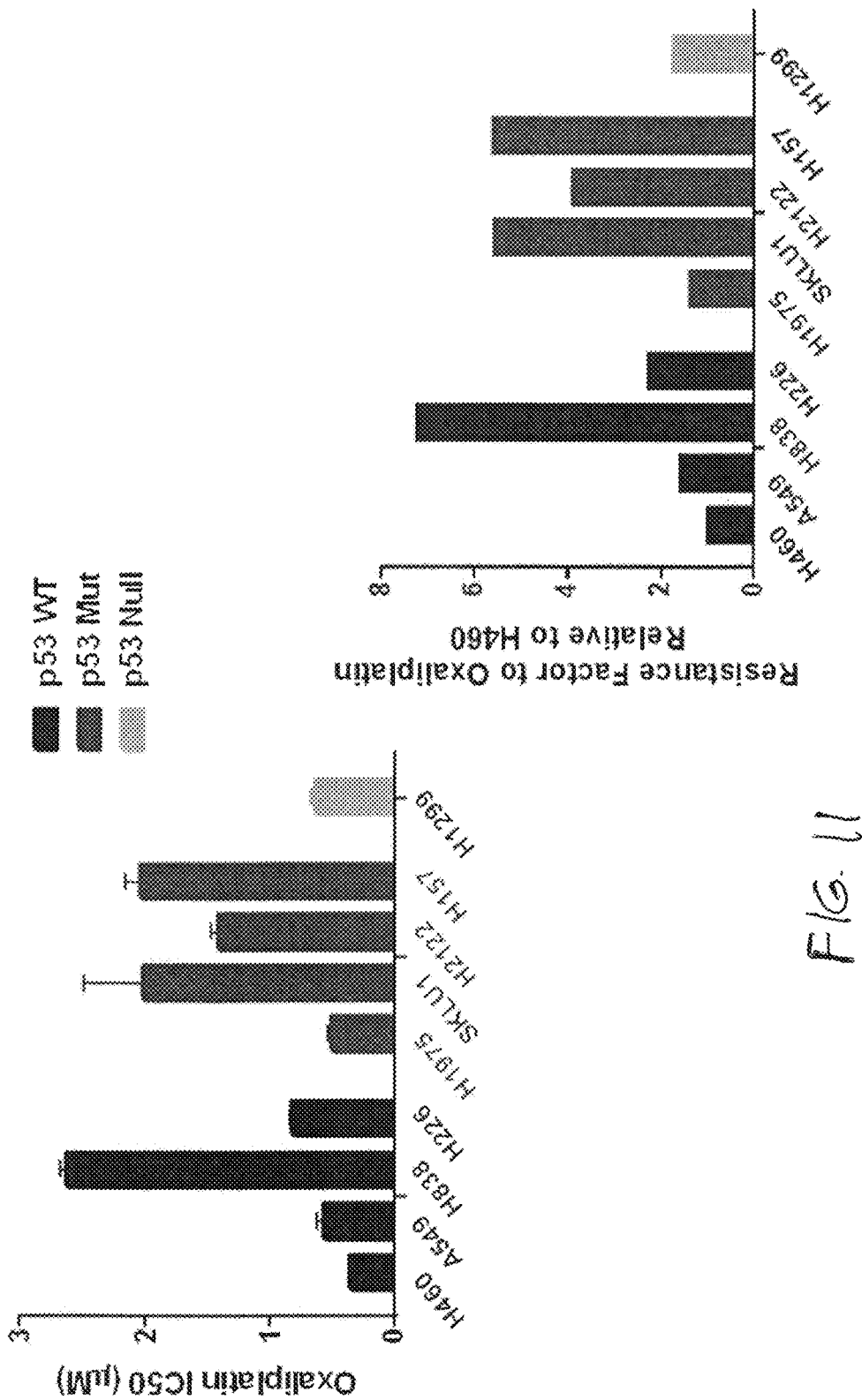
FIG. 11 is a graph showing the cytotoxicity of oxaliplatin and relative resistance in a human NSCLC tumor panel in vitro. The cell lines used are H460, A549, H838, and H226, which have a wild-type p53; H1975, SkLU1, H2122, and H157, which have a mutated p53; and H1229, which has a null p53.

FIG. 11 is a graph showing the cytotoxicity of oxaliplatin and relative resistance in a human NSCLC tumor panel in vitro. The cell lines used are H460, A549, H838, and H226, which have a wild-type p53; H1975, SkLU1, H2122, and H157, which have a mutated p53; and H1229, which has a null p53.

Figure 12:
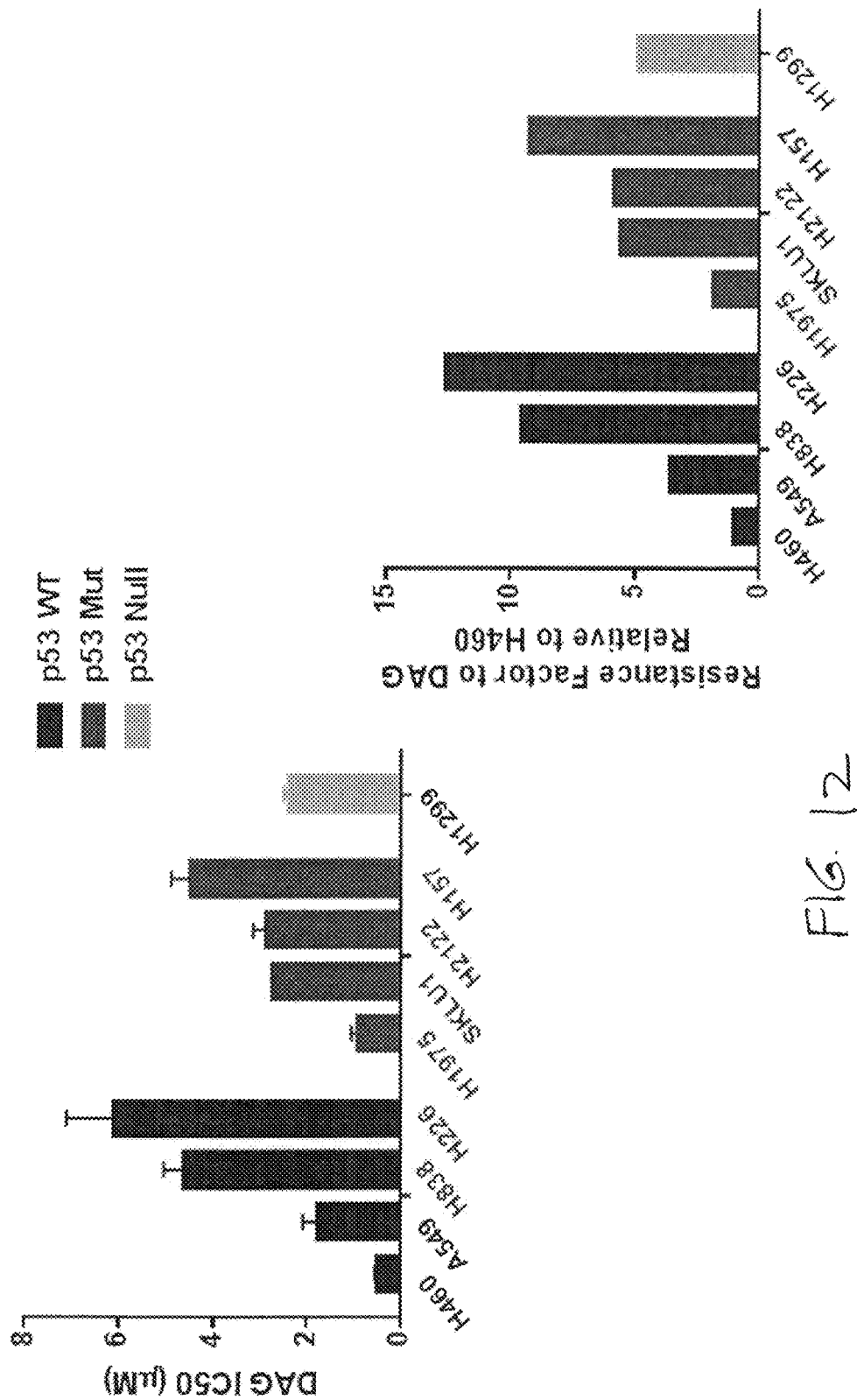
FIG. 12 is a graph showing the cytotoxicity of DAG and relative resistance in a human NSCLC tumor panel in vitro. The cell lines used are H460, A549, H838, and H226, which have a wild-type p53; H1975, SkLU1, H2122, and H157, which have a mutated p53; and H1229, which has a null p53.

FIG. 12 is a graph showing the cytotoxicity of DAG and relative resistance in a human NSCLC tumor panel in vitro. The cell lines used are H460, A549, H838, and H226, which have a wild-type p53; H1975, SkLU1, H2122, and H157, which have a mutated p53; and H1229, which has a null p53.

Figure 13:
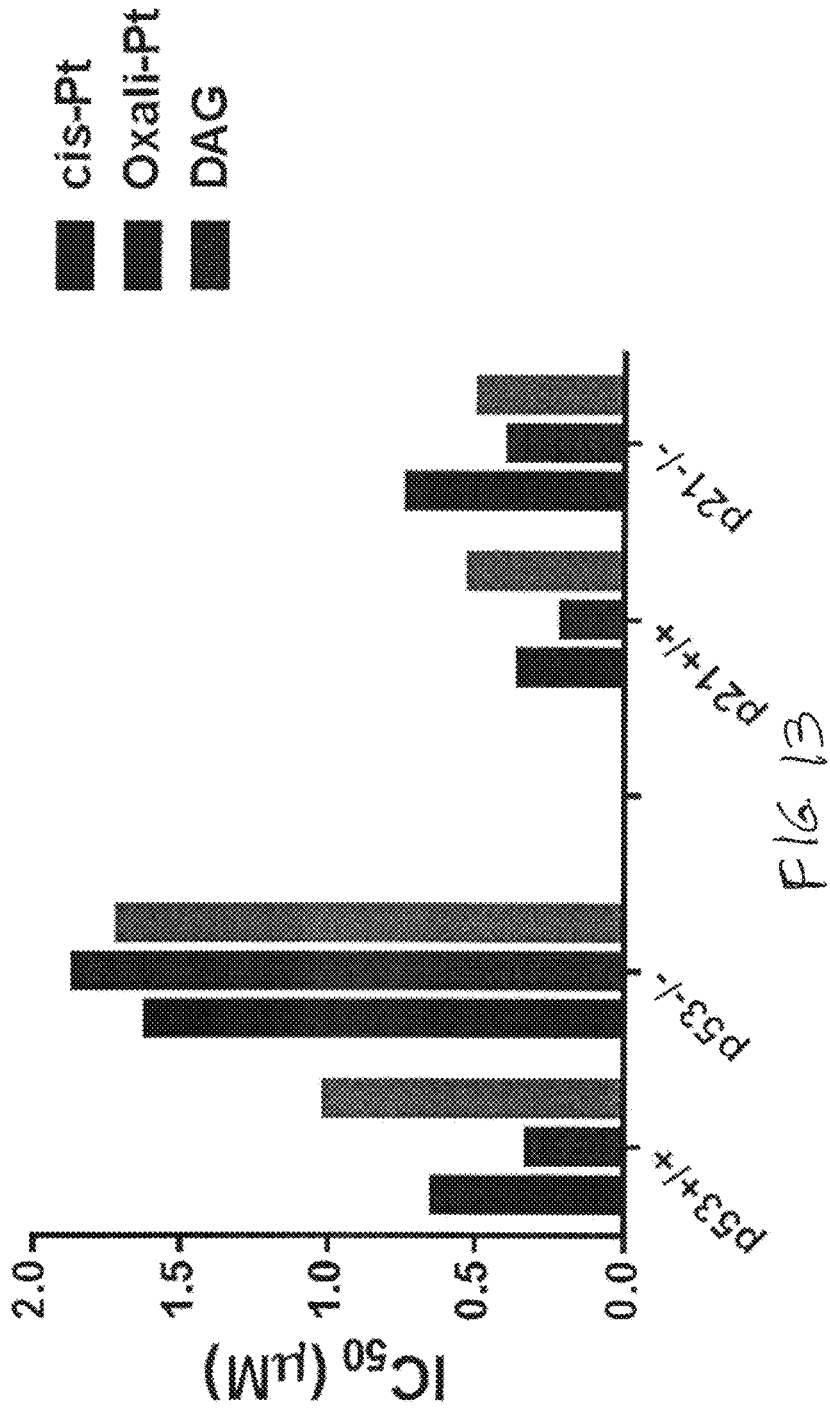
FIG. 13 is a graph showing the cytotoxicity of dianhydrogalactitol ("DAG") and the platinum drugs cisplatin ("cis-Pt") and oxaliplatin ("Oxali-Pt") against engineered HCT-116 tumor models in vitro. To better explore dependency of activity on p53 status, the molecularly engineered colorectal HCT-116 models were used. These isogenic models were molecularly engineered to knockout p53 (p53$^{-/-}$) or p21 (p21$^{-/-}$). The p53$^{+/+}$ or p21$^{+/+}$ represent the corresponding control. These IC$_{50}$ values were used to determine resistance of knockout models relative to corresponding controls.

FIG. 13 is a graph showing the cytotoxicity of dianhydrogalactitol ("DAG") and the platinum drugs cisplatin ("cis-Pt") and oxaliplatin ("Oxali-Pt") against engineered HCT-116 tumor models in vitro. To better explore dependency of activity on p53 status, the molecularly engineered colorectal HCT-116 models were used. These isogenic models were molecularly engineered to knockout p53 (p53$^{-/-}$) or p21 (p21$^{-/-}$). The p53$^{+/+}$ or p21$^{+/+}$ represent the corresponding control. The p53$^{-/-}$ cell lines are described in J. Boyer et al., "Characterization of p53 Wild-Type and Null Isogenic Colorectal Cell Lines Resistant to 5-Fluorouracil, Oxaliplatin, and Irinotecan," *Clin. Cancer Res.* 10: 2158-2167 (2004), incorporated herein by this reference. The p21$^{-/-}$ cell lines are described in Z. Han et al., "Role of p21 in Apoptosis and Senescence of Human Colon Cancer Cells Treated with Camptothecin," *J. Biol. Chem.* 277: 17154-17160 (2002), incorporated herein by this reference. These IC$_{50}$ values were used to determine resistance of knockout models relative to corresponding controls.

Figure 14:
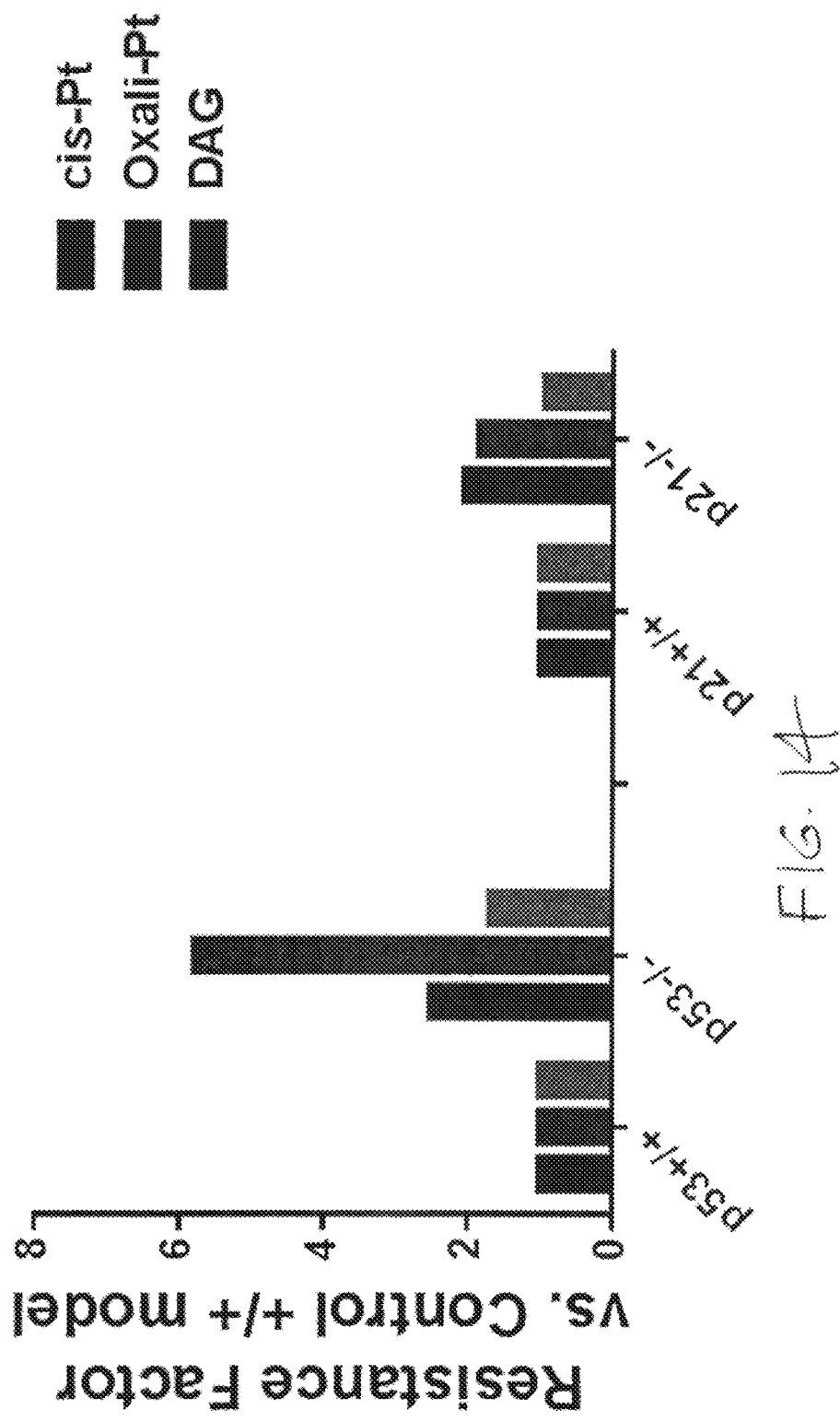
FIG. 14 is a graph showing the resistance factors for dianhydrogalactitol ("DAG") and the platinum drugs cisplatin ("cis-Pt") and oxaliplatin ("Oxali-Pt") in engineered HCT-116 tumor models in vitro. The resistance factors in the engineered colorectal HCT-116 models demonstrate that loss of p53 and p21 result in about 2-fold or greater resistance to cisplatin and oxaliplatin, but the resistance to DAG was lower ($p53^{-/-}$) or non-existent ($p21^{-/-}$).

FIG. 14 is a graph showing the resistance factors for dianhydrogalactitol ("DAG") and the platinum drugs cisplatin ("cis-Pt") and oxaliplatin ("Oxali-Pt") in engineered HCT-116 tumor models in vitro. The resistance factors in the engineered colorectal HCT-116 models demonstrate that loss of p53 and p21 result in about 2-fold or greater resistance to cisplatin and oxaliplatin, but the resistance to DAG was lower (p53$^{-/-}$) or non-existent (p21$^{-/-}$).

Figure 15:
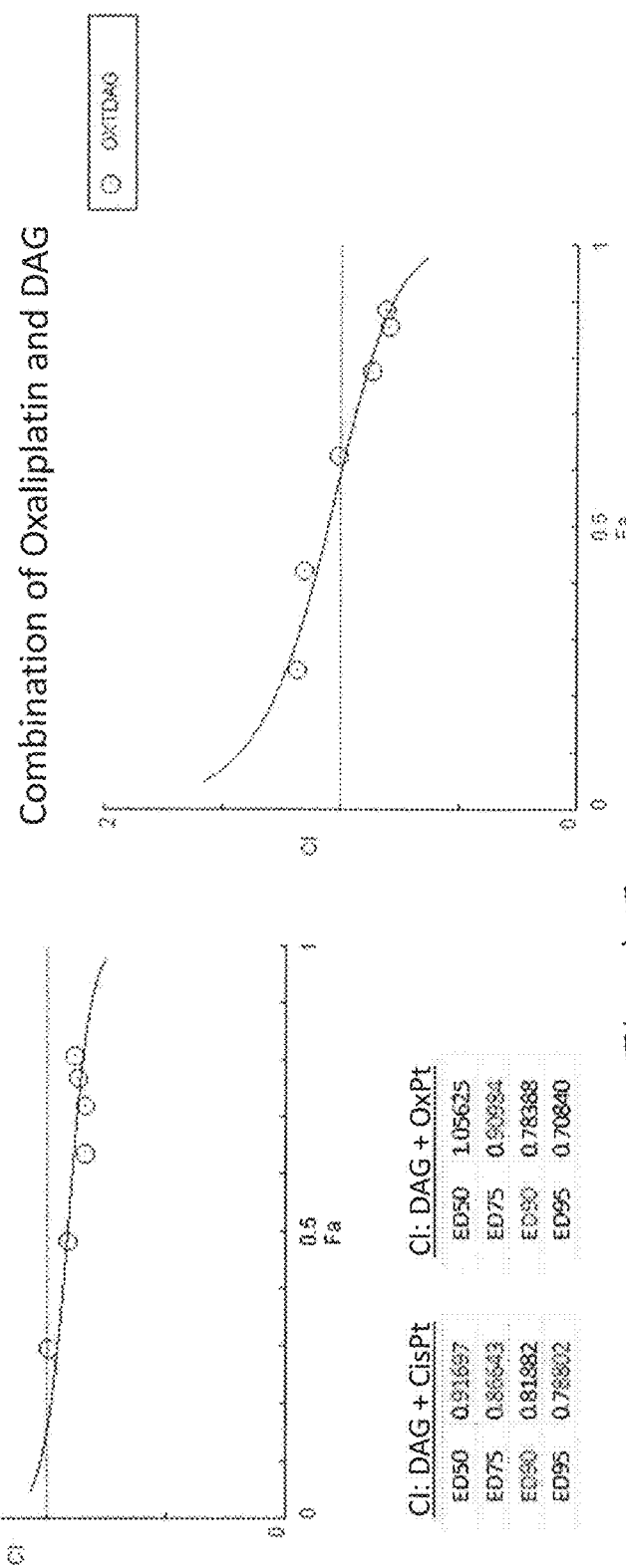
FIG. 15 shows the combination index of dianhydrogalactitol ("DAG") with cisplatin (CDDP) or oxaliplatin in an in vitro model of human A549 NSCLC model.

FIG. 15 shows the combination index of dianhydrogalactitol ("DAG") with cisplatin or oxaliplatin in vitro in a human A549 NSCLC model.

Figure 16:
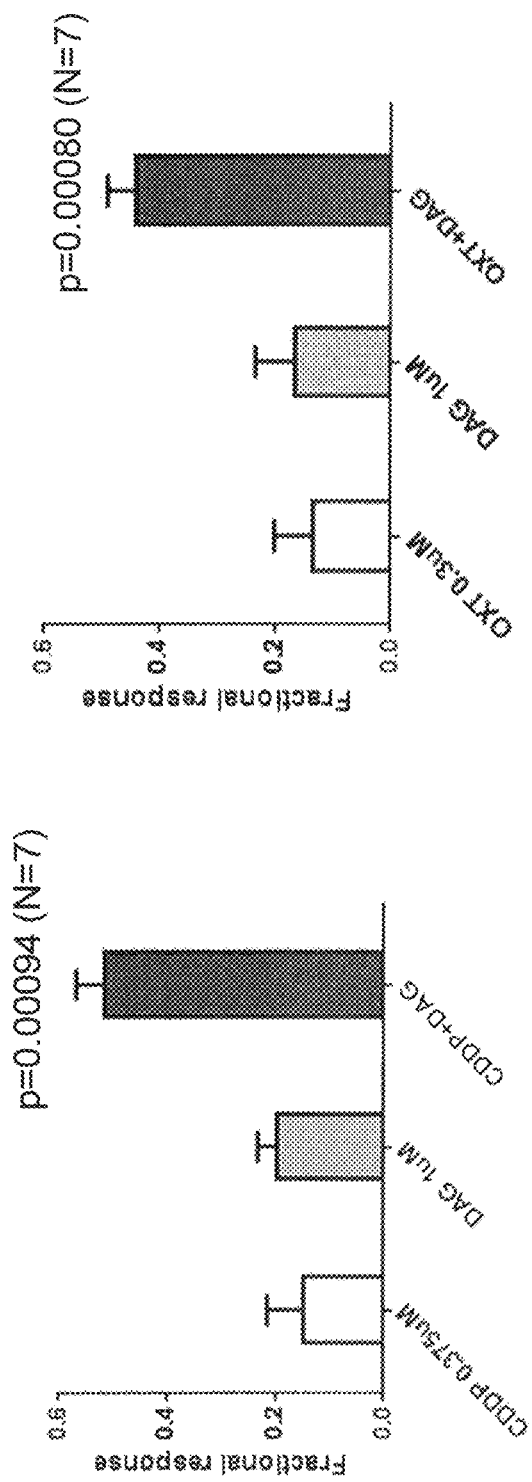
FIG. 16 is a graph showing the effect of dianhydrogalactitol (DAG) in combination with cisplatin (CDDP) or oxaliplatin (OXT) on cytotoxicity in A549 NSCLC cells in vitro. The left panel shows the results of DAG in combination with cisplatin; the right panel shows the results of DAG in combination with oxaliplatin. Data are shown as Mean+/−SE, N=7.

FIG. 16 is a graph showing the effect of dianhydrogalactitol (DAG) in combination with cisplatin or oxaliplatin on cytotoxicity in A549 cells in vitro. The left panel shows the results of DAG in combination with cisplatin; the right panel shows the results of DAG in combination with oxaliplatin.

Figure 17:
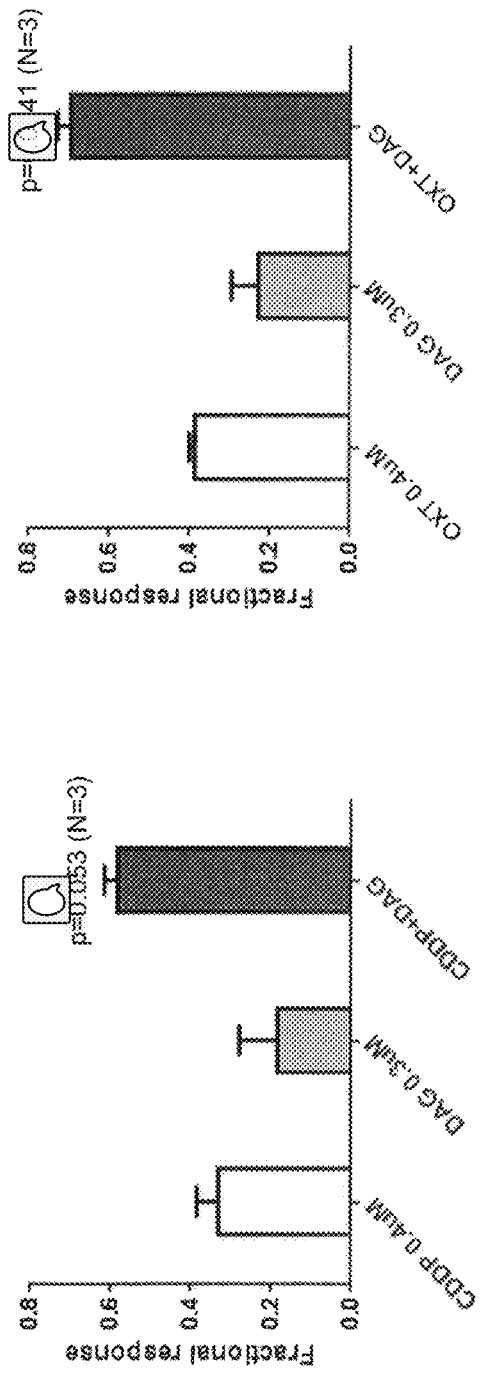
FIG. 17 is a graph showing the effect of dianhydrogalactitol (DAG) in combination with cisplatin or oxaliplatin on cytotoxicity in H460 NSCLC cells in vitro. The left panel shows the results of DAG in combination with cisplatin; the right panel shows the results of DAG in combination with oxaliplatin. With N=3 independent studies with H460 cells, the combination of cisplatin+DAG almost reaches significance for super-additivity, whereas the combination of oxaliplatin+DAG is super-additive. Data are shown as Mean+/−SE, N=4.
Figure 16:
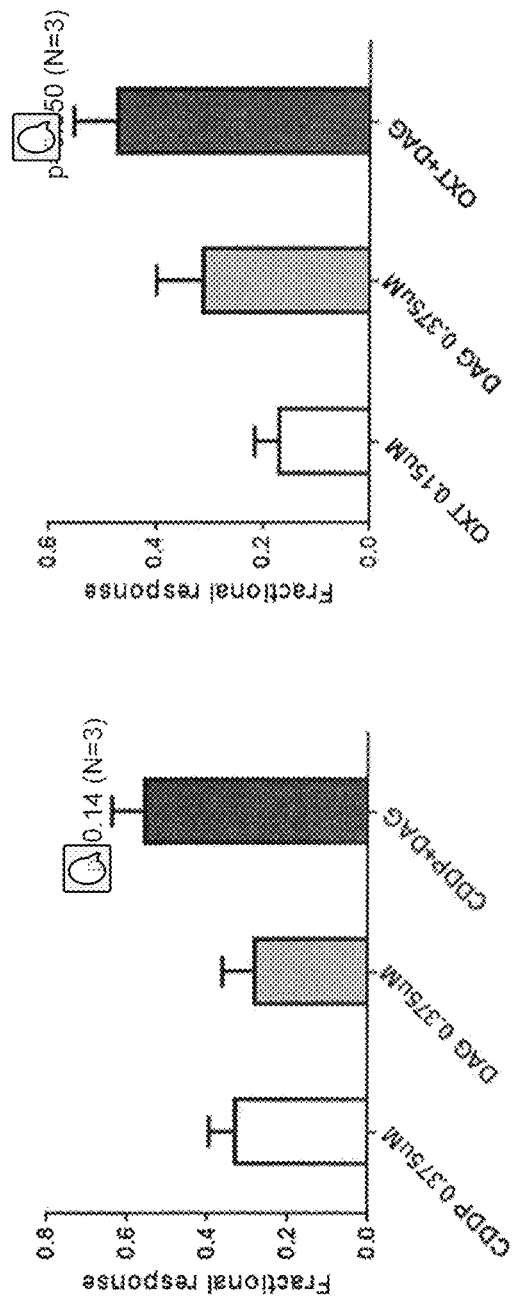

FIG. 17 is a graph showing the effect of dianhydrogalactitol (DAG) in combination with cisplatin or oxaliplatin on cytotoxicity in H460 cells in vitro. The left panel shows the results of DAG in combination with cisplatin; the right panel shows the results of DAG in combination with oxaliplatin. With N=3 independent studies with H460 cells, the combination of cisplatin+DAG almost reaches significance for super-additivity, whereas the combination of oxaliplatin+DAG is super-additive. Data are shown as Mean+/−SE.

FIG. 18 is a graph showing the effect of dianhydrogalactitol (DAG) in combination with cisplatin or oxaliplatin on cytotoxicity in H1975 cells in vitro. The left panel shows the results of DAG in combination with cisplatin; the right panel shows the results of DAG in combination with oxaliplatin. With N=3 independent studies with H1975 cells, the combination of cisplatin+DAG is additive, whereas the combination of oxaliplatin+DAG approaches significance for super-additivity. Data are shown as Mean+/−SE.

Figure 19:
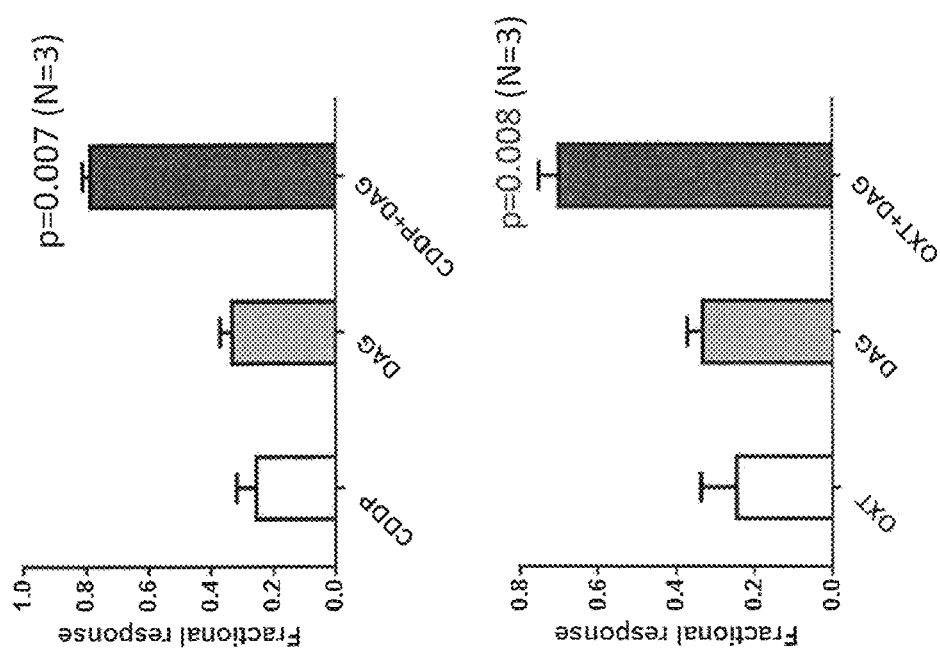
FIG. 19 is a graph showing the effect of dianhydrogalactitol (DAG) in combination with cisplatin (CDDP) or oxaliplatin (OXT) on cytotoxicity in H157 NSCLC cells in vitro. The top panel shows the results of DAG in combination with cisplatin; the bottom panel shows the results of DAG in combination with oxaliplatin. Data are shown as Mean+/−SE, N=3. Data is shown at ED75, ED90, and ED95. The H157 cell line presents a higher degree of resistance than other cell lines.

FIG. 19 is a graph showing the effect of dianhydrogalactitol (DAG) in combination with cisplatin or oxaliplatin on cytotoxicity in H157 cells in vitro. The top panel shows the results of DAG in combination with cisplatin; the bottom panel shows the results of DAG in combination with oxaliplatin. Data are shown as Mean+/−SE. Data is shown at ED75, ED90, and ED95. The H157 cell line presents a higher degree of resistance than other cell lines.

Studies in HCT-116 models demonstrated that loss of p53 increased resistance to cisplatin and oxaliplatin by 3- and 6-fold, respectively, while resistance to VAL-083 was <2-fold. As single agents, dianhydrogalactitol, cisplatin and oxaliplatin showed good cytotoxicity in all NSCLC cell lines to varying degrees, with H460 as the most sensitive (IC$_{50}$<0.5 uM). The IC50 in the other cell lines ranged from 0.9-6.1 μM, 0.5-2.2 μM and 0.6-2.6 μM for dianhydrogalactitol, cisplatin and oxaliplatin, respectively, and there was no overt difference in drug sensitivity between the wt and mutant/null p53 group. This suggests that either wt p53 is not activated and/or other genetic alterations reduce cytotoxic activities. The combination of dianhydrogalactitol with cisplatin or oxaliplatin in the A549 NSCLC model, demonstrated significant superadditivity (p<0.05) and synergism (CI<1) for both combinations. This strongly favors a non-overlapping mode of action between the platinum drugs and dianhydrogalactitol.

The results of this Example indicate that not only is dianhydrogalactitol an effective cytotoxic agent in a range of NSCLC tumor model cell lines, including cell lines that have mutated or absent p53 genes, but it is also effective in tumor model cell lines that have absent p21 genes. Furthermore, dianhydrogalactitol exhibits significant additive effects in terms of cytotoxicity with cisplatin and oxaliplatin, with super-additivity being observed with oxaliplatin.

ADVANTAGES OF THE INVENTION

The present invention provides improved methods and compositions employing dianhydrogalactitol for the treatment of non-small-cell lung carcinoma (NSCLC), a type of lung cancer that has proven resistant to chemotherapy by conventional means, as well as for the treatment of ovarian cancer.

The use of dianhydrogalactitol to treat NSCLC or ovarian cancer is expected to be well tolerated and not to result in additional side effects. Dianhydrogalactitol can be used together with radiation or other chemotherapeutic agents. Additionally, dianhydrogalactitol can be used to treat brain metastases of NSCLC or ovarian cancer and can be used to treat NSCLC or ovarian cancer in patients who have developed resistance to platinum-based therapeutic agents such as cisplatin, to tyrosine kinase inhbitors (TKIs), or to temozolomide.

Methods according to the present invention possess industrial applicability for the preparation of a medicament for the treatment of NSCLC or ovarian cancer. Compositions according to the present invention possess industrial applicability as pharmaceutical compositions.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Moreover, as used herein, unless otherwise stated, the term "comprising" is intended to encompass alternatives reciting "consisting essentially of" and "consisting." Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method of treating a patient with non-small cell lung cancer (NSCLC) resistant to a platinum-based anti-neoplastic agent consisting of the steps of:
    (a) administering a therapeutically effective quantity of dianhydrogalactitol to the patient to treat the NSCLC; and
    (b) administering a therapeutically effective quantity of the platinum-based anti-neoplastic agent to the patient to treat the NSCLC.

2. A method of treating a patient with non-small cell lung cancer (NSCLC) resistant to a platinum-based anti-neoplastic agent consisting of the steps of:
    (a) administering a therapeutically effective quantity of dianhydrogalactitol to the patient to treat the NSCLC;
    (b) administering a therapeutically effective quantity of the platinum-based anti-neoplastic agent to the patient to treat the NSCLC, and
    (c) resecting the NSCLC surgically subsequent to the administration of the dianhydrogalactitol and the platinum-based anti-neoplastic agent.

3. A method of treating a patient with non-small cell lung cancer (NSCLC) resistant to a platinum-based anti-neoplastic agent consisting of the steps of:
    (a) administering a therapeutically effective quantity of dianhydrogalactitol to the patient to treat the NSCLC;
    (b) administering a therapeutically effective quantity of the platinum-based anti-neoplastic agent to the patient to treat the NSCLC, and
    (c) resecting the NSCLC surgically prior to the administration of the dianhydrogalactitol and the platinum-based anti-neoplastic agent.

4. The method of claim 1 wherein the patient has brain metastases.

5. The method of claim 1 wherein the dianhydrogalactitol and the platinum-based anti-neoplastic agent are administered in a single pharmaceutical composition, wherein the pharmaceutical composition comprises: (i) dianhydrogalactitol; (ii) the platinum-based anti-neoplastic agent; and (iii) at least one pharmaceutically acceptable carrier.

6. The method of claim 1 wherein the dianhydrogalactitol and the platinum-based anti-neoplastic agent are administered in two pharmaceutical compositions: (i) a first pharmaceutical composition comprising dianhydrogalactitol and at least one pharmaceutically acceptable carrier; and (ii) a second pharmaceutical composition comprising the platinum-based anti-neoplastic agent and at least one pharmaceutically acceptable carrier.

7. The method of claim 1 wherein the patient has a wild-type p53 genotype.

8. The method of claim 1 wherein the patient has a mutated p53 genotype.

9. The method of claim 1 wherein the patient has a wild-type EGFR genotype.

10. The method of claim 1 wherein the patient has at least one mutation in a gene encoding a protein that is a target of at least one tyrosine kinase inhibitor (TKI).

11. The method of claim 1 wherein the patient is characterized by the presence of at least one gene in either a wild-type or mutated state encoding a product that confers resistance to the therapeutic effects of at least one tyrosine kinase inhibitor (TKI).

12. The method of claim 11 wherein the gene in either a wild-type or mutated state encoding a product that confers resistance to the therapeutic effects of at least one TKI is AHI-1.

13. The method of claim 12 wherein the AHI-1 gene is mutated as the result of a proviral insertion.

14. The method of claim 1 wherein the patient is characterized by a mutation in the kinase domain of ABL1 protein that is part of a BCR-ABL fusion protein that is a target of TKIs.

15. The method of claim 1 wherein the patient is characterized by a germline DNA deletion polymorphism conferring resistance to tyrosine kinase inhibitors (TKIs).

16. The method of claim 15 wherein the germline DNA deletion polymorphism is a germline DNA deletion polymorphism of 2903 bp located in the BIM gene.

17. The method of claim 16 wherein the germline DNA deletion polymorphism causes a splicing variation that leads to expression of an isoform of BIM protein that lacks a BH3 domain and thus inhibits the induction of apoptosis.

18. The method of claim 1 wherein the platinum-based anti-neoplastic agent is selected from the group consisting of cisplatin, carboplatin, oxaliplatin, satraplatin, picoplatin, nedaplatin, triplatin, lobaplatin, heptaplatin, and lipoplatin.

19. The method of claim 18 wherein the platinum-based anti-neoplastic agent is selected from the group consisting of cisplatin, carboplatin, and oxaliplatin.

20. The method of claim 19 wherein the platinum-based anti-neoplastic agent is cisplatin.

21. The method of claim 1 wherein the cytotoxic activity of dianhydrogalactitol and the platinum-based anti-neoplastic agent is higher than the cytotoxic activity of the dianhydrogalactitol administered at the same dosage as a single anti-neoplastic agent.

22. The method of claim 21 wherein the platinum-based anti-neoplastic agent is selected from the group consisting of cisplatin, carboplatin, and oxaliplatin.

23. The method of claim 22 wherein the platinum-based anti-neoplastic agent is cisplatin.

24. A method for treating a patient with non-small cell lung cancer (NSCLC) resistant to a platinum-based anti-neoplastic agent, wherein the patient has a mutated p53 gene consisting of the steps of:
  (a) determining the existence of a mutated p53 gene in the patient, wherein the mutated p53 gene affects the resistance of the NSCLC to at least one platinum-based anti-neoplastic agent;
  (b) administering a therapeutically effective quantity of dianhydrogalactitol to the patient to treat the NSCLC, wherein the therapeutically effective quantity of dianhydrogalactitol is determined from results on cell lines with a mutated p53 gene; and
  (c) administering a therapeutically effective quantity of the platinum-based anti-neoplastic agent to the patient to treat the NSCLC, wherein the therapeutically effective quantity of the platinum-based anti-neoplastic agent is determined from results on cell lines with a mutated p53 gene.

25. The method of claim 24, wherein the existence of the mutated p53 gene in the patient is determined by a method selected from the group consisting of gene sequencing, restriction fragment length polymorphism, and determining whether p53 in a cell sample from the patient binds to a pGL3 vector.

26. The method of claim 24, wherein the method further comprises the step of administering a therapeutically effective quantity of a p53 mimetic to the patient to treat the NSCLC.

27. The method of claim 24 wherein the platinum-based anti-neoplastic agent is selected from the group consisting of cisplatin, carboplatin, oxaliplatin, satraplatin, picoplatin, nedaplatin, triplatin, lobaplatin, heptaplatin, and lipoplatin.

28. The method of claim 27 wherein the platinum-based anti-neoplastic agent is selected from the group consisting of cisplatin, carboplatin, and oxaliplatin.

29. The method of claim 28 wherein the platinum-based anti-neoplastic agent is cisplatin.

30. The method of claim 24 wherein the cytotoxic activity of dianhydrogalactitol and the platinum-based anti-neoplastic agent is higher than the cytotoxic activity of the dianhydrogalactitol administered at the same dosage as a single anti-neoplastic agent.

31. The method of claim 30 wherein the platinum-based anti-neoplastic agent is selected from the group consisting of cisplatin, carboplatin, and oxaliplatin.

32. The method of claim 31 wherein the platinum-based anti-neoplastic agent is cisplatin.

33. The method of claim 1, wherein the combination of the therapeutically effective quantity of dianhydrogalactitol and the therapeutically effective quantity of the platinum-based anti-neoplastic agent act synergistically to treat the patient with NSCLC resistant to the platinum-based anti-neoplastic agent.

* * * * *